US007560252B2

(12) United States Patent
Salas et al.

(10) Patent No.: US 7,560,252 B2
(45) Date of Patent: Jul. 14, 2009

(54) BORRELIDIN-PRODUCING POLYKETIDE SYNTHASE AND ITS USE

(75) Inventors: Jose A Salas, Oviedo (ES); Carmen Mendez, Oviedo (ES); Carlos Olano, Oviedo (ES); Cesar Sanchez, Oviedo (ES); Alfredo F Brana, Oviedo (ES); Barrie Wilkinson, Sharnbrook (GB); Christine J Martin, Cambridge (GB); Steven Moss, Cambridge (GB); Peter F Leadlay, Cambridge (GB); Marko Oliynyk, Cambridge (GB)

(73) Assignees: Biotica Technology Limited, Essex (GB); The University of Oviedo, Oviedo (ES)

( * ) Notice: Subject to any disclaimer, the term of this patent is extended or adjusted under 35 U.S.C. 154(b) by 388 days.

(21) Appl. No.: 10/534,210

(22) PCT Filed: Dec. 24, 2003

(86) PCT No.: PCT/GB03/05704

§ 371 (c)(1),
(2), (4) Date: Mar. 17, 2006

(87) PCT Pub. No.: WO2004/058976

PCT Pub. Date: Jul. 15, 2004

(65) Prior Publication Data

US 2007/0065920 A1 Mar. 22, 2007

(30) Foreign Application Priority Data

Dec. 27, 2002 (GB) ................................ 0230217.2

(51) Int. Cl.
*C12P 19/62* (2006.01)
*C07H 21/04* (2006.01)

(52) U.S. Cl. ...................... 435/76; 435/193; 435/252.3; 435/471; 536/23.2

(58) Field of Classification Search .................. 435/76, 435/193, 252.3, 471; 536/23.2
See application file for complete search history.

(56) References Cited

U.S. PATENT DOCUMENTS

| | | | |
|---|---|---|---|
| 4,759,928 | A | 7/1988 | Gurusiddaiah |
| 6,193,964 | B1 | 2/2001 | Shiang |
| 6,815,465 | B1 | 11/2004 | Makk |

FOREIGN PATENT DOCUMENTS

| | | |
|---|---|---|
| DE | 3607287 | 1/1988 |
| JP | 8173176 | 7/1996 |
| JP | 09227549 | 9/1997 |
| WO | 01/09113 | 2/2001 |
| WO | 01/68867 | 9/2001 |

OTHER PUBLICATIONS

Thomas, I., et al., (Jul. 2002) "Skipping in a hybrid polyketide synthase: evidence for ACP-to-ACP chain transfer," Chem. Biol. 9:781-787.

Tsuchiya, E., et al., (Jan. 2001) "Borrelidin inhibits a cyclin-dependent kinase (CDK), Cdc28/Cln2, of *Saccharomyces cerevisiae*," J. Antibiot. 54:84-90.

Wakasugi, K., et al., (Jan. 8, 2002) "A human aminoacyl-tRNA synthetase as a regulator of angiogenesis," Proc. Nat. Acad. Sci. USA 99:173-177.

Wakabayashi, T., et al., (Aug. 1997) "Borrelidin is an angiogenesis inhibitor; disruption of angiogenic capillary vessels in a rat aorta matrix culture model," J. Antibiot. 50:671-676.

Waldron, C., et al., (2001) "Cloning and analysis of the spinosad biosynthetic gene cluster of *Saccharopolyspora spinosa*," Chem. Biol. 8:487-499.

Wilkinson, B., et al., (Jan. 14, 2000) "Novel octaketide macrolides related to 6-deoxyerythronolide B provide evidence for iterative operation of the erythromycin polyketide synthase," Chem. Biol. 7:111-117.

Wu, N., et al., (Jul. 11, 2001) "Assessing the balance between protein-protein interactions and enzyme-substrate interactions in the channeling of intermediates between polyketide synthase modules," J. Am. Chem. Soc. 123: 6465-6474.

Xue, Y.Q., et al., (Oct. 1998) "A gene cluster for macrolide antibiotic biosynthesis in *Streptomyces venezuelae*: architecture of metabolic diversity," Proc. Nat. Acad. Sci. USA 95:12111-12116.

Xue, Y.Q., et al., (Feb. 2000) "Alternative modular polyketide synthase expression controls macrolactone structure," Nature 403:571-575.

Bentley S.D., et al. (May 9, 2002) "Complete genome sequence of the model actinomycetes *Streptomyces coelicolor* A3(2)," Nature 417:141-147.

Kuo, M.S., et al., "Assignment of 1H and 13C NMR signals and the alkene geometry at C-7 in borrelidin," J. of Antibiotics, 42(6):1006-1007 (Jun. 1989).

Funahashi, Y., et al., "Establishment of a quantitative mouse dorsal air sac model and its application to evaluate a new angiogenesis inhibitor," Oncology Research 11:319-29 (1999).

Haddad, N., et al., "Studies towards total synthesis of borrelidin, regioselective methylation of bis-epoxides and structure determination," Tetrahedron Letters, 38(34):6079-6082 (1997).

Haddad, N., et al., "Studies towards total synthesis of borrelidin, stereoselective synthesis of the polysubstituted macrolidic part," Tetrahedron Letters, 38(34):6075-6078 (1997).

Hardt, I., et al. (Dec. 29, 2000) New Natural Epothilones from *Sorangium cellulosum*, Strains So ce90/B2 and So ce90/D13: Isolation, Structure Elucidation, and SAR Studies.

(Continued)

*Primary Examiner*—Chih-Min Kam
(74) *Attorney, Agent, or Firm*—Dann Dorfman Herrell and Skillman; Robert C. Netter, Jr.

(57) ABSTRACT

The present invention relates to the biosynthesis of polyketides and derives from the cloning of nucleic acids encoding a polyketide synthase and other associated proteins involved in the synthesis of the polyketide borrelidin. Materials and methods including enzyme systems, nucleic acids, vectors and cells are provided for the preparation of polyketides including borrelidin and analogues and derivatives thereof. Novel polyketide molecules are also provided.

17 Claims, 11 Drawing Sheets

OTHER PUBLICATIONS

Anderson, B.F., et al., (1989) "Crystal and molecular structures of two isomorphous solvates of the macrolide antibiotic borrelidin: absolute configuration determination by incorporation of a chiral solvent in the in the crystal lattice," Aust. J. Chem., 42:717-730.

Anderton, K., et al., (Apr. 17, 1965) "Some structural features of borrelidin, an anti-viral antibiotic," Nature 206:269.

Aparicio, J.F., et al., (1996) "Organization of the biosynthetic gene cluster for rapamycin in Streptomyces hygroscopicus: analysis of the enzymatic domains in the modular polyketide synthase," Gene 169:9-16.

August, P.R., et al., (Feb. 1998) "Biosynthesis of the ansamycin antibiotic rifamycin: deductions from the molecular analysis of the rif biosynthetic gene cluster of Amycolatopsis mediterranei S699," Chem. Biol. 5:69-79.

Beck, J.B., et al., (May 2002) "The hidden steps of domain skipping: macrolactone ring size determination in the pikromycin modular polyketide synthase," Chem. Biol. 9:575-583.

Berger, J., et al., (1949) "Borrelidin, a new antibiotic with anti-borrelia activity and penicillin enhancement properties," Arc. Biochem. 22:476-478.

Brautaset, T., et al., (May 23, 2000) "Biosynthesis of the polyene antifungal antibiotic nystatin in Streptomyces noursei ATCC 11455: analysis of the gene cluster and deduction of the biosynthetic pathway," Chem. Biol. 7:395-403.

Butler, A.R., et al., (Apr. 8, 1999) "Impact of thioesterase activity on tylosin biosynthesis in Streptomyces fradiae," Chem. Biol. 6:287-292.

Caffrey, P., et al., (2001) "Amphotericin biosynthesis in Streptomyces nodosus: deductions from analysis of polyketide synthase and late genes," Chem. Biol. 8:713-723.

Cheng, Y.Q., et al., (Mar. 18, 2003) "Type I polyketide synthase requiring a discrete acyltransferase for polyketide biosynthesis," Proc. Natl. Acad. Sci. USA. 100:3149-3154.

Cortés J., et al., (Nov. 8, 1990) "An unusually large multifunctional polypeptide in the erythromycin producing polyketide synthase of Saccharopolyspora erythraea," Nature 348:176-178.

Cortés, J., et al., (Jun. 9, 1995) "Repositioning of a domain in a modular polyketide synthase to promote specific chain cleavage," Science 268:1487-1489.

Cortés, J., et al., (2002) "Identification and cloning of a type III polyketide synthase required for diffusible pigment biosynthesis in Saccharopolyspora erythraea," Mol. Micro. 44:1213-1224.

Dickinson, L., et al., (Apr. 17, 1965) "Anti-viral activity of two antibiotics isolated from a species of Streptomyces," Nature 206:265-268.

Donadio, S., et al., (May 3, 1991) "Modular organization of genes required for complex polyketide biosynthesis," Science 252:675-679.

Donadio, S., et al., (1993) "An erythromycin analog produced by reprogramming of polyketide synthesis," Proc. Nat. Acad. Sci. USA 90:7119-7123.

Duffey, M.O., et al., (2003) "Enantioselective total synthesis of borrelidin," J. Am. Chem. Soc. 125:1458-1459.

Eastwood, E.L., et al., (2003) "Borrelidin induces the transcription of amino acid biosynthetic enzymes via a GCN4-dependent pathway," Bioorg. Med. Chem. Lett. 13:2235-2237.

Fernandez, E., et al., (Sep. 1998) "Identification of two genes from Streptomyces argillaceus encoding glycosyltransferases involved in transfer of a disaccharide during the biosynthesis of the antitumor drug mithramycin," J. Bacteriol. 180:4929-4937.

Floss, H.G. (2001) "Antibiotic biosynthesis: from natural to unnatural compounds," J. Ind. Micro. Biotech. 27:183-194.

Fouces, R., et al., (1999) "The tylosin biosynthetic cluster from Streptomyces fradiae: genetic organization of the left region," Microbiol. 145:855-868.

Gaisser, S., et al., (2000) "A defined system for hybrid macrolide biosynthesis in Saccharopolyspora erythraea," Mol. Microbiol. 36:391-401.

Gaisser, S., et al., (2002) "Engineered biosynthesis of novel spinosyns bearing altered deoxyhexose substituents," Chem. Commun. 618-619.

Gaitatzis, N., et al., (Apr. 12, 2002) "The biosynthesis of the aromatic myxobacterial electron transport inhibitor stigmatellin is directed by a novel type of modular polyketide synthase," J. Biol. Chem. 277:13082-13090.

Hanessian, S., et al., (2003) "Application of conformation design in acyclic stereoselection: total synthesis of borrelidin as the crystalline benzene solvate," J. Am. Chem. Soc. 125:13784-13792.

Bantleon, R., et al. (Apr. 1994) "Chloroperoxidase from Streptomyces lividans: Isolation and characterization of the enzyme and the corresponding gene," J. Bact. 176(8):2339-2347.

Hunziker, D., et al., (1998) "Primer unit specificity in rifamycin biosynthesis principally resides in the later stages of the biosynthetic pathways," J. Am. Chem. Soc. 120:1092-1093.

Kawamura, T., et al., (Aug. 2003) "Anti-angiogenesis effects of borrelidin are mediated through distinct pathways: Threonyl-tRNA synthetase and caspases are independently involved in suppression of proliferation and induction of apoptosis in endothelial cells," J. Antibiot. 56:709-715.

Kuhstoss, S., et al., (1996) "Production of a novel polyketide through the construction of a hybrid polyketide synthase," Gene 183:231-236.

Lozano, M.J., et al., (Feb. 4, 2000) "Characterization of two polyketide methyltransferases involved in the biosynthesis of the antitumor drug mithramycin by Streptomyces argillaceus," J. Biol. Chem. 275:3065-3074.

Maehr, H., et al., (Oct. 1987) "Identity of borrelidin with treponemycin," J. Antibiot. 40:1455-1456.

Marsden, A.F.A., et al., (1998) "Engineering broader specificity into an antibiotic-producing polyketide synthase," Science 279:199-202.

Moore, B.S., et al., (2001) "Discovery of a new bacterial polyketide biosynthetic pathway," Chembiochem. 2:35-38.

Olano, C., et al., (2003) "Evidence from engineered gene fusions for the repeated use of a module in a modular polyketide synthase," Chem. Commun. 2780-2782.

Oliynyk, M., et al., (1996) "A hybrid modular polyketide synthase obtained by domain swapping," Chem. Biol. 3:833-839.

Otani, A., et al., (Jan. 8, 2002) "A fragment of human TrpRS as a potent antagonist of ocular angiogenesis," Proc. Nat. Acad. Sci. USA 99:178-183.

Otoguru, K., et al., (Aug. 2003) "In vitro and in vivo antimalarial activities of a non-glycosidic 18-membered macrolide antibiotic, borrelidin, against drug-resistant strains of Plasmodia," J. Antibiot. 56:727-729.

Pacey, M.S., et al., (Nov. 1998) "Novel erythromycins from a recombinant Saccharopolyspora erythraea strain NRRL 2338 plG1 I. Fermentation, isolation and biological activity," J. Antibiot. 51:1029-1034.

Paetz, W., et al., (1973) "Biochemical and immunological characterization of threonyl-tRNA synthetase of two borrelidin-resistant mutants of Escherichia coli K12," Eur. J. Biochem. 35:331-337.

Quiros, L.M., et al., (1998) "Two glycosyltransferases and a glycosidase are involved in oleandomycin modification during its biosynthesis by Streptomyces antibioticus," Mol. Microbiol. 28:1177-1185.

Raibaud, A., et al., (Jul. 1991) "Nucleotide sequence analysis reveals linked N-acetyl hydrolase, thioesterase, transport, and regulatory genes encoded by the bialophos biosynthetic gene cluster of Streptomyces hygroscopicus," J. Bacteriol. 173:4454-4463.

Ranganathan, A., et al., (Sep. 14, 1999) "Knowledge-based design of bimodular and trimodular polyketide synthases based on domain and module swaps: a route to simple statin analogues," Chem. Biol. 6:731-741.

Reeves, C.D., et al., (2001) "Alteration of the substrate specificity of a modular polyketide synthase acyltransferase domain through site-specific mutations," Biochemistry 40:15464-15470. (7 sheets).

Rowe, C.J., et al., (2001) "Engineering a polyketide with a longer chain by insertion of an extra module into the erythromycin-producing polyketide synthase," Chem. Biol. 8:475-485. (11 sheets).

Rudd, B.A.M., et al., (Aug. 12-18, 1990) "The biosynthesis of a family of novel antiparasitic macrolides," Proceedings of the 6th International Symposium on the Genetics of Industrial Microorganisms. Strausbourg, France. Abstract A70. p. 96, ISBN 2-87805-004-5. (and 2 additional sheets).

Schwecke, T., et al., (Aug. 1995) "The biosynthetic gene cluster for the polyketide immunosuppressant rapamycin," Proc. Nat. Acad. Sci. USA 92:7839-7843.

Shaw-Reid, C.A., et al., (May 20, 1999) "Assembly line enzymology by multimodular nonribosomal peptide synthetases: the thioesterase domain of *E. coli* EntF catalyzes both elongation and cyclolactonization," Chem. Biol. 6:385-400.

Silakowski, B., et al., (2001) "Novel features in a combined polyketide synthase/non-ribosomal peptide synthetase: the myxalamid biosynthetic gene cluster of the myxobacterium *Stigmatella aurantica* Sga15," Chem. Biol. 8:59-69.

Singh, S.K., et al., (Feb. 1985) "Treponemycin, a nitrile antibiotic active against *Treponema hyodysenteriae*," Antimicrob. Agents Chemother. 27:239-245.

Swan, D.G., et al., (1994) "Characterization of a *Streptomyces antibioticus* gene encoding a type I polyketide synthase which has an unusual coding sequence," Mol. Gen. Genet. 242:258-362.

Borrelidin (1)

12-desnitrile-12-carboxyl borrelidin (2)

10-desmethyl borrelidin (3)

11-*epi* borrelidin (4)

14,15-cis-borrelidin (5)

[1,2-$^{13}$C]sodium acetate

[2,3-$^{13}$C]sodium propionate

*trans*-cyclopentane-1,2-dicarboxylic acid 5-oxo-pent-3-ene-1,2,5-tricarboxylic acid 2-hydroxy-hepta-2,4-diene-1,7-dioic acid 2-oxo-hept-3-ene-1,7-dioic acid (10)

2-oxo-hepta-1,7-dioic acid (11)

2-hydroxy-hepta-1,7-dioic acid (12)

2-OP-hepta-1,7-dioic acid (13) (P = H or activating group)

*trans*-cyclopentane-1,2-dicarboxylic acid pre-borrelidin 14

14

16

15

17

1

6

7

8

General tyrosine catabolism

L-tyrosine 4-hydroxyphenylpyruvic acid 4-hydroxyphenylacetic acid (9)

homoprotocatechuic acid 5-carboxymethyl-2-hydroxy muconic semialdehyde 5-carboxymethyl-2-hydroxy muconic acid 5-oxo-pent-3-ene-1,2,5-tricarboxylic acid 2-hydroxy-hept-2,4-diene-1,7-dioic acid 2-oxo-hept-3-ene-1,7-dioic acid 10

2,4-dihydroxy-hept-2-ene-1,7-dioic acid succinate semialdehyde pyruvate

18: m/z = 474.3 ([M-H]⁻)

19: m/z = 476.3 ([M-H]⁻)

20: m/z = 462.3 ([M-H]⁻)

21: m/z = 463.3 ([M-H]$^-$)
$\lambda_{max}$ = 240 nm

22: m/z = 465.4 ([M-H]$^-$)
$\lambda_{max}$ = 240 nm

23: m/z = 451.3 ([M-H]$^-$)
$\lambda_{max}$ = 240 nm

24: m/z = 493.3 ([M-H]$^-$)
$\lambda_{max}$ = 262 nm

25: m/z = 495.3 ([M-H]$^-$)
$\lambda_{max}$ = 262 nm

26: m/z = 481.3 ([M-H]$^-$)
$\lambda_{max}$ = 262 nm

SEQUENCE LISTING

<160> NUMBER OF SEQ ID NOS: 113

<210> SEQ ID NO 1
<211> LENGTH: 74787
<212> TYPE: DNA
<213> ORGANISM: Streptomyces parvulus Tu4055

<400> SEQUENCE: 1
gatcccgcgc ggcatcgccg tcgacgtgct gcgggccggc gaccgctggc cccacagcgc 60
ggcaccgcgc caccggggac tcctcaacgc ctggtggggc gcctgggtct gggccacggt 120
cttcgaccgc tacgcgtcga ggacctacga cgacgcccag gacgtcgacg cgatccacga 180
cgcggcggga ctggtcatgg ccggtgccgg attcgacatc ctcgccgccg tgctcgcgat 240
cctcttcgtg cgccggctga ccgccgcaca gcacgcgaag gccctcgcgg ggcccacccc 300
gccgacgcac tgagccgccc gcacccgtga tcccgccccg cgatccccgg gcccgataaa 360
tgcgttggcc ccggcgcgcg cctgtggtgg gatgagcggc gacgggggcg gctccccggc 420
gtgcatcctt ctcaccttcc tgcaaagatc ccgcgcgccc actctccgcc cccgttcttc 480
cgtcccgagc cgtcgccgcc gtggaggctt tcctgttgct cgccgccgag tccgtactgc 540
tgcgccgtga ccagagcgtc tacgtgaccc cggggtccga gccggacggt ccgccgaggg 600
ccgcactgcg ccggctcgag gccgaactgc tcggccgcgg ccacgccgtc tccgcgccgc 660
tgcacgcggt cctcgcctcc ttggactccg aggaactggc ggccgcccac gtacgcctcg 720
tcggactcgt cgacgacctg ctcggctccg accgcaccca caccccgctc ttccgccgct 780
tcccgcgcac cgtgccgcgc gacaccgagg cgctgtacgt ggaccgcgtc ttcgccttcc 840
tgctgcagca gcccgagcag ccctgcgtgc tgtgcggcga ggcgcgcacc gtcctgcccg 900
tgtcaccctg cgcgcacctg gtctgccggc tgtgctggga cggctccgac tacgcgggat 960
gcccgctgtg ccaccgcagg atcgacgggg acgacccctt cctgcgtccg gtccgtgccg 1020
tcggcgccgc cagggcgacc gtaccgggcc cgctgcgact gctgcgcctg ggcaccgaca 1080
tgaccgccga cgccaccacg gcggtggacg ccctgctggc ccgccgcacc ccgctctccc 1140
cgcaggaccg ggacgacctg ctcaccctgt tgccgctcac accggccggc cggggcgacc 1200
tgccgcagga catcccggtc cgcgagacca aggcgctggt cctgggcgcg ctggtgcgcc 1260
gggcaccgtc gcggccggcc ctgcggaggc tgctcgccga gcggctcacc accgccaccg 1320
acgtgctgcg gctgctcgcc gtgctctcgg gcggcgacgc cgggctggtg acaccggcac 1380
ggttcacgaa cgttccccgt tccctgcggc gtgacctgct cgccgtcctc gacggactgc 1440
cggcgccgta cctggtcgag gacatgctgc ggcaccccac ggcgtggaag cgggccgcgg 1500
aggtgctgca ccccttcgag gggcacaccc ggcacccgcg cgccgcgctc gccaccgccg 1560
tgctgcgcgc cacaccgttg gacccggaca ccgccttcgg cgccgccctg ctgaccacgg 1620
ccgccgcgca cccggacgcc gtgcgcccgg acggcacccg agtccgcccg gccacctggg 1680
cgggacggct ggagcaggcg atggccgagg gggacgccgc tcgggccgcg gccctcgccg 1740

-continued

```
gggagcggcc cggcgaactg gtgcgccgcc tggacgtgtt gctgcgcctg cacaccgacg   1800
aggcgctcgt gccggagctg gagaaggccc tgcggcacgg gctgccgaag gtgggcccgg   1860
gcccgctgct gtcggcgctc ggggcgctgc ggacacgcac cgaggaccgc accgggaccc   1920
ggcgcgtgtt cttcccgcgg ggcgacgtca cccgggccct gtccgtcccc gagcggcgcc   1980
ccgccctgcc cgccgggccg gtgtccgagg tggtcgccct gctggagggg gaactgctgc   2040
gccggttcgc cgccgggcgg ccctacgagc tgtcggtgct ggacgccgga ctgaccgacc   2100
tcaccgtgcc gttcaccgag cggaccgccg ccaaggccct ggtgaccgtg ggccgcggca   2160
gcgtccaggc actccccgag ggctccgtgc tccgactgtt cctgcactgg acggaacccc   2220
ggggcaaccg caccgacctg gacctgtccg tcgccttctt cgacgccgag tggacgttca   2280
ccggcctgtg cgactacacg aacctggtgc acggtccgga cgcggcgatc cactccggcg   2340
acctcacgtc ggccccggcg ccgcgcggcg ccaccgagta cgtggacctc gacctggagc   2400
ggctggcgcg gcggggagac acctacgccg tcccgctggt gttcagctac aacaacgtcc   2460
cgttcgagga actgccggac gccttcgccg ggttcatggc gctgcccgcg gaaggcccgc   2520
gcgacgcgac ctacgacccg cgcaccgtgc ggcagcgctt cgacctcgcg ggcgactcca   2580
aggtgtgcct gccgatgatc gtggacctgg cccgccggcg ggcgttgtgg accgacaccc   2640
acctgccgtc cgcgggcggc ttccagagca tcggttcgca cggcggcggt gagctggccg   2700
cggtggccgg tgacctctgg cagcagttca cctcgggcgg ccgggcgacc ctgtgggacc   2760
tcgccgtcct gcgggcggcc gccctctcgc cggaggtggc ggtggtgtcc cgggagccgg   2820
agcccgcggt gctgcgttac cggcggcggg cggccgagag cgaggccgcg ttcgccgtcc   2880
gagtcgcgtc ccacaaggac gccgaggaac ggctggcgca caccgacccc gactcggccg   2940
cggccgggct cgccgccggc cggcgggtct tcctcgcgac ggtccacggt gacgtccggc   3000
cgccgggggc gtcgggcacg tcctaccggc tcttccccgg ggccggggac gcctcaccga   3060
ccctgacccg cgtgaccgcc ggggacctgc tcgccgagct gggctgagcc aggcgccggc   3120
ccgcgccggc ccgcgccggc ccgtccctgc ccgtgccgga gggctcgccg gtcactccgg   3180
ccaggcggag ttctcgatga cctcgacgaa gtccgtacgc cggaagccgg gcgcgaagtg   3240
ctccagcaca tccgcgttca ccgtgccgaa ggtggtcgcg ggccggtgct cgaacccctc   3300
ggtgaacgcc cgcaggatct gcttcttgaa gtccgggcgg ggatgcgcgg cggtgaccgc   3360
gtcgatctgg gcccgggtga gattgcccag ccgcaggccg agcacgtcgg tctccacgcc   3420
ggcggtggtc gccgcgatct cgggggccat ccggtacggc acctccggag tggtgtgcag   3480
ggcgacggcc gtccacacgg tgtccgcgtc ggcctcgggg atgccgtggg cgagcaggaa   3540
ggcgtgggcc tggtcggcac cgtccatctc gaagcgctgg tcgtcaccgc ggtagggcgg   3600
caccaggccg gtgtcgtgga agagcgcggc gatgtacagc agctccgggt cggggcggat   3660
gcccagggcg gcggcctgga ggctgccgaa gaggtacaca cggcgtgagt ggtggaagat   3720
cagcggcgga gtggtgtcgc ggatcaggtc ggtcgcctcc cgcgccggcg cgctgtcggg   3780
aatctcgatg ccggcgatct gctcggccat ggctgccctc cggggaatcg gtgccgtcgt   3840
tgctgcctcc accctccgcc cggcgcgacc ccggcgtccg ctacccgatg gccgacaacc   3900
ccttacaagc ggccatgtgc cccgcgccgc cgcctcagcc gccgtccggg cgcgggccgg   3960
cgtccggcac ggtggtggcg aagcgctgcc ggtagcgggt gggcgacagc cccagatgac   4020
gggcgaaggc ccggcgcagg ctctcgtagc tggggaaacc cgacagcgcg gcggcctcgg   4080
tggcgttgtg cccggagtcg agcagcgcct tggcgatgtc gaaacggatc agctccacgt   4140
```

-continued

```
acttcacggg cgtgacgtcc agctcggccc ggaacatccg ggtcagatgc cgggggctga   4200
cccgcacgcg cgccgccaac gccgccagac tgtggtcggc ggccggatcg gcctgtacgg   4260
cgtcctggac ctgccgcagc acgggcgtcc gcggcgccgg gccccgcaac gaggcggaga   4320
actgcgactg gccgccggcc cgctgcaggt acaccaccag cgagcgcgcg accctgcggg   4380
cgagatcggg cccgtggtcc tcctccagca gcgcgagggc caggtcgatg cccgccgtca   4440
cgccggcgga cgtgtaggtc gccccgtcct tgacgaagat cgcgtcgggc tccacgcgtg   4500
tcgacggaca gcggcgggcc agcgcggtgg tgtgctgcca gtgcgtcgtc gcccgtctgc   4560
cctccagcag acccgcggca cccagcacga aggcgccggt gcacaccgag gcgacgcgtc   4620
cggcccgggc cgccagcgcc ttcgcggcgt cgatgagccg tgggtcgacg ggcgagccgg   4680
gcagcgcgtc accgccgacg acgacgagcg tgtccggcgg gccggcggaa cgcgcgtccg   4740
cctcggccgg gaccagcagg ccgatggacg aacgcaccgg cgccccgtcc ggggagacga   4800
cgccgagccg gtaccgggcc ccgaaccggt tggcctccgc gaagacctcc gccggccccg   4860
acaggtcgag catcttcatg ccgtcgaaga ccaggatgcc cacgctgtgc gctctcgccg   4920
tcatgtctcc ctctccgcgg gccggcgggc ccctgcgcgc cattgtcccg ccggccgtcc   4980
acgccggcgg ccggcggcgc gggcggccgg cggtcggaat gaggcgcgcc ggacatcggc   5040
gtagggtggc gagcgtgtgt tcggccgcgg tcccggagac cgcggaacgc aggacctttg   5100
gcaggcacgc ggaaggacag cgatgggtac ggtcaccacc tccgacggca cgagcatctt   5160
ctacaaggac tggggcccgc gcgacgcccc gccgatcgtc ttccaccacg gctggccgct   5220
caccgcggac gactgggaca accagatgct gttcttcctc tcgcacggct accgtgtgat   5280
cgcccacgac cggcgcggcc acggccgctc gggccagccc tcgacgggcc acgagatgga   5340
cacctacgcc gccgacgtcg cggcgctgac cgaagcgctc gacctgcggg acgccgtcca   5400
catcgggcat tcgaccggcg gcggcgaggt cgcgcgctat gtggcgcgcg ccgaaccggg   5460
ccgggtcgcc aaggccgtgc tggtcggcgc cgtgccgccg gtgatggtca agtccgacgc   5520
caaccccggc ggcaccccga tcgaggtctt cgacgggttc cgcacggccc tggccgccaa   5580
ccgggcccag ttctacatcg acgtgccctc cggccccttc tacggattca accgggaggg   5640
cgcgaaggtc tcccagggcc tgatcgacaa ctggtggcgg cagggcatgt cgggcgcggc   5700
caacgcccac tacgagtgca tcaaggcgtt ctccgagacc gacttcaccg aggacctcaa   5760
ggccatcgac gtgccggtgc tggtcgcgca cggcaccgac gaccaggtcg tgccctacgc   5820
ggactcggcg ccgctgtcgg tgaagctcct gaagaacggc accctcaagt cgtacgaagg   5880
gctcccgcac ggcatgctct ccacccaccc cgaggtggtc aaccccgacc tcctggactt   5940
cgtgaggtcc tagtcggcgc tcacgccggc gacacgggag cgggtgcggc gccgcgcacc   6000
gggtgcttgc tcaggacgga gacccggttg aaggcgttga tgctgatcgc cacccagatc   6060
acggcggaga cctcgtcgtc cgacaggacg ccccgtgcct gcgcgtaggc ggcgctctgc   6120
gcggcggcgt ccgccggacg ggtggtcgcc tccgcgaggg cgagcgccgc ccgctcccga   6180
gcggtgaaca gctcggtgtc ccgccaggcg ggcagcaccg ccaggcgctg ggtcgtctcg   6240
ccggcccgca gcgccgccct ggtgtgcaga ctgagacagt aggcacaggc attgagttgg   6300
gagacgcgga tgttcaccag ttccacgagg aggcggtcca ggccggccgc cgcggcggcc   6360
tcccgcaccg attccgccgc ggccacgaac gctttgtacg cgccgggggt ctgcttgtcg   6420
acgaagaccc gccgctcgtc cgtcgccacc ggggcctgct gtgtcacgtg gtctccttcg   6480
```

-continued

```
tcgcgctctc ttccggcggg tcctatcatc acccccatgg atgttgaaag tgaaactttc   6540
aggtcggggc cggacggggg cgcgtggtga gcaacacgga gacacggccc gcggagatgc   6600
ggtgcggcgc cctcgaagac gaggtgcccg ccgcgggcgt cgaagtcctc accgcccgtg   6660
acgtccccct cggcggcccg cgcgccatga ccgtgcggcg cacgctgccc cagcgggccc   6720
ggacgctgat cggagcctgg tgcttcgccg accactacgg tcccgacgac gtggccgcgt   6780
cgggcggcat ggacgtcgcc ccgcacccgc acatcggcct gcagacggtc agctggctgt   6840
tcagcgggga gatcgagcac cgggacagcc tcggcaccca cgccttcgtc aggcccggcg   6900
aactcaacct gatgaccggc ggcttcggca tcgcccactc cgaggtctcg acccccgaca   6960
ccactgtcct gcacggcgtc cagctctggg tggcgctgcc ggaggagcac cgcgacaccg   7020
gccgcgactt ccagcaccac gcacccgcgc cggtcgcctt cgacggcggc acggcacgcg   7080
tcttcctcgg ctcgctcgcc ggggacacct cgcccgtgag caccttcacg ccgctgctgg   7140
gcgccgagtt gacgctggtg ccgggcggca ccgccaccct ggacgtcgac cccggcttcg   7200
agcacggcgt cctcgtcgac agcggtgacg tacgcgtcga gggcgccgtc gtgcgaccgg   7260
ccgaactggg ctacgtcgcg ccgggtcgcg cgacgctgac cctgaccaac gagtcggccg   7320
cacccgcccg gctcatcctc ctcggcggcc ccccgttccc cgaggagatc atcatgtggt   7380
ggaacttcat cggccggtcg cacgacgaga tcgtgcgggc ccgcgaggac tggatgaagg   7440
gcgaccgctt cggcgaggtg cacggctacg acggggcacc cctgcccgcg ccggaactgc   7500
cgaacgcacc cttgaagccg cgacgaaggg cgcgctgatc tgcggggaca tgggttggca   7560
ccaagggttt cggcgctgct cgatcaccga acccaccgcg agtcactctc gggtgagtcc   7620
cgaacggtcg ccgggagcgc gtgagcacgt gcgcagatgc tcggcgatga tgccgagaat   7680
cgcatcccgg tgctccagca ggtagaagtg accacccgcg aaggtgtcga gtgtgaacgg   7740
gccgtccgtg tgttcggacc atgcccgggc ctcgaccggg gtgaccatcg ggtcatcatc   7800
cccggtcaag gcatggatgg ggcaccgcag cttcgggccc ggtcggtagc ggtaggtctc   7860
ggcggccctg tagtcgccgc ggatggcggg gagggccata cgcaccagct cctcgtcgtg   7920
gaagacctgc tccgcggtgc cgtcgagggt cctcagctcg gccaccaact cctcgtccga   7980
caggaggtgc accgtacccc ccgtcctctg ccgggacggt gcgggcctgg ccgagacgag   8040
gagtgcctcc agggagatgc ccgcactctc gaaccgtcgg gccagttcga aggcgagggt   8100
ggcgcccatg ctgtgtccga acagcgcgac cggctggtga acacgggccc gcagcacggg   8160
gaagagctgg ttcgcgagtt cgtcgatgtc ctccaggggc ttctccgcgc gccggtcctg   8220
ccggccgggg tactggaccg cgagcacgtc gcaccggggt gccagcgcgg cagccacggg   8280
gtggtagaac gtcgcggagc cgccggcgtg cggcagacag atcaactggg gtgccgtggg   8340
atgtgcgggg cggtactgcc tgatccacac gtcgctgtgg gtgttcgtac cggtcatcag   8400
cggtgctgcc cttccggcgt ggcgttggtg cgggggatgg ccgatccggc cgtgacgcct   8460
ccgtcgaccc cgagggtctg cccggtgacg taggcggcga gggggctgag cagccagacg   8520
accgcgttgg ccacctcctc gcacttgccc aggcggccca gcggagcccg gcgcgcccgt   8580
tgtgcgaggg cgctgggatc ggcgtacagg ctgcgcagca tgggggtgtc ggtcgaaccg   8640
gggctgacca cgttgacgcg gatgccgtcg cccgcgtact gcagggccac cgacttgctc   8700
aggccgatga ccgcgtgctt ggtggccgag tagagcgggc tctgggcgtg gccgatgtgc   8760
ccggccactg atgcgcagtt cacgatcgcg ccgccgccgg ccgtcagcat ggcctcgatc   8820
tgtccgcgca tgcacgacca gaccccacgc aggttggtgg cgatcacgcg gtcgaagttg   8880
```

-continued

```
tcggcggtgt cctggtgcag cggaccgaac gagccgaagg tcccggcgtt gttgaacgcc   8940
ccgtccagcc gtccgaaccg gctcaccgcc cgggccacgc agtccgccac ctgcttgtcg   9000
tcaccgacgt cgcagggcac caccaagtgg tgcgaggagg gtagtccggc ggttgtctcc   9060
gtgagggccg actcggtgcg gcccaccagg acgacgcgtg ctccgtgccc cacgaggagc   9120
cgggccgcgg cccggccgat gccgctgccc gctccggtga ccatcatcac gcggtcggtg   9180
agttccagac tcatcgttgt tccaacgctc cgtccctgct cgtcggatgt gcgatccgct   9240
gtgtcatatg tgcagtccgc cgttgacgtc gacgaccgtg ccggtggtgt atccggcgtc   9300
ctcgccgcac agatggcaga ccatgcccgc ggcctcggcg acgctgccga agcggccggc   9360
ggggatgtgg ctgacgcggt cggcggtcca ctgcgggggc ttgtcctccc aagcccggcg   9420
gatgcgctcg gtgccgatga cgccgtgggc gaccgcgttg accgtcacgc cgtgcggggc   9480
cagttcgtag gcgcactgct tggtgaaccc gatgacgccg gccttggcgg cgacgtaggc   9540
ggcattgctg aaccgggtgt acgtgcgacc ggccacggac gccaggttga cgaccctgcc   9600
ccaccccgcc gcgaccatcg ccgggacgca cagccgggtc atggtgaaca cgctcgccag   9660
gttgtgcgtg acggcctcct ggaggtcggc ctcggtcagt tcggtcaccg agcgggcccg   9720
ggtgtcgcca ccgacgccgt tgaccaggac gcccggccgg tgctgcgggg cgagcgagtc   9780
gacggcggac gccagggcgt gagggtcggt cacgtcggcg accagcgggt cccgggccag   9840
ccggtcgccg agcccgtccg cgacccggtg caccgcctcg gcgtccttgt cgagcaggac   9900
cacccgcagg ccccgggccg ccaggcctcg ggcgacctcc gcgcagatgc cgctgcccgc   9960
tccggtcacc agagccacgt cgtgtcgtgc cgtcatgtgt tcctccgcca gccgccgccg  10020
gattcccagg tggccgcgca ccgggtgtgt cgcagtagtt cttcggtcgg ttcgatgccc  10080
gtgcccggac cggtcaaggg ttcgacccgg tgcagtgacc ggtcgacggt gaacgccggc  10140
gtggtcagtg gcacggggaa ccactcgtcg gcccggcccg cctcgaccgt ctgccacagg  10200
tcccatgcgg tggccagggt gcgcccggcc gcccacagcg gccccacctc ggccacgtga  10260
acgccgagct ggcaaccgac gccgagctcg tcggcgcgca gtgccaggcg tgccgcggcg  10320
aggaacccgc cgcacttcga cagccgtacg ttgatgtggc tggcggcgcc gctggtggcg  10380
gcggcgtgga ggtcggccgg tccggtacag gactcgtcga gcatgacggg cagaccggtg  10440
gcccgccgca gccggcccaa ctcgggccag gaccgcggcg ggagcggctc ctccacccac  10500
cccacgccgt ccagttcgcc cgcgaccttc tccgcttcct cggccgtcca ggcgccgttg  10560
acgtccagtg agacacgggt gtcggcgggg aggcggtcct gggccgccgt cagccggtcc  10620
accgccccgg ccgggtccgc caccttgatc ttcacgtgcc gcaacgccgc cagcgcccgc  10680
ggcgtgagtg cgtccaggac ggtcgcgacg tcgcgcgaga ggtggatcac gaggctgacg  10740
gacgtcggtc cgtcccgccg tgatcgggca ggcggggcca ggacccgcag gacgtcggcg  10800
agcggccggg cgaaatgccg gcacaccgcg tcgagcaggg cgatctccac ggcggccgcc  10860
gccgacgagc cgtcgacgag cccggtcagc ggcagctgtg cgatcgaggc gacggcgctc  10920
tcgaagtccc gccactcgat gcgctcggcc agctccccgg gatcgcaggc ctggacggct  10980
cgcaccgcgc cgtccagggt ctcaccggtg acgtagtcgc ggggcgctcc ctctccccat  11040
ccgcgggtgc ccgccagctc gatctcgacc agcagggacg ccgcgctgcg acgggagcgc  11100
gtggcgtggt cgaaggccgc ggccatgggc acgacggcgg tgtgcagccg tacgcgacgg  11160
atcacgcttc ctccttcagc cgcgtggcca gccagtccca gtacgccgtc cgggccgacg  11220
```

-continued

```
tgaactccac gtagtgccga tccgtggcga agacctcctc gtgcacggct gacgtcagac  11280
gccgcagcat cgctcgcgcg gccgacaggt cgatgatcgg gtcgtgagtg gggagcgcca  11340
ggtcgacggg gagccgggtg cggggggcac cgcgggcata gtggtcctcc aggtgcacga  11400
gcgtcgcctg cgtggccgag gtgacctcgc gcagcatcag gtgatccccg gtgaggaact  11460
cccggtagcg cggcaggtcg gtgtagtcgc cgtcggcgag ccccacgggc cgtagcccgc  11520
tgccggtgag cgcgcggcgc tcggcgagcg tgtccgcggt gtggcgcgcc cgctgctgtc  11580
ccagcgcggg cgcgcacagg accaacctgc ggacgggcag atcgcgggtg caccagagcg  11640
cggccagcac gctgccgccg aggctctgcc ccagggcgac cggcccggca ccgccgacct  11700
cggccgtcac ggcgtcgagg gcgcgggcgt agtcgtcgag gacgagatcg gccgacggca  11760
ggtggccgcg aggcccctcg ctgcggcccg agcctctgcg gtccagggcg tagacgtcga  11820
tgccgcgtgc gttgagctcg ggccccgtct cgaacagcca gcccgcgtgg ctctggatgc  11880
cgtggaggta gaagacggcc gaggtggcgc cgggcgtggt ccagtggtgc agggtgagcc  11940
cggtgccgtc ggcagcggtc agcatgctcg tggtgggcat gggctgcctc ctcagtaccg  12000
gacgagattg acgtcggggt ccagccggac gtcgacgagg agcggtcctt cgagcgtcga  12060
caacaggtcg ccgacggcgt cgagttcttc cgccttgcgg acggtgaggg cacgtgcgcc  12120
catcgccgtg gccagcccgg cgaggtcggg ccaggcgaac gccgagtacg ccgggtcgta  12180
gccgtggttc ctgagtttgt agtgctcggc tccgtacgcc ccgtcgttga gtacgaccac  12240
gacgagcggc agccggtacc gtaccgccgt cgtgaactcc gacaggtgca tcatgaagcc  12300
gccgtccccc acggcggcga ccacgggccg gccggtcccg gccgtcgccg cgccgatcgc  12360
cccggcgacg ccgagcccga tcgagccgaa gccgcccatg acggtgaagt gcagcgggtc  12420
cgccacgcgc agatacggcc agacacccac gtcgaagcgg ccgatatcgc tgacgacact  12480
gcgctcggcg ggcagtatcc ggtccagccg gatcatggcc gtccggatgt cgacggtctc  12540
cgctccactg cggtcgtcga cgtcgtcctg cggcgagaac ccggccagtt gcccggcgac  12600
gcgctccgcc caggcgccgt tggccgcggt gactccggcc tgatccagca ggacgttcat  12660
ggtctcggcc gtgcggcggg catccccggc cacgggctcg tcgacggggc tgtacgagcc  12720
gaaccgtgcc ggatcggtgt ccacgtgcac gactctcttg ccgcggagca gctcgccgtt  12780
gagcacggtc cacatgttca ggctcgcccc gaacgcgatc acgcagtccg actcggcgat  12840
gaccgtgctc gccacgctgt gcgcgagcga gccgaagatg ccgacgtcgc ggggggtgacc  12900
ggcgaacatc tccttgccga gcacggtggt ggccagcgct gctccggtac ggtccgccag  12960
ctccaccagg gcctctcgcg caccggcgac ggccgcaccg tgcccggcga ggaccagcgg  13020
ccgcttggcc gagccgatca gccccagcgc gccgtccagc gcctcggcct ccggagcggc  13080
cagaggaccc ggcgccaccg ggagcgtgac cggcgcctgc tcgcccgcct ccgcctgcat  13140
gaggtcgatc ggcacattga gtacgacggg ccgccgctcg gccacgatcc gctggacggc  13200
ccggttcagg tccgcgacga gcgaggccgg tctgtggacg cgttcgtacc ccgcgcccgc  13260
cgcggccgcg accgtcgcga tgtcgaagtg gtggaagtgc gtgggcaccg gtggcggatc  13320
acctgtgatc agcaggacct ggctgtggct acgagccgct tccacaagag gggtcaaggc  13380
gttggtgaaa gccggcccgt gcgtcacgga cgccacaccg atgccgccgc acatacgtgc  13440
gcggccgtcg gccatggcga cggcgcccgc ctcgtgggcg accgccacga accgtccgcc  13500
cgcgtcggcg aaggcgggca gatagagcag attggcgttg cccatgagac cgaagacggt  13560
atcgacgccg tgtgcggtca gagcgtcggc gagcgcgtgg aaaaccttca ttgctgtccc  13620
```

-continued

```
tcggtcgggg cgggctggag ccagacggga tcgttctggt cgaccggcgc gcaggtgggt  13680
ggcgggtcct cgcggagcag ggaacgcagg tggttgccgg tgatgagcac ggtggttccg  13740
gcgcagtccc gggcgacggc catccgccgg gcgagaactt gggggtgccg caccgcgcgg  13800
gtcaggtcgt gcagcggggc cgcgggcacg ccgacggctg ccgccgcgtc cagtacggcg  13860
gcgacggggc cctcggcccg cggtggcggg ccttccgcgt cgacgaggac cgtgccgtcc  13920
gccgcccgga cgaggtgggg ggcccgtgcg ggtggggcgg tgaaccagcg gtcctgggtg  13980
agccagacag cgctgtcgaa cagcgcgacg tcggcggcgc atccgtgctc ggtgcgcaga  14040
cggacgtagg tggacacgac ggcggcggca gcggccaggt aggcaccgag gacgtcggcg  14100
ctggacactg gagtcctcag cccggcgccc gggccgccga cgaggcgcat gatgcccgac  14160
tcggcctgga tcacggtgtc gacgctgcgg tcggcggcgg ccaggccatg gccggtgacc  14220
gtgcagtgca cgacgccgtg ccgggacagg atctgatcgg gggcgaggcc ctgcgcggtg  14280
agtgtgtcgg ccgcgaggtt ggtgagcacg atgtcgcatc cggcgagcag ccgctcgaac  14340
ccggcccggt cctcggcgtc ggcgaggtcg agccgacagg agcgtttgcc cgcgttgttg  14400
acgtagtaga ggtagccgac cccggccacc tgctgggcga gccgccggga cccttcgccg  14460
tgcggcggct ccaccttcag tacgtcggcg ccgagttggg ccagcagccg gcccgcgtgc  14520
ggtccggccg tgtacgagcc gacctccagc aggcggacgc cgcgcagcgg aggagtgccg  14580
cgcgcgatcg gctcccagag gccgccctgc cggggcatcg gaccgtcggt gacggcgggt  14640
atgagggaac gcagtgggct gcccggtgta ccggacgggt cggtgaccag gccgcgacgc  14700
cgggcggcgg ctccgtcgcg tacctcctcg ggggccgcga cctgggcgca cgggatgccg  14760
gcggcccgca gggcggtcac cacgtccacg gcccgctgcc cggcggtcca cttgccgagg  14820
atctcgtcga gctcgtcggc gttgcggacg cgggcggcgg tgtcggcgaa gcgagggtcg  14880
tcggggaggt cccgtcgtcc caggactgcg gtcagcctgt gccatatcgg ctcgcccatc  14940
gtgcagatga cgacaggggc gtcctggcac gtgtagctgt tccagggtgc cgccatgccg  15000
tgtcggttgc cggtacgacg tggcggacga ccggcgagcg cgacgctcgg aagcaaggtg  15060
cccgtcagag tgaacaggct gtcgaactcg gcgatgtcca ggtagtcccc gcctcctccg  15120
cgctcgcggc cgatgagccc ggccacgacg gcgatcagac cggacagggc cgccgtacgc  15180
gacgccaggc ccaccacgga gaggaccgat ggttccccct cggtgccggt cgccgaggtc  15240
aggcccgcca gcgcctgcaa ggtccgctcg gtggccgggg cgtcacgcag cgggccggtg  15300
agcccgaacg cgctcagccg caccgcgacc aactcggggc tgcgatgcgg aagttccggc  15360
gccccgagcc ccagagcggc gagccgctca tcgccctccg cgtcgcacac cagcacatcg  15420
gccgtctgca gcagacgcga tgcctggtcc caaccggacg ccgactgcgc ggcggagtgc  15480
agccaccgct cgaacgggcc cccgtgatcg ggtgatcggc agagcgtcac gacacgtgcc  15540
ccgaggtccg cgagcagtct ccccagcagt gcggctggtg tactgcggcc ggccatgagt  15600
acggcgatgc cctcgagcgg ccctgccctt gtcatggaat tctccctcgc tccgcgcacc  15660
gatgcgggcg tcggtcgtca ccgctgattg gtcgtggacg tcggccgtga ggcgaccgcc  15720
agggaaatca caccggcgcc gcccgcatcc gcgggggatc tggccggcag tcccgatgcg  15780
ccattaaagc gcgcatgatt cgttccgtgc cgaccgtagc accgagacgg cggaaaatca  15840
tcgcacaccc ctgctccgga tccggaaacc ctgctcaggg ggcaaggggg agggggtccg  15900
taatggccaa aacgaaattt tacggagctt tacgtttgct ggacgatcta ttggtgagcg  15960
```

-continued

```
cctcgacggg ctggacatgg cagtagtgaa tgtccgcatt catggctatt agtaccgtga  16020
ccctgatcac acgagccctg gttgacgggt gaaatttggg gctggcagag tgatgacgag  16080
cttccgtccg caaagtggtt gaataactgt tccgaaatct tcggcaattc aaaggagact  16140
tacgggggat gcctctatta atgtattgct gtagggcgaa ataatgacag gcagtgctgt  16200
ttcggcccca ttcctgcagc ctcccgaacc cgtctcaggg cactccgaac ggaaaagcga  16260
tcccgtcctt ctcgtcggcg ccggacgccg tgcccgcatg gcggatgccg tacgtgccgc  16320
cggcgctcag gcgggcatcg acccggccgt cctacggcgc acccgggcca ccttgatcac  16380
cgcggggagc gcgggagccg caggccggct cgccgccgcc ctgcgcctga ccggcgccac  16440
gatctctctg gacacccgcg agacacccac actgctcgcc ctgcacctcg ccgcccaagc  16500
gctgcgggcg ggcgacacct cttacgccgt cgtcggtgcc gaacttcccg acgggaactg  16560
cgcgttgatc ctggccaggc agtcagcggc aaccgccgag ggggctgtgc cccaggcgat  16620
cgtccgcacc accacggcgg accgcaccac cacggcggat cacgccccctg cgcccgacga  16680
ccacggcagc ccggcccgtg aagccccgca tgccacccgc acgttgtccc caggcatcac  16740
ccaggccccc gccgagggct tcccgggcct gctggcgacc ctgcacgacg acacacccct  16800
gcgccccacc gcggtcaccg agcacggcag cgacgccacc accgtcctcg tcctcctcga  16860
ccagccccag gacgccgcac ccgcggcacc gctcccctgg gtggtctcgg ccccccacac  16920
ccgcgccctc cgggccacgg ccgcgaccct ggccgtccac ctcgacacca caccggccgc  16980
acccgccgac gtcgcgcaca ccctgctcac cgcgcgcccc gaccgccacc gtgccgccgt  17040
cgtcggcgcg gaccgggcca ccctcaccga cggactgcgc gcactcgcca ccggaggcga  17100
cgcgccccac ctcgtccacg gcaccgccac cggatcgccg cgtcccgtct tcgtcttccc  17160
cggccagggg tcgcagtggc ccggtatggc cgccgaactc ctcgaaacca gcgagccctt  17220
tcacgacagc gtgcacgctt gcgccgacgc gctggccgag ttcgtcgact ggtcggttct  17280
cgacgtcctg cgccaggcac cggacgcgcc accccctgcgc cgggtggacg ttctccagcc  17340
caccctgtgg gcgacgatgg tctccctggc cgaggtctgg cgctcgtacg gcgtggaacc  17400
ggccgccgtc gtcggccact gctacggcga gatcgccgcc gcgcaggtag ccggcgccct  17460
cgacatgcgt gacgccgccc gactgctcgc ccaccgcagc cgggcctggc tgcgactggt  17520
gggcaagggc acggtcatct ccgtcgccac ctcgggacag gacatcaccc ggcgcatggc  17580
ggcctggccc gactccgtcg aactggccgc gctcaacggc ccgcgctccg tggcgctcgc  17640
aggcccgccc gacgtcctgg acggcatcgt caacgacctg accgaccagg gcatccacgc  17700
caaacgcatc cccggcgtgg acaccgtcgg ccactgctcc caggtcgagg tcctccgcga  17760
ccacctgctg gacgtcctgc gcccggtctc gccccggccc gccgccgtgc cgttctactc  17820
caccgtcgac ggaaccgaac gcgacaccac cacgctggac accgactact ggtacctcaa  17880
cacccgcagc caggtccgct tccaccaggc cgtgcggaac ctgctcgccg ccggacaccg  17940
ctcgttcgtc gaggtgagcc cgcacccgct gctcggagcc tccatcgagg acaccgcggc  18000
cgagttcggc ctcgacgacg tggccgccgt cggcaccctg cgtcgaggcc agggcggcac  18060
ccgccgggtc ctgacctcgg tggcggaggc gtatgtccac ggcatcgaca tcgacttcac  18120
gcccgccttc accggcacga cccccaaccg catcgacctt ccgaccgtcg aggaccacgg  18180
catcgagggt cacggcgacg acggcggcga gacatggacc gaccgcgtca gaaccctccc  18240
ggacgagcag cgcgaagagg ctttgctgga cctcgtgtgc cgcaccgtcg ccgcggtgct  18300
cgaagcggac ccggccggca cggcggacgc cgtcgccccc gacacggcgt tcaaggagat  18360
```

-continued gggcctcggc tcactgagcg cggtccggct gcgcaacggc ctccgcgagg ccaccggcgc 18420
ccacctgccg gccaccatcg cctacgacca ccccaccccg gccgctctgg cccgccacct 18480
ggcgatgacc ctgttcgacg cgacgggcgc cgccccggcg gtcccggcac cgagccgcga 18540
cgacgaaccg atcgacgccg agaccgctgt gctgaccgcg ctggaacggg ccgacgaggc 18600
gctggaacgg ttgcgggccc cgcacgcccg cacgccccgg caggagaccg gccggcggat 18660
cgacgagctg ctgcggtccc tgaccgacaa ggccaggcgg atgagacagg ccgacgccgt 18720
cgatgatgtc gatgatccgg ccaccgaccg gttcgccgca gccaccgacg acgagatgtt 18780
cgaactcctc gagaaacgtt tcggcatctc ctgaggcgcg ccgacctccc gcactgcgag 18840
tcgcttcccc cacgatcccc gaaggcggca accgatggca catgaagaca aactgcgcca 18900
cctcctcaag cgtgtcagtg ctgaactcga cgacacccag cgccgggtgc gtgagatgga 18960
ggagagcgag cgcgagccga tcgcgatcgt ggggatgagc tgccgtctgc ccggcggggt 19020
gaacagcccg gggggagttct ggtcgctgct ggaggccggg acggacgccg tctcggagtt 19080
cccgcgggac cgtggctggg atgtggagaa cctctacgac ccggacccgg acgcccccgg 19140
gcggtcgtac gtccgcgagg gcggattcct ggacggggcc ggacagttcg acgccgcctt 19200
cttcggaatc tcgccccgtg aggcgctggc gatggatccg cagcagcggc tgctgctgga 19260
gtgctcgtgg gaggcgatcg agcggtcgcg gatcgacccg aagaccctgc acggcagccg 19320
gaccggcgtc ttcgcgggct ccaactggca ggactacaac accctgttgc tgaacgccga 19380
ggagcgctcc cagagctacc tggccaccgg cgcctccgga agcgtgctgt ccgggcgcgt 19440
ctcgtacacg ctgggcatgg aagggcccgc gatcaccgtg aacacggcgt gctcgtcctc 19500
tctggtcgcc gtccacctgg cggcccgttc cctgcgggcg ggggagtgcg acctcgccct 19560
ggccggcgcc gtcacggtca tgtccacacc gcagcttccg gtcgccttct cccggcagcg 19620
cggactcgcc cctgacggtc gctcgaaagc cttcgcggtt tcggccgacg gcatgggctt 19680
cggcgagggg gtgggcgtgc ttgtgctgga gcggttgtcg gtggcgcggc ggaacggtca 19740
tcgggtgttg gcggtggtgc ggggttcggc ggtgaaccag gacggtgcgt cgaacggtct 19800
gacggcgccg aacggtccgt cgcagcagcg ggtgatacgt gcggcgttgg cgagtgccgg 19860
gctgggtccg gccgatgtgg atgtggtgga ggcgcacggt acggggacgc ggttgggtga 19920
tccgatcgag gcgcaggcgt tgctggcgac gtacgggcgg ggccgggacg cggagcgtcc 19980
gttgtggctg gggtcggtga agtcgaacat cggtcatgcg caggctgctg ccggtgtcgc 20040
cggtgtcatc aagatggtgc tggccatgga gaagggccgt ctccctcgga cgctgcatgt 20100
ggatgagccg tcgggtgagg tggactggga ctcgggtgcg gtgcggctgc tgaccgaggc 20160
gcgggactgg ccgtcggagg aaggtcgtct gcggcgggcc ggtgtgtcgt cgttcgggat 20220
ctcaggcacc aacgcgcacg tgatcatcga ggaagcaccg gaagaggggg aggaaccgga 20280
gtccgacgcg ggtggtgtgg tgccgtgggt gctctccgcg cggacggaag ggcactgca 20340
agcacaggcg gtgcaactga gcgagttcgt cggcgagtcg agtccggtgg atgtgggttg 20400
gtcgttggtt tcgacgcgtg cggcgttcga gcatcgggcc gtggtggtgg ggcgcgggcg 20460
ggacgagttg gtgcggggct tgtccgaggt cgcgcagggt cggggcgtga ggggtgtcgc 20520
gtcttcggcg tcgggtggtc tcgcgtttgt ttttgctggt cagggcagtc agcggttggg 20580
gatggggcgg gggttgtatg agcggttccc ggtgtttgcc gaggcgttcg acgaggtgtg 20640
tgggcgggtc ggtccggggg tgcgggaggt tgttttcggt tcggatgcgg gtgagttgga 20700

-continued

```
ccggacggtg tgggcgcagg cggggttgtt cgcgttggag gtggcgctgt ttcggttgtt  20760
ggagtcctgg ggtgtgcggc cgggttgtct gatcgggcat tcggtcggtg agttgtcggc  20820
ggcgtgtgtg gcggggttgt ggtcgttgga ggatgcgtgt cgggtcgtgg ctgcccgggc  20880
gcggttgatg caggcgttgc cggcgggtgg ggtgatggtc gcggttcggg ccgaggcggg  20940
ggagctggcc ggtttcctcg gtgaggacgt ggtgatcgcg tcggtgaacg cgccggggca  21000
ggtggtgatc gctggtcctg aggggggtgt ggagcgtgtg gtggctgctt gtggggcgcg  21060
gtcgcgtcgt ctggcggtct cgcatgcttt tcattcgcct ttggtggagc cgatgcttgg  21120
ggagttccgt cgggttgtgg agtcggtggc gttcggtgtg ccgtcgttgc gggtggtttc  21180
caatgtcacg ggtgcgtggg tggatccgga ggagtggggg acgccggagt actgggtgcg  21240
tcaggtccgt gagccggtgc gtttcgccga cggggtcgcc acgttgctcg acgcgggtgt  21300
gaggacgttc gtcgagctgg gtcccgccgg ggcgctcact tcgatggtca gccactgcgc  21360
ggacgccacc gccacttcgg tgacggctgt acctaccttg cgccccgatc acgatgagtc  21420
gcggaccgtg ttgagtgccg cagcgtcctt gtacgtccag ggtcacccgg tcgactgggc  21480
cccgctgttc ccgcgggccc gcacggtgga cctgcccacc taccccttcc agcaccagca  21540
ctactggctc gacgtacctc ctctgttcac cgcctcctcg gcggcccagg acggtggctg  21600
gcgataccgc atccactggc ggcggctcgg cacgagggac tccggggacc ggctctccgg  21660
ccgctggttg ctgctggtgc ccgagtcgga cgggacggag ccctgggtgg agggggccga  21720
gaagatgctg gccgagcgcg ggtgcgaagt cgtccacgtg ccgatcgcgg cgacggccga  21780
ccgggacgcg atggtcggag ccgtgcgtga gagcgtcgag gacggtcggg tcgacggtgt  21840
gctcagcctg ctggcgctcg acggccgccc gcaccccgat gcggctgcgg tgccgacagg  21900
gttggtcgcc acggcgcagg ttgtgcaggt cagtgacgag ctgggcatcg gcccgctgtg  21960
ggtcgccacc cgacaggcgg tctccgtcga cggggccgat gaggctgacg gggccggtag  22020
gaccaggaag gccgacgacc ccgccgatgt cgcgcaggcc gctgtgtggg ggctcggccg  22080
ggtcgccgcg ctggagaagc ctcggttgtg gggcggcctc gtcgacctgc ccgcacgtgc  22140
cgacgaacgg atgcgggacc tggtggctca ggccctcacc gctcccgacg ccgaggacca  22200
acttgccgtg cgggccgacg gcatcgccgt tcgccgactg gtacgctccg ccgcgtcggc  22260
cccggccgac gactggcagc cgagcggcac cgtgctggtc accggcggca ccggaggcgt  22320
cggagccaac gtggcgcgtt ggctggtcac ccaggacatc cagcacctgt tgctggtcag  22380
ccggcgcggc ccggacgccc ccggagccgc tgagctgctg gccgaactca gcgcctcagg  22440
aacgtccgtg accatcgagc cctgcgacgt caccgacgcg gacgcggtac ggcgcctgat  22500
cggcgccgta ccggccgaac ggccgctgag cacggtcgtc cacgccgcgg gcgtactgga  22560
cgactgcttg atcgacgccc tgaccccgca gcgcctcgcc gccgcactgg aggtcaaggc  22620
caagggcgca ctgaacctcc acgaggcggc cggggaagcc cacttggtgc tcttctcctc  22680
gctggccgga acaaccggaa ccaagggaca gggcaactac gccgccgcaa acgcctatct  22740
cgacgctctg gccgaacggc ggcgtgctga cggcctgccc gccacttcgg tcgcctgggg  22800
cgcctggcag ggcgcgggca tggtggccga cgccgccgta gcccaccgca cgcgccgtta  22860
tggcctcccg ctcatgagcc ccgaccgcgc cgtcgccacc ctgcggcagg tcatggccga  22920
gccggtggcc acgcaggtgg tggcggacgt cgactggcag cgattcgtcg ccgacttcac  22980
cgcggtgcgc cccagccgcc tcctcgccga cctgccggaa gtgcgctccc tgggcgagca  23040
gcgaaaggac ggcccgggcg gtcagggcga ggaggacggc ttggccagca agctggcagc  23100
```

-continued

```
cctgcccgaa gccgaccgcc gacgagccgt gctggacctc gtggaggaac tcgtcctcgg  23160
ggttctgggc cacgagacgc gcgcggcgat cggcccggac agttccttcc acgccatcgg  23220
cttcgactcg ctcaccgccg tcgaactgcg caacctgctg accgtacgcc tcgggatgaa  23280
gctgcccgcg accctcgtct acgatcaccc gaccctgtcg tcgctggccg accacctgca  23340
cgagcaactg gttatcgacg gcaccccat gacggacacc gcggccgacc tgctcgccga  23400
actcgacgca ctcgcggcga gactcgccgc cgtcgggctg gaaccggagg cgcgcgcccg  23460
catcggacgc aggctcaagg acatgcagac cgcctgcgaa cccaggtcgg agtcctcacg  23520
cgacctgaag tccgcctcac gcaccgaagt gctcgacttc ctcaccaacg aactcggcat  23580
ctcccgctga ccagttgacc gaccgcgacg aacggcgcac ctggctgcgg ctcgtccacg  23640
ccgaccttcg accttgcccg acgcccccgg gagcggacta ccaccatgcc caacgacgaa  23700
gaactcctcg actacctgaa gcggactgcc tcgaacctcc aggaggcgcg gcagcgggtg  23760
cacgaactgg aggagagcga gcgcgagccg atcgcgatcg tggggatgag ctgccgtctg  23820
cccggcgggg tgaacagccc ggaagagttc tggtcgctgc tggaggccgg gacggacgcc  23880
gtctcggagt tcccgcggga ccgtggctgg gacgtggagc ggctgtacga cccggacccg  23940
gacgcccccg gcaagtcgta cgtgcgggaa ggcggattcc tcgacggcgc gggccggttc  24000
gaccccgcgt tcttcggtat ctccccgcgg gaggccgtgg tcatggatcc gcagcagcgg  24060
ctgctgctgg agtgctcgtg ggaggcgatc gagcggtcgc ggatcgaccc gaagaccctg  24120
cacggcagcc gcgcgggcgt gttcgtgggc tcgaacggcc aggactacgg gacgcttctc  24180
ctgcgtgccg acgaccgctc ccacgcctac ctcgccacgg gcgcctccgc gagcgtgctc  24240
tccggccgca tctcctacac gctcggactg gagggccctg cggtcacgat cagtacggcc  24300
tgctcgtcct cactggtcgc cctccacctg gcggcccgcg ccctgcgggc gggggagtgc  24360
gagctggcgc tcgccggcgg tgtgacggtc atgccgacga cccgcctgtt cgaggtcttc  24420
tcccggcagc gtggcctggc cggtgacggc cgctgcaagg ccttcgcggc cggggccgac  24480
ggcactggct ggggcgaggg cgtgggcgta ctcgtcctgg agcggttgtc ggtggcgcgg  24540
cggaacggtc atcgggtgtt ggcggtggtg cggggttcgg cggtgaacca ggacggtgcg  24600
tcgaacggtc tgacggcgcc gaacggtccg tcgcagcagc gggtgatccg cgcggccttg  24660
gccagtgcac gcctggcccc cgaggacgtg gacgccgtag aggcacacgg cacggggacc  24720
tccctgggcg acccgatcga ggcgcaggcg ttgctggcga cgtacgggcg gggccgggac  24780
gcggagcgtc cgttgtggct ggggtcggtg aagtcgaaca tcggtcacgc gcaggccgct  24840
gccggtgtcg ccggtgtcat caagatggtc aaggcgatgc aggcgggcac gctgccccgg  24900
acgctgcatg tggatgagcc gtcgggtgag gtggactggg actcgggtgc ggtgcggctg  24960
ctgaccgagg cgcgggactg gccgtcggag gaaggtcgtc tgcggcgggc cggtgtgtcg  25020
tcgttcggga tctccggcac caacgcgcac gtgattctcg aggagccgcc ggcggaggac  25080
gcggtaccgg agcctgaagc gggtgatgtg gtgccgtggg ttctttcggc gcggtcggct  25140
gaggcgttgc gggagcaggc tgcccggctg gcgtcggtgg ctggtgggtt gaacgtggtg  25200
gatgtgggct ggtcgttggc ttcgacgcgt gcggcgttcg agcaccgggc cgtagtggtg  25260
gggcgggagc gggaagagct gctcgcgggt ctgttcgctg tggctgcggg acgcccggct  25320
gcgaacgtgg tgacggggcc cgtcagctcc ggtcggcccg cctttgtttt tgctggtcag  25380
ggcagtcagc ggttggggat ggggcggggg ttgtatgagc ggttcccggt gtttgccgag  25440
```

-continued gcgttcgacg aggtgtgtgg gcgggtcggt ccgggggtgc gggaggttgt tttcggttcg 25500
gatgcgggtg agttggaccg gacggtgtgg gcgcaggcgg ggttgttcgc gttggaggtg 25560
gcgctgtttc ggttgttgga gtcctggggt gtgcggccgg gttgtctgat cgggcattcg 25620
gtcggtgagt tgtcggcggc gtgtgtggcg gggttgtggt cgttggagga tgcgtgtcgg 25680
gtcgtggctg cccgggcgcg gttgatgcag gcgttgccgg cgggtggggt gatggtcgcg 25740
gttcgggccg aggcggggga gctggccggt ttcctcggtg aggacgtggt gatcgcgtcg 25800
gtgaacgcgc cggggcaggt ggtgatcgct ggtcctgagg ggggtgtgga gcgtgtggtg 25860
gctgcttgtg gggcgcggtc gcgtcgtctg gcggtctcgc atgcttttca ttcgcctttg 25920
gtggagccga tgcttgggga gttccgtcgg gttgtggagt cggtggcgtt cggtgtgccg 25980
tcgttgcggg tggtttccaa tgtcacgggt gcgtgggtgg atccggagga gtgggggacg 26040
ccggagtact gggtgcgtca ggtccgtgag ccggtgcgtt tcgccgacgg ggtcgccacg 26100
ttgctcgacg cgggtgtgag gacgttcgtc gagctgggtc ccgctgggac gctcacttcg 26160
atggtcagcc actgcgcgga cgccaccgcc acttcggtga cggctgtacc taccttgcgc 26220
cccgatcacg atgagtcgcg gaccgtgttg agtgccgcag cgtccttgta cgtccagggt 26280
cacccggtcg actgggcccc gctgttcccg cgggcccgca cggtggacct gcccacctac 26340
cccttccagc accagcacta ctggatgatg aacaccggaa gtgccgccga gccggcggag 26400
ctggggctcg gcgatgcccg tcatccgctg ctcggttccg tcgtcaccgt cgcgggggac 26460
gacaaggtcg tcttcgccgg gcggctggcg ctgcgcacac accccctggct ggccgaccac 26520 accgtgctcg acgcggtctt gctgcccgct acggccttcc tcgaactggc cgtgcgcgcc 26580
ggtgaggagg tgagctgtcc ggtcgtacac gacctgacgc tgcaccgacc gctggtcgta 26640
cccgagcggg gcgccgtgca ggtacagatg gctgtgggcg caccggaagc cgatgggcga 26700
cgtgaggtcc gggtgtactc ccgccccgac gacgacgcgg agcacgagtg gacgctgcac 26760
gccgctggac tgctggcgtc ggccgccacg gcggagcccg ccgtggcggc cggtgcctgg 26820
ccgccgccgg aggcgcaggc cgtggacctc gacggcttct acgccggact cgccgagcac 26880
ggctaccact acggcccgct gttccagggc gtccgggccg cgtggcggct gggcgacgac 26940
gttctcgccg agatcgtgct gcccgaggcg gccggcgccg acgccgcccg gtacggcatg 27000
catccggccc tgctcgacgc cgtcctgcac gcggcacggc tgggcgcctt ccgtgagcgg 27060
tcggaggaga agtacctgcc gttcgcctgg gaaggcgtga ccctgcgtac caggggagcg 27120
accgccgtac gtgctcgaat ctcccgggcc ggtaccgacg ccatccggct ggacgtcacc 27180
gacaccgcgg accggccggt cctcacggcc gaatcgctca cgctgcgacc ggtctccgcc 27240
ggtcagctca tggccgtccc gcgcgactca ctgttccggg tcgactgggt ttccgcgccc 27300
gccgcgaacg gtcccggcct gcggctggcc cgtgccgcca ccgtggaggc ggccctcgcg 27360
gcggacgccg acatcgtggt cgtgccatgc ctcgacagtg agggtccgca tcaggcgacg 27420
taccaggcac tggagctgct acagcgctgg ctggccgccg acaccggtac caccacgctc 27480
gccctgctca cccaccgtgc cgtggcggtc ggcgacgacg tccacgacct ccaccacgcg 27540
cctctgtggg gcctggtccg caccgcccag accgaacacc ccggctgctt ccggctcgtc 27600
gactcggacg accccgaccc gacgacggac gtcctggccg cggcgctcgc caccggggaa 27660
ccccaggtcg cgatccgtga cggcgccgtc ctggccccgc ggctgaccgc ggcctccgcg 27720
ccgcgggagc cggccgagtg ggacgccgag ggaacagtcc tcatcaccgg cggatcgggc 27780
gccctcgcag ggatcgtggc ccagcacctc gtcgcacgtc acggcgtacg ccgactcgtc 27840

-continued

```
ctcgcgagcc gcagcggcag gcccgcaccg ggggccgacc tgctcgacgc cgacgtcacg  27900
gccgtgtcct gcgacgtctc cgaccgcgac gccgtggccg cgctgctcgc ctccgtgccg  27960
gacgaacacc cgctcaccgc cgtcgtgcac accgcaggcg tactggacga cggcgtcctg  28020
cacgccctca cgaccgagcg catcgacacc tcgttcgcgg cgaaggtcga cggcgcccgt  28080
catctccacg aactcacctc ccacctggat ctcaccgcgt tcgtgctgtt ctcctccgcg  28140
tcggccgtgc tgggcgccgc cggacagggc aactacgccg cggccaacgc ctacctcgac  28200
gcgctcgccg cccaccgtcg cagcaacgac ctgcccgccg tgtctctcgc gtgggggctg  28260
tgggccgagc acgagggcat ggcccgcgga ctcggtgacg ccgagctgac gcgtatttcc  28320
cggatcggcg tcaccgcgct gagcgcggag gacggcatgc ggctgttcga cgccggatgc  28380
gccggcgatc agtcacagct cgtgccgatg cgggtggaca ccgcggcgct gcgcgcacgg  28440
cgtgaccacc ttcccgcacc gatgtggagc ctggtccccg agcggacccg agcggcacgt  28500
acacagcctg ccgcctcgct tcgggacagg ctcgccgaac tgaccgcccc cgaacgcaag  28560
cgcacggtcc tcaacctggt gcgcaacgcg gtcgccgaca cactcggcca caacgccgcc  28620
gacggagtac cgcccgacca gagcctcgac gccgccgggt tcgactcgct caccgccgtc  28680
gagttccgca accggctctc cgccgtcacc gacctgcgcc tgcccgccac cctcacctac  28740
gatcacccca cccccgcggc catcgccgag cacatcctga cccgcctcac cctgctgaag  28800
gagaccgccg ccccggccgt cggcaccgcc ccggttgcgg cgccgaccga agacgatgcg  28860
atcgtcatcg tgggcatggc gggccgcttc cctggcggcg tgcgcacacc cgaaggtctt  28920
tgggacctcg tccactccgg cacggacgcc atctcggagt ggcccaccga ccgcggctgg  28980
gacgtggaga acctctacga cccggacccc gacgccgtcg gcaagtccta cgtacggcac  29040
ggcggattcc tgcacgacgt cgccggcttc gacgcgggct tcttcgggat ctcgccgcgt  29100
gaggcgctgg cgatggaccc gcagcagcgg ctcctgctgg agtgctcgta cgaggccctg  29160
gagcgggcgg gcatcgaccc ggccacgctc agaggcagcc ggtcgggcgt gtacgccgga  29220
gtgatgtacc acgagtacgc ctcccggctg ggcgccacgc ccgcaggctt cgaaggcaca  29280
ctcggcaccg gaagctcggg cagcatcgcc tccgggcgca tctcctacac attcgacctc  29340
accgggcccg cggtcaccgt cgacaccgca tgttccacct ccctcgtagg cctgcacctg  29400
gccgtgcagg ctctgcgggc cggtgagtgc gaactggccc tcgccggcgg cgtcaccgtc  29460
atgcacacgc cgcgcccctt cgtcgagttc tcccgccagc gcggcctggc cgcggacggc  29520
cggagcaagg ccttcgcggc ctccgccgac ggggtggcct gggccgaagg cgccggaatc  29580
ctcgtcctgg agcggctgtc ggcggcgcgg cggaacggtc atcgggtgtt ggcggtggtg  29640
cggggttcgg cggtgaacca ggacggtgcg tcgaacggtc tgacggcgcc gaacggtccg  29700
tcgcagcagc gggtgatacg tgcggccttg gcgagtgccg ggctgggtcc ggccgatgtg  29760
gatgtcgtcg aggcccacgg caccggcacg gccctcggcg atccgatcga ggcgcaggcg  29820
ttgctggcga cgtacgggcg ggggcgtgac gcggatcgtc cgttgtggct ggggtcggtg  29880
aagtcgaaca tcggtcacac gcaggcggcc gcgggtgtgg caagcgtgat caagatggtg  29940
caggcgatgc aggcgggcgt gctgccgcgg acgctgcatg tggacgagcc gtcgggtgag  30000
gtggattggg actcgggtgc ggtgcggctg ctgaccgagg cgcgcgagtg gccgtcgggg  30060
gaggggcgtg tgcggcgggc gggtgtgtcg tcgttcggga tctccgggac gaacgcgcac  30120
gtgatccttg aggagccgcc ggcggaggac gcgctgccgg agcctgaagc gggtgatgtg  30180
```

-continued

```
gtgccgtggg ttctttcggc gcggtcggca gaggcgttgc gggagcaggc tgcccggctg  30240
gcgtcggtgg ctggtgggtt gaacgtggtg gatgtgggct ggtcgttggc ttcgacgcgt  30300
gcggcgttcg agcaccgggc cgtcgtcgtg ggaggcgatc gggaagagct cctggggaag  30360
ctttcctcgg tttcgggggt cgaggtcggg gtcggggtcg gtgccggtgg tggtgtggtg  30420
ttggtgttcg ccggtcaggg gtgtcagtgg gtcggtatgg ggcgggagtt gctgggttcc  30480
tcgctggtgt tcgcggagtc gatgcgggag tgcgcggcgg ctctgtcgcc gtttgtggac  30540
ttttctgtgg tggatgttct gggttcggct ggggagttgg gtcgggtcga ggtggttcag  30600
cctgcgttgt gggcggtgat ggtgtcgctg gcgcgggtgt ggcggtcgtg gggtgttccg  30660
gttgctgcgg tggtgggtca ttcgcagggt gagattgccg cggcgacggt ggcgggtgcg  30720
ttgagtgtgg gtgatgcggc gcgggtggtg gcgttgcgga gccgtttgat cgcggagcgt  30780
ctgtcggggc tgggtgggat ggtttcggtg gcgttgtcgc gtgagcgggt ggtgtcgttg  30840
atcgcgggtg tgccgggtgt gtcggtggcg gcggtgaacg gttcttcgtc gacggtggtc  30900
tcgggtgagg ccgcggggct ggagagggtg ctggccgcgt gtgtgtcgtc gggggttcgg  30960
gcgcgtcgta tcgatgtgga ttacgcctcg cattcggtgc aggtggagtt gatccgtgag  31020
gagttgttgg gggttctgga cgggatcgtc ccgcgctcgg gtgagattcc gttcgtgtcc  31080
acggtgacgg gtgagcggat cgacactgtc gagctggggg cggagtactg gtaccgcaat  31140
ctccgtcaga cagtggaatt ccagtcggtg gtggagggtc tggtcgctca ggggtgtcgg  31200
gtgttcctgg agtccagtcc gcatccggtg ttgacggtcg gcatcgagga gtccgcggat  31260
cgggtcgtgg cgttggagtc gctgcgtcgt ggcgagggtg gtctgcggcg gttggtggat  31320
gcggccggtg aggcgtgggt gcgtggggtg ccgatcgact gggcggggat gctcgccggc  31380
ggccggcggg tcgacctgcc cacctatccc ttccaacacc agccctactg gctcgactca  31440
ccacgacacc ctgccggaga cgtgaccgcc gtcggtctca cagaggccgg tcacgcgttc  31500
gtgccggcgg cggtcgacct gccggacggg cagcgggtct ggacgggacg actgtcgctt  31560
ccctcctacc cgtggctggc cgatcatcag gtgctcgggc aggtgctgct ccccggcgtg  31620
gtctgggtcg aactcgccct gcacgcgggg caccaggccg gatgcgactc tgtcgatgag  31680
ctcaccctac agtcgccgct cgtgctcggt gcgtccgaca ccgtacaggt gagggtcgtc  31740
gtcacggaga ccgaagagcc cggcacccgc accgtgtcga tgcactcgcg ccgtgacgac  31800
ggcagctggg tgactcacgc cgaggggatc ctcggggcgg gcgggccgcc gccggagccg  31860
ctgccggaat ggccgccgac cggcgccatg cccctcgatg tcgagggctt ctacgacgag  31920
ctcgcggcgg gcggctacca ctacgggcct cagttccgct gcctgcggcg cgcctggcgt  31980
gccggtgagg atctcgtcgc cgagatctcg ctgccggagg gcaccgacgt cgatgcgtac  32040
ggcctgcacc ctggactctt cgacgcggcg gtgcacagcg tggcctgcgc ccggacgagc  32100
gcgggggccg gcgatgacgg tccccggctg ccgttcgcct tctcggacgt ccggctcttc  32160
gcgaccgggg tgacctcgct acgggtccgg atcgatccgc agaactcctc gtggcaggcg  32220
tgggacgaat ccgggctgcc ggtcctcacc atcgggcggc tcgccggccg gcctgtcgac  32280
gccgatcagt tcgccgtgcg gcgggcgggc cacctcttcc gcgtcgaaac gcggcacgaa  32340
gccctggccg gcccggcccc cgcctcctgg gcggtcatcg gagcggaccc ggccgggtac  32400
gccgcagccc tggaggccac gggcgcgcag gtgacgacgg ctgccgacct ggccggtctc  32460
acatcggcac ccgaagccgc cctgttcacg ctccccggca caaaggacgc gggggtcacc  32520
gaggaggtgc cgaccgctgt ccgggaggcg accgctcagg tgctggaggt gctgcaggac  32580
```

-continued tggctcaccg acggacgttt cgacgatgcc cgactggtcg tcgtaagccg cgaagcggaa 32640
gacggcgatc tcctccacgg aacggcgcgc ggactgctgc gcgccgcaca ggccgagcac 32700
ccggaccgca tcacccttgt cgacctcgat gctcatcccg cctcgctcac ggcccttccc 32760
ggtttcgccc tcggtcccga accggaggtc gtcgtacgcg cgggagacgg cagggcaccg 32820
cgcctggccc gggcgcaggc ccccaccgga gcgggctcac tgggcacggg cacggtcctg 32880
atcaccggag gcacgggcac cctcggggga ctgctcgccc ggcacctggt ggagacgcac 32940
ggagtcaccc ggctgctgct ggtcagccga cgaggaccgg ccgccgacgg cgcggaccgg 33000
ctgcacgccg agctcaccgg gcatggcgca cacgtcgaca tcgtggcggc cgacctcggc 33060
gaccgcacga gcgtggccgc gctcctcgcc acggtcgacg ccgaccaccc cctgtcggcc 33120
gtcgtgcacg ccgccggagc gctggacgac ggcgtgctcg gcacccggtc cgccgactgg 33180
ctcgacccgg tcctgcgccc caaggcggac gccgcttggc acctgcacga actcaccgcc 33240
gaactgcctc tgaccgcctt cgtcatgttc tcctcggccg catccgtgct cggcgcggcg 33300
ggacaggcca actacgccgc ggccaacgga tttctggacg cactggccgc ccatcgtgcc 33360
gcccggggac tgcccgggac ctcgctggcc tgggggctgt gggagcaccg cagcgaactg 33420
acccggcaca cgggctcccc ctcccgcagc atcgcggccg tcggcgctct gtccaccgcg 33480
gaggcccttg ccgccttcga cgccggcctg gcctccgggg agccgctggc agtgccgatc 33540
cggctggagt cgacatccag tgaggaggta ccgccgatgc tgcgcggcct ggtccgcgta 33600
cgccgccggg ccgccaccgg cacggaaccc gcggcgagcg cgggcgccgc gcaggaggtc 33660
cggcagctgg ccgagttggg cgccgacgag cgacagcggc gcgtgcagcg gatcgtgctc 33720
gacaccgcgg cggccgtcct cggccatgac agccacgacg ccatccccct cacccggggc 33780
ttcctggagc tggggttcga ctccctgaca gcggtacggc tgcgcaaccg gctcgcccgc 33840
cgactggggc tgcgcctgcc ggccacggtg gtgttcgacc accccagccc ggccgccctg 33900
gccgcccacc tggtcgagca tctcgtgggc accgtcgacc cgaccgcgca ggccatggag 33960
cagctggagg ctctgcgccg cagcgtgcac gcagccacac ccgccggtgg cctggaccgc 34020
gccctggtga cccaacgcct gacggccctg ctcgacgaaa tgcggcacgt cgacggcccc 34080
ggcggcaccg aaggccccga cggctccggg gacgacctgg agaacgcgac agcggacgag 34140
atctacgccc tcatcgacaa cgaactgggc atcgggggta cgcagtgaac ggcgacgaca 34200
aagcactggc ctatctcaag cgggtgaccg cggacctgcg gtcggcgaga gccaggctgc 34260
aggaactgga gtccgccgac accgacccca tcgccatcat cggcatgggc tgccgtctgc 34320
ccggtggcgt gcgcaccccc gaggacctgt gggacctcgt ggagaagaag catgacgcga 34380
tcggcccctt ccccgccgac cgcggatggg acctcgagaa cctgtacgac cccgacccgg 34440
acgcgccggg caaggcctac gtccgcgaag gtgggttcgt ccacgacgtc gccggcttcg 34500
acgcgggctt cttcggaatc tcgccgcgtg aggcgctggc gatggacccg caacaccggc 34560
ttctgctgga gtgctcgtgg gaggccctgg agcgggcggg catcgaccct tcctccctcg 34620
agggcacccg caccggcgtc tacaccgggc tcatgaccca tgaatacgcg acccgactgc 34680
cctcgatcga cgaggagttg gagggtgtca tcggcatcgg caacgccgga agcgttgcct 34740
cgggccgcgt ctcctacacg ctcggcctga acggccccgc tgtcaccgtc gacacggcct 34800
gctcctcctc gctcgtcgcc ctgcacctcg ccgcccaagc cctgcgccag ggccagtgca 34860
cccttgcgct ggccggaggt gcctccgtca tcgcggcgcc gaccgtgttc gccaccttca 34920

-continued

```
gccgacagcg gggcctcgcc cccgacggcc gctgcaaggc gttctcgtcc acgaccgacg  34980
gcacgggctt cggcgagggg gtgggcgtac tggtcctgga gcgcctctcg gacgcccgtc  35040
gcaacggaca cgaggtcctg gccgtcgtac ggggctcggc ggtcaaccag gacggagcca  35100
gcagcggatt caccgccccg aacggaccgt cccagcagga cgtcatccgc gaggccttgg  35160
ccgacggtcg actgacccct gcggacgtgg acgtcgtgga gggtcacggt acggggacgc  35220
ggttgggtga tccgatcgag gcgcaggcgt tgctggcgac gtacgggcgg gggcgtgacg  35280
cggatcgtcc gttgtggctg gggtcggtga agtcgaacat cggtcacacg caggcggccg  35340
cgggtgtggc aagcgtgatc aagatggtgc aggcgatgca ggcgggcgtg ctgccgcgga  35400
cgctgcatgt ggacgagccg tcgggtgagg tggattggga ctcgggtgcg gtgcggctgc  35460
tgaccgaggc gcgcgagtgg ccgtcggggg aggggcgtgt gcggcgggcg ggtgtgtcgt  35520
cgttcgggat ctccgggacg aacgcgcacg tgatccttga ggagccgccg gcggaggacg  35580
cgctgccgga gcctgaagcg ggtgatgtgg tgccgtgggt tctttcggcg cggtcggcag  35640
aggcgttgcg ggagcaggct gcccggctgg cgtcggtggc tggtgggttg aacgtggtgg  35700
atgtgggctg gtcgttggct tcgacgcgtg cggcgttcga gcaccgggcc gtcgtcgtgg  35760
gaggcgatcg ggaagagctc ctggggaagc tttcctcggt ttcgggggtc gaggtcgggg  35820
tcggggtcgg tgccggtggt ggtgtggtgt tggtgttcgc cggtcagggg tgtcagtggg  35880
tcggtatggg gcgggagttg ctgggttcct cgctggtgtt cgcggagtcg atgcgggagt  35940
gcgcggcggc tctgtcgccg tttgtggact tttctgtggt ggatgttctg ggttcggctg  36000
gggagttggg tcgggtcgag gtggttcagc ctgcgttgtg ggcggtgatg gtgtcgctgg  36060
cgcgggtgtg gcggtcgtgg ggtgttccgg ttgctgcggt ggtgggtcat tcgcagggtg  36120
agattgccgc ggcgacggtg gcgggtgcgt tgagtgtggg tgatgcggcg cgggtggtgg  36180
cgttgcggag ccgtttgatc gcggagcgtc tgtcggggct gggtgggatg gtttcggtgg  36240
cgttgtcgcg tgagcgggtg gtgtcgttga tcgcgggtgt gccgggtgtg tcggtggcgg  36300
cggtgaacgg ttcttcgtcg acggtggtct cgggtgaggc cgcggggctg gagagggtgc  36360
tggccgcgtg tgtgtcgtcg gggggttcggg cgcgtcgtat cgatgtggat tacgcctcgc  36420
attcggtgca ggtggagttg atccgtgagg agttgttggg ggttctggac gggatcgtcc  36480
cgcgctcggg tgagattccg ttcgtgtcca cggtgacggg tgagcggatc gacactgtcg  36540
agctgggggc ggagtactgg taccgcaatc tccgtcagac agtggaattc cagtcggtgg  36600
tggagggtct ggtcgctcag ggtgtcgggg tgttcctgga gtccagtccg catccggtgt  36660
tgacggtcgg catcgaggag tccgcggatc gggtcgtggc gttggagtcg ctgcgtcgtg  36720
gcgagggtgg tctgcggcgg ttggtggatg cggccggtga ggcgtgggtg cgtggggtgc  36780
cgatcgactg ggcggggatg ctcgccggcg gccggcgggt cgacctgccc acctatccct  36840
tccaacacca gccctactgg ctcgactcac cacgacaccc tgccggagac gtgaccggcc  36900
cgggcgacga cgagttctgg gcggccgtgg agcacggtga ggcgaccgag ttggcggacc  36960
tgctccggag gtcggcggcg gagccggggc aggatcttca cgcacccgtc gcggccctgc  37020
tgccgacgct tgcaacgtgg cgtcgggacc ggcagcgcag ggcggctgtg gactcctggc  37080
ggtaccggat cgtatggcgt ccggtcgcca cgccctcgta cgacagggtg ctgtcggggc  37140
gctgggctgt cgtcgtgccc gccggtcacg aggacgaccc cgtcgtcgac tgggtctgct  37200
cggcgctgcg ggaccacggg ggcgagcccg aacgcatggt gctgggcccg cgggagagcc  37260
gttcggcgct ggccacgcgg ctggccgccg atccccccgg gggcgtggtc tccctgctcg  37320
```

-continued gactgagcgg ggcggcgcac cccgaccacg aggtgctgcc cagtgccgtc gccggtaccg 37380
tcctgcttgc ccaggccctc tccgacggcg ccgtacgagc accggtgtgg accctgaccc 37440
gcaacggtgt gtccgcgacg gcgacggacc cggtggctcc cacgcacgcc gcgcaggtgt 37500
gggccgtggc acgggtggcc ggtctggagc acccggaggc gtggggtggt ctgctcgacc 37560
tgccggaccg tctcgacgac cgcgcggccg cccggttcgc cgcggtcctg tccgcgggcg 37620
aggacgagga ccaactggca ttacgcgacg ctgggttgct ggcacgaagg ctggtgcgtg 37680
cccccgttcc gcgcgacgcg gtgaccgccg gctggcagcc ccgcgacaca gcgctcgtca 37740
cgggcggcac cggcggtctc ggcgggcagg tcgcccgctg gctggcggcc gcgggcgtac 37800
ggcacctcgt gctggtcagc cgtcgggggg cggaggcgga gggcgcagac cgtctgcgcg 37860
acgacctcac cgccctcggc gtacaggtga cgttcggcgc gtgcgacgtc gcggaccgcg 37920
ccgcgctctc ggcgctcctc gaccgggttc aggaggacgg cccgccgatc cgcacggtcg 37980
tgcacgcggc gggctccggt cgcgccgcca ggctgctgga caccgacgcc gaggagaccg 38040
cggcggtgct gcgggcgaag tcggccggag cccggaacct gcacgaactc ctcgatgacg 38100
tggacgcgtt cgtgctgttc tcctccggag cgggtgtgtg gggaagcagc gcccagggcg 38160
cctacgcggc ggccaacgcc tacctggacg cactggccga acagcgcagg ggccaggggc 38220
ggccggcgac ctccgtcgcc tggggcgcct gggccggtga cggcatgaca gccgccgccg 38280
gcgaggaatg gtggagcagg cagggtctgc ggttcatggc ccctgaggcc gccctcgacg 38340
cgctgcgcca ggccgtcgac cgcgccgaga gcacgctcgt cgtcgcagac atcgactgga 38400
agacgttcgc tcccctcttc acgtcggccc gcagccgccc cctcatcacc gacatacctg 38460
aagcccgccc cgaaccgagg ccggaaggcg cggaccagcc tacgcagggc ctcgtggcca 38520
agctggcggt gctgtccgcg gacgaacggc ggcgcgccct gctcgccgag gtgcgggcgc 38580
aggcagcggt ggtgctcggc caccccggcg cggacgccgt accggtcgac cggccgttcc 38640
gcgagctcgg attcgactcc ctcagcgcgg tgaaactgcg caacaggatc gttgctgcca 38700
ccgggctcga gcttccggcc accctggtct tcgaccaccc cacgtccacg gcgctcgccg 38760
cctacctggg cgcccggctc ggaatcgacg gcgccccccgc ggggtccact ctgctggaag 38820
acctcgcgcg gctcgagtcc accgtcgcca ccctgaccgc ggcacctctc gcagagaccg 38880
tgccggacgc ccgggaccgc gcggcgctca ccacacggct gcgggcgttg ctggagcggt 38940
gggaccaggc cgatggcgag gaccaggccg ccgcccgaga agaactcgac gatctgagcg 39000
acgacgacct cttcgacttc atcgacgcga agttcggccg ttcgtgacct cggtcggccg 39060
ccgccaactc cacgtacacc ccgaagacca cgatcaccac gcgaaaagga cgggcctctc 39120
catgggggac gagcagaaac tccgcaccta cctccggcgc gtcactgccg acctggccga 39180
cgtgacggag cggttgcagc gagcagagga caagaacgcc gagccgatcg cgatcgtcgg 39240
catggggtgc cgctaccccg gtggggtgcg gtcgcccgag gagttctgga acctgctcga 39300
cgaaggcgtc gacgcagtgg ccggcttccc cgaggaccgt ggctgggacc tggagaacct 39360
gtacgacccc gaccccgacg agccgggtaa gtgctatgcc cgcgaaggcg ggttcctcta 39420
cgacgcgggc gagttcgacg ccgcgttctt cgggatatcg ccccgcgagg ccctgtccat 39480
ggacccgcag cagcggctgc tgctggagtg ctcctggagt gccctcgagc gggcgggcat 39540
cgacccgggc tcgctgcgcg gcaaagacgt cggcgtgtac gtcggcgcat ggaacagcaa 39600
ctacggcagg ggcggcgggg cggagagctc cgagggccac ctgctgaccg gcaacgcctc 39660

-continued

```
cagcgtggtc tcgggtcgcg tggcgtacgt gctggggctc gaaggccccg ccgtcaccat  39720
cgacaccgcc tgttcctcct ccctggtcgg cctgcacctg gccgcccagg ccctcaggtc  39780
cggcgagtgc ggtcttgcgc tggccggcgg cgtcaccgtg atgtccaccc ctctgtcgct  39840
ggtgtccttc tcccggcagc gggggctcgc acaggacggt cgttccaagg cgttctcggc  39900
ggacgccgat ggcatgggca tggccgaagg tgtaggcgta ctggtcctgg agcgcctctc  39960
ggaggcgcgc cgcaacgggc acgaggtcct ggccgtcctg cggagctcgg ccgtgaacca  40020
ggatggtgcc tcgaacggtc tgagcgcccc gaacgggccg gcgcagcagc gtgtcatcca  40080
gtccgccctg accgtcggcc gtctcgcccc ctccgacatc gacgtcgtcg aggcccacgg  40140
caccggcacg gccctcggcg atccgatcga ggcgcaggcg ttgctggcga cgtacgggcg  40200
ggggcgtgat gcggatcgtc cgttgtggct ggggtcggtg aagtcgaaca tcggtcacac  40260
gcaggcggcc gcgggtgtgg ccggggtcat caagatggtg ctggccctgc gcaagggcgt  40320
actgccgcgg acgttgcatg tggatgagcc aaccggtgag gtggattggg actcgggtgc  40380
ggtgcggctg ctgaccgagg cgcgcgagtg gccgtcgggg gaggggcgtg tgcggcgggc  40440
gggtgtgtcg tcgttcggga tctccgggac gaacgcgcat gtgatcgtcg aggaggctcc  40500
ggaggaggag ccccggccgg aggctccttc cgtcgacgtg gtgccgtggg ttctttcggc  40560
gcggtcggca gaggcgttgc gggagcaggc tgcccggctg gcgtcggtgg ctggtgggtt  40620
gaacgtggtg gatgtgggct ggtcgttggc ttcgacgcgt gcggcgttcg agcaccgggc  40680
cgtggtggtg gggcgggact ccgaggaatt ggtgtcgggg ctttcctcgg tttcgggggt  40740
cgaggtcggg gtcggggtcg gtgccggtgg tggtgtggtg ttggtgttcg ccggtcaggg  40800
gtgtcagtgg gtcggtatgg ggcgggagtt gctgggttcc tcgctggtgt tcgcggagtc  40860
gatgcgggag tgtgcggcgg ctctgtcgcc gtttgtggac ttttctgtgg tggatgttct  40920
gggttcggct ggggagttgg gtcgggtcga ggtggttcag cctgcgttgt gggcggtgat  40980
ggtgtcgctg gcgcgggtgt ggcggtcgtg gggtgttccg gttgctgcgg tggtgggtca  41040
ttcgcagggt gagattgccg cggcgacggt ggcgggtgcg ttgagtgtgg gtgatgcggc  41100
gcgggtggtg gcgttgcgga gccgtttgat cgcggagcgt ctgtcggggc tgggtgggat  41160
ggtttcggtg gcgttgtcgc gtgagcgggt ggtgtcgttg atcgcgggtg tgccgggtgt  41220
gtcggtggcg gcggtgaacg gttcttcgtc gacggtggtc tcgggtgagg ccgcggggct  41280
ggagagggtg ctggccgcgt gtgtgtcgtc gggggttcgg gcgcgtcgta tcgatgtgga  41340
ttacgcctcg cattcggtgc aggtggagtt gatccgtgag gagttgttgg gggttctgga  41400
cgggatcgtc ccgcgctcgg gtgagattcc gttcgtgtcc acggtgacgg gtgagcggat  41460
cgacactgtc gagctggggg cggagtactg gtaccgcaat ctccgtcaga cagtggaatt  41520
ccaagcatcc gtgcagacgc tcctcgccca ggggcaccag gtcttcctgg agtccagtcc  41580
gcacccggtt ctcaccgtcg gcatcgagga gaccgttcac gagagcgccg cacaggccgt  41640
cgttctggga agcctgcggc gggacgaggg tgccctcacc cggctcgtca cctccgccgg  41700
tgaggcatgg gcgcgcggtg tgcccgtcga ctgggcgggc atgctcgccg gcggcaggcg  41760
ggtcgagttg cccacgtatc ccttcctccg ggagcggctg tggctggagc cgtcgcgctc  41820
ccgcaccggg aacctcaaca tggccgggct ggtcgaagcc ggacatgaaa tcctgcccgc  41880
cgcagtggag ttgcccggag agcagtgggt gtggaccggc gagctgtcgc tctccgcgta  41940
cccgtggctg gccgatcacc aggtgctcgg gcagaccctg gtgccgggcg tggcgtgggt  42000
cgaactcgcc ctgcacgcgg gccaccagct cggtttcgga tccgtcgagg aactcaccct  42060
```

-continued

```
gcaggcaccg ctcgtgctcg gcgagtccga cgccgtgcag gtcagagtcg ttgtctccga  42120
tctcggggag agtgatcgcc gggcagtgtc ggtgcactcg cgtggtgacg accagacgtg  42180
ggtgacccat gcggagggat tcctcaccgc gaaaggggcg cagccggaga ccatggccgt  42240
gtggccgccg tccggtgcgg agccggtgga ggctgacggg ttctacgaac gcctcgccga  42300
tgcggggtac cactatggcc cggtcttcca gggcgtgagc aaggtctggc gagctggcga  42360
ggagatctac gccgaggtcg ggctgctcga cgacgccgac gtggacggct tcggcatcca  42420
ccccgccctg ctcgacgccg ccctgcagac cgcctacgtc gcccaacggg gccccgcaga  42480
gacgaagttg cctttcgcgt tcggcgatgt acagctgttc gccaccggtg cccggtcgct  42540
ccgcgtacgg gtctcgccgg ccgctcagca ggggatggcg tgggaggcct gggaccccac  42600
cggacttccg gtgttctccc tcgggtacct ggcgacccgg ccggtcgacc gcggccagct  42660
gaccgtgaag cggcccgagt cgctgttcaa ggtggcctgg gacgagaccg tccccgtcgt  42720
cgggaatgcg accgccgcgc atggcgtcgt gctgggcgac gacccgttcg ccctcggtgc  42780
cgcgctgcgc gcggcgggct gggaggtcgg ggccgccccg gaacccgcgt ccgccgacac  42840
cgccgccgaa gtactgctgc tgccctgcac cgcgcccggc gagccggacg cggacctgcc  42900
caccgcggtc agggccgtga ctgctcgggt gctcggcgtc ctacaggagt ggctcgccga  42960
cgaacggctc gccggcaccc gactggccgt cgtgacccgc aacgccctgc cgggtgacct  43020
cctgcacagc cccgtctggg gtctcgtgcg ctccgcccag accgagaacc ccgggcgcat  43080
caccctcgtc gacctcgacg accaccccga ctcggcggcc gtccttgccg aggccgtcca  43140
gtccgacgag ccgcgcatca tggtccgcga gggccggccc accgccgccc gcctggtccg  43200
tgccaccgca cccgagctgg tgccgcccgc cggagccgat gcctggcgcc tcgagatcac  43260
cgaaccgggc acgttcgaca acctcacgct gggcgtctac ccgcacgccg agaagaccct  43320
cgccgacaac gaggtccggg tcgccgtcca cgcgggcggc ctcaacttcc acgacgtggt  43380
cgccgcactc ggcatggtcg aggacgacct gaccctcggc cgtgaggcgg ccggcgtcgt  43440
cgtcgaggtc ggagacgccg tgccggatct gacccccggc gaccacgtga tgggcatcct  43500
gtcctccggc ttcgggccgc tcgccgtcac cgatcaccgc tacctggcac gcatgcccga  43560
gggctggacg ttcgcccagg cggcttcggt gcccgccgcg ttcctgacgg cctactacgg  43620
gctgtgcgac ctcggcggca tccgcgcggg cgaccgcgtc ctcatccacg cggccgccgg  43680
cggtgtcggc atggccgccg tacagatcgc ccggcacctc ggggcggagg tgttcggcac  43740
cgccagcccg cgcaagtggg gcgcgctgcg cgccctgggg ctcgacgacg cccacctgtc  43800
ctcctcccgc accctcgact tcgagcagga gttcctggac gccaccgacg gcaggggagt  43860
cgacctcgtt ctgaactcgc tggcccggga gttcgtcgac gcctcgctgc ggctgatgcc  43920
cggcggcggc cggttcgtgg acatgggcaa gaccgacatc cggcggccgg aacaggtggc  43980
ggaggaccac ggcggagtcg cctaccaggc attcgacctc gtcgaggccg ggccgcagcg  44040
cacgggggag atgctcgccg agatcgtccg gctcttccaa gccggcgcgt tccggccgct  44100
gccgatcacc cagtgggacg tgcgccgggc gccggaggcc ttccgacaca tcagccaggc  44160
caagcacata ggcaagatcg tcctcaccgt gccccggccc atcgacaccg acggcaccgt  44220
catggtcacc ggcgccaccg ggaccctggg cggcttcgtc gcccggcacc tggtcaccca  44280
tcacggcata cgacgactgc tgctggtcag ccgcagcgcg gagcgcaccg acctggtgcg  44340
ggaactcacc gagctgggcg ccgacgtcac ctgggcctcc tgcgacctag ccgacgccac  44400
```

-continued

```
cgccgtcgaa gagaccgttc ggtccgtcga cgaacggcat ccgctcgtgg ccgtcgtcca  44460
ctctgcggga gtactcgacg acggcgtcat cgacaagcag agccccgaac ggctcgacac  44520
cgtgatgcgt cccaaggtcg acgccgcctg gaatctgcac cgactcctcg acaacgcccc  44580
gctggccgac ttcgtgctct tctcctccgc cagcggcgtg ctcggtggcg ccggacagtc  44640
caactacgcg gccgccaacg ccttcctcga cgcgctcgcc gagcaccgcc gtgcacaggg  44700
cctcgccgga caggcgctcg cctggggact gtggtccgac cgcagcacga tgacgggaca  44760
gctcggctcc accgaactcg cccggatcgc ccgcaacggc gtcgccgaga tgtccgagac  44820
ggagggcctg gccctcttcg acgccgcccg ggacaccgcc gaggcggtgt tgctgcccat  44880
gcacctggac gtcgcgaggc tccgcagccg caacggagag gtacccgcgg tgttccgccg  44940
gctgatccac gccacggccc gccgcaccgc gagcaccgcg gtccgcagcg ccggcctcga  45000
acagcagctc gcctcgctgt ccggccccga acgcacggag ctgctcctgg gactggtgcg  45060
cgaccatgcc gccgcggtgc tcggccacgg cacctccgac gccgtctcgc cggaccggcc  45120
cttccgcgac ctgggtttcg actccctgac tgccgtggag ctgcgtaaca ggttcgccgc  45180
cctcaccggc ctgcgtctgc cggccacgct cgtcttcgac cacccgagcc cgacggccct  45240
cgccgggcac ctcgccggcc tgctgggcgc cgcgacgccc tccgcggccg agccggtcct  45300
ggccgccgtc ggacggctgc gcgccgacct ccggtcgctc accccggacg ccgagggcgc  45360
cgaggacgtg acgatccagc tggaggccct cctcgccgag tggcgggagg ccgcggagaa  45420
gcgggctccg gaggcggtcg gtgacgagga cctgtccacc gccaccgacg acgagatctt  45480
cgcgctcgtc gacagcgaac tgggtgaggc ctgatgacgg ccgaagcgtc tcaggacaag  45540
ctgcgtgact atctgcgaaa gaccctcgcc gacctgcgga ccaccaagca acggctacgc  45600
gacaccgaac gcagggcgac cgagcctgtc gcgatcgtcg gcatgagctg ccgactgccc  45660
ggcgacgtac ggacaccgga gcggttctgg gaactcctcg acactggaac cgacgccctg  45720
acgcccttgc ccaccgaccg cggctggaat ctcgacacgg cgttcgacga cgaacggccg  45780
taccggcgcg aaggcggatt cctttacgac gccggacggt tcgacgccga gttcttcggc  45840
atctcgcccc gtgaggcgct ggccatggac cctcagcagc ggctgctcct cgaaagctcg  45900
tgggaggcga tcgagcacgc ccgcatcgac cccaggtccc tgcacggcag tcgcaccggc  45960
gtctggttcg gcacgatcgg ccaggactac ttctccctct tcgccgcatc cggcggcgag  46020
cacgccaact acttggccac cgcctgctcg gccagcgtga tgtccggccg cgtctcgtac  46080
gtgctcggcc tggaggggcc cgctgtcacg gtcgacacgg cgtgctcgtc ctccctggtc  46140
gccctccact ccgccgtaca ggccctgagg tccggcgagt gcgaactggc tctcgccggg  46200
ggcgccacgg tcatggccac cccgacggtg ttcaccgcct tctcccatca gcgtggcctg  46260
gccggtgacg gccgctgcaa ggccttcgcg gcgggtgccg acggggcggg cttcgccgag  46320
ggggtgggcg tgctggtgct ggagcggttg tcggtggcgc ggcggaacgg tcatcgggtg  46380
ttggcggtgg tgcggggttc ggcggtgaac caggacggtg cgtcgaacgg tctgacggcg  46440
ccgaacggtc cgtcgcagca gcgggtgatc cgcgcggcgc tggccaacgc gcgcttggcg  46500
ccggaggacg tggacgctgt cgaaggccac ggcacgggga cttcgctggg cgacccgatc  46560
gaggcgcagg cgttgctggc gacgtacggg cggggccggg acgcggagcg tccgttgtgg  46620
ctggggtcgg tgaagtcgaa catcggtcat gcgcaggctg ctgccggtgt cgccggtgtc  46680
atcaagatgg tgctggccat ggagaagggc cgtctccctc ggacgctgca tgtggatgag  46740
ccgtcgggtg aggtggactg ggactcgggt gcggtacggc tgctgaccga ggcgcgggac  46800
```

-continued

```
tggccgtcgg gggaggggcg ggtgcggcgg gcgggagtgt cgtcgttcgg gatctccggg  46860
acgaacgcgc acgtgatcat cgaggagccg caggaggagg aagcggcacc ggattcctct  46920
gcttcgggtg ccgtgccgtg ggtgctctcg gcgcgatcgg ccgaagcgtt gcaggctctg  46980
gcttcacaac tcgccgacca cagcgccaaa tcgagtccgg tggatgtggg ttggtcgttg  47040
gtttcgacgc gtgcggcgtt cgagcatcgg gccgtggtgg tggggcgcgg gcgggacgag  47100
ttggtgcggg gcttgtccga ggtcgcgcag ggtcggggcg tgaggggtgt cgcgtcttcg  47160
gcgtcgggtg gtctcgcgtt tgtttttgct ggtcagggca gtcagcggtt ggggatgggg  47220
cgggggttgt atgagcggtt cccggtgttt gccgaggcgt tcgacgaggt gtgtgggcgg  47280
gtcggtccgg gggtgcggga ggttgttttc ggttcggatg cgggtgagtt ggaccggacg  47340
gtgtgggcgc aggcggggtt gttcgcgttg gaggtggcgc tgtttcggtt gttggagtcc  47400
tggggtgtgc ggccgggttg tctgatcggg cattcggtcg gtgagttgtc ggcggcgtgt  47460
gtggcggggt tgtggtcgtt ggaggatgcg tgtcgggtcg tggctgcccg ggcgcggttg  47520
atgcaggcgt tgccggcggg tggggtgatg gtcgcggttc gggccgaggc gggggagctg  47580
gccggtttcc tcggtgagga cgtggtgatc gcgtcggtga acgcgccggg gcaggtggtg  47640
atcgctggtc ctgagggggg tgtggagcgt gtggtggctg cttgtggggc gcggtcgcgt  47700
cgtctggcgg tctcgcatgc ttttcattcg cctttggtgg agccgatgct gggggagttc  47760
cgtcgggttg tggagtcggt ggcgttcggt gtgccgtcgt tgcgggtggt ttccaatgtc  47820
acgggtgcgt gggtggatcc ggaggagtgg gggacgccgg agtactgggt gcgtcaggtc  47880
cgtgagccgg tgcgtttcgc cgacggggtc gccacgttgc tcgacgcggg tgtgaggacg  47940
ttcgtcgagc tgggtcccgc tgggacgctc acttcgatgg tcagccactg cgcggacgcc  48000
accgccactt cggtgacggc tgtacctacc ctgcgccccg atcacgacga gtcgcggacc  48060
gtgttgagtg ccgcagcgtc cttgtacgtc cagggtcacc cggtcgactg ggccccgctg  48120
ttcccgcggg cccgcacggt ggacctgccc acctacccct tccagcacca gcactactgg  48180
atggaaagcg ccgcccggcc caccgtcgag gacaccccgc gcgagcccct cgacggctgg  48240
acgcaccgca tcgactgggt gccgctggtg gacgaggaac cggcgcccgt cctggccggt  48300
acctggctgc tcgttcgtcc cgaagaaggt ccccgcccgc tcgccgacgc cgtcgcggac  48360
gcgctgaccc ggcacggcgc ctccgtcgtc gaggccgctc gtgtcccgca ccaatccgac  48420
accgagctga ccggagtcgt ctctctgctg ggcccgggcg ccgacggcga cggcggcctg  48480
gacgcgaccc tgcggctggt acaggacttg gccaccgccg ggtccaccgc gcccttgtgg  48540
atcgtcacca gcggagccgt ggccgtcggt acgtccgaca ccgtgccgaa ccccgagcag  48600
gcgacgctct gggggttggc ccgggcggcg gccaccgagt ggcccggcct gggggcggcg  48660
cgcatcgacc tgcccgccga cctcaccgag caggtcggac gtcggctctg cgcccggctg  48720
ctcgaccgga gtgagcagga gacggcggtc cgacaggccg ggtgttcgc caggcggctg  48780
gtccgtgccc gtaccagcga cggccggtgg acgccgcgcg gcaccgtgct ggtcaccggc  48840
gggaccggcg cgctcgccgg acacgtcgcg cgatggctgg cggaggaggg ggccgagcac  48900
atcgtgctgg ccgggcgcag agggcccgac ggtcagggcg ccgaggcgct gcgcgccgac  48960
ctggtcgccg caggggtcaa ggcgacgatc gtgcgctgcg acgtcgccga ccgggatgcc  49020
gtacgtctgc tcctggacgc acaccggccc agcgccatcg tgcacacggc cggggtcgtc  49080
gacgacggac tgctcacctc gctgacgccc gcccaggtcg agcgggtgct gcggcccaag  49140
```

-continued

```
ctgctcggcg ccaggaacct gcatgagctg acccgggacc gggaactgga cgccttcgtg  49200
ctgttctcct ccctcgccgg agtcctcggc ggggcagggc aggccaacta cgccgctgcc  49260
aacgcctact tggacgccct ggccgcacac cgcaccgcgc atgggctgcc ggcggcctcg  49320
ctggcatggg ggccgtggga gggcgacggc atggccgcgg cgcaggaggc cgccgaccgg  49380
ctccgccgca gcggtctcac cccgctgccg ccggagcagg ccgtacgggc cctcggccgg  49440
ggccacgggc cgctggtggt ggccgacgcg gactgggcgc ggctggccgc cggctcgacg  49500
cagcgcctgc tcgacgagct tcccgaggtg cgtgcggtca ggccggcgga gcctgctgtc  49560
ggacagcgcc ccgacctacc ggcccggttg gcggggcgtc cggccgagga gcagtccgcg  49620
gtactgctgg aggcggtccg ggaggagatc gccgccgtac tgcgttacgc cgatccggcg  49680
cggatcggcg ccgatcacga gttcctcgcc ctcggcttcg actcgctgac atcgatcgaa  49740
ctgcgcaaca ggcttgccac gcgcatcggt ctgacgcttc ccgcgacgct caccctggaa  49800
cagcgcaccc ctgccgggct cgccgcgcac ctgcgcgagc ggatcgcgga ccggcccgtc  49860
gggtccggtg ccgtcccggt gcccgggagc gctgatgtcc cggaggcggg cggcggtagc  49920
ggcctcggtg agctgtggca ggaagccgac cggcacggcc ggcggctgga gttcatcgac  49980
gtactcaccg cggccgccgc cttccggccc gcctaccgtg aaccggccga gctggagctg  50040
ccgcctctac ggctcacctc cggcggggac gagccgcccc tgttctgcat cccctcgcac  50100
ctcggcaagg ccgacccgca caagttcctg cggttcgccg cggccctgcg gggacggcgg  50160
gacgtcttcg tcctgcgcca gcccggcttc gtacccgggc agcccctgcc cgcgggcctc  50220
gacgtcctgc tcgacaccca cgcgcgggcc atggccgggc acgaccggcc cgtgctgctc  50280
ggctactcgg ccggcggtct tgccgcgcag gcgttggccg cccgactcgc cgagctcggc  50340
aggccgccgg cggccgtcgt gctcgtcgac acctatgccc ccgacgagac ggaggtgatg  50400
gcccgtatcc agggcgccat ggagcagggc cagcgcgatc gcgacggcag gaccggtgcc  50460
gccttcggtg aggcctggct caccgcgatg ggccactact tcggcttcga ctggaccccg  50520
tgtccggtcg acgtgccggt gctgcacgta cgcgccggcg accccatgac cggtatgccc  50580
gtcgaagggc ggtggcaggc gcgctggaac ctgccgcaca ccgccgtcga cgtgcccgga  50640
gaccacttca cgatgatgga ggatcacgcc ccgcgcaccg ccgacaccgt gcacgactgg  50700
ctcggcacgg ccgtccgccg ccctgagaga acccgcgact gacgactcgc cggcgacagc  50760
ggcatcccgc cctgtcccct tcctgtccgt ccgttccctt tcctctcctc gaaacggagt  50820
tcgttctcat gccttccttc cccgtacgcc ggtccgtgcc cgacactccg cccgccgagc  50880
acctcgaact gctcaaggag agcggcggcg tctgcccctt caccatggag gacggccgtc  50940
cggcctggct cgcggccagc cacgacgccg tgcgctccct gctcgccgac cgccgtatca  51000
gcaacaaccc ggcgaagacg ccgcccttct cgcagcggga ggccctgcag aaggagcggg  51060
gccagttcag ccgtcacctg ttcaacatgg actcgccgga gcacgacgtg gcccgccgca  51120
tgatcgcgga ggacttcact ccccggcacg ccgaggcggt ccggccgtac ttcgaggagg  51180
tgttcggcga gatcgtcgac gaagtggtcc acaagggccc accggccgag atgatcgagt  51240
cgttcgcctt cccggtcgcc acccgcacca tctgcaaggt gctggacatt ccggaggacg  51300
actgcgagta cttccagaag cgcaccgagc agatcatcga gatggaccgc ggcgaggaga  51360
acctcgaagc cgtcgtcgaa ctgcgccgct acgtcgacag cgtcatgcag cagcgcaccc  51420
gcaagcccgg cgacgacctg ctcagcagga tgatcgtcaa ggcgaaggcg tccaaggaga  51480
tcgagctcag cgacgccgac ctggtcgaca acgcgatgtt cctgctggtg gccgggcacg  51540
```

-continued agccgtcggc caacatgctg ggcctcggcg tgctcgccct cgccgaattc ccggacgtgg 51600
ccgaggaact gcgggccgag ccgcacctgt ggccgggcgc gatcgacgag atgctccgct 51660
actacaccat cgcccgggcc accaagcggg tcgcggccgc cgacatcgag tacgaggggc 51720
acacgatcaa ggagggggac gccgtcatcg tgctcctcga caccagcaac cgcgacccga 51780
aggtgcacgc cgaaccgaac cggctcgaca tccaccgctc ggcgggcaac cacctggcct 51840
tcagccacgg accgcaccag tgcctgggca agcacctcgt ccgggtccaa ctggagatcg 51900
cgctgcgggc tgtcgccgag cggctgcccg gcctgcgcct ggacatcgcc aaggaggaca 51960
tccccttccg cggtgacgcc ctgtcctacg ggccgcgcca gctgcgcgtc acctggtaac 52020
agccaccatc ggcccccgcc gcggaccggg cagcacgacc cggtccgcgg cgggggcacc 52080
accaccgtca acatccccag agaggcttcc ccgtggagaa gaccgacgtc gaccggctgc 52140
gcacactcga ccgagagcac atgtggtacc cgtggacgcc gatgaccgag tggatggccc 52200
gtgatcagct cgtcgtcgaa cgcgccgaag gctgctggct gatcgacgca gacggtaagc 52260
gctacctcga cggccgctcg tcgatgggca tgaacctgca cggccacggc cgcagcgaga 52320
tagtcgaggc cctggtcgcc caggcgcgca aggccggtga gaccacgctc taccgcgtct 52380
cgcacccggc ggcggtggaa ctcgccgccc gcctggcatc gatggcgccg gccgggctcc 52440
agcgcgtctt cttcgccgag tccggatcga ccgcggtgga gacggctctc aaggctgcct 52500
acgcctactg ggtcgcgaag ggcgaaccgc agcgatccac cttcgtgtcc atggagggcg 52560
gttaccacgg cgagacccta ggcacggtca gcctgcgcgg caccaacggc gaacaggtcg 52620
acatgatccg caagacctac gagccactgt tgttcccctc cctctccttc caccagcccc 52680
actgctaccg gtgtcccgtc ggccagtcgt cggacagcga ctgcgggctg gagtgcaccg 52740
attcgctgga gaacctcctc acccgggaga agggccggat cgccgcggtc atcgtcgagc 52800
cgcgggtcca ggccctcgcc ggagtgatca ccgccccgga gggacacctc gcgaaggtcg 52860
cggagatcac ccgcaggcac ggagtgctcc tcatcgtcga cgaggtcctc accggctggg 52920
cccgcaccgg cccgacgttc tcctgcgagg ccgagggcgt cacaccggat ctgatgacgg 52980
tgggcaaggc gctgaccggc ggatatctgc cgctgtcggc caccttggcc acggaggaga 53040
tcttcggagc cttccgtgag agcgtcttcc tcagcggcag cacctactcc ggatacgcgc 53100
tcggggcggc cgtcgccctg gccagcctcg acctgttcga gaaggaggac gtaccggccc 53160
gggccaaggc gctcgccgac gtgctcacca ccgcactgga acccttccgc gcgctcaccc 53220
acgtcggtga cgtccggcag ctcggcctca tcgccggcgt cgagctggtg gccgaccggg 53280
agacccgcgc cccctacccg ccccaggagc gcgtcgtcga tcgcatctgc accctggcca 53340
gggacaacgg cgtgctggtc aacgcggtcc ccggggacgt gatcaccatg ctgccctcac 53400
cgtcgatgag ccccgacgac ctgcgcttcc tcaccggcac cctgtacacg gccgtccgag 53460
aggtgaccga agagtgaaag ggctgatgcg ggcggccgtc atccgtgcct ggggcggccc 53520
cgagcggctg accctggacc gggtcgaacg gccgtcaccc ccgcccggat ggatcgccgt 53580
acgcgtcgag gcctgcgccc tgaaccacct cgacatccac gtgcgcaacg ggcttccggg 53640
cgtacggctg gaactcccgc acgtctccgg cggcgacgtc gtcggcgtcg tcgagcaggc 53700
caccgacgag gcgggggaga gactgctcgg cagccgtgtg ctgctcgacc cgatgatcgg 53760
gcgcggcatc ctcggcgagc actactgggg cgggctcgcc gagtacgtcg tcgcacccgc 53820
ccacaacgcg ctccccgtcc ccgatcagga cgcggacccg gcacgctacg ccgcactgcc 53880

-continued

```
catctcctac ggcacggccc agcgcatgct cttcagccgc gcccggctgc gtcccggcga  53940
gagcgtgctg ctgttcggcg cgaccggcgg cgtcggcgtc gcctgcgccc agctcgccct  54000
gcgtgccggg gcccggatca tcgcctgctc cggatcaccg gccaagctcg cccggctgcg  54060
ccgactcggc gtgatcgaca cgatcgacac cggcaccgag gacgtacggc gcagggtccg  54120
cgaactcacg gacggcggtg ccgacctggt cgtcgactac cagggcaagg acacctggcc  54180
cgtctccctg cgctcggcgc gcgccggcgg ccgcatcgtc acctgcggcg cgaccaccgg  54240
gtacgaggcg acgaccgacc tgcgctacgt gtggtcgcgt cagctggaca tcctcggctc  54300
caacgcgtgg caccgcgacg atctgcacac gctggtcgac ctggtggcca ccgacgccct  54360
ggaaccggtg gtgcacgccg acttcccact ctcccgcgcc cccgaggcgg tcgccgaact  54420
ggaggagcgc cgggcgttcg ggaaggtcgt gatccgcacg gcgtgaactc actcatgtcc  54480
cggctcgatc ccagggggaa acagcgtgac cggcaacacc acatccgccg ccttcctgcg  54540
gcggacacag aacgcgctcg ccatgcagcg caagatatgc gcccagcccg aggagaccgc  54600
ggagcgcgtg ttctccgaca tcctctcggt gtcacgagac accggcttcg gccgcgaaca  54660
cggcctcgcc ggggtccgca cccgccagga gtggcggcgt gccgtgccca tccgcaccta  54720
cgacgaactg gccccctacg tcgagcggca gttctccggc gaacgccgcg tgctcaccac  54780
cgacgacccc cgcgccttcc tgcgcacctc gggatcgacc ggccgcgcga agctggtacc  54840
caccaccgat cactggcgcc gtgtctaccg cggaccggcg ctgtacgcgc agtgggggct  54900
ctacttcgaa cagatcggca cgcatcggct caccggcgac gaggtcctcg acctgtcctg  54960
ggagcccggc cccatccggc accgactgcg cggcttcccc gtctacagca tcaccgagcg  55020
ccccgtgtcg gacgaccccg acgactggaa cccgccgtgg cgtcacgcga ggtggttcac  55080
ccgcgatgcc ggtgccgcga ccatggccga cctgctctac ggcaaactgc tgcggctggc  55140
cgcccacgac ctgagactga tcgtctcggt gaacccctcc aagatcgtcc tgctcgccga  55200
gacactgaag gagaacgccg aacgcctgat ccaggacctg cacgacggcc acggcacgga  55260
ccgggcagcc cgcccggact tcctccgccg cctcaccgcc gccttcgacc gcaccggagg  55320
ccgtccgctg ctcaccgacc tgtggcccgg cctgcgtctg ctcgtctgct ggaactccgc  55380
ctccgcggcg ctgtacgggc cctggctgtc ccggctcgcg accggcgtgg cggcactgcc  55440
gttcagcacc acgggcaccg agggaatcgt cacgctgccc gtcgacgacc acctctcggc  55500
ggggccgctc gctgtcgacc aggggcattt cgaattcgtt ccgtggcagg acctggacga  55560
cggcagccct ctgcccgagg acacccccac cctcggctat gacgaactcg aactcggcgc  55620
cgactaccgg ctcgtcatga gccaggccaa cgggctctac cgctacgacg tgggcgacgt  55680
gtaccgcgtc gtcggagcgg tcggcgccac gccacggctg gagtttctgg gacgcgcggg  55740
attccagtcc tccttcaccg gcgagaagct caccgaatcc gatgtgcaca ccgccgtgat  55800
gcgggtcctc ggcagcgaac gcaccgacca cccgcacttc tccggcatcc cggtctggga  55860
caccccgccc cactacctcg tcgccatcga atgggctgac gcccacggca cgttgaacgt  55920
gcaggacaca gcccgccgca tcgacgcgac tctccaggaa gtcaacgtgg aatacgccga  55980
caagcgccgc agcggacgac tgcggcccct gcagatcctg cccctggtgc ccggcgcttt  56040
cggccagatc gccgaacgaa ggttccgcca gggcaccgcg ggagcccaga tcaaacacca  56100
ctggctgcag aaggactcgg cgttcctcga cacgctgcgc gacctcgacc tcgtccgcgc  56160
ccgcccgggg acgtgacggc atgcgcatcg gattcgccgc acccatgtcc ggcccctggg  56220
ccaccccgga caccgccgtg cacgtcgccc gcaccgccga acagctcgga tacgcctcgc  56280
```

-continued

```
tctggaccta ccagcgagtc ctcggcgcgc ccgacgactc ctggggcgag gccaaccgca  56340
gcgtccacga ccccctgacc accttggcct tcctggccgc gcacaccacc gggatccggc  56400
tcggtgtcgc cgttctgatc atgccgctgc acaccccgc ggtgctggcc aagcagctca  56460
ccaccctcga cctgctctcc ggcggccgac tcgacgtggg cctcggcaac ggctgggccg  56520
ccgaggagta cgccgccgcc ggcgtgaccc ccaccgggct cagccgccgc gccgaggact  56580
tcctcgcctg tctgcgggcc ctgtggggtg agcagaccgt ggtggaacac gacggcccct  56640
tctaccgggt cccgcccgcc cgcttcgacc cgaagcccgc ccagtccccg cacccgccgc  56700
tgctcctggg cggcgccgcg cccggcgcac tgcgccgcgc cggccgcctg tgcgacggct  56760
ggatcgcgag cagcaaggcc ggcccggccg ccatccgcga cgccatcacc gtcgtacgcg  56820
acagcgctga gcgaaccgga cgcgaccccg cgaccctgag gttcgtctgc cgcgccccgg  56880
tccggctgcg gacccggtcg gcccccaacg agccgccgct gaccggcacc gcggagacga  56940
tccgggccga tctcgccgcg ctagccgaca ctggcctgac cgagatcttc ctggacccca  57000
acttcgaccc cgagatcggc tcaccggacg cgccgaccgg cgacgtgcga caccgcgttg  57060
atctgctgct gcacgaactg gcccccgcaa actggtgaga ggaagagaac agtgctgatc  57120
gcgcgcgccg ccgtcggaga agaccgaacg tacgcccgcg tcgacacgga cacagggctg  57180
atccacctcc tggccggcac tccctacgac gagatccggc cgaccggcga aaccagaccg  57240
cttgccgagg cccgcctgct cgcaccggtc gaacccagca aagtgctggt cgcaggacgc  57300
aattacggcg atgtcgtcac accggacctg gtggtcttca tgaagccgtc cacctctgtc  57360
gtcggcccca ggagcaccgt cctgctgccg gcggaggcca agcaggtccg gtacgaggga  57420
gaactcgccg tggtgatcgg gcgccgctgc aaagacgtcc ccgaagacac cgcggaccag  57480
gccgtgttcg gctacacctg cgccaacgac gtcaccgcct gggacgtcgg ggaaccgaag  57540
ggccactgga ccaaggcgaa gagcttcgac acattctgcc cgctgggacc atggatccgc  57600
accgatctcg accccgctga cctcgtcctg cgcacaaccg tgaacggcac gctgcgccag  57660
gacggctcca ccaaggaaat gaacaggaat gtccgcgccc tcgtgtcccg ttgcagctca  57720
ctgatgacgc tgctgcccgg agacgtgatc ctcaccggca caccggcggg cgccggcgtg  57780
ctgcgtccgg gtgacgaggt cgtcgtcgag attgacggga tcggttcgct cgcgaatccg  57840
atcggcgtgg ccaagtagtt cactgactac actcgcgcga acaacacggg cccgtctgcg  57900
gcgcttcgag ctgcgccgat ccccgaggag agattccagt gtctgtaatc cgtcccaccg  57960
ccgaaaccga acgcgcagtc gtggtggtcc cggctgggac gacgtgcgcc gacgcggtca  58020
ccgcggcaaa gctgccgcgc aatggcccca acgcgatcgt cgtggtgcga gacccgtccg  58080
gcgccctgcg tgacctcgac tggacccccg attccgacgt cgaggtcgag gccgtcgcgt  58140
tgtccagcga ggacggcctc acggtgctgc gccactccac ggcacacgta ctggcccagg  58200
cggtccagca actctggccg gaggccaggc tcggtatcgg cccgccgatc gagaacggct  58260
tctactacga cttcgacgtg gagcgcccct tccagccaga ggacctcgag cgcgtcgagc  58320
agcggatgaa ggagatcatc aagtccggcc agcgcttctg ccgccgcgag ttccccgatc  58380
gggaagcggc ccgtgccgag cttgccaagg agccgtacaa gctcgagctc gttgacctca  58440
agggcgacgt ggacgccgcc gaggcaatgg aggtcggcgg gagcgacctg acgatctacg  58500
acaacctcga cgcgagaact ggagatgtgt gctggtccga cctctgccgc ggcccccact  58560
tgccgtcgac ccgcctgatc ccggcgttca agctgctgcg caacgcggca gcctactggc  58620
```

-continued gcggcagcga gaagaacccc caactgcagc gcatctacgg cacggcctgg ccgacccgcg 58680
acgagctcaa gtcccatctc gccgccttgg aggaggccgc caagcgtgac caccgccgca 58740
tcggcgagga actcgacctc ttcgcgttca acaaggagat cggccgcggc ctgccgctgt 58800
ggctgcccaa cggcgcgatc atccgcgacg aactcgagga ctgggcccgc aagaccgaac 58860
gcaagctcgg ctacaagcgc gtcgtcaccc cgcacatcac ccaggaggac ctttactacc 58920
tctcaggcca tctgccttac tacgcggagg acctgtacgc gccgatcgac atcgacggcg 58980
agaagtacta tctcaagccg atgaactgcc cgcaccacca catggtgtac aaggcgcgcc 59040
cgcacagcta tcgcgacctg ccctacaagg tcgccgaata cggcacggtg taccgattcg 59100
agcgcagcgg tcagctgcac ggcatgatgc gtacgcgcgg tttcagccag aatgacgcgc 59160
acatctactg cacggcggac caggccaagg accagttcct ggaagtcatg cgcatgcacg 59220
cggactacta ccgcactctg gggatcagcg acttctacat ggtgctcgcg ctgcgtgact 59280
cggcgaacaa ggacaagtac cacgacgacg agcagatgtg ggaggacgct gagcggatca 59340
cccgggaggc catggaagag tccgacatcc ccttccagat cgacctgggc ggtgccgcgc 59400
actacggccc gaaggtcgac ttcatgatcc gagccgtcac cggcaaggag ttcgccgcct 59460
ccaccaacca ggtcgacctg tacaccccgc agcgtttcgg gctgacctac cacgactccg 59520
acggcaccga gaagcccgtc gtggtgatcc atcgcgctcc gctcggctcg cacgagcgct 59580
tcaccgccta tctcaccgag cacttcgcag gtgccttccc ggtgtggttg gcgccggagc 59640
aggtccggat cattccgatc gtggaggaac tcacggacta cgccgaggaa gtccgcgaca 59700
tgctgctgga cgcggacgtg cgtgccgacg tcgatgccgg cgacggccgg ctgaatgcca 59760
aggtacgcgc ggccgtcacc cggaagatcc cgctcgtcgt ggtggtcggc aggcgagagg 59820
ctgagcagcg caccgtaacc gtgcgcgacc gctccggcga ggagaccccg atgtccctgg 59880
agaagttcgt ggcccatgtc actggactca tcaggaccaa gagcctggac ggcgccggcc 59940
acatccgtcc gctgtccaag gcctgaccca cagccacggg gccccggcag gtgtcccgcc 60000
tcggaccacc cccttcggtc ctcagccgac ggcgggctca tggcagccgc ccgacctgcc 60060
ggtgccgtgg ctgttcggca acccgtgggc gccgcccgcc gaggagaccg cgcgctgccg 60120
ggggatgatc tcgtccggcc cgcgccccgg gctcaccggg cggcgctgga gcgggccgga 60180
cgggagccgg gaccggccga ccgtccgtgg tcggtctcgt cccggacgag cagggacagc 60240
agtgcggcca cggtgaggcc cgcttccgcc gggtggcgca ggaccttgtc cggttcgacg 60300
cggtagatgt tgctgcgccc gtcacgggtg tgggagagat agccgtcctg ctccaggtcc 60360
gagatgatcc gctggacggc gcgctcggtg agtctgcagt gggcggcgat gtcgcggatc 60420
cgcacgttcg gattgtcggc gatggccgcc agtacacgcg cgtggttggt gacgaacgtc 60480
catccggagt gagattcagg cactgcaacc atgcacagca ttgtagggac catctttgcc 60540
ggacagccaa tacatgacat acttttcgcg ttaagagtgg catgttctgt cccatgggca 60600
actgagaagg gacccgaggg tgtctttgga tgaagcggtc gcggggtgct cgcgccacac 60660
cggccggcgt cggctcccgg ccgcggagca acccacgcag gcgcagtacg aagcgcacgg 60720
cgcctgggtc gtcagcgcac ggggcgcata cgacatgaac tcggtcgagc ccttggccga 60780
cgcgttgaaa gacgcggccg agaagtctcc gaaggtggta ctggacgcct ccggcatcac 60840
cttcgccgac tccaccctgc tgagtctgct gatcctcacc caccaggcga cggacttccg 60900
ggtggccgcg ccgacgtggc aagtgatgcg gctcatgcaa ctgacgggcg tcgacgcctt 60960
cttgaaggta cgggccacgg tggaagaggc cgccaccgct taggggcacg gcgtgccggg 61020

-continued

```
cctcggctga cgcaagccga tggcttggag ctgagaattc cgggcattcg acgttctgcc  61080
tggcccccgg ccgtcgatgg tggccggcca ggcgtgatga agacagtcac ctcctcgagg  61140
cgcgatcgac cgcgcctcgg gggagggcgg ttgacgggag agggaaggtg tccatgattc  61200
tgccggcgga gaaggaactg cgtgccgtgc tggctcggtt cgctcaggcg cgcatcgacc  61260
acgacgtacg tcccagcggc tgcaccagca ggctcctcga ggacgccacg tacaccctgt  61320
gcgtgatgac cggtgcccgt accgccgaac aggctctgcg tacggcggac gaacttctcg  61380
cacagttcgc cgagcgcacc gctgcccccg tggaggacga agccctggcc gcgtgagccg  61440
acggcacaca cctgcggcgc ctcgcgtggc aggtgtgtgc ctgccggcgg gcggacgcga  61500
gcacctgagg aaatgagaga gagtcatgag cgatacccgg cttcggcagc gcgatgagac  61560
gtcgaagggg ccggccaccg agatcccggc gccgcagtgg cgggacctct tcctcgcccc  61620
cgactggggc ggcactgatg agcaggtgat cgtcgccgaa gaggcgcgcg ggcccgagca  61680
cttcaccgga gcgcgccgtc cgcgcggcgg ccgccgatcg agtcgacggg ccgcgtgatg  61740
cgcggccctg ccgcgacggc cgcaggtcag gtgagggcga tccgtgcggt gatgcgcttg  61800
ccggacggct cgggccggat ctcgacggcc tggctcagcg ccgccacgat ctccagaccg  61860
tgctgaccca cccgggcggg atcggcgggc cggggagcgg gcagggtggt gtcaccgtct  61920
cgcacggtga cagtcaccgc gtcgtccgtg aggctcaggg tgagttctat ggggtcggcc  61980
ccgtacttga ccgcgttcgt gatcagctcg ctcaccacca ggtggacggc ctccgacgct  62040
ctctccggca ccggcgaccg aaggtcccgc tgtgaacggg tgaggtagtc ggtcgcgaag  62100
tgacgggcgt cggcgatccg cagcgcttcc cgccggtacg tcaccgaggc cgcccgcgga  62160
tccgcaccct ccggtgcccg ctgtgtcgac gaaccgtcca gtccggtctc acccatgtca  62220
accgccacgt tacccccgag ccacgcacgc gcgccgacgc ctcccgcgcg atgagaacat  62280
ctcatgtgtt cctacgatag ttctgctttc cgtcggtcac cgcacccgtc ggccagggag  62340
aaagcggggg cctggacgtg atccgggcct caggccgtgc tgagcacgcc tccgcgcaag  62400
cgggccggca gccgctccgg aatccgtgcg gtcgtcgtcg ccatgatgtc cctccccgtt  62460
ccgatggccc gctcgcgtga cggccactc ggcggctacc ccctgcgcgg gctcgcatgc  62520
acggaggcgg agatcttgtc cgaggccgtt ccgctcccgc ccgcgcgacg tgatcaggtc  62580
ggcggttacg ggatcaggaa ttccagcacg ggtcggtccc aggccaccgc gggcgggttc  62640
gcgcgggcgg ttccggtggg cagggcgccc acagcgcggt agaagccctc ggccggaggg  62700
tgcgacacca cccggacacg gtccagccct gccgcgcggg cccgcctctt catgtgatcg  62760
acaagcagcc gtccgatgcc gcggccctgg gtaccgtcct ggacgaacag caggtccagc  62820
tccgccggcg cgaggagcag cgcgtagaag ccgagcaccc ggtccgtggc gtcctcggcg  62880
tcgacgctac gaagacctgg tggttctcga tgtagtcggg cccgacgcgg tagtcggaga  62940
ccatcgccgc gtacgggccc tcgtaggctc gtgagccgcg tacgagacgc gagagccgct  63000
tggcgtcccg ggcgaccgcc cggcggatga cgatctcgcc ccgtacggac gcggaactcg  63060
attgcacggg gagcagtcta cgcgtccggg acgggccggg acctccgcgg gctccgtccg  63120
agccttccgt cagtccgtcc cgatgacgac cacctcagtc cgtcccgatg acgaccacct  63180
cgtcctcggc cgtccaccgg cgccgctcgc gtttgggcgg attgatccgc actccgtagt  63240
gggggcgcgt cgacgcgtcg gcgtggtcgc ggtaaccgat ggcgcactcg ccgcgacggc  63300
gtgccgcggc cacgacggtg gcgaaggacg tggtgctccc tggcaacagg tagtcggtcg  63360
```

-continued

```
ccggccgcag gcggaccccg gcgccctcgg cggagaacag ttcctcgaag accgcggcca  63420
ggtgccggtt ctgggagatc tgggacatga gcaggccgat gagcttgccg ctgatgatga  63480
cgtcggcccc ggggccgatg ggggccagcg cccggttgcg gtcgtcgatc agttcggtga  63540
cgaccggcag ctcgcgcccg gtggcttctt ccagttggcg caggagcaga agggtgacga  63600
gcgtgcggtt gtcgggatcg tccggcggtt ggcccggggc ggggtcccgc cccagcacga  63660
tcacgctgtc gtaggagtgg acgtccaggc gccgcagcgt ctcgggacgg gtgatgtccc  63720
cgtggtgcag agccaggctc aggccgttcc caccgttctc cccgtttccg ctgtccgctt  63780
cggcctcgct gatctcgcgg atcgtcgcct cgcccggttc cgccacgacg tcgacggccg  63840
aaccgggccg ggcgcgtcgg tgcaactggt cgaccacgag cggcgctcgg cggttccagc  63900
ccagtagcag aatccgctcc gccggcgcgg gcgtcggagg gcgggaggcc accgcggcct  63960
tctcgaccga ctccgcacag tcgtccagcc gggccgtgtc gtcgtcgccg gtgatgacga  64020
cgagcaggtc gtccggggcg accggcgtcg tcggcggcgg gttgagcaag ggggtgcagc  64080
cgcgcatcag tccgacgacg ctcgtcgtcg agtaggacag gagaacctcg ccgaacgggc  64140
ggccggtcag ggccggctcg ctgatcagat agaactcgtc tccggcgaag tcgaggagtt  64200
cccggtggac gagggagatc ccggggcggc gggcggcctg gacgatcagc cgggcggtga  64260
cggtgtcact ctccaggacg acgccgtcgg gtccggcggc gagacaggcg gccaggcggt  64320
accggtcgtc ccggacggcg gcgacgacgg gcggacgcgg tttcgccccg gccagagcgg  64380
cccgcagcgc cagcagtgtc ttcaccacct ccgcgtcggc gtgcggctcg tccggaggca  64440
gaaccagcac gacaccggcc gtggccgggc tggtcaacgg caacacggcc gggtcggtgg  64500
tggggccgct gcggcagatc aaccgcgtac cgccgcagga gcccaccttc gtgcccaggg  64560
actcctccat gacggtcttg tcccggtcgg ccagcaccac caccgccgcg ccgcgctggt  64620
tgacgttggc ggccaccagc tcgctcacca ccgtgaagac ctgttccgac catccgagga  64680
ccacggcgtg cccctgttcc agcacggtgg aacggccccg ccgcaacgag gtgagccgct  64740
ccgtgagcgc cgtcgtgatc aggccgacga gcgtggagac gtagagcagg gtgaccagcg  64800
cgagcagcac cgacaacatc gcccgcagcg gcgtacccgt ggcaccgccc agccgtagcg  64860
tctccccggt gagacgccac acctccgcca gccgctccgc gagggacggc ggggcatccg  64920
ggtcggtcca caccatcacc gcgctggccg gcacgacgac ggccagggac agcagcgcca  64980
tccagccgac gagcgcggcg gcaccgcggg ccagggtgct gtcgaaccag taacgggccc  65040
tgtcaccgaa cggagtccgc cgctgcgcca cccgtccccc ttccgtctcc ccgtactccc  65100
accaggccgc gtcggcaccg cagcggcgcc gtgccgcgcg ggcctgcccc ggagcgcgga  65160
cgtgggcacg catgtcgcag tgtgggggat cgatcagggc cgcagacgac gttcgaccag  65220
ccttcatccc ttcgggtagc cgcgtcctcc acggcggcgg acctgcgaag acgcccggct  65280
cggacacgca gatgaaagcc gccgggcctc attcgcggaa cgccgggtat ccgcgagacc  65340
ggatcaccgt cacacacagc gaggagagac cctgtgccgt ccaccgatgt cgtcgaactc  65400
atcctgcggg accaccgccg tatggaggaa ctgttccgca ccctgcgcaa cgtcgaagcg  65460
gaccgtgccg cggccctgac ggagttcgcg gacctgctca tcgcgcacgc ctcggccgag  65520
gaggacgagg tctaccccgc cctgcgtcgg tacaagaacg tcgagggtga ggatgtcgac  65580
cacagcgtcc acgagcacca cgaggccaac gaggcgctgc tggccctgct cgaggtggag  65640
gacaccgctt ccgacgagtg ggatgacaag ctcgaagagc tggtcacggc ggtcaaccac  65700
cacgccgacg aggaggaacg aacactcctc aacgacgccc gggagaacgt cgccgacgac  65760
```

-continued cgccgccggg aactggggca gaagttccag gaggcgcgtt cgcggtatct ggagaccggc 65820
tgcggcagtg tcgagaacgt gcgcaagctg gtcgccgccg ccgacgactg acccgcgtcg 65880
gcgacgtccg ggcgcggagg ggagccgccg ccgtcgggcc ccctcgccgg gcgtaccgcg 65940
gtcaggcggg tgagggctgc gtccggtccg ggacgggttc gaggcggacg acgatgccct 66000
tggacgtggg ctgattgctg atgtccgcga cgctgtccag cggtaccagg acgttggtct 66060
cgggatagta ggcggcggcc gagcccttgg ccgccgggta gggaacgacc tggaagttct 66120
cggcccggcg ctcggtgccg tccgcccaga cgctcacgag gtcgacgcga tcgccctggg 66180
cgaggccgag ttcgctcagg tcggccgggt tgacgaggac gacgtggcgg ctgccgtgga 66240
tgccgcggta gcgatcgttg tcggtgtagg ggacggtgtt ccactggtcg tgcgaacgca 66300
gtgtctgcag cagcagatga ccttcgggcg cccgtgggac cacgctctcg ttgcgagtga 66360
acagggcctt gccgacctcg gtgttgaaga cgccttcgtt gaccgggttg ggcagttgga 66420
agccaccggg ccgggtcacg cgtgcgttga agtcgtggaa gccgggcacg atgcgcgcga 66480
tgcggtcgcg gatggtgtgg tagtcgcctt cgaaggtctc ccaggggatc tccaccctgc 66540
cgtccagggt gagccgggcg agccggcaca ggatcgcgat ctcgctcagc agcatggggg 66600
aggcgggggc caggcggccc cgggaggtgt gcacctcgct catggagttc tcgacggtga 66660
cgaactgctc gccgtcggcc tggacgtcgc gctcggtgcg tcccagcgtc ggcaggatca 66720
acgcggtgtc accgcagacg gtgtgcgagc ggttgagctt ggtcgagatg tgggcggtca 66780
gccggcacga gcgcatcgcc tcctcggtga cctcgctgtc gggcgccgcc cggacgaagt 66840
tcccggccag ggcgaggaag accttgacgc ggccctcgcg cattgccttg atcgagttca 66900
ccgagtccag gccgtgggcc cgcggcggct cgaagccgaa ctcgtcccgc agggcgtcca 66960
ggaaggtgtc cggcatctgc tcccagatgc ccatggtgcg gtcgccctgg acgttgctgt 67020
ggccgcgcac cgggcaggcg ccggtgccgg cgcgtcccag gttgccgcgg agcatcagga 67080
agttgacgat ctcccggacg gtgggcacgc cgtgcttgtg ctgggtgatg cccatcgccc 67140
agcagacgac gacgcgttcg ctgtcgagga cctcgtcgcg taccttctcg atctcctcgc 67200
gggtcagtcc ggtcgccgcg cgcacgtcgt cccagtccac cgtgcgggcg tgccgggcga 67260
actcctcgaa gccggtggtg tgggcgtcga tgaagtcgtg gtccaggacg gtgccgggcc 67320
gggcgtcctc ggcctccagc agcagtcggt tgagggcctg gaagagggcg aggtcgccac 67380
cgggcttgat gtgcaggaaa cggtcggcga tccgggtgcc gcgcccgacg accccgcgcg 67440
gctgctgcgg gttcttgaag cgtcgcagcc cggcctcggg aagcgggttc acggccacga 67500
tccgggcgcc gttccgcttg gcctcctcca gcgcgctgag ctggcgcggg tggttgctgc 67560
cggggttctg cccgaccagg aagatcagat cggcgtggtg gaggtcgtcg agaccgacgg 67620
tgcccttgcc ggtccccagg gtctcgctca gggcgaagcc gctggactcg tggcacatgt 67680
tgctgcagtc gggcaggttg ttggtgccga aggcgcgggc gaagagctgc agcacgaagg 67740
cggcctcgtt gctggcgcgg cccgaggtgt agaacaccgc ctcgtcgggg gaggccagcg 67800
acttgagctc ctccgcgagg acccccaggg cgtcgttcca gccgatgggc tcgtagtgcg 67860
cggagccggg ccgtttgatc atcggctcgg tgagccggcc ctgctggttg agccacatgt 67920
cggagcggcc ggcgaggtcg gcgacgctgt gctcgcggaa gaagtcggcg gtcacccgcc 67980
gtgtggtcgc ctcgtcgttg atgtgcttgg cgccgttctc gcagtactcg ttgcggtggc 68040
gccgtcccgg ggccgggtcc gcccacgcgc agccggggca gtcgatgccg cccacctggt 68100

-continued

```
tcatggtcag cagatccacc ccggtcctgc gcggggacgt ctgctccaag gagtactcca  68160
gcgcgtgcac gaccgcgggg acgccggcgg cccacttctt cggcggtgtc acggagaggc  68220
tggtctccga ctcctcaccg tgcggcttct gcatgtgttc gcctttctct cgccgtgtcc  68280
ggccctcggt cagccgacgg gccaccgggc caccctgctc ctgggcggtt ccggtcgatc  68340
gtgttgcacg cggccgttgc ggatggtgcc gcgccaggcg ccgccctctt gtcccagtcc  68400
ctccatgaac cgtttgaatc tcgtcagctc gccgtggacc agtcgggtgg tcagccggac  68460
cgcccgcgag gaacgggtga ggatcctcgc ggctccccgc ggttccagaa gcacccggac  68520
ggtgatcgcg gtgccgccgg actccgtcgg cctgaactcg acctctcccc ggtgccacgg  68580
cctctgctcc aggccgcgcc aggccaggta ggcgtcgggg tcctgctcca ggatctcgac  68640
cgcgaagcgg cggcgcaggg ggccgtaacc gagggtccag gcggtcacgg tgggccggac  68700
ctgctcgacg tcgcggacca cggccgagaa ccgagggaag gacttgaact gcgtccactg  68760
gttgtacgcc gtccgtacgg gcaccgccac ctcgaccgtc tggtcgacgt gccgctcgcg  68820
cagcggacga cggcccgtgc tcctgtcacc gctggtgcgc gcccccggtg tgtccggcac  68880
ggcccgcggg ccctcgtgct gctccgccat cgtggtctct cctcctgtgg ggggaaccag  68940
gcgtccaggc tctcgacgtc tcctcgtgcg tcagggtccc ctcgtgcgtc agggttttcc  69000
cctcccggtt cccacctccg gcgtttcgag tcacctcggt cccgccgcgt cctcgtgcgc  69060
gtcggcctcc gacgccccgc ccggagagat ccggctcgac gtcggcctgg tcgctccggc  69120
gggcggtgag cagcaggtac tcccagtcga tggccccgtc ccgcagcgcg ccggccgcga  69180
ggtcggtgag ggccgcgtcc agggcggcgg cgcgctcggt gtcgtcgccg atgtaccggt  69240
agacggcgat gatcggcccg taggcggcct tgaagaactc aaggaagtcc ccccttcgag  69300
cggcgctcgg gaccgggggt gcgccggccg gcctgatgac cagcgtcgac ggggtcgtga  69360
gagcgtgatc gaggtgctcg acgagccgga gccaccgcag gagagtcgcg ggcagcgctc  69420
tctccagcaa cccagccttc gcacacccgt gcgcggcgca aggggcgtac gtcccctgcg  69480
caaaggggcg gctggaggcc ggtgccccac gcctcgtctc cgcacggcgc gtcggacggg  69540
gggagaacgc gtccgatgaa cacggtgtgc gccctcccga ttcctctccg tgacgtcaat  69600
gatgagccca ccgcgcctgg gtcaggcgat ccgcggtccc ctgccgctcg gtcaggggcc  69660
ggtgacggaa ggagtccacg gtgttgcttc tcatctctcc ggacggtgtc gaggaagccc  69720
tcgactgcgc gaaggcggcg gagcacctcg acatcgtcga cgtgaagaag cccgacgagg  69780
gctcgctggg cgcgaacttc ccgtgggtca tcagggagat ccgcgacgcg gtgccggcgg  69840
acaagccggt ctcggccacc gtgggggacg tcccgtacaa gcccggcacg gtggcgcagg  69900
ccgcgctggg cgcggtcgtc tcgggggcca cgtacatcaa ggtcggcctc tacggatgca  69960
cgacgcccga acagggcatc gcggtcatgc gcgcggtggt ccgggcggtg aaggaccacc  70020
gtcccgaagc gctcgtcgtc gcgtccggtt acgccgacgc ccaccggatc ggctgcgtca  70080
acccgctcgc cctgcccgac atcgccgccc gctccggcgc cgacgccgcg atgctcgaca  70140
ccgcggtcaa ggacgggacg cggctgttcg atcacgttcc gccggacacc tgcgccgagt  70200
tcgtccgtcg cgcccacgcc gccggcctgc tcgccgccct cgcgggcagc gtcaggcaga  70260
ccgacctcgg ccggctgacc cggatcggca cggacatcgt cggggtgcgc ggagcggtct  70320
gcgagggcgg cgaccgcaac gccggacgca tccggccgca cctggtggcc gccttccgga  70380
gcgagatgga ccggcacgcc cgcgagcacc gggccggcgt caccaccgcg agctgaccgc  70440
cggtatgccg acccccgcac ccgaccacgc ccccgcacag cgggccgcgc ctctcgcggt  70500
```

-continued

```
cgtcgatccg gccaccggaa cggtcttcga cgaggccccc gaccagggac cggacgtgct  70560
ggacgccgtc gtcgaccggg cccgccgggc ctggcacggc tggcgcgccg atcccgacgc  70620
ccgtaccacc gcgctgcgct cggcggccga cgcggtcgag gccgccgggg acgacctcgc  70680
ccgtctcctc acccgggaac agggaaagcc cctggccgaa tcgcatgcgg aggtcgcccg  70740
gacggcggcc cgcctgcgct acttcgccgg cctggccccc cggacccggc gcatcaccga  70800
cgggcggccg gtgcgcagcg aggtccgctg gcgccccctc ggacccgtcg ccgcgatcgt  70860
gccgtggaac ttcccccctcc aactcgcgtc ggcgaagttc gcgcccgcgc tcgccgcggg  70920
caacaccatg gtcctcaaac cctcccccctt caccccgctc gccacccggc tgctcgggtc  70980
cgtcctcgcc accgccctgc ccgaggacgt cctgacggtc gtcaccggcc gcgagccact  71040
cggcgcccgc ctcgccgcac accccggcat ccgccacgtc accttcaccg gatcggtgcc  71100
cacgggccgg gccgtcgccc gagcggcggc ggcctcgctc gcccgggtca ccctggaact  71160
gggcggcaac gacgccgcgg tcctgctgga cgacgtcgaa gtggaccgga tcgccgaccg  71220
gctgttctgg gccgcgttcc gcaactgcgg gcaggtctgc atggcggtca agcgcgtcta  71280
cgcaccggcc cgtctgcacg cacaggtcgt cgaagccctc accgagcgcg ccaaggccgt  71340
cgccgtcggg cccggcctcg acccccgcac ccggctggga ccggtcgcca acgcccccca  71400
gctggcccgg gtcgagcaga tcacccggcg cgccctggcg gacggcgccc gggcggcggc  71460
cggcggccac cggctggacg ggccgggctg cttcttcgcc cccacgatcc tcaccgacgt  71520
cccgcccgac agcccggtgg tgaccgagga gcagttcggg ccggtactgc cggtgctgcc  71580
gtaccggagc ctggacgaag ccgtcgacgc ggccaacggc acgggattcg ggctgggggg  71640
ctccgtatgg ggcaccgacc tcgaccgggc cgaggcggtg gccgaccggc tggaatgcgg  71700
cacggcctgg gtcaaccacc acgccgagct gtccctcgcc cagcccttcg ccggcgacaa  71760
ggacagcggg gtcggcgtcg cgggcgggcc gtggggactg tacggcaacc tccgtccgtt  71820
cgtcgtccac cgaccgcggg gggagtgacg gtgagcttcc gggcggccgt actgcgcggg  71880
tacgaggacc ccttcacggt cgaggaggtg accctgggga cggagcccgg cgcaggggag  71940
atcctggtcg agatcgccgg ctgcggaatg tgccggaccg atctcgcggt ccggcgctcg  72000
gccggccgga gcccgctgcc ggcggtgctc ggccacgagg gctccggggt ggtggtgcgg  72060
acgggcggcg gcccggacac cgcgatcggc gtcggtgacc acgtggtgct gagcttcgac  72120
tcctgcgggc actgccgcaa ctgccgcgcg gcggccccg cctactgtga ttccttcgcc  72180
tccctcaacc tcttcggggg ccgtgcggag gacccgccgc ggctcaccga cgggtcgggg  72240
gcggcactgg ctccccggtg gttcggacag tccgccttcg ccgagtacgc gctcgtctcc  72300
gcccgcaacg ccgttcgggt cgaccccgcc ctgcccgtcg aactgctcgg gccgctgggc  72360
tgcggcttcc tcaccggagc cggagccgtg ctcaacacct tcgccgccgg gccgggcgac  72420
accctcgtcg tgctcggcgc gggcgccgtg ggcctggccg cggtgatggc ggccaccgcc  72480
gccggcgcac cgtccgtggc cgtggaccgc aacccccgtc gcctggagct ggccgagcgg  72540
ttcggcgcgg tcccgctgcc cgccgcgacg gccggactgg ccgagcggat ccggcggctc  72600
acggacggcg gcgcgcggta cgcactggac acgaccgcct ccgtcccact gatcaacgag  72660
gcgctgcgcg cactgcgtcc caccggcgct ctcggcctgg tggcacggct ccacaccgcg  72720
ctgcccctgg aaccgggcac gctcgaccgg gggcgcagca tccgccacgt ctgcgagggg  72780
gacgcggtac ccggtctgct gataccgcag ctgacccggc tctggcaggc cggacgcttc  72840
```

-continued

```
ccccttcgacc agctcgtccg tacctacccg ctggccgaca tcaacgaggc ggagcgcgac  72900

tgcgacgccg gcctcgtggt caaacccgtg ctgctcccgc ccgcgaggag ccggtgagta  72960

cggcgcacgg caccgcggtc cgaccgcatc cgacgagcag gaagctcgcg gccccacttc  73020

cgccaacgga ggagacatga ccggcacggc gccgcagtac acggacgtgg aaggcgtgaa  73080

cggaggtgtg ggcctgacgg ccttcctggt cgccgccgcg cgggcgatcg agacccatcg  73140

cgacgacagt ctggcccagg acgtctacgc ggaacacttc gtgcgcgccg ccccggcgtg  73200

cgcggactgg ccggtgcgca tcgagcaggt ccccgacggg gacggcaacc cgctgtgggg  73260

acggttcgcc cgctatttcg gcctgcggac ccgggccctc gacgacttcc tgctccggtc  73320

ggtccggacg ggcccccgac aggtggtgct gctgggcgcg gggttggaca cccgtgcctt  73380

ccggctcgac tggccgtcgc agtgcgcggt cttcgagatc gaccggacgg gcgtgctcgc  73440

cttcaaacag caggtgctca cggacctggc ggcaaccccg agagtggagc gcgtccccgt  73500

tccggtcgat ctgcgcgcgg actgggccgg cgcgctgacc gcggccggct tcgaccccgc  73560

ggcgcccagc gtctggctgg ccgagggact gctcttctat ctgccgggcc ccgccgagtc  73620

gcttctcgtc gacacggtgg accggctgac caccgacggc agcgcgctgg ccttcgaggc  73680

caagctggag aaggacctgc tggcgtaccg cgacagtgcg atctacacgg cgacgcgcga  73740

gcagatcggc atcgacctcc tccgcctctt cgacaagggg ccccgacccg actccgcggg  73800

tgagctggcg gccagaggct ggtccacctc gatgcacacg cccttcgtct tcacccaccg  73860

gtacggacgc ggtcccctcc ccgagccgaa cgacgcgctg gaggggaacc gatgggtctt  73920

cgcccgcaag cccgggccct gacgtgccgg ccgcgcttgc cgcccacgcc cggggacgcc  73980

gctgacgagc ggtgtcagac ggtccgggcg gccaccagcc ggtcgcccgg gatcccggcc  74040

aggtccggcg cgtagtagtc ctcgatgccg gaggcccacg cggccacggt gatgcggtcc  74100

gcggcgtccg gggcgaaggc gtcgaacagc gcgtggatgt tcgcttcctc gaaaccgatc  74160

gccttcatca gcgcgacgaa gaggggacgc tcgatcagcc cgtccccgtc gggatcgccg  74220

agcgcggaca gtgcccgagc gaactcggcg atggtgggac cgaagcgctc gggatcgagt  74280

acgaacggac ggaactcctc cacggtgatc acgccgtcgc cgtcggcgtc cagttcggtg  74340

gccagcgtgg tccagtagcg gcggaacgcg gcccggacgg cggccttggc gctgtcgtcc  74400

gacccggccg ccgccgcaac gacccggtcg gtcatcaggt cgaagtcgtc ggagtcgatg  74460

actccgttgc cgttggcgtc gaagagggag aagaccagct cgacccgctt ggcggcctca  74520

tctcgcatgc acatcacctg tcttctacgg cccggtcttc gcgggcccgg ccccatgaat  74580

gctctgcgtg accgagcggg gcaggacgaa agcctccgag cggtcgcgtc ccagagaacc  74640

accatgaatg tccctgaact gcagatcggg catctgctgg cctggtgcgg gcgggggctg  74700

gcccggtgcg gcaggggagt gctctggtgc ctgggcaagg ccgtcacggg gatcatcctg  74760

ctcgccatct tcgcgtccgc gatgatc                                     74787
```

<210> SEQ ID NO 2
<211> LENGTH: 876
<212> TYPE: PRT
<213> ORGANISM: Streptomyces parvulus Tu4055

<400> SEQUENCE: 2

```
Met Thr Gly Ser Ala Val Ser Ala Pro Phe Leu Gln Pro Pro Glu Pro
  1               5                  10                  15

Val Ser Gly His Ser Glu Arg Lys Ser Asp Pro Val Leu Leu Val Gly
             20                  25                  30
```

-continued

```
Ala Gly Arg Arg Ala Arg Met Ala Asp Ala Val Arg Ala Ala Gly Ala
        35                  40                  45

Gln Ala Gly Ile Asp Pro Ala Val Leu Arg Arg Thr Arg Ala Thr Leu
    50                  55                  60

Ile Thr Ala Gly Ser Ala Gly Ala Ala Gly Arg Leu Ala Ala Ala Leu
65                  70                  75                  80

Arg Leu Thr Gly Ala Thr Ile Ser Leu Asp Thr Arg Glu Thr Pro Thr
                85                  90                  95

Leu Leu Ala Leu His Leu Ala Ala Gln Ala Leu Arg Ala Gly Asp Thr
            100                 105                 110

Ser Tyr Ala Val Val Gly Ala Glu Leu Pro Asp Gly Asn Cys Ala Leu
        115                 120                 125

Ile Leu Ala Arg Gln Ser Ala Ala Thr Ala Glu Gly Ala Val Pro Gln
    130                 135                 140

Ala Ile Val Arg Thr Thr Thr Ala Asp Arg Thr Thr Thr Ala Asp His
145                 150                 155                 160

Ala Pro Ala Pro Asp Asp His Gly Ser Pro Ala Arg Glu Ala Pro His
                165                 170                 175

Ala Thr Arg Thr Leu Ser Pro Gly Ile Thr Gln Ala Pro Ala Glu Gly
            180                 185                 190

Phe Pro Gly Leu Leu Ala Thr Leu His Asp Asp Thr Pro Leu Arg Pro
        195                 200                 205

Thr Ala Val Thr Glu His Gly Ser Asp Ala Thr Thr Val Leu Val Leu
    210                 215                 220

Leu Asp Gln Pro Gln Asp Ala Ala Pro Ala Ala Pro Leu Pro Trp Val
225                 230                 235                 240

Val Ser Ala Pro His Thr Arg Ala Leu Arg Ala Thr Ala Ala Thr Leu
                245                 250                 255

Ala Val His Leu Asp Thr Thr Pro Ala Ala Pro Ala Asp Val Ala His
            260                 265                 270

Thr Leu Leu Thr Ala Arg Pro Asp Arg His Arg Ala Ala Val Val Gly
        275                 280                 285

Ala Asp Arg Ala Thr Leu Thr Asp Gly Leu Arg Ala Leu Ala Thr Gly
    290                 295                 300

Gly Asp Ala Pro His Leu Val His Gly Thr Ala Thr Gly Ser Pro Arg
305                 310                 315                 320

Pro Val Phe Val Phe Pro Gly Gln Gly Ser Gln Trp Pro Gly Met Ala
                325                 330                 335

Ala Glu Leu Leu Glu Thr Ser Glu Pro Phe His Asp Ser Val His Ala
            340                 345                 350

Cys Ala Asp Ala Leu Ala Glu Phe Val Asp Trp Ser Val Leu Asp Val
        355                 360                 365

Leu Arg Gln Ala Pro Asp Ala Pro Pro Leu Arg Arg Val Asp Val Leu
    370                 375                 380

Gln Pro Thr Leu Trp Ala Thr Met Val Ser Leu Ala Glu Val Trp Arg
385                 390                 395                 400

Ser Tyr Gly Val Glu Pro Ala Ala Val Val Gly His Cys Tyr Gly Glu
                405                 410                 415

Ile Ala Ala Ala Gln Val Ala Gly Ala Leu Asp Met Arg Asp Ala Ala
            420                 425                 430

Arg Leu Leu Ala His Arg Ser Arg Ala Trp Leu Arg Leu Val Gly Lys
        435                 440                 445
```

-continued

```
Gly Thr Val Ile Ser Val Ala Thr Ser Gly Gln Asp Ile Thr Arg Arg
    450                 455                 460

Met Ala Ala Trp Pro Asp Ser Val Glu Leu Ala Ala Leu Asn Gly Pro
465                 470                 475                 480

Arg Ser Val Ala Leu Ala Gly Pro Pro Asp Val Leu Asp Gly Ile Val
                485                 490                 495

Asn Asp Leu Thr Asp Gln Gly Ile His Ala Lys Arg Ile Pro Gly Val
            500                 505                 510

Asp Thr Val Gly His Cys Ser Gln Val Glu Val Leu Arg Asp His Leu
        515                 520                 525

Leu Asp Val Leu Arg Pro Val Ser Pro Arg Pro Ala Ala Val Pro Phe
    530                 535                 540

Tyr Ser Thr Val Asp Gly Thr Glu Arg Asp Thr Thr Thr Leu Asp Thr
545                 550                 555                 560

Asp Tyr Trp Tyr Leu Asn Thr Arg Ser Gln Val Arg Phe His Gln Ala
                565                 570                 575

Val Arg Asn Leu Leu Ala Ala Gly His Arg Ser Phe Val Glu Val Ser
            580                 585                 590

Pro His Pro Leu Leu Gly Ala Ser Ile Glu Asp Thr Ala Ala Glu Phe
        595                 600                 605

Gly Leu Asp Asp Val Ala Ala Val Gly Thr Leu Arg Arg Gly Gln Gly
    610                 615                 620

Gly Thr Arg Arg Val Leu Thr Ser Val Ala Glu Ala Tyr Val His Gly
625                 630                 635                 640

Ile Asp Ile Asp Phe Thr Pro Ala Phe Thr Gly Thr Thr Pro Asn Arg
                645                 650                 655

Ile Asp Leu Pro Thr Val Glu Asp His Gly Ile Glu Gly His Gly Asp
            660                 665                 670

Asp Gly Gly Glu Thr Trp Thr Asp Arg Val Arg Thr Leu Pro Asp Glu
        675                 680                 685

Gln Arg Glu Glu Ala Leu Leu Asp Leu Val Cys Arg Thr Val Ala Ala
    690                 695                 700

Val Leu Glu Ala Asp Pro Ala Gly Thr Ala Asp Ala Val Ala Pro Asp
705                 710                 715                 720

Thr Ala Phe Lys Glu Met Gly Leu Gly Ser Leu Ser Ala Val Arg Leu
                725                 730                 735

Arg Asn Gly Leu Arg Glu Ala Thr Gly Ala His Leu Pro Ala Thr Ile
            740                 745                 750

Ala Tyr Asp His Pro Thr Pro Ala Ala Leu Ala Arg His Leu Ala Met
        755                 760                 765

Thr Leu Phe Asp Ala Thr Gly Ala Ala Pro Ala Val Pro Ala Pro Ser
    770                 775                 780

Arg Asp Asp Glu Pro Ile Asp Ala Glu Thr Ala Val Leu Thr Ala Leu
785                 790                 795                 800

Glu Arg Ala Asp Glu Ala Leu Glu Arg Leu Arg Ala Pro His Ala Arg
                805                 810                 815

Thr Pro Arg Gln Glu Thr Gly Arg Arg Ile Asp Glu Leu Leu Arg Ser
            820                 825                 830

Leu Thr Asp Lys Ala Arg Arg Met Arg Gln Ala Asp Ala Val Asp Asp
        835                 840                 845

Val Asp Asp Pro Ala Thr Asp Arg Phe Ala Ala Ala Thr Asp Asp Glu
    850                 855                 860

Met Phe Glu Leu Leu Glu Lys Arg Phe Gly Ile Ser
```

-continued

```
865                 870                 875


<210> SEQ ID NO 3
<211> LENGTH: 1571
<212> TYPE: PRT
<213> ORGANISM: Streptomyces Parvulus Tu4055

<400> SEQUENCE: 3

Met Ala His Glu Asp Lys Leu Arg His Leu Leu Lys Arg Val Ser Ala
  1               5                  10                  15

Glu Leu Asp Asp Thr Gln Arg Arg Val Arg Glu Met Glu Glu Ser Glu
            20                  25                  30

Arg Glu Pro Ile Ala Ile Val Gly Met Ser Cys Arg Leu Pro Gly Gly
        35                  40                  45

Val Asn Ser Pro Gly Glu Phe Trp Ser Leu Leu Glu Ala Gly Thr Asp
     50                  55                  60

Ala Val Ser Glu Phe Pro Arg Asp Arg Gly Trp Asp Val Glu Asn Leu
 65                  70                  75                  80

Tyr Asp Pro Asp Pro Asp Ala Pro Gly Arg Ser Tyr Val Arg Glu Gly
                 85                  90                  95

Gly Phe Leu Asp Gly Ala Gly Gln Phe Asp Ala Ala Phe Phe Gly Ile
            100                 105                 110

Ser Pro Arg Glu Ala Leu Ala Met Asp Pro Gln Gln Arg Leu Leu Leu
        115                 120                 125

Glu Cys Ser Trp Glu Ala Ile Glu Arg Ser Arg Ile Asp Pro Lys Thr
    130                 135                 140

Leu His Gly Ser Arg Thr Gly Val Phe Ala Gly Ser Asn Trp Gln Asp
145                 150                 155                 160

Tyr Asn Thr Leu Leu Leu Asn Ala Glu Glu Arg Ser Gln Ser Tyr Leu
                165                 170                 175

Ala Thr Gly Ala Ser Gly Ser Val Leu Ser Gly Arg Val Ser Tyr Thr
            180                 185                 190

Leu Gly Met Glu Gly Pro Ala Ile Thr Val Asn Thr Ala Cys Ser Ser
        195                 200                 205

Ser Leu Val Ala Val His Leu Ala Ala Arg Ser Leu Arg Ala Gly Glu
    210                 215                 220

Cys Asp Leu Ala Leu Ala Gly Ala Val Thr Val Met Ser Thr Pro Gln
225                 230                 235                 240

Leu Pro Val Ala Phe Ser Arg Gln Arg Gly Leu Ala Pro Asp Gly Arg
                245                 250                 255

Ser Lys Ala Phe Ala Val Ser Ala Asp Gly Met Gly Phe Gly Glu Gly
            260                 265                 270

Val Gly Val Leu Val Leu Glu Arg Leu Ser Val Ala Arg Arg Asn Gly
        275                 280                 285

His Arg Val Leu Ala Val Val Arg Gly Ser Ala Val Asn Gln Asp Gly
    290                 295                 300

Ala Ser Asn Gly Leu Thr Ala Pro Asn Gly Pro Ser Gln Gln Arg Val
305                 310                 315                 320

Ile Arg Ala Ala Leu Ala Ser Ala Gly Leu Gly Pro Ala Asp Val Asp
                325                 330                 335

Val Val Glu Ala His Gly Thr Gly Thr Arg Leu Gly Asp Pro Ile Glu
            340                 345                 350

Ala Gln Ala Leu Leu Ala Thr Tyr Gly Arg Gly Arg Asp Ala Glu Arg
        355                 360                 365
```

-continued

```
Pro Leu Trp Leu Gly Ser Val Lys Ser Asn Ile Gly His Ala Gln Ala
    370                 375                 380

Ala Ala Gly Val Ala Gly Val Ile Lys Met Val Leu Ala Met Glu Lys
385                 390                 395                 400

Gly Arg Leu Pro Arg Thr Leu His Val Asp Glu Pro Ser Gly Glu Val
                405                 410                 415

Asp Trp Asp Ser Gly Ala Val Arg Leu Leu Thr Glu Ala Arg Asp Trp
            420                 425                 430

Pro Ser Glu Glu Gly Arg Leu Arg Arg Ala Gly Val Ser Ser Phe Gly
        435                 440                 445

Ile Ser Gly Thr Asn Ala His Val Ile Ile Glu Glu Ala Pro Glu Glu
    450                 455                 460

Gly Glu Glu Pro Glu Ser Asp Ala Gly Gly Val Val Pro Trp Val Leu
465                 470                 475                 480

Ser Ala Arg Thr Glu Gly Ala Leu Gln Ala Gln Ala Val Gln Leu Ser
                485                 490                 495

Glu Phe Val Gly Glu Ser Ser Pro Val Asp Val Gly Trp Ser Leu Val
            500                 505                 510

Ser Thr Arg Ala Ala Phe Glu His Arg Ala Val Val Val Gly Arg Gly
        515                 520                 525

Arg Asp Glu Leu Val Arg Gly Leu Ser Glu Val Ala Gln Gly Arg Gly
    530                 535                 540

Val Arg Gly Val Ala Ser Ser Ala Ser Gly Gly Leu Ala Phe Val Phe
545                 550                 555                 560

Ala Gly Gln Gly Ser Gln Arg Leu Gly Met Gly Arg Gly Leu Tyr Glu
                565                 570                 575

Arg Phe Pro Val Phe Ala Glu Ala Phe Asp Glu Val Cys Gly Arg Val
            580                 585                 590

Gly Pro Gly Val Arg Glu Val Val Phe Gly Ser Asp Ala Gly Glu Leu
        595                 600                 605

Asp Arg Thr Val Trp Ala Gln Ala Gly Leu Phe Ala Leu Glu Val Ala
    610                 615                 620

Leu Phe Arg Leu Leu Glu Ser Trp Gly Val Arg Pro Gly Cys Leu Ile
625                 630                 635                 640

Gly His Ser Val Gly Glu Leu Ser Ala Ala Cys Val Ala Gly Leu Trp
                645                 650                 655

Ser Leu Glu Asp Ala Cys Arg Val Val Ala Ala Arg Ala Arg Leu Met
            660                 665                 670

Gln Ala Leu Pro Ala Gly Gly Val Met Val Ala Val Arg Ala Glu Ala
        675                 680                 685

Gly Glu Leu Ala Gly Phe Leu Gly Glu Asp Val Val Ile Ala Ser Val
    690                 695                 700

Asn Ala Pro Gly Gln Val Val Ile Ala Gly Pro Glu Gly Gly Val Glu
705                 710                 715                 720

Arg Val Val Ala Ala Cys Gly Ala Arg Ser Arg Arg Leu Ala Val Ser
                725                 730                 735

His Ala Phe His Ser Pro Leu Val Glu Pro Met Leu Gly Glu Phe Arg
            740                 745                 750

Arg Val Val Glu Ser Val Ala Phe Gly Val Pro Ser Leu Arg Val Val
        755                 760                 765

Ser Asn Val Thr Gly Ala Trp Val Asp Pro Glu Glu Trp Gly Thr Pro
    770                 775                 780

Glu Tyr Trp Val Arg Gln Val Arg Glu Pro Val Arg Phe Ala Asp Gly
```

-continued

```
785                 790                 795                 800

Val Ala Thr Leu Leu Asp Ala Gly Val Arg Thr Phe Val Glu Leu Gly
                805                 810                 815

Pro Ala Gly Ala Leu Thr Ser Met Val Ser His Cys Ala Asp Ala Thr
            820                 825                 830

Ala Thr Ser Val Thr Ala Val Pro Thr Leu Arg Pro Asp His Asp Glu
        835                 840                 845

Ser Arg Thr Val Leu Ser Ala Ala Ala Ser Leu Tyr Val Gln Gly His
    850                 855                 860

Pro Val Asp Trp Ala Pro Leu Phe Pro Arg Ala Arg Thr Val Asp Leu
865                 870                 875                 880

Pro Thr Tyr Pro Phe Gln His Gln His Tyr Trp Leu Asp Val Pro Pro
                885                 890                 895

Leu Phe Thr Ala Ser Ser Ala Ala Gln Asp Gly Gly Trp Arg Tyr Arg
            900                 905                 910

Ile His Trp Arg Arg Leu Gly Thr Arg Asp Ser Gly Asp Arg Leu Ser
        915                 920                 925

Gly Arg Trp Leu Leu Leu Val Pro Glu Ser Asp Gly Thr Glu Pro Trp
    930                 935                 940

Val Glu Gly Ala Glu Lys Met Leu Ala Glu Arg Gly Cys Glu Val Val
945                 950                 955                 960

His Val Pro Ile Ala Ala Thr Ala Asp Arg Asp Ala Met Val Gly Ala
                965                 970                 975

Val Arg Glu Ser Val Glu Asp Gly Arg Val Asp Gly Val Leu Ser Leu
            980                 985                 990

Leu Ala Leu Asp Gly Arg Pro His Pro Asp Ala Ala Ala Val Pro Thr
        995                 1000                1005

Gly Leu Val Ala Thr Ala Gln Val Val Gln Val Ser Asp Glu Leu Gly
   1010                1015                1020

Ile Gly Pro Leu Trp Val Ala Thr Arg Gln Ala Val Ser Val Asp Gly
1025               1030                1035                1040

Ala Asp Glu Ala Asp Gly Ala Gly Arg Thr Arg Lys Ala Asp Asp Pro
               1045                1050                1055

Ala Asp Val Ala Gln Ala Ala Val Trp Gly Leu Gly Arg Val Ala Ala
           1060                1065                1070

Leu Glu Lys Pro Arg Leu Trp Gly Gly Leu Val Asp Leu Pro Ala Arg
       1075                1080                1085

Ala Asp Glu Arg Met Arg Asp Leu Val Ala Gln Ala Leu Thr Ala Pro
   1090                1095                1100

Asp Ala Glu Asp Gln Leu Ala Val Arg Ala Asp Gly Ile Ala Val Arg
1105               1110                1115                1120

Arg Leu Val Arg Ser Ala Ala Ser Ala Pro Ala Asp Asp Trp Gln Pro
               1125                1130                1135

Ser Gly Thr Val Leu Val Thr Gly Gly Thr Gly Gly Val Gly Ala Asn
           1140                1145                1150

Val Ala Arg Trp Leu Val Thr Gln Asp Ile Gln His Leu Leu Leu Val
       1155                1160                1165

Ser Arg Arg Gly Pro Asp Ala Pro Gly Ala Ala Glu Leu Leu Ala Glu
   1170                1175                1180

Leu Ser Ala Ser Gly Thr Ser Val Thr Ile Glu Pro Cys Asp Val Thr
1185               1190                1195                1200

Asp Ala Asp Ala Val Arg Arg Leu Ile Gly Ala Val Pro Ala Glu Arg
               1205                1210                1215
```

-continued

Pro Leu Ser Thr Val Val His Ala Ala Gly Val Leu Asp Asp Cys Leu
1220 1225 1230

Ile Asp Ala Leu Thr Pro Gln Arg Leu Ala Ala Ala Leu Glu Val Lys
1235 1240 1245

Ala Lys Gly Ala Leu Asn Leu His Glu Ala Ala Gly Glu Ala His Leu
1250 1255 1260

Val Leu Phe Ser Ser Leu Ala Gly Thr Thr Gly Thr Lys Gly Gln Gly
1265 1270 1275 1280

Asn Tyr Ala Ala Ala Asn Ala Tyr Leu Asp Ala Leu Ala Glu Arg Arg
1285 1290 1295

Arg Ala Asp Gly Leu Pro Ala Thr Ser Val Ala Trp Gly Ala Trp Gln
1300 1305 1310

Gly Ala Gly Met Val Ala Asp Ala Ala Val Ala His Arg Thr Arg Arg
1315 1320 1325

Tyr Gly Leu Pro Leu Met Ser Pro Asp Arg Ala Val Ala Thr Leu Arg
1330 1335 1340

Gln Val Met Ala Glu Pro Val Ala Thr Gln Val Val Ala Asp Val Asp
1345 1350 1355 1360

Trp Gln Arg Phe Val Ala Asp Phe Thr Ala Val Arg Pro Ser Arg Leu
1365 1370 1375

Leu Ala Asp Leu Pro Glu Val Arg Ser Leu Gly Glu Gln Arg Lys Asp
1380 1385 1390

Gly Pro Gly Gly Gln Gly Glu Glu Asp Gly Leu Ala Ser Lys Leu Ala
1395 1400 1405

Ala Leu Pro Glu Ala Asp Arg Arg Arg Ala Val Leu Asp Leu Val Glu
1410 1415 1420

Glu Leu Val Leu Gly Val Leu Gly His Glu Thr Arg Ala Ala Ile Gly
1425 1430 1435 1440

Pro Asp Ser Ser Phe His Ala Ile Gly Phe Asp Ser Leu Thr Ala Val
1445 1450 1455

Glu Leu Arg Asn Leu Leu Thr Val Arg Leu Gly Met Lys Leu Pro Ala
1460 1465 1470

Thr Leu Val Tyr Asp His Pro Thr Leu Ser Ser Leu Ala Asp His Leu
1475 1480 1485

His Glu Gln Leu Val Ile Asp Gly Thr Pro Met Thr Asp Thr Ala Ala
1490 1495 1500

Asp Leu Leu Ala Glu Leu Asp Ala Leu Ala Ala Arg Leu Ala Ala Val
1505 1510 1515 1520

Gly Leu Glu Pro Glu Ala Arg Ala Arg Ile Gly Arg Arg Leu Lys Asp
1525 1530 1535

Met Gln Thr Ala Cys Glu Pro Arg Ser Glu Ser Ser Arg Asp Leu Lys
1540 1545 1550

Ser Ala Ser Arg Thr Glu Val Leu Asp Phe Leu Thr Asn Glu Leu Gly
1555 1560 1565

Ile Ser Arg
1570

<210> SEQ ID NO 4
<211> LENGTH: 3500
<212> TYPE: PRT
<213> ORGANISM: Streptomyces parvulus Tu4055

<400> SEQUENCE: 4

Met Pro Asn Asp Glu Glu Leu Leu Asp Tyr Leu Lys Arg Thr Ala Ser

-continued

```
1               5                   10                  15

Asn Leu Gln Glu Ala Arg Gln Arg Val His Glu Leu Glu Glu Ser Glu
            20                  25                  30

Arg Glu Pro Ile Ala Ile Val Gly Met Ser Cys Arg Leu Pro Gly Gly
        35                  40                  45

Val Asn Ser Pro Glu Glu Phe Trp Ser Leu Leu Glu Ala Gly Thr Asp
    50                  55                  60

Ala Val Ser Glu Phe Pro Arg Asp Arg Gly Trp Asp Val Glu Arg Leu
 65                  70                  75                  80

Tyr Asp Pro Asp Pro Asp Ala Pro Gly Lys Ser Tyr Val Arg Glu Gly
                85                  90                  95

Gly Phe Leu Asp Gly Ala Gly Arg Phe Asp Pro Ala Phe Phe Gly Ile
            100                 105                 110

Ser Pro Arg Glu Ala Val Val Met Asp Pro Gln Gln Arg Leu Leu Leu
        115                 120                 125

Glu Cys Ser Trp Glu Ala Ile Glu Arg Ser Arg Ile Asp Pro Lys Thr
    130                 135                 140

Leu His Gly Ser Arg Ala Gly Val Phe Val Gly Ser Asn Gly Gln Asp
145                 150                 155                 160

Tyr Gly Thr Leu Leu Leu Arg Ala Asp Asp Arg Ser His Ala Tyr Leu
                165                 170                 175

Ala Thr Gly Ala Ser Ala Ser Val Leu Ser Gly Arg Ile Ser Tyr Thr
            180                 185                 190

Leu Gly Leu Glu Gly Pro Ala Val Thr Ile Ser Thr Ala Cys Ser Ser
        195                 200                 205

Ser Leu Val Ala Leu His Leu Ala Ala Arg Ala Leu Arg Ala Gly Glu
    210                 215                 220

Cys Glu Leu Ala Leu Ala Gly Gly Val Thr Val Met Pro Thr Thr Arg
225                 230                 235                 240

Leu Phe Glu Val Phe Ser Arg Gln Arg Gly Leu Ala Gly Asp Gly Arg
                245                 250                 255

Cys Lys Ala Phe Ala Ala Gly Ala Asp Gly Thr Gly Trp Gly Glu Gly
            260                 265                 270

Val Gly Val Leu Val Leu Glu Arg Leu Ser Val Ala Arg Arg Asn Gly
        275                 280                 285

His Arg Val Leu Ala Val Val Arg Gly Ser Ala Val Asn Gln Asp Gly
    290                 295                 300

Ala Ser Asn Gly Leu Thr Ala Pro Asn Gly Pro Ser Gln Gln Arg Val
305                 310                 315                 320

Ile Arg Ala Ala Leu Ala Ser Ala Arg Leu Ala Pro Glu Asp Val Asp
                325                 330                 335

Ala Val Glu Ala His Gly Thr Gly Thr Ser Leu Gly Asp Pro Ile Glu
            340                 345                 350

Ala Gln Ala Leu Leu Ala Thr Tyr Gly Arg Gly Arg Asp Ala Glu Arg
        355                 360                 365

Pro Leu Trp Leu Gly Ser Val Lys Ser Asn Ile Gly His Ala Gln Ala
    370                 375                 380

Ala Ala Gly Val Ala Gly Val Ile Lys Met Val Lys Ala Met Gln Ala
385                 390                 395                 400

Gly Thr Leu Pro Arg Thr Leu His Val Asp Glu Pro Ser Gly Glu Val
                405                 410                 415

Asp Trp Asp Ser Gly Ala Val Arg Leu Leu Thr Glu Ala Arg Asp Trp
            420                 425                 430
```

-continued

```
Pro Ser Glu Glu Gly Arg Leu Arg Arg Ala Gly Val Ser Ser Phe Gly
        435                 440                 445

Ile Ser Gly Thr Asn Ala His Val Ile Leu Glu Glu Pro Pro Ala Glu
    450                 455                 460

Asp Ala Val Pro Glu Pro Glu Ala Gly Asp Val Val Pro Trp Val Leu
465                 470                 475                 480

Ser Ala Arg Ser Ala Glu Ala Leu Arg Glu Gln Ala Ala Arg Leu Ala
                485                 490                 495

Ser Val Ala Gly Gly Leu Asn Val Val Asp Val Gly Trp Ser Leu Ala
            500                 505                 510

Ser Thr Arg Ala Ala Phe Glu His Arg Ala Val Val Val Gly Arg Glu
        515                 520                 525

Arg Glu Glu Leu Leu Ala Gly Leu Phe Ala Val Ala Ala Gly Arg Pro
    530                 535                 540

Ala Ala Asn Val Val Thr Gly Pro Val Ser Ser Gly Arg Pro Ala Phe
545                 550                 555                 560

Val Phe Ala Gly Gln Gly Ser Gln Arg Leu Gly Met Gly Arg Gly Leu
                565                 570                 575

Tyr Glu Arg Phe Pro Val Phe Ala Glu Ala Phe Asp Glu Val Cys Gly
            580                 585                 590

Arg Val Gly Pro Gly Val Arg Glu Val Val Phe Gly Ser Asp Ala Gly
        595                 600                 605

Glu Leu Asp Arg Thr Val Trp Ala Gln Ala Gly Leu Phe Ala Leu Glu
    610                 615                 620

Val Ala Leu Phe Arg Leu Leu Glu Ser Trp Gly Val Arg Pro Gly Cys
625                 630                 635                 640

Leu Ile Gly His Ser Val Gly Glu Leu Ser Ala Ala Cys Val Ala Gly
                645                 650                 655

Leu Trp Ser Leu Glu Asp Ala Cys Arg Val Val Ala Ala Arg Ala Arg
            660                 665                 670

Leu Met Gln Ala Leu Pro Ala Gly Gly Val Met Val Ala Val Arg Ala
        675                 680                 685

Glu Ala Gly Glu Leu Ala Gly Phe Leu Gly Glu Asp Val Val Ile Ala
    690                 695                 700

Ser Val Asn Ala Pro Gly Gln Val Val Ile Ala Gly Pro Glu Gly Gly
705                 710                 715                 720

Val Glu Arg Val Val Ala Ala Cys Gly Ala Arg Ser Arg Arg Leu Ala
                725                 730                 735

Val Ser His Ala Phe His Ser Pro Leu Val Glu Pro Met Leu Gly Glu
            740                 745                 750

Phe Arg Arg Val Val Glu Ser Val Ala Phe Gly Val Pro Ser Leu Arg
        755                 760                 765

Val Val Ser Asn Val Thr Gly Ala Trp Val Asp Pro Glu Glu Trp Gly
    770                 775                 780

Thr Pro Glu Tyr Trp Val Arg Gln Val Arg Glu Pro Val Arg Phe Ala
785                 790                 795                 800

Asp Gly Val Ala Thr Leu Leu Asp Ala Gly Val Arg Thr Phe Val Glu
                805                 810                 815

Leu Gly Pro Ala Gly Thr Leu Thr Ser Met Val Ser His Cys Ala Asp
            820                 825                 830

Ala Thr Ala Thr Ser Val Thr Ala Val Pro Thr Leu Arg Pro Asp His
        835                 840                 845
```

-continued

```
Asp Glu Ser Arg Thr Val Leu Ser Ala Ala Ala Ser Leu Tyr Val Gln
    850                 855                 860

Gly His Pro Val Asp Trp Ala Pro Leu Phe Pro Arg Ala Arg Thr Val
865                 870                 875                 880

Asp Leu Pro Thr Tyr Pro Phe Gln His Gln His Tyr Trp Met Met Asn
                885                 890                 895

Thr Gly Ser Ala Ala Glu Pro Ala Glu Leu Gly Leu Gly Asp Ala Arg
            900                 905                 910

His Pro Leu Leu Gly Ser Val Val Thr Val Ala Gly Asp Asp Lys Val
        915                 920                 925

Val Phe Ala Gly Arg Leu Ala Leu Arg Thr His Pro Trp Leu Ala Asp
    930                 935                 940

His Thr Val Leu Asp Ala Val Leu Leu Pro Ala Thr Ala Phe Leu Glu
945                 950                 955                 960

Leu Ala Val Arg Ala Gly Glu Glu Val Ser Cys Pro Val Val His Asp
                965                 970                 975

Leu Thr Leu His Arg Pro Leu Val Val Pro Glu Arg Gly Ala Val Gln
            980                 985                 990

Val Gln Met Ala Val Gly Ala Pro Glu Ala Asp Gly Arg Arg Glu Val
        995                 1000                1005

Arg Val Tyr Ser Arg Pro Asp Asp Asp Ala Glu His Glu Trp Thr Leu
   1010                 1015                1020

His Ala Ala Gly Leu Leu Ala Ser Ala Ala Thr Ala Glu Pro Ala Val
1025                1030                1035                1040

Ala Ala Gly Ala Trp Pro Pro Pro Glu Ala Gln Ala Val Asp Leu Asp
               1045                1050                1055

Gly Phe Tyr Ala Gly Leu Ala Glu His Gly Tyr His Tyr Gly Pro Leu
           1060                1065                1070

Phe Gln Gly Val Arg Ala Ala Trp Arg Leu Gly Asp Asp Val Leu Ala
       1075                1080                1085

Glu Ile Val Leu Pro Glu Ala Ala Gly Ala Asp Ala Ala Arg Tyr Gly
   1090                1095                1100

Met His Pro Ala Leu Leu Asp Ala Val Leu His Ala Ala Arg Leu Gly
1105                1110                1115                1120

Ala Phe Arg Glu Arg Ser Glu Glu Lys Tyr Leu Pro Phe Ala Trp Glu
               1125                1130                1135

Gly Val Thr Leu Arg Thr Arg Gly Ala Thr Ala Val Arg Ala Arg Ile
           1140                1145                1150

Ser Arg Ala Gly Thr Asp Ala Ile Arg Leu Asp Val Thr Asp Thr Ala
       1155                1160                1165

Asp Arg Pro Val Leu Thr Ala Glu Ser Leu Thr Leu Arg Pro Val Ser
   1170                1175                1180

Ala Gly Gln Leu Met Ala Val Pro Arg Asp Ser Leu Phe Arg Val Asp
1185                1190                1195                1200

Trp Val Ser Ala Pro Ala Ala Asn Gly Pro Gly Leu Arg Leu Ala Arg
               1205                1210                1215

Ala Ala Thr Val Glu Ala Ala Leu Ala Ala Asp Ala Asp Ile Val Val
           1220                1225                1230

Val Pro Cys Leu Asp Ser Glu Gly Pro His Gln Ala Thr Tyr Gln Ala
       1235                1240                1245

Leu Glu Leu Leu Gln Arg Trp Leu Ala Ala Asp Thr Gly Thr Thr Thr
   1250                1255                1260

Leu Ala Leu Leu Thr His Arg Ala Val Ala Val Gly Asp Asp Val His
```

-continued 1265 1270 1275 1280

Asp Leu His His Ala Pro Leu Trp Gly Leu Val Arg Thr Ala Gln Thr
1285 1290 1295

Glu His Pro Gly Cys Phe Arg Leu Val Asp Ser Asp Asp Pro Asp Pro
1300 1305 1310

Thr Thr Asp Val Leu Ala Ala Ala Leu Ala Thr Gly Glu Pro Gln Val
1315 1320 1325

Ala Ile Arg Asp Gly Ala Val Leu Ala Pro Arg Leu Thr Ala Ala Ser
1330 1335 1340

Ala Pro Arg Glu Pro Ala Glu Trp Asp Ala Glu Gly Thr Val Leu Ile
1345 1350 1355 1360

Thr Gly Gly Ser Gly Ala Leu Ala Gly Ile Val Ala Gln His Leu Val
1365 1370 1375

Ala Arg His Gly Val Arg Arg Leu Val Leu Ala Ser Arg Ser Gly Arg
1380 1385 1390

Pro Ala Pro Gly Ala Asp Leu Leu Asp Ala Asp Val Thr Ala Val Ser
1395 1400 1405

Cys Asp Val Ser Asp Arg Asp Ala Val Ala Ala Leu Leu Ala Ser Val
1410 1415 1420

Pro Asp Glu His Pro Leu Thr Ala Val Val His Thr Ala Gly Val Leu
1425 1430 1435 1440

Asp Asp Gly Val Leu His Ala Leu Thr Thr Glu Arg Ile Asp Thr Ser
1445 1450 1455

Phe Ala Ala Lys Val Asp Gly Ala Arg His Leu His Glu Leu Thr Ser
1460 1465 1470

His Leu Asp Leu Thr Ala Phe Val Leu Phe Ser Ser Ala Ser Ala Val
1475 1480 1485

Leu Gly Ala Ala Gly Gln Gly Asn Tyr Ala Ala Ala Asn Ala Tyr Leu
1490 1495 1500

Asp Ala Leu Ala Ala His Arg Arg Ser Asn Asp Leu Pro Ala Val Ser
1505 1510 1515 1520

Leu Ala Trp Gly Leu Trp Ala Glu His Glu Gly Met Ala Arg Gly Leu
1525 1530 1535

Gly Asp Ala Glu Leu Thr Arg Ile Ser Arg Ile Gly Val Thr Ala Leu
1540 1545 1550

Ser Ala Glu Asp Gly Met Arg Leu Phe Asp Ala Gly Cys Ala Gly Asp
1555 1560 1565

Gln Ser Gln Leu Val Pro Met Arg Val Asp Thr Ala Ala Leu Arg Ala
1570 1575 1580

Arg Arg Asp His Leu Pro Ala Pro Met Trp Ser Leu Val Pro Glu Arg
1585 1590 1595 1600

Thr Arg Ala Ala Arg Thr Gln Pro Ala Ala Ser Leu Arg Asp Arg Leu
1605 1610 1615

Ala Glu Leu Thr Ala Pro Glu Arg Lys Arg Thr Val Leu Asn Leu Val
1620 1625 1630

Arg Asn Ala Val Ala Asp Thr Leu Gly His Asn Ala Ala Asp Gly Val
1635 1640 1645

Pro Pro Asp Gln Ser Leu Asp Ala Ala Gly Phe Asp Ser Leu Thr Ala
1650 1655 1660

Val Glu Phe Arg Asn Arg Leu Ser Ala Val Thr Asp Leu Arg Leu Pro
1665 1670 1675 1680

Ala Thr Leu Thr Tyr Asp His Pro Thr Pro Ala Ala Ile Ala Glu His
1685 1690 1695

-continued

```
Ile Leu Thr Arg Leu Thr Leu Leu Lys Glu Thr Ala Ala Pro Ala Val
            1700                1705                1710

Gly Thr Ala Pro Val Ala Ala Pro Thr Glu Asp Asp Ala Ile Val Ile
        1715                1720                1725

Val Gly Met Ala Gly Arg Phe Pro Gly Gly Val Arg Thr Pro Glu Gly
    1730                1735                1740

Leu Trp Asp Leu Val His Ser Gly Thr Asp Ala Ile Ser Glu Trp Pro
1745                1750                1755                1760

Thr Asp Arg Gly Trp Asp Val Glu Asn Leu Tyr Asp Pro Asp Pro Asp
                1765                1770                1775

Ala Val Gly Lys Ser Tyr Val Arg His Gly Gly Phe Leu His Asp Val
            1780                1785                1790

Ala Gly Phe Asp Ala Gly Phe Phe Gly Ile Ser Pro Arg Glu Ala Leu
        1795                1800                1805

Ala Met Asp Pro Gln Gln Arg Leu Leu Leu Glu Cys Ser Tyr Glu Ala
    1810                1815                1820

Leu Glu Arg Ala Gly Ile Asp Pro Ala Thr Leu Arg Gly Ser Arg Ser
1825                1830                1835                1840

Gly Val Tyr Ala Gly Val Met Tyr His Glu Tyr Ala Ser Arg Leu Gly
                1845                1850                1855

Ala Thr Pro Ala Gly Phe Glu Gly Thr Leu Gly Thr Gly Ser Ser Gly
            1860                1865                1870

Ser Ile Ala Ser Gly Arg Ile Ser Tyr Thr Phe Asp Leu Thr Gly Pro
        1875                1880                1885

Ala Val Thr Val Asp Thr Ala Cys Ser Thr Ser Leu Val Gly Leu His
    1890                1895                1900

Leu Ala Val Gln Ala Leu Arg Ala Gly Glu Cys Glu Leu Ala Leu Ala
1905                1910                1915                1920

Gly Gly Val Thr Val Met His Thr Pro Arg Pro Phe Val Glu Phe Ser
                1925                1930                1935

Arg Gln Arg Gly Leu Ala Ala Asp Gly Arg Ser Lys Ala Phe Ala Ala
            1940                1945                1950

Ser Ala Asp Gly Val Ala Trp Ala Glu Gly Ala Gly Ile Leu Val Leu
        1955                1960                1965

Glu Arg Leu Ser Ala Ala Arg Arg Asn Gly His Arg Val Leu Ala Val
    1970                1975                1980

Val Arg Gly Ser Ala Val Asn Gln Asp Gly Ala Ser Asn Gly Leu Thr
1985                1990                1995                2000

Ala Pro Asn Gly Pro Ser Gln Gln Arg Val Ile Arg Ala Ala Leu Ala
                2005                2010                2015

Ser Ala Gly Leu Gly Pro Ala Asp Val Asp Val Val Glu Ala His Gly
            2020                2025                2030

Thr Gly Thr Ala Leu Gly Asp Pro Ile Glu Ala Gln Ala Leu Leu Ala
        2035                2040                2045

Thr Tyr Gly Arg Gly Arg Asp Ala Asp Arg Pro Leu Trp Leu Gly Ser
    2050                2055                2060

Val Lys Ser Asn Ile Gly His Thr Gln Ala Ala Ala Gly Val Ala Ser
2065                2070                2075                2080

Val Ile Lys Met Val Gln Ala Met Gln Ala Gly Val Leu Pro Arg Thr
                2085                2090                2095

Leu His Val Asp Glu Pro Ser Gly Glu Val Asp Trp Asp Ser Gly Ala
            2100                2105                2110
```

-continued

```
Val Arg Leu Leu Thr Glu Ala Arg Glu Trp Pro Ser Gly Glu Gly Arg
       2115                2120                2125

Val Arg Arg Ala Gly Val Ser Ser Phe Gly Ile Ser Gly Thr Asn Ala
   2130                2135                2140

His Val Ile Leu Glu Glu Pro Pro Ala Glu Asp Ala Leu Pro Glu Pro
2145                2150                2155                2160

Glu Ala Gly Asp Val Val Pro Trp Val Leu Ser Ala Arg Ser Ala Glu
               2165                2170                2175

Ala Leu Arg Glu Gln Ala Ala Arg Leu Ala Ser Val Ala Gly Gly Leu
           2180                2185                2190

Asn Val Val Asp Val Gly Trp Ser Leu Ala Ser Thr Arg Ala Ala Phe
       2195                2200                2205

Glu His Arg Ala Val Val Val Gly Gly Asp Arg Glu Glu Leu Leu Gly
   2210                2215                2220

Lys Leu Ser Ser Val Ser Gly Val Glu Val Gly Val Gly Val Gly Ala
2225                2230                2235                2240

Gly Gly Gly Val Val Leu Val Phe Ala Gly Gln Gly Cys Gln Trp Val
               2245                2250                2255

Gly Met Gly Arg Glu Leu Leu Gly Ser Ser Leu Val Phe Ala Glu Ser
           2260                2265                2270

Met Arg Glu Cys Ala Ala Ala Leu Ser Pro Phe Val Asp Phe Ser Val
       2275                2280                2285

Val Asp Val Leu Gly Ser Ala Gly Glu Leu Gly Arg Val Glu Val Val
   2290                2295                2300

Gln Pro Ala Leu Trp Ala Val Met Val Ser Leu Ala Arg Val Trp Arg
2305                2310                2315                2320

Ser Trp Gly Val Pro Val Ala Ala Val Val Gly His Ser Gln Gly Glu
               2325                2330                2335

Ile Ala Ala Ala Thr Val Ala Gly Ala Leu Ser Val Gly Asp Ala Ala
           2340                2345                2350

Arg Val Val Ala Leu Arg Ser Arg Leu Ile Ala Glu Arg Leu Ser Gly
       2355                2360                2365

Leu Gly Gly Met Val Ser Val Ala Leu Ser Arg Glu Arg Val Val Ser
   2370                2375                2380

Leu Ile Ala Gly Val Pro Gly Val Ser Val Ala Ala Val Asn Gly Ser
2385                2390                2395                2400

Ser Ser Thr Val Val Ser Gly Glu Ala Ala Gly Leu Glu Arg Val Leu
               2405                2410                2415

Ala Ala Cys Val Ser Ser Gly Val Arg Ala Arg Arg Ile Asp Val Asp
           2420                2425                2430

Tyr Ala Ser His Ser Val Gln Val Glu Leu Ile Arg Glu Glu Leu Leu
       2435                2440                2445

Gly Val Leu Asp Gly Ile Val Pro Arg Ser Gly Glu Ile Pro Phe Val
   2450                2455                2460

Ser Thr Val Thr Gly Glu Arg Ile Asp Thr Val Glu Leu Gly Ala Glu
2465                2470                2475                2480

Tyr Trp Tyr Arg Asn Leu Arg Gln Thr Val Glu Phe Gln Ser Val Val
               2485                2490                2495

Glu Gly Leu Val Ala Gln Gly Cys Arg Val Phe Leu Glu Ser Ser Pro
           2500                2505                2510

His Pro Val Leu Thr Val Gly Ile Glu Glu Ser Ala Asp Arg Val Val
       2515                2520                2525

Ala Leu Glu Ser Leu Arg Arg Gly Glu Gly Gly Leu Arg Arg Leu Val
```

-continued

```
    2530                2535                2540

Asp Ala Ala Gly Glu Ala Trp Val Arg Gly Val Pro Ile Asp Trp Ala
2545                2550                2555                2560

Gly Met Leu Ala Gly Gly Arg Arg Val Asp Leu Pro Thr Tyr Pro Phe
                2565                2570                2575

Gln His Gln Pro Tyr Trp Leu Asp Ser Pro Arg His Pro Ala Gly Asp
            2580                2585                2590

Val Thr Ala Val Gly Leu Thr Glu Ala Gly His Ala Phe Val Pro Ala
        2595                2600                2605

Ala Val Asp Leu Pro Asp Gly Gln Arg Val Trp Thr Gly Arg Leu Ser
    2610                2615                2620

Leu Pro Ser Tyr Pro Trp Leu Ala Asp His Gln Val Leu Gly Gln Val
2625                2630                2635                2640

Leu Leu Pro Gly Val Val Trp Val Glu Leu Ala Leu His Ala Gly His
                2645                2650                2655

Gln Ala Gly Cys Asp Ser Val Asp Glu Leu Thr Leu Gln Ser Pro Leu
            2660                2665                2670

Val Leu Gly Ala Ser Asp Thr Val Gln Val Arg Val Val Val Thr Glu
        2675                2680                2685

Thr Glu Glu Pro Gly Thr Arg Thr Val Ser Met His Ser Arg Arg Asp
    2690                2695                2700

Asp Gly Ser Trp Val Thr His Ala Glu Gly Ile Leu Gly Ala Gly Gly
2705                2710                2715                2720

Pro Pro Pro Glu Pro Leu Pro Glu Trp Pro Pro Thr Gly Ala Met Pro
                2725                2730                2735

Leu Asp Val Glu Gly Phe Tyr Asp Glu Leu Ala Ala Gly Gly Tyr His
            2740                2745                2750

Tyr Gly Pro Gln Phe Arg Cys Leu Arg Arg Ala Trp Arg Ala Gly Glu
        2755                2760                2765

Asp Leu Val Ala Glu Ile Ser Leu Pro Glu Gly Thr Asp Val Asp Ala
    2770                2775                2780

Tyr Gly Leu His Pro Gly Leu Phe Asp Ala Ala Val His Ser Val Ala
2785                2790                2795                2800

Cys Ala Arg Thr Ser Ala Gly Ala Gly Asp Asp Gly Pro Arg Leu Pro
                2805                2810                2815

Phe Ala Phe Ser Asp Val Arg Leu Phe Ala Thr Gly Val Thr Ser Leu
            2820                2825                2830

Arg Val Arg Ile Asp Pro Gln Asn Ser Ser Trp Gln Ala Trp Asp Glu
        2835                2840                2845

Ser Gly Leu Pro Val Leu Thr Ile Gly Arg Leu Ala Gly Arg Pro Val
    2850                2855                2860

Asp Ala Asp Gln Phe Ala Val Arg Arg Ala Gly His Leu Phe Arg Val
2865                2870                2875                2880

Glu Thr Arg His Glu Ala Leu Ala Gly Pro Ala Pro Ala Ser Trp Ala
                2885                2890                2895

Val Ile Gly Ala Asp Pro Ala Gly Tyr Ala Ala Ala Leu Glu Ala Thr
            2900                2905                2910

Gly Ala Gln Val Thr Thr Ala Ala Asp Leu Ala Gly Leu Thr Ser Ala
        2915                2920                2925

Pro Glu Ala Ala Leu Phe Thr Leu Pro Gly Thr Lys Asp Ala Gly Val
    2930                2935                2940

Thr Glu Glu Val Pro Thr Ala Val Arg Glu Ala Thr Ala Gln Val Leu
2945                2950                2955                2960
```

-continued

```
Glu Val Leu Gln Asp Trp Leu Thr Asp Gly Arg Phe Asp Asp Ala Arg
                2965                2970                2975

Leu Val Val Val Ser Arg Glu Ala Glu Asp Gly Asp Leu Leu His Gly
            2980                2985                2990

Thr Ala Arg Gly Leu Leu Arg Ala Ala Gln Ala Glu His Pro Asp Arg
        2995                3000                3005

Ile Thr Leu Val Asp Leu Asp Ala His Pro Ala Ser Leu Thr Ala Leu
    3010                3015                3020

Pro Gly Phe Ala Leu Gly Pro Glu Pro Glu Val Val Val Arg Ala Gly
3025                3030                3035                3040

Asp Gly Arg Ala Pro Arg Leu Ala Arg Ala Gln Ala Pro Thr Gly Ala
                3045                3050                3055

Gly Ser Leu Gly Thr Gly Thr Val Leu Ile Thr Gly Gly Thr Gly Thr
            3060                3065                3070

Leu Gly Gly Leu Leu Ala Arg His Leu Val Glu Thr His Gly Val Thr
        3075                3080                3085

Arg Leu Leu Leu Val Ser Arg Arg Gly Pro Ala Ala Asp Gly Ala Asp
    3090                3095                3100

Arg Leu His Ala Glu Leu Thr Gly His Gly Ala His Val Asp Ile Val
3105                3110                3115                3120

Ala Ala Asp Leu Gly Asp Arg Thr Ser Val Ala Ala Leu Leu Ala Thr
                3125                3130                3135

Val Asp Ala Asp His Pro Leu Ser Ala Val Val His Ala Ala Gly Ala
            3140                3145                3150

Leu Asp Asp Gly Val Leu Gly Thr Arg Ser Ala Asp Trp Leu Asp Pro
        3155                3160                3165

Val Leu Arg Pro Lys Ala Asp Ala Ala Trp His Leu His Glu Leu Thr
    3170                3175                3180

Ala Glu Leu Pro Leu Thr Ala Phe Val Met Phe Ser Ser Ala Ala Ser
3185                3190                3195                3200

Val Leu Gly Ala Ala Gly Gln Ala Asn Tyr Ala Ala Ala Asn Gly Phe
                3205                3210                3215

Leu Asp Ala Leu Ala Ala His Arg Ala Ala Arg Gly Leu Pro Gly Thr
            3220                3225                3230

Ser Leu Ala Trp Gly Leu Trp Glu His Arg Ser Glu Leu Thr Arg His
        3235                3240                3245

Thr Gly Ser Pro Ser Arg Ser Ile Ala Ala Val Gly Ala Leu Ser Thr
    3250                3255                3260

Ala Glu Ala Leu Ala Ala Phe Asp Ala Gly Leu Ala Ser Gly Glu Pro
3265                3270                3275                3280

Leu Ala Val Pro Ile Arg Leu Glu Ser Thr Ser Ser Glu Glu Val Pro
                3285                3290                3295

Pro Met Leu Arg Gly Leu Val Arg Val Arg Arg Arg Ala Ala Thr Gly
            3300                3305                3310

Thr Glu Pro Ala Ala Ser Ala Gly Ala Ala Gln Glu Val Arg Gln Leu
        3315                3320                3325

Ala Glu Leu Gly Ala Asp Glu Arg Gln Arg Arg Val Gln Arg Ile Val
    3330                3335                3340

Leu Asp Thr Ala Ala Ala Val Leu Gly His Asp Ser His Asp Ala Ile
3345                3350                3355                3360

Pro Leu Thr Arg Gly Phe Leu Glu Leu Gly Phe Asp Ser Leu Thr Ala
                3365                3370                3375
```

-continued

```
Val Arg Leu Arg Asn Arg Leu Ala Arg Arg Leu Gly Leu Arg Leu Pro
           3380                3385                3390

Ala Thr Val Val Phe Asp His Pro Ser Pro Ala Ala Leu Ala Ala His
       3395                3400                3405

Leu Val Glu His Leu Val Gly Thr Val Asp Pro Thr Ala Gln Ala Met
   3410                3415                3420

Glu Gln Leu Glu Ala Leu Arg Arg Ser Val His Ala Ala Thr Pro Ala
3425                3430                3435                3440

Gly Gly Leu Asp Arg Ala Leu Val Thr Gln Arg Leu Thr Ala Leu Leu
               3445                3450                3455

Asp Glu Met Arg His Val Asp Gly Pro Gly Gly Thr Glu Gly Pro Asp
           3460                3465                3470

Gly Ser Gly Asp Asp Leu Glu Asn Ala Thr Ala Asp Glu Ile Tyr Ala
       3475                3480                3485

Leu Ile Asp Asn Glu Leu Gly Ile Gly Gly Thr Gln
   3490                3495                3500


<210> SEQ ID NO 5
<211> LENGTH: 1620
<212> TYPE: PRT
<213> ORGANISM: Streptomyces parvulus Tu4055

<400> SEQUENCE: 5

Met Asn Gly Asp Asp Lys Ala Leu Ala Tyr Leu Lys Arg Val Thr Ala
  1               5                  10                  15

Asp Leu Arg Ser Ala Arg Ala Arg Leu Gln Glu Leu Glu Ser Ala Asp
             20                  25                  30

Thr Asp Pro Ile Ala Ile Ile Gly Met Gly Cys Arg Leu Pro Gly Gly
         35                  40                  45

Val Arg Thr Pro Glu Asp Leu Trp Asp Leu Val Glu Lys Lys His Asp
     50                  55                  60

Ala Ile Gly Pro Phe Pro Ala Asp Arg Gly Trp Asp Leu Glu Asn Leu
 65                  70                  75                  80

Tyr Asp Pro Asp Pro Asp Ala Pro Gly Lys Ala Tyr Val Arg Glu Gly
                 85                  90                  95

Gly Phe Val His Asp Val Ala Gly Phe Asp Ala Gly Phe Phe Gly Ile
            100                 105                 110

Ser Pro Arg Glu Ala Leu Ala Met Asp Pro Gln His Arg Leu Leu Leu
        115                 120                 125

Glu Cys Ser Trp Glu Ala Leu Glu Arg Ala Gly Ile Asp Pro Ser Ser
    130                 135                 140

Leu Glu Gly Thr Arg Thr Gly Val Tyr Thr Gly Leu Met Thr His Glu
145                 150                 155                 160

Tyr Ala Thr Arg Leu Pro Ser Ile Asp Glu Glu Leu Glu Gly Val Ile
                165                 170                 175

Gly Ile Gly Asn Ala Gly Ser Val Ala Ser Gly Arg Val Ser Tyr Thr
            180                 185                 190

Leu Gly Leu Asn Gly Pro Ala Val Thr Val Asp Thr Ala Cys Ser Ser
        195                 200                 205

Ser Leu Val Ala Leu His Leu Ala Ala Gln Ala Leu Arg Gln Gly Gln
    210                 215                 220

Cys Thr Leu Ala Leu Ala Gly Gly Ala Ser Val Ile Ala Ala Pro Thr
225                 230                 235                 240

Val Phe Ala Thr Phe Ser Arg Gln Arg Gly Leu Ala Pro Asp Gly Arg
                245                 250                 255
```

-continued

```
Cys Lys Ala Phe Ser Ser Thr Thr Asp Gly Thr Gly Phe Gly Glu Gly
            260                 265                 270

Val Gly Val Leu Val Leu Glu Arg Leu Ser Asp Ala Arg Arg Asn Gly
        275                 280                 285

His Glu Val Leu Ala Val Val Arg Gly Ser Ala Val Asn Gln Asp Gly
    290                 295                 300

Ala Ser Ser Gly Phe Thr Ala Pro Asn Gly Pro Ser Gln Gln Asp Val
305                 310                 315                 320

Ile Arg Glu Ala Leu Ala Asp Gly Arg Leu Thr Pro Ala Asp Val Asp
                325                 330                 335

Val Val Glu Gly His Gly Thr Gly Thr Arg Leu Gly Asp Pro Ile Glu
            340                 345                 350

Ala Gln Ala Leu Leu Ala Thr Tyr Gly Arg Gly Arg Asp Ala Asp Arg
        355                 360                 365

Pro Leu Trp Leu Gly Ser Val Lys Ser Asn Ile Gly His Thr Gln Ala
    370                 375                 380

Ala Ala Gly Val Ala Ser Val Ile Lys Met Val Gln Ala Met Gln Ala
385                 390                 395                 400

Gly Val Leu Pro Arg Thr Leu His Val Asp Glu Pro Ser Gly Glu Val
                405                 410                 415

Asp Trp Asp Ser Gly Ala Val Arg Leu Leu Thr Glu Ala Arg Glu Trp
            420                 425                 430

Pro Ser Gly Glu Gly Arg Val Arg Arg Ala Gly Val Ser Ser Phe Gly
        435                 440                 445

Ile Ser Gly Thr Asn Ala His Val Ile Leu Glu Glu Pro Pro Ala Glu
    450                 455                 460

Asp Ala Leu Pro Glu Pro Glu Ala Gly Asp Val Val Pro Trp Val Leu
465                 470                 475                 480

Ser Ala Arg Ser Ala Glu Ala Leu Arg Glu Gln Ala Ala Arg Leu Ala
                485                 490                 495

Ser Val Ala Gly Gly Leu Asn Val Val Asp Val Gly Trp Ser Leu Ala
            500                 505                 510

Ser Thr Arg Ala Ala Phe Glu His Arg Ala Val Val Val Gly Gly Asp
        515                 520                 525

Arg Glu Glu Leu Leu Gly Lys Leu Ser Ser Val Ser Gly Val Glu Val
    530                 535                 540

Gly Val Gly Val Gly Ala Gly Gly Gly Val Val Leu Val Phe Ala Gly
545                 550                 555                 560

Gln Gly Cys Gln Trp Val Gly Met Gly Arg Glu Leu Leu Gly Ser Ser
                565                 570                 575

Leu Val Phe Ala Glu Ser Met Arg Glu Cys Ala Ala Ala Leu Ser Pro
            580                 585                 590

Phe Val Asp Phe Ser Val Val Asp Val Leu Gly Ser Ala Gly Glu Leu
        595                 600                 605

Gly Arg Val Glu Val Val Gln Pro Ala Leu Trp Ala Val Met Val Ser
    610                 615                 620

Leu Ala Arg Val Trp Arg Ser Trp Gly Val Pro Val Ala Ala Val Val
625                 630                 635                 640

Gly His Ser Gln Gly Glu Ile Ala Ala Ala Thr Val Ala Gly Ala Leu
                645                 650                 655

Ser Val Gly Asp Ala Ala Arg Val Val Ala Leu Arg Ser Arg Leu Ile
            660                 665                 670
```

-continued

```
Ala Glu Arg Leu Ser Gly Leu Gly Gly Met Val Ser Val Ala Leu Ser
        675                 680                 685

Arg Glu Arg Val Val Ser Leu Ile Ala Gly Val Pro Gly Val Ser Val
    690                 695                 700

Ala Ala Val Asn Gly Ser Ser Ser Thr Val Val Ser Gly Glu Ala Ala
705                 710                 715                 720

Gly Leu Glu Arg Val Leu Ala Ala Cys Val Ser Ser Gly Val Arg Ala
                725                 730                 735

Arg Arg Ile Asp Val Asp Tyr Ala Ser His Ser Val Gln Val Glu Leu
            740                 745                 750

Ile Arg Glu Glu Leu Leu Gly Val Leu Asp Gly Ile Val Pro Arg Ser
        755                 760                 765

Gly Glu Ile Pro Phe Val Ser Thr Val Thr Gly Glu Arg Ile Asp Thr
    770                 775                 780

Val Glu Leu Gly Ala Glu Tyr Trp Tyr Arg Asn Leu Arg Gln Thr Val
785                 790                 795                 800

Glu Phe Gln Ser Val Val Glu Gly Leu Val Ala Gln Gly Cys Arg Val
                805                 810                 815

Phe Leu Glu Ser Ser Pro His Pro Val Leu Thr Val Gly Ile Glu Glu
            820                 825                 830

Ser Ala Asp Arg Val Val Ala Leu Glu Ser Leu Arg Arg Gly Glu Gly
        835                 840                 845

Gly Leu Arg Arg Leu Val Asp Ala Ala Gly Glu Ala Trp Val Arg Gly
    850                 855                 860

Val Pro Ile Asp Trp Ala Gly Met Leu Ala Gly Gly Arg Arg Val Asp
865                 870                 875                 880

Leu Pro Thr Tyr Pro Phe Gln His Gln Pro Tyr Trp Leu Asp Ser Pro
                885                 890                 895

Arg His Pro Ala Gly Asp Val Thr Gly Pro Gly Asp Asp Glu Phe Trp
            900                 905                 910

Ala Ala Val Glu His Gly Glu Ala Thr Glu Leu Ala Asp Leu Leu Arg
        915                 920                 925

Arg Ser Ala Ala Glu Pro Gly Gln Asp Leu His Ala Pro Val Ala Ala
    930                 935                 940

Leu Leu Pro Thr Leu Ala Thr Trp Arg Arg Asp Arg Gln Arg Arg Ala
945                 950                 955                 960

Ala Val Asp Ser Trp Arg Tyr Arg Ile Val Trp Arg Pro Val Ala Thr
                965                 970                 975

Pro Ser Tyr Asp Arg Val Leu Ser Gly Arg Trp Ala Val Val Val Pro
            980                 985                 990

Ala Gly His Glu Asp Asp Pro Val Val Asp Trp Val Cys Ser Ala Leu
        995                 1000                1005

Arg Asp His Gly Gly Glu Pro Glu Arg Met Val Leu Gly Pro Arg Glu
   1010                1015                1020

Ser Arg Ser Ala Leu Ala Thr Arg Leu Ala Ala Asp Pro Pro Gly Gly
1025                1030                1035                1040

Val Val Ser Leu Leu Gly Leu Ser Gly Ala Ala His Pro Asp His Glu
               1045                1050                1055

Val Leu Pro Ser Ala Val Ala Gly Thr Val Leu Leu Ala Gln Ala Leu
           1060                1065                1070

Ser Asp Gly Ala Val Arg Ala Pro Val Trp Thr Leu Thr Arg Asn Gly
       1075                1080                1085

Val Ser Ala Thr Ala Thr Asp Pro Val Ala Pro Thr His Ala Ala Gln
```

-continued

```
   1090                1095                1100

Val Trp Ala Val Ala Arg Val Ala Gly Leu Glu His Pro Glu Ala Trp
1105                1110                1115                1120

Gly Gly Leu Leu Asp Leu Pro Asp Arg Leu Asp Asp Arg Ala Ala Ala
                1125                1130                1135

Arg Phe Ala Ala Val Leu Ser Ala Gly Glu Asp Glu Asp Gln Leu Ala
            1140                1145                1150

Leu Arg Asp Ala Gly Leu Leu Ala Arg Arg Leu Val Arg Ala Pro Val
        1155                1160                1165

Pro Arg Asp Ala Val Thr Ala Gly Trp Gln Pro Arg Asp Thr Ala Leu
    1170                1175                1180

Val Thr Gly Gly Thr Gly Gly Leu Gly Gly Gln Val Ala Arg Trp Leu
1185                1190                1195                1200

Ala Ala Ala Gly Val Arg His Leu Val Leu Val Ser Arg Arg Gly Ala
                1205                1210                1215

Glu Ala Glu Gly Ala Asp Arg Leu Arg Asp Asp Leu Thr Ala Leu Gly
            1220                1225                1230

Val Gln Val Thr Phe Gly Ala Cys Asp Val Ala Asp Arg Ala Ala Leu
        1235                1240                1245

Ser Ala Leu Leu Asp Arg Val Gln Glu Asp Gly Pro Pro Ile Arg Thr
    1250                1255                1260

Val Val His Ala Ala Gly Ser Gly Arg Ala Ala Arg Leu Leu Asp Thr
1265                1270                1275                1280

Asp Ala Glu Glu Thr Ala Ala Val Leu Arg Ala Lys Ser Ala Gly Ala
                1285                1290                1295

Arg Asn Leu His Glu Leu Leu Asp Asp Val Asp Ala Phe Val Leu Phe
            1300                1305                1310

Ser Ser Gly Ala Gly Val Trp Gly Ser Ser Ala Gln Gly Ala Tyr Ala
        1315                1320                1325

Ala Ala Asn Ala Tyr Leu Asp Ala Leu Ala Glu Gln Arg Arg Gly Gln
    1330                1335                1340

Gly Arg Pro Ala Thr Ser Val Ala Trp Gly Ala Trp Ala Gly Asp Gly
1345                1350                1355                1360

Met Thr Ala Ala Ala Gly Glu Glu Trp Trp Ser Arg Gln Gly Leu Arg
                1365                1370                1375

Phe Met Ala Pro Glu Ala Ala Leu Asp Ala Leu Arg Gln Ala Val Asp
            1380                1385                1390

Arg Ala Glu Ser Thr Leu Val Val Ala Asp Ile Asp Trp Lys Thr Phe
        1395                1400                1405

Ala Pro Leu Phe Thr Ser Ala Arg Ser Arg Pro Leu Ile Thr Asp Ile
    1410                1415                1420

Pro Glu Ala Arg Pro Glu Pro Arg Pro Glu Gly Ala Asp Gln Pro Thr
1425                1430                1435                1440

Gln Gly Leu Val Ala Lys Leu Ala Val Leu Ser Ala Asp Glu Arg Arg
                1445                1450                1455

Arg Ala Leu Leu Ala Glu Val Arg Ala Gln Ala Ala Val Val Leu Gly
            1460                1465                1470

His Pro Gly Ala Asp Ala Val Pro Val Asp Arg Pro Phe Arg Glu Leu
        1475                1480                1485

Gly Phe Asp Ser Leu Ser Ala Val Lys Leu Arg Asn Arg Ile Val Ala
    1490                1495                1500

Ala Thr Gly Leu Glu Leu Pro Ala Thr Leu Val Phe Asp His Pro Thr
1505                1510                1515                1520
```

Ser Thr Ala Leu Ala Ala Tyr Leu Gly Ala Arg Leu Gly Ile Asp Gly
1525 1530 1535

Ala Pro Ala Gly Ser Thr Leu Leu Glu Asp Leu Ala Arg Leu Glu Ser
1540 1545 1550

Thr Val Ala Thr Leu Thr Ala Ala Pro Leu Ala Glu Thr Val Pro Asp
1555 1560 1565

Ala Arg Asp Arg Ala Ala Leu Thr Thr Arg Leu Arg Ala Leu Leu Glu
1570 1575 1580

Arg Trp Asp Gln Ala Asp Gly Glu Asp Gln Ala Ala Ala Arg Glu Glu
1585 1590 1595 1600

Leu Asp Asp Leu Ser Asp Asp Asp Leu Phe Asp Phe Ile Asp Ala Lys
1605 1610 1615

Phe Gly Arg Ser
1620

<210> SEQ ID NO 6
<211> LENGTH: 2130
<212> TYPE: PRT
<213> ORGANISM: Streptomyces parvulus Tu4055

<400> SEQUENCE: 6

Met Gly Asp Glu Gln Lys Leu Arg Thr Tyr Leu Arg Arg Val Thr Ala
1 5 10 15

Asp Leu Ala Asp Val Thr Glu Arg Leu Gln Arg Ala Glu Asp Lys Asn
20 25 30

Ala Glu Pro Ile Ala Ile Val Gly Met Gly Cys Arg Tyr Pro Gly Gly
35 40 45

Val Arg Ser Pro Glu Glu Phe Trp Asn Leu Leu Asp Glu Gly Val Asp
50 55 60

Ala Val Ala Gly Phe Pro Glu Asp Arg Gly Trp Asp Leu Glu Asn Leu
65 70 75 80

Tyr Asp Pro Asp Pro Asp Glu Pro Gly Lys Cys Tyr Ala Arg Glu Gly
85 90 95

Gly Phe Leu Tyr Asp Ala Gly Glu Phe Asp Ala Ala Phe Phe Gly Ile
100 105 110

Ser Pro Arg Glu Ala Leu Ser Met Asp Pro Gln Gln Arg Leu Leu Leu
115 120 125

Glu Cys Ser Trp Ser Ala Leu Glu Arg Ala Gly Ile Asp Pro Gly Ser
130 135 140

Leu Arg Gly Lys Asp Val Gly Val Tyr Val Gly Ala Trp Asn Ser Asn
145 150 155 160

Tyr Gly Arg Gly Gly Gly Ala Glu Ser Ser Glu Gly His Leu Leu Thr
165 170 175

Gly Asn Ala Ser Ser Val Val Ser Gly Arg Val Ala Tyr Val Leu Gly
180 185 190

Leu Glu Gly Pro Ala Val Thr Ile Asp Thr Ala Cys Ser Ser Ser Leu
195 200 205

Val Gly Leu His Leu Ala Ala Gln Ala Leu Arg Ser Gly Glu Cys Gly
210 215 220

Leu Ala Leu Ala Gly Gly Val Thr Val Met Ser Thr Pro Leu Ser Leu
225 230 235 240

Val Ser Phe Ser Arg Gln Arg Gly Leu Ala Gln Asp Gly Arg Ser Lys
245 250 255

Ala Phe Ser Ala Asp Ala Asp Gly Met Gly Met Ala Glu Gly Val Gly

-continued

```
            260                 265                 270

Val Leu Val Leu Glu Arg Leu Ser Glu Ala Arg Arg Asn Gly His Glu
        275                 280                 285

Val Leu Ala Val Leu Arg Ser Ser Ala Val Asn Gln Asp Gly Ala Ser
    290                 295                 300

Asn Gly Leu Ser Ala Pro Asn Gly Pro Ala Gln Gln Arg Val Ile Gln
305                 310                 315                 320

Ser Ala Leu Thr Val Gly Arg Leu Ala Pro Ser Asp Ile Asp Val Val
                325                 330                 335

Glu Ala His Gly Thr Gly Thr Ala Leu Gly Asp Pro Ile Glu Ala Gln
            340                 345                 350

Ala Leu Leu Ala Thr Tyr Gly Arg Gly Arg Asp Ala Asp Arg Pro Leu
        355                 360                 365

Trp Leu Gly Ser Val Lys Ser Asn Ile Gly His Thr Gln Ala Ala Ala
    370                 375                 380

Gly Val Ala Gly Val Ile Lys Met Val Leu Ala Leu Arg Lys Gly Val
385                 390                 395                 400

Leu Pro Arg Thr Leu His Val Asp Glu Pro Thr Gly Glu Val Asp Trp
                405                 410                 415

Asp Ser Gly Ala Val Arg Leu Leu Thr Glu Ala Arg Glu Trp Pro Ser
            420                 425                 430

Gly Glu Gly Arg Val Arg Arg Ala Gly Val Ser Ser Phe Gly Ile Ser
        435                 440                 445

Gly Thr Asn Ala His Val Ile Val Glu Glu Ala Pro Glu Glu Glu Pro
    450                 455                 460

Arg Pro Glu Ala Pro Ser Val Asp Val Val Pro Trp Val Leu Ser Ala
465                 470                 475                 480

Arg Ser Ala Glu Ala Leu Arg Glu Gln Ala Ala Arg Leu Ala Ser Val
                485                 490                 495

Ala Gly Gly Leu Asn Val Val Asp Val Gly Trp Ser Leu Ala Ser Thr
            500                 505                 510

Arg Ala Ala Phe Glu His Arg Ala Val Val Val Gly Arg Asp Ser Glu
        515                 520                 525

Glu Leu Val Ser Gly Leu Ser Ser Val Ser Gly Val Glu Val Gly Val
    530                 535                 540

Gly Val Gly Ala Gly Gly Gly Val Val Leu Val Phe Ala Gly Gln Gly
545                 550                 555                 560

Cys Gln Trp Val Gly Met Gly Arg Glu Leu Leu Gly Ser Ser Leu Val
                565                 570                 575

Phe Ala Glu Ser Met Arg Glu Cys Ala Ala Ala Leu Ser Pro Phe Val
            580                 585                 590

Asp Phe Ser Val Val Asp Val Leu Gly Ser Ala Gly Glu Leu Gly Arg
        595                 600                 605

Val Glu Val Val Gln Pro Ala Leu Trp Ala Val Met Val Ser Leu Ala
    610                 615                 620

Arg Val Trp Arg Ser Trp Gly Val Pro Val Ala Ala Val Val Gly His
625                 630                 635                 640

Ser Gln Gly Glu Ile Ala Ala Ala Thr Val Ala Gly Ala Leu Ser Val
                645                 650                 655

Gly Asp Ala Ala Arg Val Val Ala Leu Arg Ser Arg Leu Ile Ala Glu
            660                 665                 670

Arg Leu Ser Gly Leu Gly Gly Met Val Ser Val Ala Leu Ser Arg Glu
        675                 680                 685
```

-continued

```
Arg Val Val Ser Leu Ile Ala Gly Val Pro Gly Val Ser Val Ala Ala
    690                 695                 700

Val Asn Gly Ser Ser Ser Thr Val Val Ser Gly Glu Ala Ala Gly Leu
705                 710                 715                 720

Glu Arg Val Leu Ala Ala Cys Val Ser Ser Gly Val Arg Ala Arg Arg
                725                 730                 735

Ile Asp Val Asp Tyr Ala Ser His Ser Val Gln Val Glu Leu Ile Arg
            740                 745                 750

Glu Glu Leu Leu Gly Val Leu Asp Gly Ile Val Pro Arg Ser Gly Glu
        755                 760                 765

Ile Pro Phe Val Ser Thr Val Thr Gly Glu Arg Ile Asp Thr Val Glu
    770                 775                 780

Leu Gly Ala Glu Tyr Trp Tyr Arg Asn Leu Arg Gln Thr Val Glu Phe
785                 790                 795                 800

Gln Ala Ser Val Gln Thr Leu Leu Ala Gln Gly His Gln Val Phe Leu
                805                 810                 815

Glu Ser Ser Pro His Pro Val Leu Thr Val Gly Ile Glu Glu Thr Val
            820                 825                 830

His Glu Ser Ala Ala Gln Ala Val Val Leu Gly Ser Leu Arg Arg Asp
        835                 840                 845

Glu Gly Ala Leu Thr Arg Leu Val Thr Ser Ala Gly Glu Ala Trp Ala
    850                 855                 860

Arg Gly Val Pro Val Asp Trp Ala Gly Met Leu Ala Gly Gly Arg Arg
865                 870                 875                 880

Val Glu Leu Pro Thr Tyr Pro Phe Leu Arg Glu Arg Leu Trp Leu Glu
                885                 890                 895

Pro Ser Arg Ser Arg Thr Gly Asn Leu Asn Met Ala Gly Leu Val Glu
            900                 905                 910

Ala Gly His Glu Ile Leu Pro Ala Ala Val Glu Leu Pro Gly Glu Gln
        915                 920                 925

Trp Val Trp Thr Gly Glu Leu Ser Leu Ser Ala Tyr Pro Trp Leu Ala
    930                 935                 940

Asp His Gln Val Leu Gly Gln Thr Leu Val Pro Gly Val Ala Trp Val
945                 950                 955                 960

Glu Leu Ala Leu His Ala Gly His Gln Leu Gly Phe Gly Ser Val Glu
                965                 970                 975

Glu Leu Thr Leu Gln Ala Pro Leu Val Leu Gly Glu Ser Asp Ala Val
            980                 985                 990

Gln Val Arg Val Val Val Ser Asp Leu Gly Glu Ser Asp Arg Arg Ala
        995                 1000                1005

Val Ser Val His Ser Arg Gly Asp Asp Gln Thr Trp Val Thr His Ala
   1010                 1015                1020

Glu Gly Phe Leu Thr Ala Lys Gly Ala Gln Pro Glu Thr Met Ala Val
1025                1030                1035                1040

Trp Pro Pro Ser Gly Ala Glu Pro Val Glu Ala Asp Gly Phe Tyr Glu
               1045                1050                1055

Arg Leu Ala Asp Ala Gly Tyr His Tyr Gly Pro Val Phe Gln Gly Val
           1060                1065                1070

Ser Lys Val Trp Arg Ala Gly Glu Glu Ile Tyr Ala Glu Val Gly Leu
       1075                1080                1085

Leu Asp Asp Ala Asp Val Asp Gly Phe Gly Ile His Pro Ala Leu Leu
   1090                1095                1100
```

-continued

```
Asp Ala Ala Leu Gln Thr Ala Tyr Val Ala Gln Arg Gly Pro Ala Glu
1105                1110                1115                1120

Thr Lys Leu Pro Phe Ala Phe Gly Asp Val Gln Leu Phe Ala Thr Gly
                1125                1130                1135

Ala Arg Ser Leu Arg Val Arg Val Ser Pro Ala Ala Gln Gln Gly Met
            1140                1145                1150

Ala Trp Glu Ala Trp Asp Pro Thr Gly Leu Pro Val Phe Ser Leu Gly
        1155                1160                1165

Tyr Leu Ala Thr Arg Pro Val Asp Arg Gly Gln Leu Thr Val Lys Arg
    1170                1175                1180

Pro Glu Ser Leu Phe Lys Val Ala Trp Asp Glu Thr Val Pro Val Val
1185                1190                1195                1200

Gly Asn Ala Thr Ala Ala His Gly Val Val Leu Gly Asp Asp Pro Phe
                1205                1210                1215

Ala Leu Gly Ala Ala Leu Arg Ala Ala Gly Trp Glu Val Gly Ala Ala
            1220                1225                1230

Pro Glu Pro Ala Ser Ala Asp Thr Ala Ala Glu Val Leu Leu Leu Pro
        1235                1240                1245

Cys Thr Ala Pro Gly Glu Pro Asp Ala Asp Leu Pro Thr Ala Val Arg
    1250                1255                1260

Ala Val Thr Ala Arg Val Leu Gly Val Leu Gln Glu Trp Leu Ala Asp
1265                1270                1275                1280

Glu Arg Leu Ala Gly Thr Arg Leu Ala Val Val Thr Arg Asn Ala Leu
                1285                1290                1295

Pro Gly Asp Leu Leu His Ser Pro Val Trp Gly Leu Val Arg Ser Ala
            1300                1305                1310

Gln Thr Glu Asn Pro Gly Arg Ile Thr Leu Val Asp Leu Asp Asp His
        1315                1320                1325

Pro Asp Ser Ala Ala Val Leu Ala Glu Ala Val Gln Ser Asp Glu Pro
    1330                1335                1340

Arg Ile Met Val Arg Glu Gly Arg Pro Thr Ala Ala Arg Leu Val Arg
1345                1350                1355                1360

Ala Thr Ala Pro Glu Leu Val Pro Pro Ala Gly Ala Asp Ala Trp Arg
                1365                1370                1375

Leu Glu Ile Thr Glu Pro Gly Thr Phe Asp Asn Leu Thr Leu Gly Val
            1380                1385                1390

Tyr Pro His Ala Glu Lys Thr Leu Ala Asp Asn Glu Val Arg Val Ala
        1395                1400                1405

Val His Ala Gly Gly Leu Asn Phe His Asp Val Val Ala Ala Leu Gly
    1410                1415                1420

Met Val Glu Asp Asp Leu Thr Leu Gly Arg Glu Ala Ala Gly Val Val
1425                1430                1435                1440

Val Glu Val Gly Asp Ala Val Pro Asp Leu Thr Pro Gly Asp His Val
                1445                1450                1455

Met Gly Ile Leu Ser Ser Gly Phe Gly Pro Leu Ala Val Thr Asp His
            1460                1465                1470

Arg Tyr Leu Ala Arg Met Pro Glu Gly Trp Thr Phe Ala Gln Ala Ala
        1475                1480                1485

Ser Val Pro Ala Ala Phe Leu Thr Ala Tyr Tyr Gly Leu Cys Asp Leu
    1490                1495                1500

Gly Gly Ile Arg Ala Gly Asp Arg Val Leu Ile His Ala Ala Ala Gly
1505                1510                1515                1520

Gly Val Gly Met Ala Ala Val Gln Ile Ala Arg His Leu Gly Ala Glu
```

-continued

```
            1525                1530                1535

Val Phe Gly Thr Ala Ser Pro Arg Lys Trp Gly Ala Leu Arg Ala Leu
        1540                1545                1550

Gly Leu Asp Asp Ala His Leu Ser Ser Ser Arg Thr Leu Asp Phe Glu
     1555                1560                1565

Gln Glu Phe Leu Asp Ala Thr Asp Gly Arg Gly Val Asp Leu Val Leu
  1570                1575                1580

Asn Ser Leu Ala Arg Glu Phe Val Asp Ala Ser Leu Arg Leu Met Pro
1585                1590                1595                1600

Gly Gly Gly Arg Phe Val Asp Met Gly Lys Thr Asp Ile Arg Arg Pro
            1605                1610                1615

Glu Gln Val Ala Glu Asp His Gly Gly Val Ala Tyr Gln Ala Phe Asp
        1620                1625                1630

Leu Val Glu Ala Gly Pro Gln Arg Thr Gly Glu Met Leu Ala Glu Ile
     1635                1640                1645

Val Arg Leu Phe Gln Ala Gly Ala Phe Arg Pro Leu Pro Ile Thr Gln
  1650                1655                1660

Trp Asp Val Arg Arg Ala Pro Glu Ala Phe Arg His Ile Ser Gln Ala
1665                1670                1675                1680

Lys His Ile Gly Lys Ile Val Leu Thr Val Pro Arg Pro Ile Asp Thr
            1685                1690                1695

Asp Gly Thr Val Met Val Thr Gly Ala Thr Gly Thr Leu Gly Gly Phe
        1700                1705                1710

Val Ala Arg His Leu Val Thr His His Gly Ile Arg Arg Leu Leu Leu
     1715                1720                1725

Val Ser Arg Ser Ala Glu Arg Thr Asp Leu Val Arg Glu Leu Thr Glu
  1730                1735                1740

Leu Gly Ala Asp Val Thr Trp Ala Ser Cys Asp Leu Ala Asp Ala Thr
1745                1750                1755                1760

Ala Val Glu Glu Thr Val Arg Ser Val Asp Glu Arg His Pro Leu Val
            1765                1770                1775

Ala Val Val His Ser Ala Gly Val Leu Asp Asp Gly Val Ile Asp Lys
        1780                1785                1790

Gln Ser Pro Glu Arg Leu Asp Thr Val Met Arg Pro Lys Val Asp Ala
     1795                1800                1805

Ala Trp Asn Leu His Arg Leu Leu Asp Asn Ala Pro Leu Ala Asp Phe
  1810                1815                1820

Val Leu Phe Ser Ser Ala Ser Gly Val Leu Gly Gly Ala Gly Gln Ser
1825                1830                1835                1840

Asn Tyr Ala Ala Ala Asn Ala Phe Leu Asp Ala Leu Ala Glu His Arg
            1845                1850                1855

Arg Ala Gln Gly Leu Ala Gly Gln Ala Leu Ala Trp Gly Leu Trp Ser
        1860                1865                1870

Asp Arg Ser Thr Met Thr Gly Gln Leu Gly Ser Thr Glu Leu Ala Arg
     1875                1880                1885

Ile Ala Arg Asn Gly Val Ala Glu Met Ser Glu Thr Glu Gly Leu Ala
  1890                1895                1900

Leu Phe Asp Ala Ala Arg Asp Thr Ala Glu Ala Val Leu Leu Pro Met
1905                1910                1915                1920

His Leu Asp Val Ala Arg Leu Arg Ser Arg Asn Gly Glu Val Pro Ala
            1925                1930                1935

Val Phe Arg Arg Leu Ile His Ala Thr Ala Arg Arg Thr Ala Ser Thr
        1940                1945                1950
```

-continued

```
Ala Val Arg Ser Ala Gly Leu Glu Gln Gln Leu Ala Ser Leu Ser Gly
       1955                1960                1965

Pro Glu Arg Thr Glu Leu Leu Leu Gly Leu Val Arg Asp His Ala Ala
   1970                1975                1980

Ala Val Leu Gly His Gly Thr Ser Asp Ala Val Ser Pro Asp Arg Pro
1985                1990                1995                2000

Phe Arg Asp Leu Gly Phe Asp Ser Leu Thr Ala Val Glu Leu Arg Asn
               2005                2010                2015

Arg Phe Ala Ala Leu Thr Gly Leu Arg Leu Pro Ala Thr Leu Val Phe
           2020                2025                2030

Asp His Pro Ser Pro Thr Ala Leu Ala Gly His Leu Ala Gly Leu Leu
       2035                2040                2045

Gly Ala Ala Thr Pro Ser Ala Ala Glu Pro Val Leu Ala Ala Val Gly
   2050                2055                2060

Arg Leu Arg Ala Asp Leu Arg Ser Leu Thr Pro Asp Ala Glu Gly Ala
2065                2070                2075                2080

Glu Asp Val Thr Ile Gln Leu Glu Ala Leu Leu Ala Glu Trp Arg Glu
               2085                2090                2095

Ala Ala Glu Lys Arg Ala Pro Glu Ala Val Gly Asp Glu Asp Leu Ser
           2100                2105                2110

Thr Ala Thr Asp Asp Glu Ile Phe Ala Leu Val Asp Ser Glu Leu Gly
       2115                2120                2125

Glu Ala
   2130


<210> SEQ ID NO 7
<211> LENGTH: 1742
<212> TYPE: PRT
<213> ORGANISM: Streptomyces parvulus Tu4055

<400> SEQUENCE: 7

Met Thr Ala Glu Ala Ser Gln Asp Lys Leu Arg Asp Tyr Leu Arg Lys
  1               5                  10                  15

Thr Leu Ala Asp Leu Arg Thr Thr Lys Gln Arg Leu Arg Asp Thr Glu
             20                  25                  30

Arg Arg Ala Thr Glu Pro Val Ala Ile Val Gly Met Ser Cys Arg Leu
         35                  40                  45

Pro Gly Asp Val Arg Thr Pro Glu Arg Phe Trp Glu Leu Leu Asp Thr
     50                  55                  60

Gly Thr Asp Ala Leu Thr Pro Leu Pro Thr Asp Arg Gly Trp Asn Leu
 65                  70                  75                  80

Asp Thr Ala Phe Asp Asp Glu Arg Pro Tyr Arg Arg Glu Gly Gly Phe
                 85                  90                  95

Leu Tyr Asp Ala Gly Arg Phe Asp Ala Glu Phe Phe Gly Ile Ser Pro
            100                 105                 110

Arg Glu Ala Leu Ala Met Asp Pro Gln Gln Arg Leu Leu Leu Glu Ser
        115                 120                 125

Ser Trp Glu Ala Ile Glu His Ala Arg Ile Asp Pro Arg Ser Leu His
    130                 135                 140

Gly Ser Arg Thr Gly Val Trp Phe Gly Thr Ile Gly Gln Asp Tyr Phe
145                 150                 155                 160

Ser Leu Phe Ala Ala Ser Gly Gly Glu His Ala Asn Tyr Leu Ala Thr
                165                 170                 175

Ala Cys Ser Ala Ser Val Met Ser Gly Arg Val Ser Tyr Val Leu Gly
```

-continued

```
            180                 185                 190

Leu Glu Gly Pro Ala Val Thr Val Asp Thr Ala Cys Ser Ser Ser Leu
        195                 200                 205

Val Ala Leu His Ser Ala Val Gln Ala Leu Arg Ser Gly Glu Cys Glu
    210                 215                 220

Leu Ala Leu Ala Gly Gly Ala Thr Val Met Ala Thr Pro Thr Val Phe
225                 230                 235                 240

Thr Ala Phe Ser His Gln Arg Gly Leu Ala Gly Asp Gly Arg Cys Lys
                245                 250                 255

Ala Phe Ala Ala Gly Ala Asp Gly Ala Gly Phe Ala Glu Gly Val Gly
            260                 265                 270

Val Leu Val Leu Glu Arg Leu Ser Val Ala Arg Arg Asn Gly His Arg
        275                 280                 285

Val Leu Ala Val Val Arg Gly Ser Ala Val Asn Gln Asp Gly Ala Ser
    290                 295                 300

Asn Gly Leu Thr Ala Pro Asn Gly Pro Ser Gln Gln Arg Val Ile Arg
305                 310                 315                 320

Ala Ala Leu Ala Asn Ala Arg Leu Ala Pro Glu Asp Val Asp Ala Val
                325                 330                 335

Glu Gly His Gly Thr Gly Thr Ser Leu Gly Asp Pro Ile Glu Ala Gln
            340                 345                 350

Ala Leu Leu Ala Thr Tyr Gly Arg Gly Arg Asp Ala Glu Arg Pro Leu
        355                 360                 365

Trp Leu Gly Ser Val Lys Ser Asn Ile Gly His Ala Gln Ala Ala Ala
    370                 375                 380

Gly Val Ala Gly Val Ile Lys Met Val Leu Ala Met Glu Lys Gly Arg
385                 390                 395                 400

Leu Pro Arg Thr Leu His Val Asp Glu Pro Ser Gly Glu Val Asp Trp
                405                 410                 415

Asp Ser Gly Ala Val Arg Leu Leu Thr Glu Ala Arg Asp Trp Pro Ser
            420                 425                 430

Gly Glu Gly Arg Val Arg Arg Ala Gly Val Ser Ser Phe Gly Ile Ser
        435                 440                 445

Gly Thr Asn Ala His Val Ile Ile Glu Glu Pro Gln Glu Glu Glu Ala
    450                 455                 460

Ala Pro Asp Ser Ser Ala Ser Gly Ala Val Pro Trp Val Leu Ser Ala
465                 470                 475                 480

Arg Ser Ala Glu Ala Leu Gln Ala Leu Ala Ser Gln Leu Ala Asp His
                485                 490                 495

Ser Ala Lys Ser Ser Pro Val Asp Val Gly Trp Ser Leu Val Ser Thr
            500                 505                 510

Arg Ala Ala Phe Glu His Arg Ala Val Val Val Gly Arg Gly Arg Asp
        515                 520                 525

Glu Leu Val Arg Gly Leu Ser Glu Val Ala Gln Gly Arg Gly Val Arg
    530                 535                 540

Gly Val Ala Ser Ser Ala Ser Gly Gly Leu Ala Phe Val Phe Ala Gly
545                 550                 555                 560

Gln Gly Ser Gln Arg Leu Gly Met Gly Arg Gly Leu Tyr Glu Arg Phe
                565                 570                 575

Pro Val Phe Ala Glu Ala Phe Asp Glu Val Cys Gly Arg Val Gly Pro
            580                 585                 590

Gly Val Arg Glu Val Val Phe Gly Ser Asp Ala Gly Glu Leu Asp Arg
        595                 600                 605
```

-continued

```
Thr Val Trp Ala Gln Ala Gly Leu Phe Ala Leu Glu Val Ala Leu Phe
    610                 615                 620

Arg Leu Leu Glu Ser Trp Gly Val Arg Pro Gly Cys Leu Ile Gly His
625                 630                 635                 640

Ser Val Gly Glu Leu Ser Ala Ala Cys Val Ala Gly Leu Trp Ser Leu
                645                 650                 655

Glu Asp Ala Cys Arg Val Val Ala Ala Arg Ala Arg Leu Met Gln Ala
            660                 665                 670

Leu Pro Ala Gly Gly Val Met Val Ala Val Arg Ala Glu Ala Gly Glu
        675                 680                 685

Leu Ala Gly Phe Leu Gly Glu Asp Val Val Ile Ala Ser Val Asn Ala
    690                 695                 700

Pro Gly Gln Val Val Ile Ala Gly Pro Glu Gly Gly Val Glu Arg Val
705                 710                 715                 720

Val Ala Ala Cys Gly Ala Arg Ser Arg Arg Leu Ala Val Ser His Ala
                725                 730                 735

Phe His Ser Pro Leu Val Glu Pro Met Leu Gly Glu Phe Arg Arg Val
            740                 745                 750

Val Glu Ser Val Ala Phe Gly Val Pro Ser Leu Arg Val Val Ser Asn
        755                 760                 765

Val Thr Gly Ala Trp Val Asp Pro Glu Glu Trp Gly Thr Pro Glu Tyr
    770                 775                 780

Trp Val Arg Gln Val Arg Glu Pro Val Arg Phe Ala Asp Gly Val Ala
785                 790                 795                 800

Thr Leu Leu Asp Ala Gly Val Arg Thr Phe Val Glu Leu Gly Pro Ala
                805                 810                 815

Gly Thr Leu Thr Ser Met Val Ser His Cys Ala Asp Ala Thr Ala Thr
            820                 825                 830

Ser Val Thr Ala Val Pro Thr Leu Arg Pro Asp His Asp Glu Ser Arg
        835                 840                 845

Thr Val Leu Ser Ala Ala Ala Ser Leu Tyr Val Gln Gly His Pro Val
    850                 855                 860

Asp Trp Ala Pro Leu Phe Pro Arg Ala Arg Thr Val Asp Leu Pro Thr
865                 870                 875                 880

Tyr Pro Phe Gln His Gln His Tyr Trp Met Glu Ser Ala Ala Arg Pro
                885                 890                 895

Thr Val Glu Asp Thr Pro Arg Glu Pro Leu Asp Gly Trp Thr His Arg
            900                 905                 910

Ile Asp Trp Val Pro Leu Val Asp Glu Glu Pro Ala Pro Val Leu Ala
        915                 920                 925

Gly Thr Trp Leu Leu Val Arg Pro Glu Glu Gly Pro Arg Pro Leu Ala
    930                 935                 940

Asp Ala Val Ala Asp Ala Leu Thr Arg His Gly Ala Ser Val Val Glu
945                 950                 955                 960

Ala Ala Arg Val Pro His Gln Ser Asp Thr Glu Leu Thr Gly Val Val
                965                 970                 975

Ser Leu Leu Gly Pro Gly Ala Asp Gly Asp Gly Gly Leu Asp Ala Thr
            980                 985                 990

Leu Arg Leu Val Gln Asp Leu Ala Thr Ala Gly Ser Thr Ala Pro Leu
        995                1000                1005

Trp Ile Val Thr Ser Gly Ala Val Ala Val Gly Thr Ser Asp Thr Val
   1010                1015                1020
```

-continued

```
Pro Asn Pro Glu Gln Ala Thr Leu Trp Gly Leu Ala Arg Ala Ala Ala
1025                1030                1035                1040

Thr Glu Trp Pro Gly Leu Gly Ala Ala Arg Ile Asp Leu Pro Ala Asp
               1045                1050                1055

Leu Thr Glu Gln Val Gly Arg Arg Leu Cys Ala Arg Leu Leu Asp Arg
           1060                1065                1070

Ser Glu Gln Glu Thr Ala Val Arg Gln Ala Gly Val Phe Ala Arg Arg
       1075                1080                1085

Leu Val Arg Ala Arg Thr Ser Asp Gly Arg Trp Thr Pro Arg Gly Thr
   1090                1095                1100

Val Leu Val Thr Gly Gly Thr Gly Ala Leu Ala Gly His Val Ala Arg
1105                1110                1115                1120

Trp Leu Ala Glu Glu Gly Ala Glu His Ile Val Leu Ala Gly Arg Arg
               1125                1130                1135

Gly Pro Asp Gly Gln Gly Ala Glu Ala Leu Arg Ala Asp Leu Val Ala
           1140                1145                1150

Ala Gly Val Lys Ala Thr Ile Val Arg Cys Asp Val Ala Asp Arg Asp
       1155                1160                1165

Ala Val Arg Leu Leu Leu Asp Ala His Arg Pro Ser Ala Ile Val His
   1170                1175                1180

Thr Ala Gly Val Val Asp Asp Gly Leu Leu Thr Ser Leu Thr Pro Ala
1185                1190                1195                1200

Gln Val Glu Arg Val Leu Arg Pro Lys Leu Leu Gly Ala Arg Asn Leu
               1205                1210                1215

His Glu Leu Thr Arg Asp Arg Glu Leu Asp Ala Phe Val Leu Phe Ser
           1220                1225                1230

Ser Leu Ala Gly Val Leu Gly Gly Ala Gly Gln Ala Asn Tyr Ala Ala
       1235                1240                1245

Ala Asn Ala Tyr Leu Asp Ala Leu Ala Ala His Arg Thr Ala His Gly
   1250                1255                1260

Leu Pro Ala Ala Ser Leu Ala Trp Gly Pro Trp Glu Gly Asp Gly Met
1265                1270                1275                1280

Ala Ala Ala Gln Glu Ala Ala Asp Arg Leu Arg Arg Ser Gly Leu Thr
               1285                1290                1295

Pro Leu Pro Pro Glu Gln Ala Val Arg Ala Leu Gly Arg Gly His Gly
           1300                1305                1310

Pro Leu Val Val Ala Asp Ala Asp Trp Ala Arg Leu Ala Ala Gly Ser
       1315                1320                1325

Thr Gln Arg Leu Leu Asp Glu Leu Pro Glu Val Arg Ala Val Arg Pro
   1330                1335                1340

Ala Glu Pro Ala Val Gly Gln Arg Pro Asp Leu Pro Ala Arg Leu Ala
1345                1350                1355                1360

Gly Arg Pro Ala Glu Glu Gln Ser Ala Val Leu Leu Glu Ala Val Arg
               1365                1370                1375

Glu Glu Ile Ala Ala Val Leu Arg Tyr Ala Asp Pro Ala Arg Ile Gly
           1380                1385                1390

Ala Asp His Glu Phe Leu Ala Leu Gly Phe Asp Ser Leu Thr Ser Ile
       1395                1400                1405

Glu Leu Arg Asn Arg Leu Ala Thr Arg Ile Gly Leu Thr Leu Pro Ala
   1410                1415                1420

Thr Leu Thr Leu Glu Gln Arg Thr Pro Ala Gly Leu Ala Ala His Leu
1425                1430                1435                1440

Arg Glu Arg Ile Ala Asp Arg Pro Val Gly Ser Gly Ala Val Pro Val
```

-continued

```
                1445                1450                1455

Pro Gly Ser Ala Asp Val Pro Glu Ala Gly Gly Gly Ser Gly Leu Gly
            1460                1465                1470

Glu Leu Trp Gln Glu Ala Asp Arg His Gly Arg Arg Leu Glu Phe Ile
        1475                1480                1485

Asp Val Leu Thr Ala Ala Ala Ala Phe Arg Pro Ala Tyr Arg Glu Pro
    1490                1495                1500

Ala Glu Leu Glu Leu Pro Pro Leu Arg Leu Thr Ser Gly Gly Asp Glu
1505                1510                1515                1520

Pro Pro Leu Phe Cys Ile Pro Ser His Leu Gly Lys Ala Asp Pro His
                1525                1530                1535

Lys Phe Leu Arg Phe Ala Ala Ala Leu Arg Gly Arg Arg Asp Val Phe
            1540                1545                1550

Val Leu Arg Gln Pro Gly Phe Val Pro Gly Gln Pro Leu Pro Ala Gly
        1555                1560                1565

Leu Asp Val Leu Leu Asp Thr His Ala Arg Ala Met Ala Gly His Asp
    1570                1575                1580

Arg Pro Val Leu Leu Gly Tyr Ser Ala Gly Gly Leu Ala Ala Gln Ala
1585                1590                1595                1600

Leu Ala Ala Arg Leu Ala Glu Leu Gly Arg Pro Pro Ala Ala Val Val
                1605                1610                1615

Leu Val Asp Thr Tyr Ala Pro Asp Glu Thr Glu Val Met Ala Arg Ile
            1620                1625                1630

Gln Gly Ala Met Glu Gln Gly Gln Arg Asp Arg Asp Gly Arg Thr Gly
        1635                1640                1645

Ala Ala Phe Gly Glu Ala Trp Leu Thr Ala Met Gly His Tyr Phe Gly
    1650                1655                1660

Phe Asp Trp Thr Pro Cys Pro Val Asp Val Pro Val Leu His Val Arg
1665                1670                1675                1680

Ala Gly Asp Pro Met Thr Gly Met Pro Val Glu Gly Arg Trp Gln Ala
                1685                1690                1695

Arg Trp Asn Leu Pro His Thr Ala Val Asp Val Pro Gly Asp His Phe
            1700                1705                1710

Thr Met Met Glu Asp His Ala Pro Arg Thr Ala Asp Thr Val His Asp
        1715                1720                1725

Trp Leu Gly Thr Ala Val Arg Arg Pro Glu Arg Thr Arg Asp
    1730                1735                1740


<210> SEQ ID NO 8
<211> LENGTH: 264
<212> TYPE: PRT
<213> ORGANISM: Streptomyces parvulus Tu4055

<400> SEQUENCE: 8

Met Thr Gly Thr Asn Thr His Ser Asp Val Trp Ile Arg Gln Tyr Arg
1               5                   10                  15

Pro Ala His Pro Thr Ala Pro Gln Leu Ile Cys Leu Pro His Ala Gly
            20                  25                  30

Gly Ser Ala Thr Phe Tyr His Pro Val Ala Ala Ala Leu Ala Pro Arg
        35                  40                  45

Cys Asp Val Leu Ala Val Gln Tyr Pro Gly Arg Gln Asp Arg Arg Ala
    50                  55                  60

Glu Lys Pro Leu Glu Asp Ile Asp Glu Leu Ala Asn Gln Leu Phe Pro
65                  70                  75                  80
```

-continued

```
Val Leu Arg Ala Arg Val His Gln Pro Val Ala Leu Phe Gly His Ser
                85                  90                  95

Met Gly Ala Thr Leu Ala Phe Glu Leu Ala Arg Arg Phe Glu Ser Ala
            100                 105                 110

Gly Ile Ser Leu Glu Ala Leu Leu Val Ser Ala Arg Pro Ala Pro Ser
        115                 120                 125

Arg Gln Arg Thr Gly Gly Thr Val His Leu Leu Ser Asp Glu Glu Leu
    130                 135                 140

Val Ala Glu Leu Arg Thr Leu Asp Gly Thr Ala Glu Gln Val Phe His
145                 150                 155                 160

Asp Glu Glu Leu Val Arg Met Ala Leu Pro Ala Ile Arg Gly Asp Tyr
                165                 170                 175

Arg Ala Ala Glu Thr Tyr Arg Tyr Arg Pro Gly Pro Lys Leu Arg Cys
            180                 185                 190

Pro Ile His Ala Leu Thr Gly Asp Asp Asp Pro Met Val Thr Pro Val
        195                 200                 205

Glu Ala Arg Ala Trp Ser Glu His Thr Asp Gly Pro Phe Thr Leu Asp
    210                 215                 220

Thr Phe Ala Gly Gly His Phe Tyr Leu Leu Glu His Arg Asp Ala Ile
225                 230                 235                 240

Leu Gly Ile Ile Ala Glu His Leu Arg Thr Cys Ser Arg Ala Pro Gly
                245                 250                 255

Asp Arg Ser Gly Leu Thr Arg Glu
            260
```

<210> SEQ ID NO 9
<211> LENGTH: 265
<212> TYPE: PRT
<213> ORGANISM: Streptomyces parvulus Tu4055

<400> SEQUENCE: 9

```
Met Ser Leu Glu Leu Thr Asp Arg Val Met Met Val Thr Gly Ala Gly
  1               5                  10                  15

Ser Gly Ile Gly Arg Ala Ala Ala Arg Leu Leu Val Gly His Gly Ala
             20                  25                  30

Arg Val Val Leu Val Gly Arg Thr Glu Ser Ala Leu Thr Glu Thr Thr
         35                  40                  45

Ala Gly Leu Pro Ser Ser His His Leu Val Val Pro Cys Asp Val Gly
     50                  55                  60

Asp Asp Lys Gln Val Ala Asp Cys Val Ala Arg Ala Val Ser Arg Phe
 65                  70                  75                  80

Gly Arg Leu Asp Gly Ala Phe Asn Asn Ala Gly Thr Phe Gly Ser Phe
                 85                  90                  95

Gly Pro Leu His Gln Asp Thr Ala Asp Asn Phe Asp Arg Val Ile Ala
            100                 105                 110

Thr Asn Leu Arg Gly Val Trp Ser Cys Met Arg Gly Gln Ile Glu Ala
        115                 120                 125

Met Leu Thr Ala Gly Gly Gly Ala Ile Val Asn Cys Ala Ser Val Ala
    130                 135                 140

Gly His Ile Gly His Ala Gln Ser Pro Leu Tyr Ser Ala Thr Lys His
145                 150                 155                 160

Ala Val Ile Gly Leu Ser Lys Ser Val Ala Leu Gln Tyr Ala Gly Asp
                165                 170                 175

Gly Ile Arg Val Asn Val Val Ser Pro Gly Ser Thr Asp Thr Pro Met
            180                 185                 190
```

-continued

```
Leu Arg Ser Leu Tyr Ala Asp Pro Ser Ala Leu Ala Gln Arg Ala Arg
        195                 200                 205

Arg Ala Pro Leu Gly Arg Leu Gly Lys Cys Glu Glu Val Ala Asn Ala
    210                 215                 220

Val Val Trp Leu Leu Ser Pro Leu Ala Ala Tyr Val Thr Gly Gln Thr
225                 230                 235                 240

Leu Gly Val Asp Gly Gly Val Thr Ala Gly Ser Ala Ile Pro Arg Thr
                245                 250                 255

Asn Ala Thr Pro Glu Gly Gln His Arg
            260                 265


<210> SEQ ID NO 10
<211> LENGTH: 250
<212> TYPE: PRT
<213> ORGANISM: Streptomyces parvulus Tu4055

<400> SEQUENCE: 10

Met Thr Ala Arg His Asp Val Ala Leu Val Thr Gly Ala Gly Ser Gly
  1               5                  10                  15

Ile Cys Ala Glu Val Ala Arg Gly Leu Ala Ala Arg Gly Leu Arg Val
             20                  25                  30

Val Leu Leu Asp Lys Asp Ala Glu Ala Val His Arg Val Ala Asp Gly
         35                  40                  45

Leu Gly Asp Arg Leu Ala Arg Asp Pro Leu Val Ala Asp Val Thr Asp
     50                  55                  60

Pro His Ala Leu Ala Ser Ala Val Asp Ser Leu Ala Pro Gln His Arg
 65                  70                  75                  80

Pro Gly Val Leu Val Asn Gly Val Gly Gly Asp Thr Arg Ala Arg Ser
                 85                  90                  95

Val Thr Glu Leu Thr Glu Ala Asp Leu Gln Glu Ala Val Thr His Asn
            100                 105                 110

Leu Ala Ser Val Phe Thr Met Thr Arg Leu Cys Val Pro Ala Met Val
        115                 120                 125

Ala Ala Gly Trp Gly Arg Val Val Asn Leu Ala Ser Val Ala Gly Arg
    130                 135                 140

Thr Tyr Thr Arg Phe Ser Asn Ala Ala Tyr Val Ala Ala Lys Ala Gly
145                 150                 155                 160

Val Ile Gly Phe Thr Lys Gln Cys Ala Tyr Glu Leu Ala Pro His Gly
                165                 170                 175

Val Thr Val Asn Ala Val Ala His Gly Val Ile Gly Thr Glu Arg Ile
            180                 185                 190

Arg Arg Ala Trp Glu Asp Lys Pro Pro Gln Trp Thr Ala Asp Arg Val
        195                 200                 205

Ser His Ile Pro Ala Gly Arg Phe Gly Ser Val Ala Glu Ala Ala Gly
    210                 215                 220

Met Val Cys His Leu Cys Gly Glu Asp Ala Gly Tyr Thr Thr Gly Thr
225                 230                 235                 240

Val Val Asp Val Asn Gly Gly Leu His Ile
                245                 250


<210> SEQ ID NO 11
<211> LENGTH: 390
<212> TYPE: PRT
<213> ORGANISM: Streptomyces parvulus Tu4055

<400> SEQUENCE: 11
```

-continued

```
Met Ile Arg Arg Val Arg Leu His Thr Ala Val Val Pro Met Ala Ala
  1               5                  10                  15

Ala Phe Asp His Ala Thr Arg Ser Arg Arg Ser Ala Ala Ser Leu Leu
             20                  25                  30

Val Glu Ile Glu Leu Ala Gly Thr Arg Gly Trp Gly Glu Gly Ala Pro
        35                  40                  45

Arg Asp Tyr Val Thr Gly Glu Thr Leu Asp Gly Ala Val Arg Ala Val
    50                  55                  60

Gln Ala Cys Asp Pro Gly Glu Leu Ala Glu Arg Ile Glu Trp Arg Asp
65                  70                  75                  80

Phe Glu Ser Ala Val Ala Ser Ile Ala Gln Leu Pro Leu Thr Gly Leu
                 85                  90                  95

Val Asp Gly Ser Ser Ala Ala Ala Ala Val Glu Ile Ala Leu Leu Asp
            100                 105                 110

Ala Val Cys Arg His Phe Ala Arg Pro Leu Ala Asp Val Leu Arg Val
        115                 120                 125

Leu Ala Pro Pro Ala Arg Ser Arg Arg Asp Gly Pro Thr Ser Val Ser
    130                 135                 140

Leu Val Ile His Leu Ser Arg Asp Val Ala Thr Val Leu Asp Ala Leu
145                 150                 155                 160

Thr Pro Arg Ala Leu Ala Ala Leu Arg His Val Lys Ile Lys Val Ala
                165                 170                 175

Asp Pro Ala Gly Ala Val Asp Arg Leu Thr Ala Ala Gln Asp Arg Leu
            180                 185                 190

Pro Ala Asp Thr Arg Val Ser Leu Asp Val Asn Gly Ala Trp Thr Ala
        195                 200                 205

Glu Glu Ala Glu Lys Val Ala Gly Glu Leu Asp Gly Val Gly Trp Val
    210                 215                 220

Glu Glu Pro Leu Pro Pro Arg Ser Trp Pro Glu Leu Gly Arg Leu Arg
225                 230                 235                 240

Arg Ala Thr Gly Leu Pro Val Met Leu Asp Glu Ser Cys Thr Gly Pro
                245                 250                 255

Ala Asp Leu His Ala Ala Ala Thr Ser Gly Ala Ala Ser His Ile Asn
            260                 265                 270

Val Arg Leu Ser Lys Cys Gly Gly Phe Leu Ala Ala Ala Arg Leu Ala
        275                 280                 285

Leu Arg Ala Asp Glu Leu Gly Val Gly Cys Gln Leu Gly Val His Val
    290                 295                 300

Ala Glu Val Gly Pro Leu Trp Ala Ala Gly Arg Thr Leu Ala Thr Ala
305                 310                 315                 320

Trp Asp Leu Trp Gln Thr Val Glu Ala Gly Arg Ala Asp Glu Trp Phe
                325                 330                 335

Pro Val Pro Leu Thr Thr Pro Ala Phe Thr Val Asp Arg Ser Leu His
            340                 345                 350

Arg Val Glu Pro Leu Thr Gly Pro Gly Thr Gly Ile Glu Pro Thr Glu
        355                 360                 365

Glu Leu Leu Arg His Thr Arg Cys Ala Ala Thr Trp Glu Ser Gly Gly
    370                 375                 380

Gly Trp Arg Arg Asn Thr
385                 390
```

<210> SEQ ID NO 12
<211> LENGTH: 272

-continued

<212> TYPE: PRT
<213> ORGANISM: Streptomyces parvulus Tu4055

<400> SEQUENCE: 12

Met Pro Thr Thr Ser Met Leu Thr Ala Ala Asp Gly Thr Gly Leu Thr
1 5 10 15

Leu His His Trp Thr Thr Pro Gly Ala Thr Ser Ala Val Phe Tyr Leu
20 25 30

His Gly Ile Gln Ser His Ala Gly Trp Leu Phe Glu Thr Gly Pro Glu
35 40 45

Leu Asn Ala Arg Gly Ile Asp Val Tyr Ala Leu Asp Arg Arg Gly Ser
50 55 60

Gly Arg Ser Glu Gly Pro Arg Gly His Leu Pro Ser Ala Asp Leu Val
65 70 75 80

Leu Asp Asp Tyr Ala Arg Ala Leu Asp Ala Val Thr Ala Glu Val Gly
85 90 95

Gly Ala Gly Pro Val Ala Leu Gly Gln Ser Leu Gly Gly Ser Val Leu
100 105 110

Ala Ala Leu Trp Cys Thr Arg Asp Leu Pro Val Arg Arg Leu Val Leu
115 120 125

Cys Ala Pro Ala Leu Gly Gln Gln Arg Ala Arg His Thr Ala Asp Thr
130 135 140

Leu Ala Glu Arg Arg Ala Leu Thr Gly Ser Gly Leu Arg Pro Val Gly
145 150 155 160

Leu Ala Asp Gly Asp Tyr Thr Asp Leu Pro Arg Tyr Arg Glu Phe Leu
165 170 175

Thr Gly Asp His Leu Met Leu Arg Glu Val Thr Ser Ala Thr Gln Ala
180 185 190

Thr Leu Val His Leu Glu Asp His Tyr Ala Arg Gly Ala Pro Arg Thr
195 200 205

Arg Leu Pro Val Asp Leu Ala Leu Pro Thr His Asp Pro Ile Ile Asp
210 215 220

Leu Ser Ala Ala Arg Ala Met Leu Arg Arg Leu Thr Ser Ala Val His
225 230 235 240

Glu Glu Val Phe Ala Thr Asp Arg His Tyr Val Glu Phe Thr Ser Ala
245 250 255

Arg Thr Ala Tyr Trp Asp Trp Leu Ala Thr Arg Leu Lys Glu Glu Ala
260 265 270

<210> SEQ ID NO 13
<211> LENGTH: 539
<212> TYPE: PRT
<213> ORGANISM: Streptomyces parvulus Tu4055

<400> SEQUENCE: 13

Met Lys Val Phe His Ala Leu Ala Asp Ala Leu Thr Ala His Gly Val
1 5 10 15

Asp Thr Val Phe Gly Leu Met Gly Asn Ala Asn Leu Leu Tyr Leu Pro
20 25 30

Ala Phe Ala Asp Ala Gly Gly Arg Phe Val Ala Val Ala His Glu Ala
35 40 45

Gly Ala Val Ala Met Ala Asp Gly Arg Ala Arg Met Cys Gly Gly Ile
50 55 60

Gly Val Ala Ser Val Thr His Gly Pro Ala Phe Thr Asn Ala Leu Thr
65 70 75 80

-continued

```
Pro Leu Val Glu Ala Ala Arg Ser His Ser Gln Val Leu Leu Ile Thr
                85                  90                  95

Gly Asp Pro Pro Pro Val Pro Thr His Phe His His Phe Asp Ile Ala
            100                 105                 110

Thr Val Ala Ala Ala Ala Gly Ala Gly Tyr Glu Arg Val His Arg Pro
        115                 120                 125

Ala Ser Leu Val Ala Asp Leu Asn Arg Ala Val Gln Arg Ile Val Ala
    130                 135                 140

Glu Arg Arg Pro Val Val Leu Asn Val Pro Ile Asp Leu Met Gln Ala
145                 150                 155                 160

Glu Ala Gly Glu Gln Ala Pro Val Thr Leu Pro Val Ala Pro Gly Pro
                165                 170                 175

Leu Ala Ala Pro Glu Ala Glu Ala Leu Asp Gly Ala Leu Gly Leu Ile
            180                 185                 190

Gly Ser Ala Lys Arg Pro Leu Val Leu Ala Gly His Gly Ala Ala Val
        195                 200                 205

Ala Gly Ala Arg Glu Ala Leu Val Glu Leu Ala Asp Arg Thr Gly Ala
    210                 215                 220

Ala Leu Ala Thr Thr Val Leu Gly Lys Glu Met Phe Ala Gly His Pro
225                 230                 235                 240

Arg Asp Val Gly Ile Phe Gly Ser Leu Ala His Ser Val Ala Ser Thr
                245                 250                 255

Val Ile Ala Glu Ser Asp Cys Val Ile Ala Phe Gly Ala Ser Leu Asn
            260                 265                 270

Met Trp Thr Val Leu Asn Gly Glu Leu Leu Arg Gly Lys Arg Val Val
        275                 280                 285

His Val Asp Thr Asp Pro Ala Arg Phe Gly Ser Tyr Ser Pro Val Asp
    290                 295                 300

Glu Pro Val Ala Gly Asp Ala Arg Arg Thr Ala Glu Thr Met Asn Val
305                 310                 315                 320

Leu Leu Asp Gln Ala Gly Val Thr Ala Ala Asn Gly Ala Trp Ala Glu
                325                 330                 335

Arg Val Ala Gly Gln Leu Ala Gly Phe Ser Pro Gln Asp Asp Val Asp
            340                 345                 350

Asp Arg Ser Gly Ala Glu Thr Val Asp Ile Arg Thr Ala Met Ile Arg
        355                 360                 365

Leu Asp Arg Ile Leu Pro Ala Glu Arg Ser Val Val Ser Asp Ile Gly
    370                 375                 380

Arg Phe Asp Val Gly Val Trp Pro Tyr Leu Arg Val Ala Asp Pro Leu
385                 390                 395                 400

His Phe Thr Val Met Gly Gly Phe Gly Ser Ile Gly Leu Gly Val Ala
                405                 410                 415

Gly Ala Ile Gly Ala Ala Thr Ala Gly Thr Gly Arg Pro Val Val Ala
            420                 425                 430

Ala Val Gly Asp Gly Gly Phe Met Met His Leu Ser Glu Phe Thr Thr
        435                 440                 445

Ala Val Arg Tyr Arg Leu Pro Leu Val Val Val Val Leu Asn Asp Gly
    450                 455                 460

Ala Tyr Gly Ala Glu His Tyr Lys Leu Arg Asn His Gly Tyr Asp Pro
465                 470                 475                 480

Ala Tyr Ser Ala Phe Ala Trp Pro Asp Leu Ala Gly Leu Ala Thr Ala
                485                 490                 495

Met Gly Ala Arg Ala Leu Thr Val Arg Lys Ala Glu Glu Leu Asp Ala
```

-continued

```
            500                 505                 510

Val Gly Asp Leu Leu Ser Thr Leu Glu Gly Pro Leu Leu Val Asp Val
        515                 520                 525

Arg Leu Asp Pro Asp Val Asn Leu Val Arg Tyr
    530                 535


<210> SEQ ID NO 14
<211> LENGTH: 683
<212> TYPE: PRT
<213> ORGANISM: Streptomyces parvulus Tu4055

<400> SEQUENCE: 14

Met Arg Gly Ala Arg Glu Asn Ser Met Thr Arg Ala Gly Pro Leu Glu
  1               5                  10                  15

Gly Ile Ala Val Leu Met Ala Gly Arg Ser Thr Pro Ala Ala Leu Leu
             20                  25                  30

Gly Arg Leu Leu Ala Asp Leu Gly Ala Arg Val Val Thr Leu Cys Arg
         35                  40                  45

Ser Pro Asp His Gly Gly Pro Phe Glu Arg Trp Leu His Ser Ala Ala
     50                  55                  60

Gln Ser Ala Ser Gly Trp Asp Gln Ala Ser Arg Leu Leu Gln Thr Ala
 65                  70                  75                  80

Asp Val Leu Val Cys Asp Ala Glu Gly Asp Glu Arg Leu Ala Ala Leu
                 85                  90                  95

Gly Leu Gly Ala Pro Glu Leu Pro His Arg Ser Pro Glu Leu Val Ala
            100                 105                 110

Val Arg Leu Ser Ala Phe Gly Leu Thr Gly Pro Leu Arg Asp Ala Pro
        115                 120                 125

Ala Thr Glu Arg Thr Leu Gln Ala Leu Ala Gly Leu Thr Ser Ala Thr
    130                 135                 140

Gly Thr Glu Gly Glu Pro Ser Val Leu Ser Val Val Gly Leu Ala Ser
145                 150                 155                 160

Arg Thr Ala Ala Leu Ser Gly Leu Ile Ala Val Val Ala Gly Leu Ile
                165                 170                 175

Gly Arg Glu Arg Gly Gly Gly Gly Asp Tyr Leu Asp Ile Ala Glu Phe
            180                 185                 190

Asp Ser Leu Phe Thr Leu Thr Gly Thr Leu Leu Pro Ser Val Ala Leu
        195                 200                 205

Ala Gly Arg Pro Pro Arg Arg Thr Gly Asn Arg His Gly Met Ala Ala
    210                 215                 220

Pro Trp Asn Ser Tyr Thr Cys Gln Asp Ala Pro Val Val Ile Cys Thr
225                 230                 235                 240

Met Gly Glu Pro Ile Trp His Arg Leu Thr Ala Val Leu Gly Arg Arg
                245                 250                 255

Asp Leu Pro Asp Asp Pro Arg Phe Ala Asp Thr Ala Ala Arg Val Arg
            260                 265                 270

Asn Ala Asp Glu Leu Asp Glu Ile Leu Gly Lys Trp Thr Ala Gly Gln
        275                 280                 285

Arg Ala Val Asp Val Val Thr Ala Leu Arg Ala Ala Gly Ile Pro Cys
    290                 295                 300

Ala Gln Val Ala Ala Pro Glu Glu Val Arg Asp Gly Ala Ala Ala Arg
305                 310                 315                 320

Arg Arg Gly Leu Val Thr Asp Pro Ser Gly Thr Pro Gly Ser Pro Leu
                325                 330                 335
```

-continued

Arg Ser Leu Ile Pro Ala Val Thr Asp Gly Pro Met Pro Arg Gln Gly
340 345 350

Gly Leu Trp Glu Pro Ile Ala Arg Gly Thr Pro Pro Leu Arg Gly Val
355 360 365

Arg Leu Leu Glu Val Gly Ser Tyr Thr Ala Gly Pro His Ala Gly Arg
370 375 380

Leu Leu Ala Gln Leu Gly Ala Asp Val Leu Lys Val Glu Pro Pro His
385 390 395 400

Gly Glu Gly Ser Arg Arg Leu Ala Gln Gln Val Ala Gly Val Gly Tyr
405 410 415

Leu Tyr Tyr Val Asn Asn Ala Gly Lys Arg Ser Cys Arg Leu Asp Leu
420 425 430

Ala Asp Ala Glu Asp Arg Ala Gly Phe Glu Arg Leu Leu Ala Gly Cys
435 440 445

Asp Ile Val Leu Thr Asn Leu Ala Ala Asp Thr Leu Thr Ala Gln Gly
450 455 460

Leu Ala Pro Asp Gln Ile Leu Ser Arg His Gly Val Val His Cys Thr
465 470 475 480

Val Thr Gly His Gly Leu Ala Ala Ala Asp Arg Ser Val Asp Thr Val
485 490 495

Ile Gln Ala Glu Ser Gly Ile Met Arg Leu Val Gly Gly Pro Gly Ala
500 505 510

Gly Leu Arg Thr Pro Val Ser Ser Ala Asp Val Leu Gly Ala Tyr Leu
515 520 525

Ala Ala Ala Ala Ala Val Val Ser Thr Tyr Val Arg Leu Arg Thr Glu
530 535 540

His Gly Cys Ala Ala Asp Val Ala Leu Phe Asp Ser Ala Val Trp Leu
545 550 555 560

Thr Gln Asp Arg Trp Phe Thr Ala Pro Pro Ala Arg Ala Pro His Leu
565 570 575

Val Arg Ala Ala Asp Gly Thr Val Leu Val Asp Ala Glu Gly Pro Pro
580 585 590

Pro Arg Ala Glu Gly Pro Val Ala Ala Val Leu Asp Ala Ala Ala Ala
595 600 605

Val Gly Val Pro Ala Ala Pro Leu His Asp Leu Thr Arg Ala Val Arg
610 615 620

His Pro Gln Val Leu Ala Arg Arg Met Ala Val Ala Arg Asp Cys Ala
625 630 635 640

Gly Thr Thr Val Leu Ile Thr Gly Asn His Leu Arg Ser Leu Leu Arg
645 650 655

Glu Asp Pro Pro Pro Thr Cys Ala Pro Val Asp Gln Asn Asp Pro Val
660 665 670

Trp Leu Gln Pro Ala Pro Thr Glu Gly Gln Gln
675 680

<210> SEQ ID NO 15
<211> LENGTH: 426
<212> TYPE: PRT
<213> ORGANISM: Streptomyces parvulus Tu4055

<400> SEQUENCE: 15

Met Thr Thr Arg Arg Arg Gln Arg His Pro Ala Leu Ser Pro Ser Cys
1 5 10 15

Pro Ser Val Pro Phe Pro Leu Leu Glu Thr Glu Phe Val Leu Met Pro
20 25 30

-continued

```
Ser Phe Pro Val Arg Arg Ser Val Pro Asp Thr Pro Pro Ala Glu His
        35                  40                  45

Leu Glu Leu Leu Lys Glu Ser Gly Gly Val Cys Pro Phe Thr Met Glu
    50                  55                  60

Asp Gly Arg Pro Ala Trp Leu Ala Ala Ser His Asp Ala Val Arg Ser
65                  70                  75                  80

Leu Leu Ala Asp Arg Arg Ile Ser Asn Asn Pro Ala Lys Thr Pro Pro
                85                  90                  95

Phe Ser Gln Arg Glu Ala Leu Gln Lys Glu Arg Gly Gln Phe Ser Arg
            100                 105                 110

His Leu Phe Asn Met Asp Ser Pro Glu His Asp Val Ala Arg Arg Met
        115                 120                 125

Ile Ala Glu Asp Phe Thr Pro Arg His Ala Glu Ala Val Arg Pro Tyr
    130                 135                 140

Phe Glu Glu Val Phe Gly Glu Ile Val Asp Glu Val Val His Lys Gly
145                 150                 155                 160

Pro Pro Ala Glu Met Ile Glu Ser Phe Ala Phe Pro Val Ala Thr Arg
                165                 170                 175

Thr Ile Cys Lys Val Leu Asp Ile Pro Glu Asp Asp Cys Glu Tyr Phe
            180                 185                 190

Gln Lys Arg Thr Glu Gln Ile Ile Glu Met Asp Arg Gly Glu Glu Asn
        195                 200                 205

Leu Glu Ala Val Val Glu Leu Arg Arg Tyr Val Asp Ser Val Met Gln
    210                 215                 220

Gln Arg Thr Arg Lys Pro Gly Asp Asp Leu Leu Ser Arg Met Ile Val
225                 230                 235                 240

Lys Ala Lys Ala Ser Lys Glu Ile Glu Leu Ser Asp Ala Asp Leu Val
                245                 250                 255

Asp Asn Ala Met Phe Leu Leu Val Ala Gly His Glu Pro Ser Ala Asn
            260                 265                 270

Met Leu Gly Leu Gly Val Leu Ala Leu Ala Glu Phe Pro Asp Val Ala
        275                 280                 285

Glu Glu Leu Arg Ala Glu Pro His Leu Trp Pro Gly Ala Ile Asp Glu
    290                 295                 300

Met Leu Arg Tyr Tyr Thr Ile Ala Arg Ala Thr Lys Arg Val Ala Ala
305                 310                 315                 320

Ala Asp Ile Glu Tyr Glu Gly His Thr Ile Lys Glu Gly Asp Ala Val
                325                 330                 335

Ile Val Leu Leu Asp Thr Ser Asn Arg Asp Pro Lys Val His Ala Glu
            340                 345                 350

Pro Asn Arg Leu Asp Ile His Arg Ser Ala Gly Asn His Leu Ala Phe
        355                 360                 365

Ser His Gly Pro His Gln Cys Leu Gly Lys His Leu Val Arg Val Gln
    370                 375                 380

Leu Glu Ile Ala Leu Arg Ala Val Ala Glu Arg Leu Pro Gly Leu Arg
385                 390                 395                 400

Leu Asp Ile Ala Lys Glu Asp Ile Pro Phe Arg Gly Asp Ala Leu Ser
                405                 410                 415

Tyr Gly Pro Arg Gln Leu Arg Val Thr Trp
            420                 425
```

<210> SEQ ID NO 16
<211> LENGTH: 454

-continued

<212> TYPE: PRT
<213> ORGANISM: Streptomyces parvulus Tu4055

<400> SEQUENCE: 16

```
Met Glu Lys Thr Asp Val Asp Arg Leu Arg Thr Leu Asp Arg Glu His
  1               5                  10                  15

Met Trp Tyr Pro Trp Thr Pro Met Thr Glu Trp Met Ala Arg Asp Gln
             20                  25                  30

Leu Val Val Glu Arg Ala Glu Gly Cys Trp Leu Ile Asp Ala Asp Gly
         35                  40                  45

Lys Arg Tyr Leu Asp Gly Arg Ser Ser Met Gly Met Asn Leu His Gly
     50                  55                  60

His Gly Arg Ser Glu Ile Val Glu Ala Leu Val Ala Gln Ala Arg Lys
 65                  70                  75                  80

Ala Gly Glu Thr Thr Leu Tyr Arg Val Ser His Pro Ala Ala Val Glu
                 85                  90                  95

Leu Ala Ala Arg Leu Ala Ser Met Ala Pro Ala Gly Leu Gln Arg Val
            100                 105                 110

Phe Phe Ala Glu Ser Gly Ser Thr Ala Val Glu Thr Ala Leu Lys Ala
        115                 120                 125

Ala Tyr Ala Tyr Trp Val Ala Lys Gly Glu Pro Gln Arg Ser Thr Phe
    130                 135                 140

Val Ser Met Glu Gly Gly Tyr His Gly Glu Thr Leu Gly Thr Val Ser
145                 150                 155                 160

Leu Arg Gly Thr Asn Gly Glu Gln Val Asp Met Ile Arg Lys Thr Tyr
                165                 170                 175

Glu Pro Leu Leu Phe Pro Ser Leu Ser Phe His Gln Pro His Cys Tyr
            180                 185                 190

Arg Cys Pro Val Gly Gln Ser Ser Asp Ser Asp Cys Gly Leu Glu Cys
        195                 200                 205

Thr Asp Ser Leu Glu Asn Leu Leu Thr Arg Glu Lys Gly Arg Ile Ala
    210                 215                 220

Ala Val Ile Val Glu Pro Arg Val Gln Ala Leu Ala Gly Val Ile Thr
225                 230                 235                 240

Ala Pro Glu Gly His Leu Ala Lys Val Ala Glu Ile Thr Arg Arg His
                245                 250                 255

Gly Val Leu Leu Ile Val Asp Glu Val Leu Thr Gly Trp Ala Arg Thr
            260                 265                 270

Gly Pro Thr Phe Ser Cys Glu Ala Glu Gly Val Thr Pro Asp Leu Met
        275                 280                 285

Thr Val Gly Lys Ala Leu Thr Gly Gly Tyr Leu Pro Leu Ser Ala Thr
    290                 295                 300

Leu Ala Thr Glu Glu Ile Phe Gly Ala Phe Arg Glu Ser Val Phe Leu
305                 310                 315                 320

Ser Gly Ser Thr Tyr Ser Gly Tyr Ala Leu Gly Ala Ala Val Ala Leu
                325                 330                 335

Ala Ser Leu Asp Leu Phe Glu Lys Glu Asp Val Pro Ala Arg Ala Lys
            340                 345                 350

Ala Leu Ala Asp Val Leu Thr Thr Ala Leu Glu Pro Phe Arg Ala Leu
        355                 360                 365

Thr His Val Gly Asp Val Arg Gln Leu Gly Leu Ile Ala Gly Val Glu
    370                 375                 380

Leu Val Ala Asp Arg Glu Thr Arg Ala Pro Tyr Pro Pro Gln Glu Arg
385                 390                 395                 400
```

-continued

```
Val Val Asp Arg Ile Cys Thr Leu Ala Arg Asp Asn Gly Val Leu Val
                405                 410                 415

Asn Ala Val Pro Gly Asp Val Ile Thr Met Leu Pro Ser Pro Ser Met
            420                 425                 430

Ser Pro Asp Asp Leu Arg Phe Leu Thr Gly Thr Leu Tyr Thr Ala Val
        435                 440                 445

Arg Glu Val Thr Glu Glu
    450


<210> SEQ ID NO 17
<211> LENGTH: 326
<212> TYPE: PRT
<213> ORGANISM: Streptomyces parvulus Tu4055

<400> SEQUENCE: 17

Met Arg Ala Ala Val Ile Arg Ala Trp Gly Gly Pro Glu Arg Leu Thr
  1               5                  10                  15

Leu Asp Arg Val Glu Arg Pro Ser Pro Pro Pro Gly Trp Ile Ala Val
             20                  25                  30

Arg Val Glu Ala Cys Ala Leu Asn His Leu Asp Ile His Val Arg Asn
         35                  40                  45

Gly Leu Pro Gly Val Arg Leu Glu Leu Pro His Val Ser Gly Gly Asp
     50                  55                  60

Val Val Gly Val Val Glu Gln Ala Thr Asp Glu Ala Gly Glu Arg Leu
 65                  70                  75                  80

Leu Gly Ser Arg Val Leu Leu Asp Pro Met Ile Gly Arg Gly Ile Leu
                 85                  90                  95

Gly Glu His Tyr Trp Gly Gly Leu Ala Glu Tyr Val Val Ala Pro Ala
            100                 105                 110

His Asn Ala Leu Pro Val Pro Asp Gln Asp Ala Asp Pro Ala Arg Tyr
        115                 120                 125

Ala Ala Leu Pro Ile Ser Tyr Gly Thr Ala Gln Arg Met Leu Phe Ser
    130                 135                 140

Arg Ala Arg Leu Arg Pro Gly Glu Ser Val Leu Leu Phe Gly Ala Thr
145                 150                 155                 160

Gly Gly Val Gly Val Ala Cys Ala Gln Leu Ala Leu Arg Ala Gly Ala
                165                 170                 175

Arg Ile Ile Ala Cys Ser Gly Ser Pro Ala Lys Leu Ala Arg Leu Arg
            180                 185                 190

Arg Leu Gly Val Ile Asp Thr Ile Asp Thr Gly Thr Glu Asp Val Arg
        195                 200                 205

Arg Arg Val Arg Glu Leu Thr Asp Gly Gly Ala Asp Leu Val Val Asp
    210                 215                 220

Tyr Gln Gly Lys Asp Thr Trp Pro Val Ser Leu Arg Ser Ala Arg Ala
225                 230                 235                 240

Gly Gly Arg Ile Val Thr Cys Gly Ala Thr Thr Gly Tyr Glu Ala Thr
                245                 250                 255

Thr Asp Leu Arg Tyr Val Trp Ser Arg Gln Leu Asp Ile Leu Gly Ser
            260                 265                 270

Asn Ala Trp His Arg Asp Asp Leu His Thr Leu Val Asp Leu Val Ala
        275                 280                 285

Thr Asp Ala Leu Glu Pro Val Val His Ala Asp Phe Pro Leu Ser Arg
    290                 295                 300

Ala Pro Glu Ala Val Ala Glu Leu Glu Glu Arg Arg Ala Phe Gly Lys
```

-continued 305 310 315 320

Val Val Ile Arg Thr Ala
325

<210> SEQ ID NO 18
<211> LENGTH: 556
<212> TYPE: PRT
<213> ORGANISM: Streptomyces parvulus Tu4055

<400> SEQUENCE: 18

Met Thr Gly Asn Thr Thr Ser Ala Ala Phe Leu Arg Arg Thr Gln Asn
1 5 10 15

Ala Leu Ala Met Gln Arg Lys Ile Cys Ala Gln Pro Glu Glu Thr Ala
20 25 30

Glu Arg Val Phe Ser Asp Ile Leu Ser Val Ser Arg Asp Thr Gly Phe
35 40 45

Gly Arg Glu His Gly Leu Ala Gly Val Arg Thr Arg Gln Glu Trp Arg
50 55 60

Arg Ala Val Pro Ile Arg Thr Tyr Asp Glu Leu Ala Pro Tyr Val Glu
65 70 75 80

Arg Gln Phe Ser Gly Glu Arg Arg Val Leu Thr Thr Asp Asp Pro Arg
85 90 95

Ala Phe Leu Arg Thr Ser Gly Ser Thr Gly Arg Ala Lys Leu Val Pro
100 105 110

Thr Thr Asp His Trp Arg Arg Val Tyr Arg Gly Pro Ala Leu Tyr Ala
115 120 125

Gln Trp Gly Leu Tyr Phe Glu Gln Ile Gly Thr His Arg Leu Thr Gly
130 135 140

Asp Glu Val Leu Asp Leu Ser Trp Glu Pro Gly Pro Ile Arg His Arg
145 150 155 160

Leu Arg Gly Phe Pro Val Tyr Ser Ile Thr Glu Arg Pro Val Ser Asp
165 170 175

Asp Pro Asp Asp Trp Asn Pro Pro Trp Arg His Ala Arg Trp Phe Thr
180 185 190

Arg Asp Ala Gly Ala Ala Thr Met Ala Asp Leu Leu Tyr Gly Lys Leu
195 200 205

Leu Arg Leu Ala Ala His Asp Leu Arg Leu Ile Val Ser Val Asn Pro
210 215 220

Ser Lys Ile Val Leu Leu Ala Glu Thr Leu Lys Glu Asn Ala Glu Arg
225 230 235 240

Leu Ile Gln Asp Leu His Asp Gly His Gly Thr Asp Arg Ala Ala Arg
245 250 255

Pro Asp Phe Leu Arg Arg Leu Thr Ala Ala Phe Asp Arg Thr Gly Gly
260 265 270

Arg Pro Leu Leu Thr Asp Leu Trp Pro Gly Leu Arg Leu Leu Val Cys
275 280 285

Trp Asn Ser Ala Ser Ala Ala Leu Tyr Gly Pro Trp Leu Ser Arg Leu
290 295 300

Ala Thr Gly Val Ala Ala Leu Pro Phe Ser Thr Thr Gly Thr Glu Gly
305 310 315 320

Ile Val Thr Leu Pro Val Asp Asp His Leu Ser Ala Gly Pro Leu Ala
325 330 335

Val Asp Gln Gly His Phe Glu Phe Val Pro Trp Gln Asp Leu Asp Asp
340 345 350

-continued

Gly Ser Pro Leu Pro Glu Asp Thr Pro Thr Leu Gly Tyr Asp Glu Leu
355 360 365

Glu Leu Gly Ala Asp Tyr Arg Leu Val Met Ser Gln Ala Asn Gly Leu
370 375 380

Tyr Arg Tyr Asp Val Gly Asp Val Tyr Arg Val Val Gly Ala Val Gly
385 390 395 400

Ala Thr Pro Arg Leu Glu Phe Leu Gly Arg Ala Gly Phe Gln Ser Ser
405 410 415

Phe Thr Gly Glu Lys Leu Thr Glu Ser Asp Val His Thr Ala Val Met
420 425 430

Arg Val Leu Gly Ser Glu Arg Thr Asp His Pro His Phe Ser Gly Ile
435 440 445

Pro Val Trp Asp Thr Pro Pro His Tyr Leu Val Ala Ile Glu Trp Ala
450 455 460

Asp Ala His Gly Thr Leu Asn Val Gln Asp Thr Ala Arg Arg Ile Asp
465 470 475 480

Ala Thr Leu Gln Glu Val Asn Val Glu Tyr Ala Asp Lys Arg Arg Ser
485 490 495

Gly Arg Leu Arg Pro Leu Gln Ile Leu Pro Leu Val Pro Gly Ala Phe
500 505 510

Gly Gln Ile Ala Glu Arg Arg Phe Arg Gln Gly Thr Ala Gly Ala Gln
515 520 525

Ile Lys His His Trp Leu Gln Lys Asp Ser Ala Phe Leu Asp Thr Leu
530 535 540

Arg Asp Leu Asp Leu Val Arg Ala Arg Pro Gly Thr
545 550 555

<210> SEQ ID NO 19
<211> LENGTH: 305
<212> TYPE: PRT
<213> ORGANISM: Streptomyces parvulus Tu4055

<400> SEQUENCE: 19

Met Arg Ile Gly Phe Ala Ala Pro Met Ser Gly Pro Trp Ala Thr Pro
1 5 10 15

Asp Thr Ala Val His Val Ala Arg Thr Ala Glu Gln Leu Gly Tyr Ala
20 25 30

Ser Leu Trp Thr Tyr Gln Arg Val Leu Gly Ala Pro Asp Asp Ser Trp
35 40 45

Gly Glu Ala Asn Arg Ser Val His Asp Pro Leu Thr Thr Leu Ala Phe
50 55 60

Leu Ala Ala His Thr Thr Gly Ile Arg Leu Gly Val Ala Val Leu Ile
65 70 75 80

Met Pro Leu His Thr Pro Ala Val Leu Ala Lys Gln Leu Thr Thr Leu
85 90 95

Asp Leu Leu Ser Gly Gly Arg Leu Asp Val Gly Leu Gly Asn Gly Trp
100 105 110

Ala Ala Glu Glu Tyr Ala Ala Ala Gly Val Thr Pro Thr Gly Leu Ser
115 120 125

Arg Arg Ala Glu Asp Phe Leu Ala Cys Leu Arg Ala Leu Trp Gly Glu
130 135 140

Gln Thr Val Val Glu His Asp Gly Pro Phe Tyr Arg Val Pro Pro Ala
145 150 155 160

Arg Phe Asp Pro Lys Pro Ala Gln Ser Pro His Pro Pro Leu Leu Leu
165 170 175

-continued

```
Gly Gly Ala Ala Pro Gly Ala Leu Arg Arg Ala Gly Arg Leu Cys Asp
            180                 185                 190

Gly Trp Ile Ala Ser Ser Lys Ala Gly Pro Ala Ala Ile Arg Asp Ala
        195                 200                 205

Ile Thr Val Val Arg Asp Ser Ala Glu Arg Thr Gly Arg Asp Pro Ala
    210                 215                 220

Thr Leu Arg Phe Val Cys Arg Ala Pro Val Arg Leu Arg Thr Arg Ser
225                 230                 235                 240

Ala Pro Asn Glu Pro Pro Leu Thr Gly Thr Ala Glu Thr Ile Arg Ala
                245                 250                 255

Asp Leu Ala Ala Leu Ala Asp Thr Gly Leu Thr Glu Ile Phe Leu Asp
            260                 265                 270

Pro Asn Phe Asp Pro Glu Ile Gly Ser Pro Asp Ala Pro Thr Gly Asp
        275                 280                 285

Val Arg His Arg Val Asp Leu Leu Leu His Glu Leu Ala Pro Ala Asn
    290                 295                 300

Trp
305


<210> SEQ ID NO 20
<211> LENGTH: 248
<212> TYPE: PRT
<213> ORGANISM: Streptomyces parvulus Tu4055

<400> SEQUENCE: 20

Met Leu Ile Ala Arg Ala Ala Val Gly Glu Asp Arg Thr Tyr Ala Arg
  1               5                  10                  15

Val Asp Thr Asp Thr Gly Leu Ile His Leu Leu Ala Gly Thr Pro Tyr
             20                  25                  30

Asp Glu Ile Arg Pro Thr Gly Glu Thr Arg Pro Leu Ala Glu Ala Arg
         35                  40                  45

Leu Leu Ala Pro Val Glu Pro Ser Lys Val Leu Val Ala Gly Arg Asn
     50                  55                  60

Tyr Gly Asp Val Val Thr Pro Asp Leu Val Val Phe Met Lys Pro Ser
 65                  70                  75                  80

Thr Ser Val Val Gly Pro Arg Ser Thr Val Leu Leu Pro Ala Glu Ala
                 85                  90                  95

Lys Gln Val Arg Tyr Glu Gly Glu Leu Ala Val Val Ile Gly Arg Arg
            100                 105                 110

Cys Lys Asp Val Pro Glu Asp Thr Ala Asp Gln Ala Val Phe Gly Tyr
        115                 120                 125

Thr Cys Ala Asn Asp Val Thr Ala Trp Asp Val Gly Glu Pro Lys Gly
    130                 135                 140

His Trp Thr Lys Ala Lys Ser Phe Asp Thr Phe Cys Pro Leu Gly Pro
145                 150                 155                 160

Trp Ile Arg Thr Asp Leu Asp Pro Ala Asp Leu Val Leu Arg Thr Thr
                165                 170                 175

Val Asn Gly Thr Leu Arg Gln Asp Gly Ser Thr Lys Glu Met Asn Arg
            180                 185                 190

Asn Val Arg Ala Leu Val Ser Arg Cys Ser Ser Leu Met Thr Leu Leu
        195                 200                 205

Pro Gly Asp Val Ile Leu Thr Gly Thr Pro Ala Gly Ala Gly Val Leu
    210                 215                 220

Arg Pro Gly Asp Glu Val Val Val Glu Ile Asp Gly Ile Gly Ser Leu
```

-continued

```
225                 230                 235                 240

Ala Asn Pro Ile Gly Val Ala Lys
                245


<210> SEQ ID NO 21
<211> LENGTH: 675
<212> TYPE: PRT
<213> ORGANISM: Streptomyces parvulus Tu4055

<400> SEQUENCE: 21

Met Ser Val Ile Arg Pro Thr Ala Glu Thr Glu Arg Ala Val Val Val
  1               5                  10                  15

Val Pro Ala Gly Thr Thr Cys Ala Asp Ala Val Thr Ala Ala Lys Leu
             20                  25                  30

Pro Arg Asn Gly Pro Asn Ala Ile Val Val Val Arg Asp Pro Ser Gly
         35                  40                  45

Ala Leu Arg Asp Leu Asp Trp Thr Pro Asp Ser Asp Val Glu Val Glu
     50                  55                  60

Ala Val Ala Leu Ser Ser Glu Asp Gly Leu Thr Val Leu Arg His Ser
 65                  70                  75                  80

Thr Ala His Val Leu Ala Gln Ala Val Gln Gln Leu Trp Pro Glu Ala
                 85                  90                  95

Arg Leu Gly Ile Gly Pro Pro Ile Glu Asn Gly Phe Tyr Tyr Asp Phe
            100                 105                 110

Asp Val Glu Arg Pro Phe Gln Pro Glu Asp Leu Glu Arg Val Glu Gln
        115                 120                 125

Arg Met Lys Glu Ile Ile Lys Ser Gly Gln Arg Phe Cys Arg Arg Glu
    130                 135                 140

Phe Pro Asp Arg Glu Ala Ala Arg Ala Glu Leu Ala Lys Glu Pro Tyr
145                 150                 155                 160

Lys Leu Glu Leu Val Asp Leu Lys Gly Asp Val Asp Ala Ala Glu Ala
                165                 170                 175

Met Glu Val Gly Gly Ser Asp Leu Thr Ile Tyr Asp Asn Leu Asp Ala
            180                 185                 190

Arg Thr Gly Asp Val Cys Trp Ser Asp Leu Cys Arg Gly Pro His Leu
        195                 200                 205

Pro Ser Thr Arg Leu Ile Pro Ala Phe Lys Leu Leu Arg Asn Ala Ala
    210                 215                 220

Ala Tyr Trp Arg Gly Ser Glu Lys Asn Pro Gln Leu Gln Arg Ile Tyr
225                 230                 235                 240

Gly Thr Ala Trp Pro Thr Arg Asp Glu Leu Lys Ser His Leu Ala Ala
                245                 250                 255

Leu Glu Glu Ala Ala Lys Arg Asp His Arg Arg Ile Gly Glu Glu Leu
            260                 265                 270

Asp Leu Phe Ala Phe Asn Lys Glu Ile Gly Arg Gly Leu Pro Leu Trp
        275                 280                 285

Leu Pro Asn Gly Ala Ile Ile Arg Asp Glu Leu Glu Asp Trp Ala Arg
    290                 295                 300

Lys Thr Glu Arg Lys Leu Gly Tyr Lys Arg Val Val Thr Pro His Ile
305                 310                 315                 320

Thr Gln Glu Asp Leu Tyr Tyr Leu Ser Gly His Leu Pro Tyr Tyr Ala
                325                 330                 335

Glu Asp Leu Tyr Ala Pro Ile Asp Ile Asp Gly Glu Lys Tyr Tyr Leu
            340                 345                 350
```

-continued

```
Lys Pro Met Asn Cys Pro His His His Met Val Tyr Lys Ala Arg Pro
        355                 360                 365

His Ser Tyr Arg Asp Leu Pro Tyr Lys Val Ala Glu Tyr Gly Thr Val
    370                 375                 380

Tyr Arg Phe Glu Arg Ser Gly Gln Leu His Gly Met Met Arg Thr Arg
385                 390                 395                 400

Gly Phe Ser Gln Asn Asp Ala His Ile Tyr Cys Thr Ala Asp Gln Ala
                405                 410                 415

Lys Asp Gln Phe Leu Glu Val Met Arg Met His Ala Asp Tyr Tyr Arg
            420                 425                 430

Thr Leu Gly Ile Ser Asp Phe Tyr Met Val Leu Ala Leu Arg Asp Ser
        435                 440                 445

Ala Asn Lys Asp Lys Tyr His Asp Asp Glu Gln Met Trp Glu Asp Ala
    450                 455                 460

Glu Arg Ile Thr Arg Glu Ala Met Glu Glu Ser Asp Ile Pro Phe Gln
465                 470                 475                 480

Ile Asp Leu Gly Gly Ala Ala His Tyr Gly Pro Lys Val Asp Phe Met
                485                 490                 495

Ile Arg Ala Val Thr Gly Lys Glu Phe Ala Ala Ser Thr Asn Gln Val
            500                 505                 510

Asp Leu Tyr Thr Pro Gln Arg Phe Gly Leu Thr Tyr His Asp Ser Asp
        515                 520                 525

Gly Thr Glu Lys Pro Val Val Val Ile His Arg Ala Pro Leu Gly Ser
    530                 535                 540

His Glu Arg Phe Thr Ala Tyr Leu Thr Glu His Phe Ala Gly Ala Phe
545                 550                 555                 560

Pro Val Trp Leu Ala Pro Glu Gln Val Arg Ile Ile Pro Ile Val Glu
                565                 570                 575

Glu Leu Thr Asp Tyr Ala Glu Glu Val Arg Asp Met Leu Leu Asp Ala
            580                 585                 590

Asp Val Arg Ala Asp Val Asp Ala Gly Asp Gly Arg Leu Asn Ala Lys
        595                 600                 605

Val Arg Ala Ala Val Thr Arg Lys Ile Pro Leu Val Val Val Val Gly
    610                 615                 620

Arg Arg Glu Ala Glu Gln Arg Thr Val Thr Val Arg Asp Arg Ser Gly
625                 630                 635                 640

Glu Glu Thr Pro Met Ser Leu Glu Lys Phe Val Ala His Val Thr Gly
                645                 650                 655

Leu Ile Arg Thr Lys Ser Leu Asp Gly Ala Gly His Ile Arg Pro Leu
            660                 665                 670

Ser Lys Ala
        675


<210> SEQ ID NO 22
<211> LENGTH: 103
<212> TYPE: PRT
<213> ORGANISM: Streptomyces parvulus Tu4055

<400> SEQUENCE: 22

Met Pro Arg Gly Ile Ala Val Asp Val Leu Arg Ala Gly Asp Arg Trp
  1               5                  10                  15

Pro His Ser Ala Ala Pro Arg His Arg Gly Leu Leu Asn Ala Trp Trp
            20                  25                  30

Gly Ala Trp Val Trp Ala Thr Val Phe Asp Arg Tyr Ala Ser Arg Thr
        35                  40                  45
```

-continued

Tyr Asp Asp Ala Gln Asp Val Asp Ala Ile His Asp Ala Ala Gly Leu
50 55 60

Val Met Ala Gly Ala Gly Phe Asp Ile Leu Ala Ala Val Leu Ala Ile
65 70 75 80

Leu Phe Val Arg Arg Leu Thr Ala Ala Gln His Ala Lys Ala Leu Ala
85 90 95

Gly Pro Thr Pro Pro Thr His
100

<210> SEQ ID NO 23
<211> LENGTH: 868
<212> TYPE: PRT
<213> ORGANISM: Streptomyces parvulus Tu4055

<400> SEQUENCE: 23

Met Glu Ala Phe Leu Leu Leu Ala Ala Glu Ser Val Leu Leu Arg Arg
1 5 10 15

Asp Gln Ser Val Tyr Val Thr Pro Gly Ser Glu Pro Asp Gly Pro Pro
20 25 30

Arg Ala Ala Leu Arg Arg Leu Glu Ala Glu Leu Leu Gly Arg Gly His
35 40 45

Ala Val Ser Ala Pro Leu His Ala Val Leu Ala Ser Leu Asp Ser Glu
50 55 60

Glu Leu Ala Ala Ala His Val Arg Leu Val Gly Leu Val Asp Asp Leu
65 70 75 80

Leu Gly Ser Asp Arg Thr His Thr Pro Leu Phe Arg Arg Phe Pro Arg
85 90 95

Thr Val Pro Arg Asp Thr Glu Ala Leu Tyr Val Asp Arg Val Phe Ala
100 105 110

Phe Leu Leu Gln Gln Pro Glu Gln Pro Cys Val Leu Cys Gly Glu Ala
115 120 125

Arg Thr Val Leu Pro Val Ser Pro Cys Ala His Leu Val Cys Arg Leu
130 135 140

Cys Trp Asp Gly Ser Asp Tyr Ala Gly Cys Pro Leu Cys His Arg Arg
145 150 155 160

Ile Asp Gly Asp Asp Pro Phe Leu Arg Pro Val Arg Ala Val Gly Ala
165 170 175

Ala Arg Ala Thr Val Pro Gly Pro Leu Arg Leu Leu Arg Leu Gly Thr
180 185 190

Asp Met Thr Ala Asp Ala Thr Thr Ala Val Asp Ala Leu Leu Ala Arg
195 200 205

Arg Thr Pro Leu Ser Pro Gln Asp Arg Asp Asp Leu Leu Thr Leu Leu
210 215 220

Pro Leu Thr Pro Ala Gly Arg Gly Asp Leu Pro Gln Asp Ile Pro Val
225 230 235 240

Arg Glu Thr Lys Ala Leu Val Leu Gly Ala Leu Val Arg Arg Ala Pro
245 250 255

Ser Arg Pro Ala Leu Arg Arg Leu Leu Ala Glu Arg Leu Thr Thr Ala
260 265 270

Thr Asp Val Leu Arg Leu Leu Ala Val Leu Ser Gly Gly Asp Ala Gly
275 280 285

Leu Val Thr Pro Ala Arg Phe Thr Asn Val Pro Arg Ser Leu Arg Arg
290 295 300

Asp Leu Leu Ala Val Leu Asp Gly Leu Pro Ala Pro Tyr Leu Val Glu

-continued

```
305                 310                 315                 320

Asp Met Leu Arg His Pro Thr Ala Trp Lys Arg Ala Ala Glu Val Leu
                325                 330                 335

His Pro Phe Glu Gly His Thr Arg His Pro Arg Ala Ala Leu Ala Thr
            340                 345                 350

Ala Val Leu Arg Ala Thr Pro Leu Asp Pro Asp Thr Ala Phe Gly Ala
        355                 360                 365

Ala Leu Leu Thr Thr Ala Ala Ala His Pro Asp Ala Val Arg Pro Asp
    370                 375                 380

Gly Thr Arg Val Arg Pro Ala Thr Trp Ala Gly Arg Leu Glu Gln Ala
385                 390                 395                 400

Met Ala Glu Gly Asp Ala Ala Arg Ala Ala Ala Leu Ala Gly Glu Arg
                405                 410                 415

Pro Gly Glu Leu Val Arg Arg Leu Asp Val Leu Leu Arg Leu His Thr
            420                 425                 430

Asp Glu Ala Leu Val Pro Glu Leu Glu Lys Ala Leu Arg His Gly Leu
        435                 440                 445

Pro Lys Val Gly Pro Gly Pro Leu Leu Ser Ala Leu Gly Ala Leu Arg
    450                 455                 460

Thr Arg Thr Glu Asp Arg Thr Gly Thr Arg Arg Val Phe Phe Pro Arg
465                 470                 475                 480

Gly Asp Val Thr Arg Ala Leu Ser Val Pro Glu Arg Arg Pro Ala Leu
                485                 490                 495

Pro Ala Gly Pro Val Ser Glu Val Val Ala Leu Leu Glu Gly Glu Leu
            500                 505                 510

Leu Arg Arg Phe Ala Ala Gly Arg Pro Tyr Glu Leu Ser Val Leu Asp
        515                 520                 525

Ala Gly Leu Thr Asp Leu Thr Val Pro Phe Thr Glu Arg Thr Ala Ala
    530                 535                 540

Lys Ala Leu Val Thr Val Gly Arg Gly Ser Val Gln Ala Leu Pro Glu
545                 550                 555                 560

Gly Ser Val Leu Arg Leu Phe Leu His Trp Thr Glu Pro Arg Gly Asn
                565                 570                 575

Arg Thr Asp Leu Asp Leu Ser Val Ala Phe Phe Asp Ala Glu Trp Thr
            580                 585                 590

Phe Thr Gly Leu Cys Asp Tyr Thr Asn Leu Val His Gly Pro Asp Ala
        595                 600                 605

Ala Ile His Ser Gly Asp Leu Thr Ser Ala Pro Ala Pro Arg Gly Ala
    610                 615                 620

Thr Glu Tyr Val Asp Leu Asp Leu Glu Arg Leu Ala Arg Arg Gly Asp
625                 630                 635                 640

Thr Tyr Ala Val Pro Leu Val Phe Ser Tyr Asn Asn Val Pro Phe Glu
                645                 650                 655

Glu Leu Pro Asp Ala Phe Ala Gly Phe Met Ala Leu Pro Ala Glu Gly
            660                 665                 670

Pro Arg Asp Ala Thr Tyr Asp Pro Arg Thr Val Arg Gln Arg Phe Asp
        675                 680                 685

Leu Ala Gly Asp Ser Lys Val Cys Leu Pro Met Ile Val Asp Leu Ala
    690                 695                 700

Arg Arg Arg Ala Leu Trp Thr Asp Thr His Leu Pro Ser Ala Gly Gly
705                 710                 715                 720

Phe Gln Ser Ile Gly Ser His Gly Gly Gly Glu Leu Ala Ala Val Ala
                725                 730                 735
```

```
Gly Asp Leu Trp Gln Gln Phe Thr Ser Gly Gly Arg Ala Thr Leu Trp
            740                 745                 750

Asp Leu Ala Val Leu Arg Ala Ala Ala Leu Ser Pro Glu Val Ala Val
        755                 760                 765

Val Ser Arg Glu Pro Glu Pro Ala Val Leu Arg Tyr Arg Arg Arg Ala
    770                 775                 780

Ala Glu Ser Glu Ala Ala Phe Ala Val Arg Val Ala Ser His Lys Asp
785                 790                 795                 800

Ala Glu Glu Arg Leu Ala His Thr Asp Pro Asp Ser Ala Ala Ala Gly
                805                 810                 815

Leu Ala Ala Gly Arg Arg Val Phe Leu Ala Thr Val His Gly Asp Val
            820                 825                 830

Arg Pro Pro Gly Ala Ser Gly Thr Ser Tyr Arg Leu Phe Pro Gly Ala
        835                 840                 845

Gly Asp Ala Ser Pro Thr Leu Thr Arg Val Thr Ala Gly Asp Leu Leu
    850                 855                 860

Ala Glu Leu Gly
865


<210> SEQ ID NO 24
<211> LENGTH: 212
<212> TYPE: PRT
<213> ORGANISM: Streptomyces parvulus Tu4055

<400> SEQUENCE: 24

Met Ala Glu Gln Ile Ala Gly Ile Glu Ile Pro Asp Ser Ala Pro Ala
  1               5                  10                  15

Arg Glu Ala Thr Asp Leu Ile Arg Asp Thr Thr Pro Pro Leu Ile Phe
             20                  25                  30

His His Ser Arg Arg Val Tyr Leu Phe Gly Ser Leu Gln Ala Ala Ala
         35                  40                  45

Leu Gly Ile Arg Pro Asp Pro Glu Leu Leu Tyr Ile Ala Ala Leu Phe
     50                  55                  60

His Asp Thr Gly Leu Val Pro Pro Tyr Arg Gly Asp Asp Gln Arg Phe
 65                  70                  75                  80

Glu Met Asp Gly Ala Asp Gln Ala His Ala Phe Leu Leu Ala His Gly
                 85                  90                  95

Ile Pro Glu Ala Asp Ala Asp Thr Val Trp Thr Ala Val Ala Leu His
            100                 105                 110

Thr Thr Pro Glu Val Pro Tyr Arg Met Ala Pro Glu Ile Ala Ala Thr
        115                 120                 125

Thr Ala Gly Val Glu Thr Asp Val Leu Gly Leu Arg Leu Gly Asn Leu
    130                 135                 140

Thr Arg Ala Gln Ile Asp Ala Val Thr Ala Ala His Pro Arg Pro Asp
145                 150                 155                 160

Phe Lys Lys Gln Ile Leu Arg Ala Phe Thr Glu Gly Phe Glu His Arg
                165                 170                 175

Pro Ala Thr Thr Phe Gly Thr Val Asn Ala Asp Val Leu Glu His Phe
            180                 185                 190

Ala Pro Gly Phe Arg Arg Thr Asp Phe Val Glu Val Ile Glu Asn Ser
        195                 200                 205

Ala Trp Pro Glu
    210
```

-continued

<210> SEQ ID NO 25
<211> LENGTH: 329
<212> TYPE: PRT
<213> ORGANISM: Streptomyces parvulus Tu4055

<400> SEQUENCE: 25

```
Met Thr Ala Arg Ala His Ser Val Gly Ile Leu Val Phe Asp Gly Met
  1               5                  10                  15

Lys Met Leu Asp Leu Ser Gly Pro Ala Glu Val Phe Ala Glu Ala Asn
             20                  25                  30

Arg Phe Gly Ala Arg Tyr Arg Leu Gly Val Val Ser Pro Asp Gly Ala
         35                  40                  45

Pro Val Arg Ser Ser Ile Gly Leu Leu Val Pro Ala Glu Ala Asp Ala
     50                  55                  60

Arg Ser Ala Gly Pro Pro Asp Thr Leu Val Val Val Gly Gly Asp Ala
 65                  70                  75                  80

Leu Pro Gly Ser Pro Val Asp Pro Arg Leu Ile Asp Ala Ala Lys Ala
                 85                  90                  95

Leu Ala Ala Arg Ala Gly Arg Val Ala Ser Val Cys Thr Gly Ala Phe
            100                 105                 110

Val Leu Gly Ala Ala Gly Leu Leu Glu Gly Arg Arg Ala Thr Thr His
        115                 120                 125

Trp Gln His Thr Thr Ala Leu Ala Arg Arg Cys Pro Ser Thr Arg Val
    130                 135                 140

Glu Pro Asp Ala Ile Phe Val Lys Asp Gly Ala Thr Tyr Thr Ser Ala
145                 150                 155                 160

Gly Val Thr Ala Gly Ile Asp Leu Ala Leu Ala Leu Leu Glu Glu Asp
                165                 170                 175

His Gly Pro Asp Leu Ala Arg Arg Val Ala Arg Ser Leu Val Val Tyr
            180                 185                 190

Leu Gln Arg Ala Gly Gly Gln Ser Gln Phe Ser Ala Ser Leu Arg Gly
        195                 200                 205

Pro Ala Pro Arg Thr Pro Val Leu Arg Gln Val Gln Asp Ala Val Gln
    210                 215                 220

Ala Asp Pro Ala Ala Asp His Ser Leu Ala Ala Leu Ala Ala Arg Val
225                 230                 235                 240

Arg Val Ser Pro Arg His Leu Thr Arg Met Phe Arg Ala Glu Leu Asp
                245                 250                 255

Val Thr Pro Val Lys Tyr Val Glu Leu Ile Arg Phe Asp Ile Ala Lys
            260                 265                 270

Ala Leu Leu Asp Ser Gly His Asn Ala Thr Glu Ala Ala Ala Leu Ser
        275                 280                 285

Gly Phe Pro Ser Tyr Glu Ser Leu Arg Arg Ala Phe Ala Arg His Leu
    290                 295                 300

Gly Leu Ser Pro Thr Arg Tyr Arg Gln Arg Phe Ala Thr Thr Val Pro
305                 310                 315                 320

Asp Ala Gly Pro Arg Pro Asp Gly Gly
                325
```

<210> SEQ ID NO 26
<211> LENGTH: 276
<212> TYPE: PRT
<213> ORGANISM: Streptomyces parvulus Tu4055

<400> SEQUENCE: 26

```
Met Gly Thr Val Thr Thr Ser Asp Gly Thr Ser Ile Phe Tyr Lys Asp
```

-continued

```
  1               5                  10                  15

Trp Gly Pro Arg Asp Ala Pro Pro Ile Val Phe His His Gly Trp Pro
            20                  25                  30

Leu Thr Ala Asp Asp Trp Asp Asn Gln Met Leu Phe Phe Leu Ser His
        35                  40                  45

Gly Tyr Arg Val Ile Ala His Asp Arg Arg Gly His Gly Arg Ser Gly
     50                  55                  60

Gln Pro Ser Thr Gly His Glu Met Asp Thr Tyr Ala Ala Asp Val Ala
 65                  70                  75                  80

Ala Leu Thr Glu Ala Leu Asp Leu Arg Asp Ala Val His Ile Gly His
                 85                  90                  95

Ser Thr Gly Gly Gly Glu Val Ala Arg Tyr Val Ala Arg Ala Glu Pro
            100                 105                 110

Gly Arg Val Ala Lys Ala Val Leu Val Gly Ala Val Pro Pro Val Met
        115                 120                 125

Val Lys Ser Asp Ala Asn Pro Gly Gly Thr Pro Ile Glu Val Phe Asp
    130                 135                 140

Gly Phe Arg Thr Ala Leu Ala Ala Asn Arg Ala Gln Phe Tyr Ile Asp
145                 150                 155                 160

Val Pro Ser Gly Pro Phe Tyr Gly Phe Asn Arg Glu Gly Ala Lys Val
                165                 170                 175

Ser Gln Gly Leu Ile Asp Asn Trp Trp Arg Gln Gly Met Ser Gly Ala
            180                 185                 190

Ala Asn Ala His Tyr Glu Cys Ile Lys Ala Phe Ser Glu Thr Asp Phe
        195                 200                 205

Thr Glu Asp Leu Lys Ala Ile Asp Val Pro Val Leu Val Ala His Gly
    210                 215                 220

Thr Asp Asp Gln Val Val Pro Tyr Ala Asp Ser Ala Pro Leu Ser Val
225                 230                 235                 240

Lys Leu Leu Lys Asn Gly Thr Leu Lys Ser Tyr Glu Gly Leu Pro His
                245                 250                 255

Gly Met Leu Ser Thr His Pro Glu Val Val Asn Pro Asp Leu Leu Asp
            260                 265                 270

Phe Val Arg Ser
        275


<210> SEQ ID NO 27
<211> LENGTH: 185
<212> TYPE: PRT
<213> ORGANISM: Streptomyces parvulus Tu4055

<400> SEQUENCE: 27

Met Gly Val Met Ile Gly Pro Ala Gly Arg Glu Arg Asp Glu Gly Asp
  1               5                  10                  15

His Val Thr Gln Gln Ala Pro Val Ala Thr Asp Glu Arg Arg Val Phe
            20                  25                  30

Val Asp Lys Gln Thr Pro Gly Ala Tyr Lys Ala Phe Val Ala Ala Ala
        35                  40                  45

Glu Ser Val Arg Glu Ala Ala Ala Ala Ala Gly Leu Asp Arg Leu Leu
     50                  55                  60

Val Glu Leu Val Asn Ile Arg Val Ser Gln Leu Asn Ala Cys Ala Tyr
 65                  70                  75                  80

Cys Leu Ser Leu His Thr Arg Ala Ala Leu Arg Ala Gly Glu Thr Thr
                 85                  90                  95
```

-continued

```
Gln Arg Leu Ala Val Leu Pro Ala Trp Arg Asp Thr Glu Leu Phe Thr
            100                 105                 110

Ala Arg Glu Arg Ala Ala Leu Ala Leu Ala Glu Ala Thr Thr Arg Pro
        115                 120                 125

Ala Asp Ala Ala Ala Gln Ser Ala Ala Tyr Ala Gln Ala Arg Gly Val
    130                 135                 140

Leu Ser Asp Asp Glu Val Ser Ala Val Ile Trp Val Ala Ile Ser Ile
145                 150                 155                 160

Asn Ala Phe Asn Arg Val Ser Val Leu Ser Lys His Pro Val Arg Gly
                165                 170                 175

Ala Ala Pro Ala Pro Val Ser Pro Ala
            180                 185


<210> SEQ ID NO 28
<211> LENGTH: 324
<212> TYPE: PRT
<213> ORGANISM: Streptomyces parvulus Tu4055

<400> SEQUENCE: 28

Met Val Ser Asn Thr Glu Thr Arg Pro Ala Glu Met Arg Cys Gly Ala
  1               5                  10                  15

Leu Glu Asp Glu Val Pro Ala Ala Gly Val Glu Val Leu Thr Ala Arg
             20                  25                  30

Asp Val Pro Leu Gly Gly Pro Arg Ala Met Thr Val Arg Arg Thr Leu
         35                  40                  45

Pro Gln Arg Ala Arg Thr Leu Ile Gly Ala Trp Cys Phe Ala Asp His
     50                  55                  60

Tyr Gly Pro Asp Asp Val Ala Ala Ser Gly Gly Met Asp Val Ala Pro
 65                  70                  75                  80

His Pro His Ile Gly Leu Gln Thr Val Ser Trp Leu Phe Ser Gly Glu
                 85                  90                  95

Ile Glu His Arg Asp Ser Leu Gly Thr His Ala Phe Val Arg Pro Gly
            100                 105                 110

Glu Leu Asn Leu Met Thr Gly Gly Phe Gly Ile Ala His Ser Glu Val
        115                 120                 125

Ser Thr Pro Asp Thr Thr Val Leu His Gly Val Gln Leu Trp Val Ala
    130                 135                 140

Leu Pro Glu Glu His Arg Asp Thr Gly Arg Asp Phe Gln His His Ala
145                 150                 155                 160

Pro Ala Pro Val Ala Phe Asp Gly Gly Thr Ala Arg Val Phe Leu Gly
                165                 170                 175

Ser Leu Ala Gly Asp Thr Ser Pro Val Ser Thr Phe Thr Pro Leu Leu
            180                 185                 190

Gly Ala Glu Leu Thr Leu Val Pro Gly Gly Thr Ala Thr Leu Asp Val
        195                 200                 205

Asp Pro Gly Phe Glu His Gly Val Leu Val Asp Ser Gly Asp Val Arg
    210                 215                 220

Val Glu Gly Ala Val Val Arg Pro Ala Glu Leu Gly Tyr Val Ala Pro
225                 230                 235                 240

Gly Arg Ala Thr Leu Thr Leu Thr Asn Glu Ser Ala Ala Pro Ala Arg
                245                 250                 255

Leu Ile Leu Leu Gly Gly Pro Pro Phe Pro Glu Glu Ile Ile Met Trp
            260                 265                 270

Trp Asn Phe Ile Gly Arg Ser His Asp Glu Ile Val Arg Ala Arg Glu
        275                 280                 285
```

-continued

```
Asp Trp Met Lys Gly Asp Arg Phe Gly Glu Val His Gly Tyr Asp Gly
    290                 295                 300

Ala Pro Leu Pro Ala Pro Glu Leu Pro Asn Ala Pro Leu Lys Pro Arg
305                 310                 315                 320

Arg Arg Ala Arg


<210> SEQ ID NO 29
<211> LENGTH: 126
<212> TYPE: PRT
<213> ORGANISM: Streptomyces parvulus Tu4055

<400> SEQUENCE: 29

Met Val Pro Thr Met Leu Cys Met Val Ala Val Pro Glu Ser His Ser
  1               5                  10                  15

Gly Trp Thr Phe Val Thr Asn His Ala Arg Val Leu Ala Ala Ile Ala
             20                  25                  30

Asp Asn Pro Asn Val Arg Ile Arg Asp Ile Ala Ala His Cys Arg Leu
         35                  40                  45

Thr Glu Arg Ala Val Gln Arg Ile Ile Ser Asp Leu Glu Gln Asp Gly
     50                  55                  60

Tyr Leu Ser His Thr Arg Asp Gly Arg Ser Asn Ile Tyr Arg Val Glu
 65                  70                  75                  80

Pro Asp Lys Val Leu Arg His Pro Ala Glu Ala Gly Leu Thr Val Ala
                 85                  90                  95

Ala Leu Leu Ser Leu Leu Val Arg Asp Glu Thr Asp His Gly Arg Ser
            100                 105                 110

Ala Gly Pro Gly Ser Arg Pro Ala Arg Ser Ser Ala Ala Arg
        115                 120                 125


<210> SEQ ID NO 30
<211> LENGTH: 127
<212> TYPE: PRT
<213> ORGANISM: Streptomyces parvulus Tu4055

<400> SEQUENCE: 30

Met Ser Leu Asp Glu Ala Val Ala Gly Cys Ser Arg His Thr Gly Arg
  1               5                  10                  15

Arg Arg Leu Pro Ala Ala Glu Gln Pro Thr Gln Ala Gln Tyr Glu Ala
             20                  25                  30

His Gly Ala Trp Val Val Ser Ala Arg Gly Ala Tyr Asp Met Asn Ser
         35                  40                  45

Val Glu Pro Leu Ala Asp Ala Leu Lys Asp Ala Ala Glu Lys Ser Pro
     50                  55                  60

Lys Val Val Leu Asp Ala Ser Gly Ile Thr Phe Ala Asp Ser Thr Leu
 65                  70                  75                  80

Leu Ser Leu Leu Ile Leu Thr His Gln Ala Thr Asp Phe Arg Val Ala
                 85                  90                  95

Ala Pro Thr Trp Gln Val Met Arg Leu Met Gln Leu Thr Gly Val Asp
            100                 105                 110

Ala Phe Leu Lys Val Arg Ala Thr Val Glu Glu Ala Ala Thr Ala
        115                 120                 125


<210> SEQ ID NO 31
<211> LENGTH: 82
<212> TYPE: PRT
<213> ORGANISM: Streptomyces parvulus Tu4055
```

-continued

<400> SEQUENCE: 31

```
Met Ser Met Ile Leu Pro Ala Glu Lys Glu Leu Arg Ala Val Leu Ala
  1               5                  10                  15

Arg Phe Ala Gln Ala Arg Ile Asp His Asp Val Arg Pro Ser Gly Cys
             20                  25                  30

Thr Ser Arg Leu Leu Glu Asp Ala Thr Tyr Thr Leu Cys Val Met Thr
         35                  40                  45

Gly Ala Arg Thr Ala Glu Gln Ala Leu Arg Thr Ala Asp Glu Leu Leu
     50                  55                  60

Ala Gln Phe Ala Glu Arg Thr Ala Ala Pro Val Glu Asp Glu Ala Leu
 65                  70                  75                  80

Ala Ala
```

<210> SEQ ID NO 32
<211> LENGTH: 70
<212> TYPE: PRT
<213> ORGANISM: Streptomyces parvulus Tu4055

<400> SEQUENCE: 32

```
Met Ser Asp Thr Arg Leu Arg Gln Arg Asp Glu Thr Ser Lys Gly Pro
  1               5                  10                  15

Ala Thr Glu Ile Pro Ala Pro Gln Trp Arg Asp Leu Phe Leu Ala Pro
             20                  25                  30

Asp Trp Gly Gly Thr Asp Glu Gln Val Ile Val Ala Glu Glu Ala Arg
         35                  40                  45

Gly Pro Glu His Phe Thr Gly Ala Arg Arg Pro Arg Gly Gly Arg Arg
     50                  55                  60

Ser Ser Arg Arg Ala Ala
 65                  70
```

<210> SEQ ID NO 33
<211> LENGTH: 172
<212> TYPE: PRT
<213> ORGANISM: Streptomyces parvulus Tu4055

<400> SEQUENCE: 33

```
Met Arg Cys Ser His Arg Ala Gly Gly Val Gly Ala Arg Ala Trp Leu
  1               5                  10                  15

Gly Gly Asn Val Ala Val Asp Met Gly Glu Thr Gly Leu Asp Gly Ser
             20                  25                  30

Ser Thr Gln Arg Ala Pro Glu Gly Ala Asp Pro Arg Ala Ala Ser Val
         35                  40                  45

Thr Tyr Arg Arg Glu Ala Leu Arg Ile Ala Asp Ala Arg His Phe Ala
     50                  55                  60

Thr Asp Tyr Leu Thr Arg Ser Gln Arg Asp Leu Arg Ser Pro Val Pro
 65                  70                  75                  80

Glu Arg Ala Ser Glu Ala Val His Leu Val Val Ser Glu Leu Ile Thr
                 85                  90                  95

Asn Ala Val Lys Tyr Gly Ala Asp Pro Ile Glu Leu Thr Leu Ser Leu
            100                 105                 110

Thr Asp Asp Ala Val Thr Val Thr Val Arg Asp Gly Asp Thr Thr Leu
        115                 120                 125

Pro Ala Pro Arg Pro Ala Asp Pro Ala Arg Val Gly Gln His Gly Leu
    130                 135                 140

Glu Ile Val Ala Ala Leu Ser Gln Ala Val Glu Ile Arg Pro Glu Pro
145                 150                 155                 160
```

-continued

```
Ser Gly Lys Arg Ile Thr Ala Arg Ile Ala Leu Thr
                165                 170
```

<210> SEQ ID NO 34
<211> LENGTH: 105
<212> TYPE: PRT
<213> ORGANISM: Streptomyces parvulus Tu4055

<400> SEQUENCE: 34

```
Met Gln Ser Ser Ser Ala Ser Val Arg Gly Glu Ile Val Ile Arg Arg
  1               5                  10                  15

Ala Val Ala Arg Asp Ala Lys Arg Leu Ser Arg Leu Val Arg Gly Ser
             20                  25                  30

Arg Ala Tyr Glu Gly Pro Tyr Ala Ala Met Val Ser Asp Tyr Arg Val
         35                  40                  45

Gly Pro Asp Tyr Ile Glu Asn His Gln Val Phe Val Ala Ser Thr Pro
     50                  55                  60

Arg Thr Pro Arg Thr Gly Cys Ser Ala Ser Thr Arg Cys Ser Ser Arg
 65                  70                  75                  80

Arg Arg Ser Trp Thr Cys Cys Ser Ser Arg Thr Val Pro Arg Ala Ala
                 85                  90                  95

Ala Ser Asp Gly Cys Leu Ser Ile Thr
            100                 105
```

<210> SEQ ID NO 35
<211> LENGTH: 638
<212> TYPE: PRT
<213> ORGANISM: Streptomyces parvulus Tu4055

<400> SEQUENCE: 35

```
Met Ala Gln Arg Arg Thr Pro Phe Gly Asp Arg Ala Arg Tyr Trp Phe
  1               5                  10                  15

Asp Ser Thr Leu Ala Arg Gly Ala Ala Ala Leu Val Gly Trp Met Ala
             20                  25                  30

Leu Leu Ser Leu Ala Val Val Val Pro Ala Ser Ala Val Met Val Trp
         35                  40                  45

Thr Asp Pro Asp Ala Pro Pro Ser Leu Ala Glu Arg Leu Ala Glu Val
     50                  55                  60

Trp Arg Leu Thr Gly Glu Thr Leu Arg Leu Gly Gly Ala Thr Gly Thr
 65                  70                  75                  80

Pro Leu Arg Ala Met Leu Ser Val Leu Leu Ala Leu Val Thr Leu Leu
                 85                  90                  95

Tyr Val Ser Thr Leu Val Gly Leu Ile Thr Thr Ala Leu Thr Glu Arg
            100                 105                 110

Leu Thr Ser Leu Arg Arg Gly Arg Ser Thr Val Leu Glu Gln Gly His
        115                 120                 125

Ala Val Val Leu Gly Trp Ser Glu Gln Val Phe Thr Val Val Ser Glu
    130                 135                 140

Leu Val Ala Ala Asn Val Asn Gln Arg Gly Ala Ala Val Val Val Leu
145                 150                 155                 160

Ala Asp Arg Asp Lys Thr Val Met Glu Glu Ser Leu Gly Thr Lys Val
                165                 170                 175

Gly Ser Cys Gly Gly Thr Arg Leu Ile Cys Arg Ser Gly Pro Thr Thr
            180                 185                 190

Asp Pro Ala Val Leu Pro Leu Thr Ser Pro Ala Thr Ala Gly Val Val
        195                 200                 205
```

-continued

```
Leu Val Leu Pro Pro Asp Glu Pro His Ala Asp Ala Glu Val Val Lys
    210                 215                 220

Thr Leu Leu Ala Leu Arg Ala Ala Leu Ala Gly Ala Lys Pro Arg Pro
225                 230                 235                 240

Pro Val Val Ala Ala Val Arg Asp Asp Arg Tyr Arg Leu Ala Ala Cys
                245                 250                 255

Leu Ala Ala Gly Pro Asp Gly Val Val Leu Glu Ser Asp Thr Val Thr
            260                 265                 270

Ala Arg Leu Ile Val Gln Ala Ala Arg Arg Pro Gly Ile Ser Leu Val
        275                 280                 285

His Arg Glu Leu Leu Asp Phe Ala Gly Asp Glu Phe Tyr Leu Ile Ser
    290                 295                 300

Glu Pro Ala Leu Thr Gly Arg Pro Phe Gly Glu Val Leu Leu Ser Tyr
305                 310                 315                 320

Ser Thr Thr Ser Val Val Gly Leu Met Arg Gly Cys Thr Pro Leu Leu
                325                 330                 335

Asn Pro Pro Pro Thr Thr Pro Val Ala Pro Asp Asp Leu Leu Val Val
            340                 345                 350

Ile Thr Gly Asp Asp Asp Thr Ala Arg Leu Asp Asp Cys Ala Glu Ser
        355                 360                 365

Val Glu Lys Ala Ala Val Ala Ser Arg Pro Pro Thr Pro Ala Pro Ala
    370                 375                 380

Glu Arg Ile Leu Leu Leu Gly Trp Asn Arg Arg Ala Pro Leu Val Val
385                 390                 395                 400

Asp Gln Leu His Arg Arg Ala Arg Pro Gly Ser Ala Val Asp Val Val
                405                 410                 415

Ala Glu Pro Gly Glu Ala Thr Ile Arg Glu Ile Ser Glu Ala Glu Ala
            420                 425                 430

Asp Ser Gly Asn Gly Glu Asn Gly Gly Asn Gly Leu Ser Leu Ala Leu
        435                 440                 445

His His Gly Asp Ile Thr Arg Pro Glu Thr Leu Arg Arg Leu Asp Val
    450                 455                 460

His Ser Tyr Asp Ser Val Ile Val Leu Gly Arg Asp Pro Ala Pro Gly
465                 470                 475                 480

Gln Pro Pro Asp Asp Pro Asp Asn Arg Thr Leu Val Thr Leu Leu Leu
                485                 490                 495

Leu Arg Gln Leu Glu Glu Ala Thr Gly Arg Glu Leu Pro Val Val Thr
            500                 505                 510

Glu Leu Ile Asp Asp Arg Asn Arg Ala Leu Ala Pro Ile Gly Pro Gly
        515                 520                 525

Ala Asp Val Ile Ile Ser Gly Lys Leu Ile Gly Leu Leu Met Ser Gln
    530                 535                 540

Ile Ser Gln Asn Arg His Leu Ala Ala Val Phe Glu Glu Leu Phe Ser
545                 550                 555                 560

Ala Glu Gly Ala Gly Val Arg Leu Arg Pro Ala Thr Asp Tyr Leu Leu
                565                 570                 575

Pro Gly Ser Thr Thr Ser Phe Ala Thr Val Val Ala Ala Ala Arg Arg
            580                 585                 590

Arg Gly Glu Cys Ala Ile Gly Tyr Arg Asp His Ala Asp Ala Ser Thr
        595                 600                 605

Arg Pro His Tyr Gly Val Arg Ile Asn Pro Pro Lys Arg Glu Arg Arg
    610                 615                 620
```

-continued

Arg Trp Thr Ala Glu Asp Glu Val Val Val Ile Gly Thr Asp
625 630 635

<210> SEQ ID NO 36
<211> LENGTH: 165
<212> TYPE: PRT
<213> ORGANISM: Streptomyces parvulus Tu4055

<400> SEQUENCE: 36

Met Pro Ser Thr Asp Val Val Glu Leu Ile Leu Arg Asp His Arg Arg
1 5 10 15

Met Glu Glu Leu Phe Arg Thr Leu Arg Asn Val Glu Ala Asp Arg Ala
20 25 30

Ala Ala Leu Thr Glu Phe Ala Asp Leu Leu Ile Ala His Ala Ser Ala
35 40 45

Glu Glu Asp Glu Val Tyr Pro Ala Leu Arg Arg Tyr Lys Asn Val Glu
50 55 60

Gly Glu Asp Val Asp His Ser Val His Glu His His Glu Ala Asn Glu
65 70 75 80

Ala Leu Leu Ala Leu Leu Glu Val Glu Asp Thr Ala Ser Asp Glu Trp
85 90 95

Asp Asp Lys Leu Glu Glu Leu Val Thr Ala Val Asn His His Ala Asp
100 105 110

Glu Glu Glu Arg Thr Leu Leu Asn Asp Ala Arg Glu Asn Val Ala Asp
115 120 125

Asp Arg Arg Arg Glu Leu Gly Gln Lys Phe Gln Glu Ala Arg Ser Arg
130 135 140

Tyr Leu Glu Thr Gly Cys Gly Ser Val Glu Asn Val Arg Lys Leu Val
145 150 155 160

Ala Ala Ala Asp Asp
165

<210> SEQ ID NO 37
<211> LENGTH: 787
<212> TYPE: PRT
<213> ORGANISM: Streptomyces parvulus Tu4055

<400> SEQUENCE: 37

Met Ala Arg Arg Leu Thr Glu Gly Arg Thr Arg Arg Glu Lys Gly Glu
1 5 10 15

His Met Gln Lys Pro His Gly Glu Glu Ser Glu Thr Ser Leu Ser Val
20 25 30

Thr Pro Pro Lys Lys Trp Ala Ala Gly Val Pro Ala Val Val His Ala
35 40 45

Leu Glu Tyr Ser Leu Glu Gln Thr Ser Pro Arg Arg Thr Gly Val Asp
50 55 60

Leu Leu Thr Met Asn Gln Val Gly Gly Ile Asp Cys Pro Gly Cys Ala
65 70 75 80

Trp Ala Asp Pro Ala Pro Gly Arg Arg His Arg Asn Glu Tyr Cys Glu
85 90 95

Asn Gly Ala Lys His Ile Asn Asp Glu Ala Thr Thr Arg Arg Val Thr
100 105 110

Ala Asp Phe Phe Arg Glu His Ser Val Ala Asp Leu Ala Gly Arg Ser
115 120 125

Asp Met Trp Leu Asn Gln Gln Gly Arg Leu Thr Glu Pro Met Ile Lys
130 135 140

-continued

```
Arg Pro Gly Ser Ala His Tyr Glu Pro Ile Gly Trp Asn Asp Ala Leu
145                 150                 155                 160

Gly Val Leu Ala Glu Glu Leu Lys Ser Leu Ala Ser Pro Asp Glu Ala
                165                 170                 175

Val Phe Tyr Thr Ser Gly Arg Ala Ser Asn Glu Ala Ala Phe Val Leu
            180                 185                 190

Gln Leu Phe Ala Arg Ala Phe Gly Thr Asn Asn Leu Pro Asp Cys Ser
        195                 200                 205

Asn Met Cys His Glu Ser Ser Gly Phe Ala Leu Ser Glu Thr Leu Gly
    210                 215                 220

Thr Gly Lys Gly Thr Val Gly Leu Asp Asp Leu His His Ala Asp Leu
225                 230                 235                 240

Ile Phe Leu Val Gly Gln Asn Pro Gly Ser Asn His Pro Arg Gln Leu
                245                 250                 255

Ser Ala Leu Glu Glu Ala Lys Arg Asn Gly Ala Arg Ile Val Ala Val
            260                 265                 270

Asn Pro Leu Pro Glu Ala Gly Leu Arg Arg Phe Lys Asn Pro Gln Gln
        275                 280                 285

Pro Arg Gly Val Val Gly Arg Gly Thr Arg Ile Ala Asp Arg Phe Leu
    290                 295                 300

His Ile Lys Pro Gly Gly Asp Leu Ala Leu Phe Gln Ala Leu Asn Arg
305                 310                 315                 320

Leu Leu Leu Glu Ala Glu Asp Ala Arg Pro Gly Thr Val Leu Asp His
                325                 330                 335

Asp Phe Ile Asp Ala His Thr Thr Gly Phe Glu Glu Phe Ala Arg His
            340                 345                 350

Ala Arg Thr Val Asp Trp Asp Asp Val Arg Ala Ala Thr Gly Leu Thr
        355                 360                 365

Arg Glu Glu Ile Glu Lys Val Arg Asp Glu Val Leu Asp Ser Glu Arg
    370                 375                 380

Val Val Val Cys Trp Ala Met Gly Ile Thr Gln His Lys His Gly Val
385                 390                 395                 400

Pro Thr Val Arg Glu Ile Val Asn Phe Leu Met Leu Arg Gly Asn Leu
                405                 410                 415

Gly Arg Ala Gly Thr Gly Ala Cys Pro Val Arg Gly His Ser Asn Val
            420                 425                 430

Gln Gly Asp Arg Thr Met Gly Ile Trp Glu Gln Met Pro Asp Thr Phe
        435                 440                 445

Leu Asp Ala Leu Arg Asp Glu Phe Gly Phe Glu Pro Pro Arg Ala His
    450                 455                 460

Gly Leu Asp Ser Val Asn Ser Ile Lys Ala Met Arg Glu Gly Arg Val
465                 470                 475                 480

Lys Val Phe Leu Ala Leu Ala Gly Asn Phe Val Arg Ala Ala Pro Asp
                485                 490                 495

Ser Glu Val Thr Glu Glu Ala Met Arg Ser Cys Arg Leu Thr Ala His
            500                 505                 510

Ile Ser Thr Lys Leu Asn Arg Ser His Thr Val Cys Gly Asp Thr Ala
        515                 520                 525

Leu Ile Leu Pro Thr Leu Gly Arg Thr Glu Arg Asp Val Gln Ala Asp
    530                 535                 540

Gly Glu Gln Phe Val Thr Val Glu Asn Ser Met Ser Glu Val His Thr
545                 550                 555                 560

Ser Arg Gly Arg Leu Ala Pro Ala Ser Pro Met Leu Leu Ser Glu Ile
```

-continued

```
                565                 570                 575

Ala Ile Leu Cys Arg Leu Ala Arg Leu Thr Leu Asp Gly Arg Val Glu
            580                 585                 590

Ile Pro Trp Glu Thr Phe Glu Gly Asp Tyr His Thr Ile Arg Asp Arg
        595                 600                 605

Ile Ala Arg Ile Val Pro Gly Phe His Asp Phe Asn Ala Arg Val Thr
    610                 615                 620

Arg Pro Gly Gly Phe Gln Leu Pro Asn Pro Val Asn Glu Gly Val Phe
625                 630                 635                 640

Asn Thr Glu Val Gly Lys Ala Leu Phe Thr Arg Asn Glu Ser Val Val
                645                 650                 655

Pro Arg Ala Pro Glu Gly His Leu Leu Leu Gln Thr Leu Arg Ser His
            660                 665                 670

Asp Gln Trp Asn Thr Val Pro Tyr Thr Asp Asn Asp Arg Tyr Arg Gly
        675                 680                 685

Ile His Gly Ser Arg His Val Val Leu Val Asn Pro Ala Asp Leu Ser
    690                 695                 700

Glu Leu Gly Leu Ala Gln Gly Asp Arg Val Asp Leu Val Ser Val Trp
705                 710                 715                 720

Ala Asp Gly Thr Glu Arg Arg Ala Glu Asn Phe Gln Val Val Pro Tyr
                725                 730                 735

Pro Ala Ala Lys Gly Ser Ala Ala Ala Tyr Tyr Pro Glu Thr Asn Val
            740                 745                 750

Leu Val Pro Leu Asp Ser Val Ala Asp Ile Ser Asn Gln Pro Thr Ser
        755                 760                 765

Lys Gly Ile Val Val Arg Leu Glu Pro Val Pro Asp Arg Thr Gln Pro
    770                 775                 780

Ser Pro Ala
785


<210> SEQ ID NO 38
<211> LENGTH: 206
<212> TYPE: PRT
<213> ORGANISM: Streptomyces parvulus Tu4055

<400> SEQUENCE: 38

Met Ala Glu Gln His Glu Gly Pro Arg Ala Val Pro Asp Thr Pro Gly
  1               5                  10                  15

Ala Arg Thr Ser Gly Asp Arg Ser Thr Gly Arg Arg Pro Leu Arg Glu
            20                  25                  30

Arg His Val Asp Gln Thr Val Glu Val Ala Val Pro Val Arg Thr Ala
        35                  40                  45

Tyr Asn Gln Trp Thr Gln Phe Lys Ser Phe Pro Arg Phe Ser Ala Val
     50                  55                  60

Val Arg Asp Val Glu Gln Val Arg Pro Thr Val Thr Ala Trp Thr Leu
 65                  70                  75                  80

Gly Tyr Gly Pro Leu Arg Arg Arg Phe Ala Val Glu Ile Leu Glu Gln
                 85                  90                  95

Asp Pro Asp Ala Tyr Leu Ala Trp Arg Gly Leu Glu Gln Arg Pro Trp
            100                 105                 110

His Arg Gly Glu Val Glu Phe Arg Pro Thr Glu Ser Gly Gly Thr Ala
        115                 120                 125

Ile Thr Val Arg Val Leu Leu Glu Pro Arg Gly Ala Ala Arg Ile Leu
    130                 135                 140
```

-continued

```
Thr Arg Ser Ser Arg Ala Val Arg Leu Thr Thr Arg Leu Val His Gly
145                 150                 155                 160

Glu Leu Thr Arg Phe Lys Arg Phe Met Glu Gly Leu Gly Gln Glu Gly
                165                 170                 175

Gly Ala Trp Arg Gly Thr Ile Arg Asn Gly Arg Val Gln His Asp Arg
            180                 185                 190

Pro Glu Pro Pro Arg Ser Arg Val Ala Arg Trp Pro Val Gly
        195                 200                 205


<210> SEQ ID NO 39
<211> LENGTH: 251
<212> TYPE: PRT
<213> ORGANISM: Streptomyces parvulus Tu4055

<400> SEQUENCE: 39

Met Leu Leu Leu Ile Ser Pro Asp Gly Val Glu Glu Ala Leu Asp Cys
  1               5                  10                  15

Ala Lys Ala Ala Glu His Leu Asp Ile Val Asp Val Lys Lys Pro Asp
             20                  25                  30

Glu Gly Ser Leu Gly Ala Asn Phe Pro Trp Val Ile Arg Glu Ile Arg
         35                  40                  45

Asp Ala Val Pro Ala Asp Lys Pro Val Ser Ala Thr Val Gly Asp Val
     50                  55                  60

Pro Tyr Lys Pro Gly Thr Val Ala Gln Ala Ala Leu Gly Ala Val Val
 65                  70                  75                  80

Ser Gly Ala Thr Tyr Ile Lys Val Gly Leu Tyr Gly Cys Thr Thr Pro
                 85                  90                  95

Glu Gln Gly Ile Ala Val Met Arg Ala Val Val Arg Ala Val Lys Asp
            100                 105                 110

His Arg Pro Glu Ala Leu Val Val Ala Ser Gly Tyr Ala Asp Ala His
        115                 120                 125

Arg Ile Gly Cys Val Asn Pro Leu Ala Leu Pro Asp Ile Ala Ala Arg
    130                 135                 140

Ser Gly Ala Asp Ala Ala Met Leu Asp Thr Ala Val Lys Asp Gly Thr
145                 150                 155                 160

Arg Leu Phe Asp His Val Pro Pro Asp Thr Cys Ala Glu Phe Val Arg
                165                 170                 175

Arg Ala His Ala Ala Gly Leu Leu Ala Ala Leu Ala Gly Ser Val Arg
            180                 185                 190

Gln Thr Asp Leu Gly Arg Leu Thr Arg Ile Gly Thr Asp Ile Val Gly
        195                 200                 205

Val Arg Gly Ala Val Cys Glu Gly Gly Asp Arg Asn Ala Gly Arg Ile
    210                 215                 220

Arg Pro His Leu Val Ala Ala Phe Arg Ser Glu Met Asp Arg His Ala
225                 230                 235                 240

Arg Glu His Arg Ala Gly Val Thr Thr Ala Ser
                245                 250


<210> SEQ ID NO 40
<211> LENGTH: 467
<212> TYPE: PRT
<213> ORGANISM: Streptomyces parvulus Tu4055

<400> SEQUENCE: 40

Met Pro Thr Pro Ala Pro Asp His Ala Pro Ala Gln Arg Ala Ala Pro
  1               5                  10                  15
```

-continued

```
Leu Ala Val Val Asp Pro Ala Thr Gly Thr Val Phe Asp Glu Ala Pro
            20                  25                  30

Asp Gln Gly Pro Asp Val Leu Asp Ala Val Val Asp Arg Ala Arg Arg
        35                  40                  45

Ala Trp His Gly Trp Arg Ala Asp Pro Asp Ala Arg Thr Thr Ala Leu
    50                  55                  60

Arg Ser Ala Ala Asp Ala Val Glu Ala Ala Gly Asp Asp Leu Ala Arg
65                  70                  75                  80

Leu Leu Thr Arg Glu Gln Gly Lys Pro Leu Ala Glu Ser His Ala Glu
                85                  90                  95

Val Ala Arg Thr Ala Ala Arg Leu Arg Tyr Phe Ala Gly Leu Ala Pro
            100                 105                 110

Arg Thr Arg Arg Ile Thr Asp Gly Arg Pro Val Arg Ser Glu Val Arg
        115                 120                 125

Trp Arg Pro Leu Gly Pro Val Ala Ala Ile Val Pro Trp Asn Phe Pro
    130                 135                 140

Leu Gln Leu Ala Ser Ala Lys Phe Ala Pro Ala Leu Ala Ala Gly Asn
145                 150                 155                 160

Thr Met Val Leu Lys Pro Ser Pro Phe Thr Pro Leu Ala Thr Arg Leu
                165                 170                 175

Leu Gly Ser Val Leu Ala Thr Ala Leu Pro Glu Asp Val Leu Thr Val
            180                 185                 190

Val Thr Gly Arg Glu Pro Leu Gly Ala Arg Leu Ala Ala His Pro Gly
        195                 200                 205

Ile Arg His Val Thr Phe Thr Gly Ser Val Pro Thr Gly Arg Ala Val
    210                 215                 220

Ala Arg Ala Ala Ala Ala Ser Leu Ala Arg Val Thr Leu Glu Leu Gly
225                 230                 235                 240

Gly Asn Asp Ala Ala Val Leu Leu Asp Asp Val Glu Val Asp Arg Ile
                245                 250                 255

Ala Asp Arg Leu Phe Trp Ala Ala Phe Arg Asn Cys Gly Gln Val Cys
            260                 265                 270

Met Ala Val Lys Arg Val Tyr Ala Pro Ala Arg Leu His Ala Gln Val
        275                 280                 285

Val Glu Ala Leu Thr Glu Arg Ala Lys Ala Val Ala Val Gly Pro Gly
    290                 295                 300

Leu Asp Pro Arg Thr Arg Leu Gly Pro Val Ala Asn Ala Pro Gln Leu
305                 310                 315                 320

Ala Arg Val Glu Gln Ile Thr Arg Arg Ala Leu Ala Asp Gly Ala Arg
                325                 330                 335

Ala Ala Ala Gly Gly His Arg Leu Asp Gly Pro Gly Cys Phe Phe Ala
            340                 345                 350

Pro Thr Ile Leu Thr Asp Val Pro Pro Asp Ser Pro Val Val Thr Glu
        355                 360                 365

Glu Gln Phe Gly Pro Val Leu Pro Val Leu Pro Tyr Arg Ser Leu Asp
    370                 375                 380

Glu Ala Val Asp Ala Ala Asn Gly Thr Gly Phe Gly Leu Gly Gly Ser
385                 390                 395                 400

Val Trp Gly Thr Asp Leu Asp Arg Ala Glu Ala Val Ala Asp Arg Leu
                405                 410                 415

Glu Cys Gly Thr Ala Trp Val Asn His His Ala Glu Leu Ser Leu Ala
            420                 425                 430

Gln Pro Phe Ala Gly Asp Lys Asp Ser Gly Val Gly Val Ala Gly Gly
```

```
        435                 440                 445

Pro Trp Gly Leu Tyr Gly Asn Leu Arg Pro Phe Val Val His Arg Pro
    450                 455                 460

Arg Gly Glu
465


<210> SEQ ID NO 41
<211> LENGTH: 368
<212> TYPE: PRT
<213> ORGANISM: Streptomyces parvulus Tu4055

<400> SEQUENCE: 41

Met Ser Phe Arg Ala Ala Val Leu Arg Gly Tyr Glu Asp Pro Phe Thr
  1               5                  10                  15

Val Glu Glu Val Thr Leu Gly Thr Glu Pro Gly Ala Gly Glu Ile Leu
             20                  25                  30

Val Glu Ile Ala Gly Cys Gly Met Cys Arg Thr Asp Leu Ala Val Arg
         35                  40                  45

Arg Ser Ala Gly Arg Ser Pro Leu Pro Ala Val Leu Gly His Glu Gly
     50                  55                  60

Ser Gly Val Val Val Arg Thr Gly Gly Gly Pro Asp Thr Ala Ile Gly
 65                  70                  75                  80

Val Gly Asp His Val Val Leu Ser Phe Asp Ser Cys Gly His Cys Arg
                 85                  90                  95

Asn Cys Arg Ala Ala Ala Pro Ala Tyr Cys Asp Ser Phe Ala Ser Leu
            100                 105                 110

Asn Leu Phe Gly Gly Arg Ala Glu Asp Pro Pro Arg Leu Thr Asp Gly
        115                 120                 125

Ser Gly Ala Ala Leu Ala Pro Arg Trp Phe Gly Gln Ser Ala Phe Ala
    130                 135                 140

Glu Tyr Ala Leu Val Ser Ala Arg Asn Ala Val Arg Val Asp Pro Ala
145                 150                 155                 160

Leu Pro Val Glu Leu Leu Gly Pro Leu Gly Cys Gly Phe Leu Thr Gly
                165                 170                 175

Ala Gly Ala Val Leu Asn Thr Phe Ala Ala Gly Pro Gly Asp Thr Leu
            180                 185                 190

Val Val Leu Gly Ala Gly Ala Val Gly Leu Ala Ala Val Met Ala Ala
        195                 200                 205

Thr Ala Ala Gly Ala Pro Ser Val Ala Val Asp Arg Asn Pro Arg Arg
    210                 215                 220

Leu Glu Leu Ala Glu Arg Phe Gly Ala Val Pro Leu Pro Ala Ala Thr
225                 230                 235                 240

Ala Gly Leu Ala Glu Arg Ile Arg Arg Leu Thr Asp Gly Gly Ala Arg
                245                 250                 255

Tyr Ala Leu Asp Thr Thr Ala Ser Val Pro Leu Ile Asn Glu Ala Leu
            260                 265                 270

Arg Ala Leu Arg Pro Thr Gly Ala Leu Gly Leu Val Ala Arg Leu His
        275                 280                 285

Thr Ala Leu Pro Leu Glu Pro Gly Thr Leu Asp Arg Gly Arg Ser Ile
    290                 295                 300

Arg His Val Cys Glu Gly Asp Ala Val Pro Gly Leu Leu Ile Pro Gln
305                 310                 315                 320

Leu Thr Arg Leu Trp Gln Ala Gly Arg Phe Pro Phe Asp Gln Leu Val
                325                 330                 335
```

-continued

```
Arg Thr Tyr Pro Leu Ala Asp Ile Asn Glu Ala Glu Arg Asp Cys Asp
            340                 345                 350

Ala Gly Leu Val Val Lys Pro Val Leu Leu Pro Pro Ala Arg Ser Arg
        355                 360                 365
```

<210> SEQ ID NO 42
<211> LENGTH: 301
<212> TYPE: PRT
<213> ORGANISM: Streptomyces parvulus Tu4055

<400> SEQUENCE: 42

```
Met Thr Gly Thr Ala Pro Gln Tyr Thr Asp Val Glu Gly Val Asn Gly
  1               5                  10                  15

Gly Val Gly Leu Thr Ala Phe Leu Val Ala Ala Ala Arg Ala Ile Glu
            20                  25                  30

Thr His Arg Asp Asp Ser Leu Ala Gln Asp Val Tyr Ala Glu His Phe
        35                  40                  45

Val Arg Ala Ala Pro Ala Cys Ala Asp Trp Pro Val Arg Ile Glu Gln
     50                  55                  60

Val Pro Asp Gly Asp Gly Asn Pro Leu Trp Gly Arg Phe Ala Arg Tyr
 65                  70                  75                  80

Phe Gly Leu Arg Thr Arg Ala Leu Asp Asp Phe Leu Leu Arg Ser Val
                 85                  90                  95

Arg Thr Gly Pro Arg Gln Val Val Leu Leu Gly Ala Gly Leu Asp Thr
            100                 105                 110

Arg Ala Phe Arg Leu Asp Trp Pro Ser Gln Cys Ala Val Phe Glu Ile
        115                 120                 125

Asp Arg Thr Gly Val Leu Ala Phe Lys Gln Gln Val Leu Thr Asp Leu
    130                 135                 140

Ala Ala Thr Pro Arg Val Glu Arg Val Pro Val Pro Val Asp Leu Arg
145                 150                 155                 160

Ala Asp Trp Ala Gly Ala Leu Thr Ala Ala Gly Phe Asp Pro Ala Ala
                165                 170                 175

Pro Ser Val Trp Leu Ala Glu Gly Leu Leu Phe Tyr Leu Pro Gly Pro
            180                 185                 190

Ala Glu Ser Leu Leu Val Asp Thr Val Asp Arg Leu Thr Thr Asp Gly
        195                 200                 205

Ser Ala Leu Ala Phe Glu Ala Lys Leu Glu Lys Asp Leu Leu Ala Tyr
    210                 215                 220

Arg Asp Ser Ala Ile Tyr Thr Ala Thr Arg Glu Gln Ile Gly Ile Asp
225                 230                 235                 240

Leu Leu Arg Leu Phe Asp Lys Gly Pro Arg Pro Asp Ser Ala Gly Glu
                245                 250                 255

Leu Ala Ala Arg Gly Trp Ser Thr Ser Met His Thr Pro Phe Val Phe
            260                 265                 270

Thr His Arg Tyr Gly Arg Gly Pro Leu Pro Glu Pro Asn Asp Ala Leu
        275                 280                 285

Glu Gly Asn Arg Trp Val Phe Ala Arg Lys Pro Gly Pro
    290                 295                 300
```

<210> SEQ ID NO 43
<211> LENGTH: 179
<212> TYPE: PRT
<213> ORGANISM: Streptomyces parvulus Tu4055

<400> SEQUENCE: 43

-continued

```
Met Cys Met Arg Asp Glu Ala Ala Lys Arg Val Glu Leu Val Phe Ser
  1               5                  10                  15

Leu Phe Asp Ala Asn Gly Asn Gly Val Ile Asp Ser Asp Asp Phe Asp
             20                  25                  30

Leu Met Thr Asp Arg Val Val Ala Ala Ala Ala Gly Ser Asp Asp Ser
         35                  40                  45

Ala Lys Ala Ala Val Arg Ala Ala Phe Arg Arg Tyr Trp Thr Thr Leu
     50                  55                  60

Ala Thr Glu Leu Asp Ala Asp Gly Asp Gly Val Ile Thr Val Glu Glu
 65                  70                  75                  80

Phe Arg Pro Phe Val Leu Asp Pro Glu Arg Phe Gly Pro Thr Ile Ala
                 85                  90                  95

Glu Phe Ala Arg Ala Leu Ser Ala Leu Gly Asp Pro Asp Gly Asp Gly
            100                 105                 110

Leu Ile Glu Arg Pro Leu Phe Val Ala Leu Met Lys Ala Ile Gly Phe
        115                 120                 125

Glu Glu Ala Asn Ile His Ala Leu Phe Asp Ala Phe Ala Pro Asp Ala
    130                 135                 140

Ala Asp Arg Ile Thr Val Ala Ala Trp Ala Ser Gly Ile Glu Asp Tyr
145                 150                 155                 160

Tyr Ala Pro Asp Leu Ala Gly Ile Pro Gly Asp Arg Leu Val Ala Ala
                165                 170                 175

Arg Thr Val
```

<210> SEQ ID NO 44
<211> LENGTH: 33
<212> TYPE: DNA
<213> ORGANISM: Artificial Sequence
<220> FEATURE:
<223> OTHER INFORMATION: Description of Artificial Sequence:
oligo CM410

<400> SEQUENCE: 44
aaaatgcatt cggcctgaac ggccccgctg tca 33

<210> SEQ ID NO 45
<211> LENGTH: 33
<212> TYPE: DNA
<213> ORGANISM: Artificial Sequence
<220> FEATURE:
<223> OTHER INFORMATION: Description of Artificial Sequence:
oligo CM411

<400> SEQUENCE: 45
aaatggccag cgaacaccaa caccacacca cca 33

<210> SEQ ID NO 46
<211> LENGTH: 32
<212> TYPE: DNA
<213> ORGANISM: Artificial Sequence
<220> FEATURE:
<223> OTHER INFORMATION: Description of Artificial Sequence:
oligo CM412

<400> SEQUENCE: 46
aaagtcctag gcggcggccg gcgggtcgac ct 32

<210> SEQ ID NO 47
<211> LENGTH: 35
<212> TYPE: DNA
<213> ORGANISM: Artificial Sequence -continued
<220> FEATURE:
<223> OTHER INFORMATION: Description of Artificial Sequence:
      oligo CM413

<400> SEQUENCE: 47
tttagatctc gcgacgtcgc acgcgccgaa cgtca 35

<210> SEQ ID NO 48
<211> LENGTH: 34
<212> TYPE: DNA
<213> ORGANISM: Artificial Sequence
<220> FEATURE:
<223> OTHER INFORMATION: Description of Artificial Sequence:
      oligo CM414

<400> SEQUENCE: 48
aaactgcaga gtcgaacatc ggtcacacgc aggc 34

<210> SEQ ID NO 49
<211> LENGTH: 35
<212> TYPE: DNA
<213> ORGANISM: Artificial Sequence
<220> FEATURE:
<223> OTHER INFORMATION: Description of Artificial Sequence:
      oligo CM415

<400> SEQUENCE: 49
aaaatgcatg atccacatcg atacgacgcg cccga 35

<210> SEQ ID NO 50
<211> LENGTH: 36
<212> TYPE: DNA
<213> ORGANISM: Artificial Sequence
<220> FEATURE:
<223> OTHER INFORMATION: Description of Artificial Sequence:
      oligo CM416

<400> SEQUENCE: 50
taaatgcatt ccattcggtg caggtggagt tgatcc 36

<210> SEQ ID NO 51
<211> LENGTH: 36
<212> TYPE: DNA
<213> ORGANISM: Artificial Sequence
<220> FEATURE:
<223> OTHER INFORMATION: Description of Artificial Sequence:
      oligo CM417

<400> SEQUENCE: 51
ataggatccc ctccgggtgc tccagaccgg ccaccc 36

<210> SEQ ID NO 52
<211> LENGTH: 35
<212> TYPE: DNA
<213> ORGANISM: Artificial Sequence
<220> FEATURE:
<223> OTHER INFORMATION: Description of Artificial Sequence:
      oligo CM368

<400> SEQUENCE: 52
tttcctgcag gccatcccca cgatcgcgat cggct 35

<210> SEQ ID NO 53
<211> LENGTH: 35
<212> TYPE: DNA
<213> ORGANISM: Artificial Sequence
<220> FEATURE:

-continued

<223> OTHER INFORMATION: Description of Artificial Sequence:
oligo CM369

<400> SEQUENCE: 53
tttcatatga caggcagtgc tgtttcggcc ccatt 35

<210> SEQ ID NO 54
<211> LENGTH: 36
<212> TYPE: DNA
<213> ORGANISM: Artificial Sequence
<220> FEATURE:
<223> OTHER INFORMATION: Description of Artificial Sequence:
oligo CM370

<400> SEQUENCE: 54
tttcatatgg cggatgccgt acgtgccgcc ggcgct 36

<210> SEQ ID NO 55
<211> LENGTH: 32
<212> TYPE: DNA
<213> ORGANISM: Artificial Sequence
<220> FEATURE:
<223> OTHER INFORMATION: Description of Artificial Sequence:
oligo CM371

<400> SEQUENCE: 55
tttcatatgc cccaggcgat cgtccgcacc ac 32

<210> SEQ ID NO 56
<211> LENGTH: 41
<212> TYPE: DNA
<213> ORGANISM: Artificial Sequence
<220> FEATURE:
<223> OTHER INFORMATION: Description of Artificial Sequence:
oligo CM372

<400> SEQUENCE: 56
tttcatatgg tctcggcccc ccacacaaga gccctccggg c 41

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence:
oligo B1819A

<400> SEQUENCE: 57
gtcatgcatg cggcgggctc 20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence:
oligo B1819B

<400> SEQUENCE: 58
ggtctagaac ggccgaactt 20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence:

-continued oligo B1819C

<400> SEQUENCE: 59
gttctagaac ctcggtcggc 20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence:
oligo B1819D

<400> SEQUENCE: 60
ctggatccca cgctgctgcg 20

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence:
oligo BLDA

<400> SEQUENCE: 61
ggagacttac gggggatgc 19

<210> SEQ ID NO 62
<211> LENGTH: 19
<212> TYPE: DNA
<213> ORGANISM: Artificial Sequence
<220> FEATURE:
<223> OTHER INFORMATION: Description of Artificial Sequence:
oligo BLDB

<400> SEQUENCE: 62
ctccagcagc gaccagaac 19

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence:
oligo B19A

<400> SEQUENCE: 63
cccatgcatc accgacatac 20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence:
oligo B19B

<400> SEQUENCE: 64
gcgatatccc gaagaacgcg 20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence:
oligo B1920A -continued

<400> SEQUENCE: 65
gccaagcttc ctcgacgcgc 20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence:
oligo B1920B

<400> SEQUENCE: 66
cactagtgcc tcacccagtt 20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence:
oligo B1920C

<400> SEQUENCE: 67
cactagtgac ggccgaagcg 20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence:
oligo B1920D

<400> SEQUENCE: 68
tcggatccgt cagaccgttc 20

<210> SEQ ID NO 69
<211> LENGTH: 36
<212> TYPE: DNA
<213> ORGANISM: Artificial Sequence
<220> FEATURE:
<223> OTHER INFORMATION: Description of Artificial Sequence:
oligo CM384

<400> SEQUENCE: 69
aacctgcagg taccccggtg gggtgcggtc gcccga 36

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence:
oligo CM385

<400> SEQUENCE: 70
cgccgcacgc gtcgaagcca acga 24

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence:
oligo CM386

-continued

<400> SEQUENCE: 71
tgtgggctgg tcgttggctt cgac 24

<210> SEQ ID NO 72
<211> LENGTH: 34
<212> TYPE: DNA
<213> ORGANISM: Artificial Sequence
<220> FEATURE:
<223> OTHER INFORMATION: Description of Artificial Sequence:
oligo CM387

<400> SEQUENCE: 72
ggtgcctgca gcgtgagttc ctcgacggat ccga 34

<210> SEQ ID NO 73
<211> LENGTH: 26
<212> TYPE: DNA
<213> ORGANISM: Artificial Sequence
<220> FEATURE:
<223> OTHER INFORMATION: Description of Artificial Sequence:
oligo CM388

<400> SEQUENCE: 73
gaggaactca ccctgcaggc accgct 26

<210> SEQ ID NO 74
<211> LENGTH: 26
<212> TYPE: DNA
<213> ORGANISM: Artificial Sequence
<220> FEATURE:
<223> OTHER INFORMATION: Description of Artificial Sequence:
oligo CM395

<400> SEQUENCE: 74
cgaacgtcca gccctcgggc atgcgt 26

<210> SEQ ID NO 75
<211> LENGTH: 28
<212> TYPE: DNA
<213> ORGANISM: Artificial Sequence
<220> FEATURE:
<223> OTHER INFORMATION: Description of Artificial Sequence:
oligo CM396

<400> SEQUENCE: 75
tggcacgcat gcccgagggc tggacgtt 28

<210> SEQ ID NO 76
<211> LENGTH: 35
<212> TYPE: DNA
<213> ORGANISM: Artificial Sequence
<220> FEATURE:
<223> OTHER INFORMATION: Description of Artificial Sequence:
oligo CM397

<400> SEQUENCE: 76
tttcctgcag gccatgccga cgatcgcgac aggct 35

<210> SEQ ID NO 77
<211> LENGTH: 36
<212> TYPE: DNA
<213> ORGANISM: Artificial Sequence
<220> FEATURE:
<223> OTHER INFORMATION: Description of Artificial Sequence:
oligo CM398

<400> SEQUENCE: 77

-continued aaacatatgg tcctggcgct gcgcaacggg gaactg 36

<210> SEQ ID NO 78
<211> LENGTH: 35
<212> TYPE: DNA
<213> ORGANISM: Artificial Sequence
<220> FEATURE:
<223> OTHER INFORMATION: Description of Artificial Sequence:
oligo CM399

<400> SEQUENCE: 78
tttcctgcag gcgatgccga cgatggcgat gggct 35

<210> SEQ ID NO 79
<211> LENGTH: 43
<212> TYPE: DNA
<213> ORGANISM: Artificial Sequence
<220> FEATURE:
<223> OTHER INFORMATION: Description of Artificial Sequence:
oligo CM400

<400> SEQUENCE: 79
aaacctgcag gttccccggc gacgtggact cgccggagtc gtt 43

<210> SEQ ID NO 80
<211> LENGTH: 41
<212> TYPE: DNA
<213> ORGANISM: Artificial Sequence
<220> FEATURE:
<223> OTHER INFORMATION: Description of Artificial Sequence:
oligo CM401

<400> SEQUENCE: 80
ttttctagag cgacgtcgca ggcggcgatg gtcacgcccg t 41

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence:
oligo B25A

<400> SEQUENCE: 81
ttctgcagcc gcggccttcg 20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence:
oligo B25B

<400> SEQUENCE: 82
agaattcgcc ggcgccgctg 20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence:
oligo B7T1

<400> SEQUENCE: 83

-continued ggctgcagac gcggctgaag 20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence:
oligo B7T2

<400> SEQUENCE: 84
ccggatccca gagccacgtc 20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence:
oligo BP4501

<400> SEQUENCE: 85
cgtatgcatg gcgccatgga 20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence:
oligo BP4502

<400> SEQUENCE: 86
agccaattgg tgcactccag 20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence:
oligo BNHT1

<400> SEQUENCE: 87
gtcatgcatc agcgcacccg 20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence:
oligo BNHT2

<400> SEQUENCE: 88
gtgcaattgc cctggtagtc 20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence:
oligo BTRNAS1

<400> SEQUENCE: 89
tgtctagact cgcgcgaaca 20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence:
oligo BTRNAS2

<400> SEQUENCE: 90
tgaattccga agggggtggt 20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence:
oligo B5B

<400> SEQUENCE: 91
aactagtccg cagtggaccg 20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence:
oligo B5A

<400> SEQUENCE: 92
tcgatatcct caccgcccgt 20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence:
oligo B6B

<400> SEQUENCE: 93
aactagtgtg gcagacggtc 20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence:
oligo B5A

<400> SEQUENCE: 94
tcgatatcct caccgcccgt 20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence:
oligo B6T1

<400> SEQUENCE: 95
cggatgcatc accggcacgg 20

-continued

```
<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence:
      oligo B6T2

<400> SEQUENCE: 96

tgggatccgc ggggcggtac                                                20


<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence:
      oligo BBB

<400> SEQUENCE: 97

aactagtgcg atcccgggga                                                20


<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence:
      oligo BBA

<400> SEQUENCE: 98

cgtcgatatc ctccaggggc                                                20


<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence:
      oligo BBT1

<400> SEQUENCE: 99

tactgcagca cacccggtgc                                                20


<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence:
      oligo BBT2

<400> SEQUENCE: 100

tgggatccgc tgtgtcatat                                                20


<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence:
      oligo BCB

<400> SEQUENCE: 101

cactagtcct cgccgggcac                                                20
```

-continued

```
<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence:
      oligo BCA

<400> SEQUENCE: 102

gaggatcccg gtcagcggca                                              20


<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence:
      oligo BCT1

<400> SEQUENCE: 103

gcctgcagcg acctcgccgg                                              20


<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence:
      oligo BCT2

<400> SEQUENCE: 104

cgggatcccg tggcgtggtc                                              20


<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence:
      oligo B23A

<400> SEQUENCE: 105

atctgcagcg gcatcggtgt                                              20


<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence:
      oligo B23B

<400> SEQUENCE: 106

agaattctcc actgcggtcg                                              20


<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence:
      oligo B9A

<400> SEQUENCE: 107

acctgcaggc cgggctcatc                                              20


<210> SEQ ID NO 108
```

-continued

<211> LENGTH: 20
<212> TYPE: DNA
<213> ORGANISM: Artificial Sequence
<220> FEATURE:
<223> OTHER INFORMATION: Description of Artificial Sequence:
oligo B9B

<400> SEQUENCE: 108
agaattcggg cgagccgccg 20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence:
oligo B231

<400> SEQUENCE: 109
atcaagcttc gtgtccatgg 20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence:
oligo B232

<400> SEQUENCE: 110
gtcatgcatc aggcgttcgg 20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence:
oligo B251

<400> SEQUENCE: 111
cttctagatg aacccctcca 20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence:
oligo B252

<400> SEQUENCE: 112
gggcaattgc gcggcagctt 20

<210> SEQ ID NO 113
<211> LENGTH: 90
<212> TYPE: PRT
<213> ORGANISM: Streptomyces parvulus Tu4055

<400> SEQUENCE: 113

Met Leu Gly Phe Tyr Ala Leu Leu Leu Ala Pro Ala Glu Leu Asp Leu
1 5 10 15

Leu Phe Val Gln Asp Gly Thr Gln Gly Arg Gly Ile Gly Arg Leu Leu
20 25 30

Val Asp His Met Lys Arg Arg Ala Arg Ala Ala Gly Leu Asp Arg Val
35 40 45

-continued

```
Arg Val Val Ser His Pro Pro Ala Glu Gly Phe Tyr Arg Ala Val Gly
     50                  55                  60

Ala Leu Pro Thr Gly Thr Ala Arg Ala Asn Pro Pro Ala Val Ala Trp
 65                  70                  75                  80

Asp Arg Pro Val Leu Glu Phe Leu Ile Pro
                 85                  90
```

BORRELIDIN-PRODUCING POLYKETIDE SYNTHASE AND ITS USE

This application is a 371 of PCT/GB03/05704, filed Dec. 24, 2003, which claims the priority of United Kingdom 0230217.2, filed Dec. 27, 2002.

FIELD OF THE INVENTION

The present invention relates to materials and methods for the preparation of polyketides. Enzyme systems, nucleic acids, vectors and cells are provided for the preparation of polyketides, and in particular the polyketide macrolide borrelidin.

BACKGROUND TO THE INVENTION

Polyketides are natural products produced by a wide range of organisms, and particularly by microorganisms. Polyketides have many important pharmaceutical, veterinary and agricultural uses. Polyketides encompass a huge range of chemical structural space, and have a wide range of associated biological activities. Polyketides with use in medical treatments include antibiotics, immunosuppressants, antitumor agents, other chemotherapeutic agents, and other compounds possessing a broad range of therapeutic and biological properties. The Gram-positive bacteria *Streptomyces* and their allied genera are prodigious producers of polyketides, and the genetics and biochemistry of polyketide biosynthesis in these organisms are relatively well characterised (Hopwood, 1997). The genes for polyketide biosynthesis in *Streptomyces* are clustered and the exploitation of DNA technology has made it possible to isolate complete biosynthetic gene clusters by screening gene libraries with DNA probes encoding the genes responsible for their biosynthesis. Thus, increasing numbers of gene clusters for polyketide biosynthesis in *Streptomyces* and other microorganisms have been isolated and sequenced, including, for example, those for the polyether monensin (WO 01/68867), the polyene nystatin (WO 01/59126) and for rapamycin (Schwecke et al., 1995).

Polyketides are synthesised through the repeated condensation of building blocks that contain a carboxylic acid function. At each stage of the process this results in the formation of a new β-keto function and an α-side chain branch into the growing chain. The structural diversity of polyketides derives from a number of aspects of their biosynthetic pathway including: the wide variety of starter units that may be utilised in their biosynthesis; the different lengths of polyketide chains that are possible; the various α-side chains that are introduced either during or after assembly of the polyketide chain; the various β-substitutions that may be introduced during or after assembly of the polyketide chain; the various degrees of processing that the β-keto groups can undergo (keto, hydroxyl, enoyl, and methylene); and the various stereochemistries that are possible at the α- and β-centres.

The synthesis of polyketides is catalysed by an enzyme, or by a complex of enzymes, called the polyketide synthase (PKS) in a manner similar to that of fatty acid biosynthesis. *Streptomyces* and related genera PKSs fall into three main categories: type-I, type-II and type-III. The type-III PKSs are small proteins related to plant chalcone synthases that have been discovered only recently (Moore & Hopke, 2000). Type-III systems have been implicated in the biosynthesis of a small number of secondary metabolites but may be more generally involved in the biosynthesis of soluble pigments (Cortés et al., 2002). The type-II PKSs consist of several monofunctional proteins that act as a multi-polypeptide complex. Simple aromatic polyketides such as actinorhodin are formed by several rounds of chain assembly, which are performed iteratively on one set of type-II PKS enzymes that are encoded for by one set of PKS genes (Hopwood, 1997). Type-I PKSs are multifunctional proteins and are required for the synthesis of more complex polyketides such as erythromycin and rapamycin. As the focus of this patent, type-I PKS organisation and function are described in detail below:

Type-I PKSs are organised into modules, whereby each module consists of several catalytic 'domains' that are required to carry out one round of chain assembly (Staunton & Wilkinson, 1997). In general a modular PKS contains the correct number of modules (loading plus extension modules) to select and condense the correct number of loading and extension units. For example the erythromycin PKS consists of 7 modules (one loading and six extension modules) to select and condense the one starter and six extension units required for the biosynthesis of the erythromycin precursor 6-deoxyerythronolide B. Thus, there exists a one to one relationship between the number of modules present in the PKS and the number of units incorporated. This one to one relationship is described as 'co-linearity'.

The term 'extension module' as used herein refers to the set of contiguous domains, from the β-ketoacyl-acyl carrier protein synthase (KS) domain to the next acyl carrier protein (ACP) domain, which accomplishes one cycle of polyketide chain extension. The term 'loading module' as used herein refers to any group of contiguous domains that accomplishes the loading of the starter unit onto the PKS and thus renders it available to the KS domain of the first extension module. Besides condensation of the next extender carboxylic acid (or ketide) unit onto the growing polyketide chain, which is performed by the catalytic activity of the essential KS domain, modules of type-I PKSs may contain domains with β-ketoreductase (KR), dehydratase (DH), and enoyl reductase (ER) activities which are responsible for the further processing of the newly formed β-keto groups during chain extension. The acyl transferase (AT) and the ACP domains present in each module are responsible for the choice of extender unit, and the tethering of the growing chain during its passage on the PKS respectively. The AT domains of a modular PKS can also be found as discrete proteins (Cheng et al., 2003). The completed polyketide chain is generally released from PKSs by the action of a terminal thioesterase (TE) domain that is also generally involved in the cyclisation (lactonisation) of the final product. Other chain terminating/cyclising strategies are also employed such as that for the addition of an amino acid residue and macrolactam formation as observed for rapamycin (Schwecke et al., 1995), for macrolactam formation as for rifamycin (August et al., 1998), and for amino acid incorporation followed by reductive elimination as for myxalamid biosynthesis (Silakowski et al., 2001). In summary, there is a single enzymatic domain present for each successive catalytic step that occurs during biosynthesis on the PKS, and they are used in defined sequence that depends upon their location within the protein and the particular function they perform. This mechanism is termed 'processive'.

The modular arrangement of type-I PKSs was first confirmed by mutation of the erythromycin PKS (also known as 6-deoxyerythronolide B synthase, DEBS) through an in-frame deletion of a region of the KR domain of module 5 (Donadio et al., 1991). This led to the production of the erythromycin analogues, 5,6-dideoxy-3-α-mycarosyl-5-oxoerythronolide B and 5,6-dideoxy-5-oxoerythronolide B, due to the inability of the mutated KR domain to reduce the β-keto group 5 at this stage of processive biosynthesis. Likewise, alteration of the active site residues in the ER domain of module 4 of DEBS2, by genetic engineering of the corresponding PKS-encoding DNA and its introduction into *Saccharopolyspora erythraea*, led to the production of 6,7-anhydroerythromycin C (Donadio et al., 1993). In addition, the length of the polyketide chain formed by DEBS has been altered through the specific relocation of the TE domain of DEBS3 to the end of DEBS1; the expected triketide lactone product was produced in good yield (Cortés et al., 1995). It should be noted that the changes described involved modification by deletion of sequence, or by sequence specific inactivation, or by the alternative juxtaposition of DNA sequence from within the same PKS cluster (ie. they are considered 'homologous changes'). Other such 'homologous' changes to the erythromycin PKS are described in WO 93/13663.

The modular organisation of type-I PKS genes lends itself to the manipulation of these genes to produce altered polyketide structures. Type I PKSs represent an assembly line for polyketide biosynthesis that can be manipulated by changing the number of modules; by changing their specificities towards different carboxylic acid starter units and extender units; by inactivating, mutating, removing, swapping or inserting domains with different activities and specificities; and by altering the chain or ring size through the repositioning of termination or cyclisation domains (Staunton & Wilkinson, 1997).

WO 98/01546 describes the production of hybrid PKS gene assemblies comprising the incorporation of heterologous DNA. WO 98/01546 describes methods for generating hybrid PKSs in which the substitution of genes encoding heterologous modules, sub-modules or domains for the native genes generates novel polyketides with altered structures. Specifically, for example the AT domains of heterologous DNA from the rapamycin or monensin PKSs can be exchanged for that native to the erythromycin PKS in order to generate novel polyketides with altered alkyl branching. Such an AT domain swap represented the first example of the production of a truly hybrid PKS (Oliynyk et al., 1996). WO 98/01546 also describes in general terms the production of hybrid PKS assemblies comprising a loading module and at least one extension module. It specifically describes the construction of a hybrid PKS gene assembly by grafting the broad-specificity loading module for the avermectin-producing PKS onto the first protein of the erythromycin PKS (DEBS1) in place of the normal loading module (see also Marsden et al., 1998). Additional examples comprising loading module swaps that are substrate specific have also been described (WO 00/00618; U.S. Pat. No. 5,876,991; Kuhstoss et al., 1996). WO 00/01827 describes methods for varying the β-keto processing capability of a PKS module through the ability to swap 'reductive loops', ie. the ability to rapidly and in a combinatorial manner, alter the number and type of ketoreductase, dehydratase and enoyl reductase domains within a module. In addition to changing the level of β-keto group processing, such changes may also lead to changes in stereochemistry of the α-alkyl and β-hydroxyl groups thus formed by the altered modules.

Although modular PKSs operate 'normally' in a co-linear and processive manner as described above, examples of a deviation from this mode of operation have been described and are discussed below.

The picromycin PKS gene cluster in *Streptomyces venezuelae* is responsible for the biosynthesis of both picromycin (a 14-membered, heptaketide macrolide) and methymycin (a 12-membered, hexaketide macrolide) (Xue et al., 1998). The ability of a single PKS to produce two related macrolides, of different ring sizes, derives from the alternative expression of the final PKS gene pikA4 (Xue & Sherman, 2000). When 'normal' expression occurs and full-length PikA4 is formed, a sixth extension unit is incorporated and the picromycin aglycone is produced; when alternative expression occurs and an N-terminally truncated form of PikA4 is produced, no sixth extension unit is incorporated and the growing polyketide chain is passed directly to the TE domain which leads to formation of the methymycin aglycone. Thus, a breakdown of co-linearity occurs and a 'ring contracted' product is formed. The biochemical basis for this phenomenon has been investigated and shown to be an ACP5 to ACP6 transfer, missing out covalent attachment to the intervening KS6 domain; such a breakdown of co-linearity has been called 'skipping' (Beck et al., 2002).

Skipping has also been observed to occur when an extra extension module from the rapamycin PKS was interpolated into the erythromycin PKS in order to convert the natural heptketide-producing PKS Into an octaketide-producing one (Rowe et al., 2001). The expected octaketide, 16-membered macrolide was produced, but the major product was the normal heptaketide product 6-deoxyerythronolide. This 'skipping' of the interpolated module is believed to occur due to the interpolated module acting on some occasions as a 'shuttle', passing the growing chain from the preceding module to the following downstream module without performing a round of chain extension. It was subsequently shown that the ACP domain of the interpolated module is essential in passing the growing polyketide chain from the preceding ACP domain and passing it to the KS domain of the following module during skipping (Thomas et al., 2002), a mechanism similar to that described for methymycin biosynthesis above. It is shown that skipping can occur without the active site nucleophile of the KS domain. A ring-contracted (skipped) nemadectin (an antiparasitic macrolide) has been reported from a mutant of a *Streptomyces* soil isolate that was modified by chemical mutation (Rudd et al., 1990); the biosynthesis of the natural PKS product was abolished.

An alternative manner in which modular PKSs deviate from co-linear operation involves the iterative operation of modules. For example, module 4 of the erythromycin PKS appears to operate iteratively, at a low level, to produce a ring expanded 16-membered, octaketide macrolide related to 6-deoxyerythronolide B (Wilkinson et al., 2000). The ability of the erythromycin PKS to perform this operation has been termed 'stuttering'. The 'stuttering' of the erythromycin PKS is considered an aberrant process, as the products of this stuttering are formed in low yield and the major product of the erythromycin PKS is the normal heptaketide 6-deoxyerythonolide B formed by co-linear operation. Products that appear to be formed by both stuttering and skipping have also been reported as minor components from the epothilone producer *Sorangium cellulosum* (Hardt et al., 2001). The stigmatellin biosynthetic cluster of *Stigmatella aurantiaca* encodes for a PKS that comprises ten (one loading and nine extension) modules (Gaitatzis et al., 2002); however, based on results from structural elucidation and the feeding of stable isotope labelled substrates, stigmatellin is formed from eleven modular derived units. Thus, it would appear that one of the stigmatellin PKS modules operates (twice) iteratively.

Since the priority filing of the present application, the sequence of the PKS responsible for biosynthesis of the macrolide lankacidin by *Streptomyces rochei* has been described (Mochizuki et al., 2003). This PKS also appears to contain too few modules in comparison to the number of extension cycles required for lankacidin biosynthesis, although the mechanism by which this would occur is not clear.

Additional structural diversity can be generated through the modification of polyketides by enzymes other than the PKS, either during the process of chain assembly as seen during the biosynthesis of some ansamycins (Floss, 2001), or after the process of chain assembly following release from the PKS. Such non-PKS mediated reactions may include, but are not limited to the following: reduction, oxidation, hydroxylation, acylation, alkylation, amination, decarboxylation, dehydration, double bond isomerisation/migration, cyclisation, ring cleavage, conjugation, glycosylation, reductive elimination and any combination of these. When these reactions occur after chain assembly they are termed the post-PKS or tailoring steps. Such tailoring steps are generally, but not always, essential for endowing the polyketide natural product with biological activity.

In addition, the structural diversity of polyketides obtainable biosynthetically can be further enhanced through the use of defined heterologous post-PKS tailoring enzymes as well as through the use of those which naturally modify the natural polyketide (Gaisser et al., 2000). WO 01/79520 describes the heterologous modification of polyketide macrolide structures through glycosylation, epoxidation, hydroxylation, and methylation. The ability to generate analogues of the agricultural compound spinosyn through glycosylation with alternative deoxyhexose substituents has been reported (Gaisser et al., 2002).

Borrelidin 1 (FIG. 1) is an 18-membered macrolide produced by several bacterial strains including, but not limited to, *Streptomyces rochei* ATCC23956, *Streptomyces parvulus* Tü113 and *Streptomyces parvulus* Tü4055. Borrelidin is herein shown to be derived from a trans-cyclopentane-1,2-dicarboxylic acid starter acid, three malonyl-CoA and five methylmalonyl-CoA extender units (see FIG. 2). From the absolute stereochemistry of borrelidin, based on the crystal structure and recently confirmed through total synthesis, the actual starter acid is predicted to be trans-cyclopentane-(1R,2R)-dicarboxylic acid. Borrelidin isolated after the feeding of stable isotope labelled acetate and propionate substrates clearly indicated the expected incorporation of these building blocks; in addition, it has been demonstrated in the present application that feeding of trans-cyclopentane-1,2-dicarboxylic acid was sufficient to re-establish borrelidin biosynthesis in mutants where specific genes believed to be involved in the formation of the starter unit had been disrupted. Borrelidin contains a nitrile group attached to the C12 position, which is shown herein to arise through the action of tailoring enzymes acting upon a methylmalonyl-CoA derived methyl branch present at this position. The gross structure of borrelidin was first elucidated in 1967 (Keller-Scheirlein, 1967), and was subsequently refined by detailed NMR analysis (Kuo et al., 1989). The absolute configuration of borrelidin was confirmed by X-ray crystallography (Anderson et al., 1989). Its co-identity as the antibiotic treponemycin has been verified (Maehr & Evans, 1987).

A number of groups have reported the synthesis of fragments of the borrelidin structure, and since the priority filing of the present application, two independent total syntheses of borrelidin have been reported (Hanessian et al., 2003; Duffey et al., 2003).

Borrelidin was first discovered due to its antibacterial activity (Berger et al., 1949), although this antibacterial activity extends only to a limited number of micrococci, and is not found against all common test bacteria. The mode of action in sensitive microorganisms involves selective inhibition of threonyl tRNA synthetase (Paetz & Nass, 1973). Other activities against spirochetes of the genus *Treponema* (Singh et al., 1985; U.S. Pat. No. 4,759,928), against viruses (Dickinson et al., 1965), uses for the control of animal pests and weeds (DE 3607287) and use as an agricultural fungicide (DE 19835669; U.S. Pat. No. 6,193,964) have been reported. Additionally, since the priority filing of the present application, borrelidin has been reported to have antimalarial activity against drug resistant *Plasmodium falciparum* strains (Otoguro et al., 2003). Between all of these reports only two reported any synthetically modified derivatives. The first of these describes the benzyl ester and its bis-O-(4-nitrobenzoyl) derivative (Berger et al., 1949). The second of these describes the borrelidin methyl ester, the methyl ester bis O-acetyl derivative, and the methyl ester $\Delta_{14-15}$-dihydro-, $\Delta_{14-15,12-13}$-tetrahydro-, and $\Delta_{14-15,12-13}$-tetrahydro-C12-amino derivatives (Anderton & Rickards, 1965). No biological activity was reported for any of these compounds.

A recent disclosure of particular interest is the discovery that borrelidin displays anti-angiogenesis activity (Wakabayashi et al., 1997). Angiogenesis is the process of the formation of new blood vessels. Angiogenesis occurs only locally and transiently in adults, being involved in, for example, repair following local trauma and the female reproductive cycle. It has been established as a key component in several pathogenic processes including cancer, rheumatoid arthritis and diabetic retinopathy. Its importance in enabling tumours to grow beyond a diameter of 1-2 cm was established by Folkman (Folkman, 1986), and is provoked by the tumour responding to hypoxia. In its downstream consequences angiogenesis is mostly a host-derived process, thus inhibition of angiogenesis offers significant potential in the treatment of cancers, avoiding the hurdles of other anticancer therapeutic modalities such as the diversity of cancer types and drug resistance (Matter, 2001). It is of additional interest that recent publications have described the functional involvement of tyrosinyl- and tryptophanyl tRNA synthetases in the regulation of angiogenesis (Wakasugi et al., 2002; Otani et al., 2002).

In the rat aorta matrix culture model of angiogenesis, borrelidin exhibits a potent angiogenesis-inhibiting effect and also causes disruption of formed capillary tubes in a dose dependent manner by inducing apoptosis of the capillary-forming cells (Wakabayashi et al., 1997). Borrelidin inhibited capillary tube formation with an $IC_{50}$ value of 0.4 ng/ml (0.8 nM). In the same study, borrelidin was shown to possess anti-proliferative activity towards human umbilical vein endothelial cells (HUVEC) in a cell growth assay; the $IC_{50}$ value was measured at 6 ng/ml, which is 15-fold weaker than the anti-angiogenesis activity measured in the same medium. This anti-proliferative activity of borrelidin was shown to be general towards various cell lines. In addition to these data the authors report that borrelidin inhibits tRNA synthetase and protein synthesis in the cultured rat cells; however the $IC_{50}$ value for anti-angiogenesis activity (0.4 ng/ml) was 50-fold lower than that reported for inhibition of protein synthesis (20 ng/ml), indicating different activities of the compound.

Borrelidin also displays potent inhibition of angiogenesis in vivo using the mouse dorsal air sac model (Funahashi et al., 1999), which examines VEGF-induced angiogenesis and is an excellent model for studying tumour-angiogenesis. Borrelidin was administered at a dose of 1.8 mg/kg by intraperitoneal injection and shown to significantly reduce the increment of vascular volume induced by WiDr cells, and to a higher degree than does TNP-470, which is a synthetic angiogenesis inhibitor in clinical trials. Detailed controls verified that these data are for angiogenesis inhibition and not inhibition of growth of the tumour cells. The authors also showed that borrelidin is effective for the inhibition of the formation of spontaneous lung metastases of B16-BL6 melanoma cells at the same dosage by inhibiting the angiogenic processes involved in their formation.

JP 9-227,549 and JP 8-173,167 confirm that borrelidin is effective against WiDr cell lines of human colon cancer, and also against PC-3 cell lines of human prostate cancer. JP 9-227,549 describes the production of borrelidin by *Streptomyces rochei* Mer-N7167 (Ferm P-14670) and its isolation from the resulting fermentation culture. In addition to borrelidin 1,12-desnitrile-12-carboxyl borrelidin 2 (presumably a biosynthetic intermediate or shunt metabolite), 10-desmethyl borrelidin 3 (presumably a biosynthetic analogue arising from the mis-incorporation of an alternative malonyl-CoA extender unit in module 4 of the borrelidin PKS), 11-epiborrelidin 4 and the C14,C15-cis borrelidin analogue 5 were described (see FIG. 1). Thus, JP 9-227,549 specifies borrelidin and borrelidin analogues wherein a nitrile or carboxyl group is attached the carbon skeleton at C12, and a hydrogen atom or lower alkyl group is attached to the carbon skeleton at C10.

WO 01/09113 discloses the preparation of borrelidin analogues that have undergone synthetic modification at the carboxylic acid moiety of the cyclopentane ring. The activity of these compounds was examined using endothelial cell proliferation and endothelial capillary formation assays In a similar manner to that described above. In general, modification of the carboxyl moiety improved the selectivity for inhibiting capillary formation: the major reason for this improvement in selectivity is through a decrease in the cell proliferation inhibition activity whereas the capillary formation inhibitory activity was altered to a much lower degree. Specifically, the borrelidin-morpholinoethyl ester showed a 60-fold selectivity index, the borrelidin-amide showed a 37-fold selectivity index, the borrelidin-(2-pyridyl)-ethyl ester showed a 7.5-fold selectivity index and the borrelidin-morpholinoethyl amide showed a 6-fold selectivity index, for the capillary formation inhibitory activity versus cell proliferation with respect to borrelidin. The capillary formation inhibitory activity of these and other borrelidin derivatives was verified using a micro-vessel formation assay. In addition, the authors showed that borrelidin weakly inhibited the propagation of metastatic nodules, after removal of the primary tumour, when using a Lewis lung adenocarcinoma model. However, the borrelidin-(3-picolylamide) derivative was reported to inhibit very considerably the increase of micrometastases in rats after intraperitoneal and also with per os administration at subtoxic doses. Similarly, using the colon 38 spleen liver model, the metastasis-forming ability of mouse colon adenocarcinoma cells transplanted into mouse spleen was considerably decreased after treatment with a subtoxic dose of this borrelidin derivative. These data confirm the earlier reported ability of borrelidin and its derivatives to inhibit the formation of metastases.

Borrelidin has also been identified as an inhibitor of cyclin-dependant kinase Cdc28/Cln2 of *Saccharomyces cerivisiae* with an $IC_{50}$ value of 12 μg/ml (24 μM) (Tsuchiya et al., 2001). It was shown that borrelidin arrests both haploid and diploid cells in late $G_1$ phase (at a time point indistinguishable from α-mating pheromone), and at concentrations that do not affect gross protein biosynthesis. These data were taken to indicate that borrelidin has potential as a lead compound to develop anti-tumour agents.

Since the priority filing of the present application, two further reports have been published concerning the biological activity of borrelidin. The first of these indicates that the anti-angiogenic effects of borrelidin are mediated through distinct pathways (Kawamura et al., 2003). High concentrations of threonine were found to attenuate the ability of borrelidin to inhibit both capillary tube formation in the rat aorta culture model and HUVEC cells proliferation; however, it did not affect the ability of borrelidin to collapse formed capillary tubes or to induce apoptosis in HUVEC. Borrelidin was also found to activate caspase-3 and caspase-8, and inhibitors of both of these suppressed borrelidin induced apoptosis in HUVEC. The second of these papers used the method of global cellular mRNA profiling to provide insight into the effects of borrelidin on *Saccharomyces cerevisiae* (Eastwood and Schaus, 2003). This analysis showed the induction of amino acid biosynthetic enzymes in a time-dependent fashion upon treatment with borrelidin, and it was ascertained that the induction of this pathway involves the GCN4 transcription factor.

In summary, the angiogenesis-inhibitory effect of borrelidin is directed towards the twin tumour-biological effects of proliferation and capillary formation. In addition, borrelidin, and derivatives thereof, have been shown to inhibit the propagation of metastases. Borrelidin also has indications for use in cell cycle modulation. Thus, borrelidin and related compounds are particularly attractive targets for investigation as therapeutic agents for the treatment of tumour tissues, either as single agents or for use as an adjunct to other therapies. In addition, they may be used for treating other diseases in which angiogenesis is implicated in the pathogenic process, including, but not restricted to, the following list: rheumatoid arthritis, psoriasis, atherosclerosis, diabetic retinopathy and various ophthalmic disorders.

SUMMARY OF THE INVENTION

The present invention provides the entire nucleic acid sequence of the biosynthetic gene cluster responsible for governing the synthesis of the polyketide macrolide borrelidin in *Streptomyces parvulus* Tü4055. Also provided is the use of all or part of the cloned DNA and the nucleic acid sequences thereof in the specific detection of other polyketide biosynthetic gene clusters, in the engineering of mutant strains of *Streptomyces parvulus* and other suitable host strains for the production of enhanced levels of borrelidin, or for the production of modified or novel polyketides, and of recombinant genes encoding PKS systems for the biosynthesis of modified or novel polyketides.

The present invention provides an isolated nucleic acid molecule comprising all or part of a borrelidin biosynthetic gene cluster.

The complete nucleotide sequence of the borrelidin biosynthetic gene cluster from *Streptomyces parvulus* Tü4055 is shown in SEQ ID No.1. Its organisation is presented in FIG. 3 and comprises genes and open reading frames designated hereinafter as: borA1, borA2, borA3, borA4, borA5, borA6, borB, borC, borD, borE, borF, borG, borH, borI, borJ, borK, borL, borM, borN, borO, orfB1, orfB2, orfB3, orfB4, orfB5, orfB6, orfB7, orfB8, orfB9, orfB10, orfB11, orfB12, orfB13, orfB14, orfB15, orfB16, orfB17, orfB18, orfB19, orfB20, orfB21 and orfB22.

The proposed functions of the cloned genes are described in FIG. 4 (proposed biosynthesis of the starter unit), 5 (organisation of the borrelidin PKS and biosynthesis of pre-borrelidin) and 6 (introduction of the C12-nitrile moiety) and are described below.

The present invention thus provides an isolated nucleic acid molecule comprising:

(a) a nucleotide sequence as shown in SEQ ID No.1, or a portion or fragment thereof; or (b) a nucleotide sequence which is the complement of SEQ ID No.1, or a portion or fragment thereof; or (c) a nucleotide sequence which is degenerate with a coding sequence of SEQ ID No.1, or a portion or fragment thereof.

As used herein the term "fragment" with respect to nucleotide sequences refers to a stretch of nucleic acid residues that are at least 10, preferably at least 20, at least 30, at least 50, at least 75, at least 100, at least 150 or at least 200 nucleotides in length. A preferred portion or fragment of SEQ ID NO:1 is the sequence extending between nucleotide positions 7603 and 59966 of SEQ ID No.1.

The sequence may encode or be complementary to a sequence encoding a polypeptide of a polyketide biosynthetic gene cluster, or a portion thereof. By "a polypeptide of a polyketide biosynthetic gene cluster" is meant a polypeptide encoded by one or more open reading frames of a polyketide biosynthetic gene cluster, and particularly the borrelidin biosynthetic gene cluster.

A polyketide biosynthetic gene cluster is a segment of DNA comprising a plurality of genes encoding polypeptides having activity in the biosynthesis of a polyketide or macrolide moiety. This is not restricted to components of the polyketide synthase (PKS) which function inter alia in the synthesis of the polyketide backbone and reductive processing of side groups, but also encompasses polypeptides having ancillary functions in the synthesis of the polyketide. Thus polypeptides of the biosynthetic gene cluster may also act in macrolide ring or polyketide chain modification (e.g. catalysing a reaction in the formation of the C12 nitrile moiety of borrelidin), in the synthesis of a precursor or starter unit for a polyketide or macrolide moiety (e.g. catalysing a reaction in the synthesis of the trans-cyclopentane-1,2-dicarboxylic acid starter unit for the borrelidin PKS, or responsible for the activation of such molecules as the coenzyme-A thioesters of the starter and extender units of the chain), regulatory activity (e.g. regulation of the expression of the genes or proteins involved in polyketide or macrolide synthesis), transporter activity (e.g. in transport of substrates for the polyketide or macrolide moiety into the cell, or of synthesis products such as the polyketide or macrolide molecule out of the cell), and in conferring resistance of the producing cell to the synthesised products (e.g. through specific binding to the synthesised molecule, or as a replacement for other endogenous proteins to which the synthesised molecule may bind within or outside of the cell).

The gene cluster also includes non-coding regions, such as promoters and other transcriptional regulatory sequences which are operably linked to the coding regions of the gene cluster. The skilled person is well able to identify such elements based upon the information provided herein, and these are within the scope of the present invention.

Genes and open reading frames encoded within SEQ ID No.1 represent preferred parts or fragments of SEQ ID No.1. Thus an isolated nucleic acid molecule may comprise a sequence that encodes a polypeptide from a borrelidin biosynthetic gene cluster, wherein said polypeptide has an amino acid sequence selected from the group consisting of SEQ ID Nos.2 to 43 and 113.

In preferred embodiments, the nucleic acid sequence comprises an open reading frame selected from the group of open reading frames of SEQ ID NO: 1 consisting of borA1, borA2, borA3, borA4, borA5, borA6, borB, borC, borD, borE, borF, borG, borH, borI, borJ, borK, borL, borM, borN, borO, orfB1, orfB2, orfB3, orfB4, orfB5, orfB6, orfB7, orfB8, orfB9, orfB10, orfB11, orfB12, orfB13a, orfB13b, orfB14, orfB15, orfB16, orfB17, orfB18, orfB19, orfB20, orfB21 and orfB22, said open reading frames being described by, respectively, bases 16184*-18814, 18875-23590, 23686-34188, 34185*-39047, 39122*-45514, 45514-50742, 7603-8397c, 8397-9194c, 9244-9996c, 9993-11165c, 11162-11980c, 11992-13611c, 13608-15659*c, 50739*-52019, 52113-53477, 53486-54466, 54506-56176, 56181*-57098, 57112-57858, 57939-59966, 2-313 (incomplete), 501*-3107, 3172-3810c, 3935-4924c, 5123-5953, 5961-6518*c, 6564*-7538, 60153-60533*c, 60620-61003, 61188*-61436, 61526-61738, 61767-62285c, 62750-63067c, 62586-62858c, 63155-65071c, 65374-65871, 65942-68305*c, 68290-68910*c, 69681-70436, 70445-71848, 71851-72957, 73037-73942 and 73995-74534c of SEQ ID No.1.

In the above list, 'c' indicates that the gene is encoded by the complementary strand to that shown in SEQ ID NO: 1. Each open reading frame above represents the longest probable open reading frame present. It is sometimes the case that more than one potential start codon can be identified. One skilled in the art will recognise this and be able to identify alternative possible start codons. Those genes which have more than one possible start codon are indicated with a '*' symbol. Throughout we have indicated what we believe to be the start codon, however, a person of skill in the art will appreciate that it may be possible to generate active protein using an alternative start codon, proteins generated using these alternative start codons are also considered within the scope of the present invention.

It should be noted that a number of these open reading frames begin with a codon (GTG, CTG or TTG) other than the more normal ATG initiation codon. It is well known that in some bacterial systems such codons, which normally denote valine (GTG) or leucine (CTG, TTG), may be read as initiation codons encoding methionine at the N terminus of the polypeptide chain. In the amino acid sequences (SEQ ID Nos: 2 to 43 and 113) provided herein, such codons are therefore translated as methionine.

Also provided are nucleic acid molecules comprising portions of the open reading frames identified herein. For example, such a nucleic acid sequence may comprise one or more isolated domains derived from the open reading frames identified herein. The polypeptides encoded by these isolated portions of the open reading frames may have independent activity, e.g. catalytic activity. In particular, the polypeptides which make up the borrelidin PKS have modular structures in which individual domains have particular catalytic activities as set out above. Thus any of these domains may be expressed alone or in combination, with other polypeptides from the borrelidin PKS described herein or domains thereof, or with polypeptides from the PKS of other polyketides. In particular, any of these domains may be substituted for the equivalent domains either within the borrelidin PKS or in other polyketide synthases and additionally equivalent domains from other PKSs may be substituted for domains within the borrelidin PKS. In this context an equivalent domain includes domains which have the same type of function but differ in for example, their specificity, an example of substitutions contemplated by the present invention include: the substitution of a malonyl-CoA specific AT domain for a methylmalonyl-CoA specific AT domain, or the substitute of a reductive loop containing a KR domain only for one containing KR, DH and ER. In preferred embodiments the expressed domains represent at least one PKS module as described below.

The term 'PKS domain' as used herein refers to a polypeptide sequence, capable of folding independently of the remainder of the PKS, and having a single distinct enzymatic activity or other function in polyketide or macrolide synthesis including, but not restricted to β-ketoacyl-acyl carrier protein synthase (KS), acyl carrier protein (ACP), acyl transferase (AT), β-ketoreductase (KR), dehydratase (DH), enoyl reductase (ER) or terminal thioesterase (TE).

Accordingly, the invention further provides:

(a) an isolated nucleic acid molecule comprising a sequence that encodes a PKS domain selected from AT0 and ACP0, said domains being described by, respectively, amino acids 322-664 and 694-763 of SEQ ID No.2. In a preferred embodiment, the PKS domain comprises a sequence selected from the group consisting of bases 17147-18175 and 18263-18472 of SEQ ID No.1;

(b) an isolated nucleic acid molecule comprising a sequence that encodes a PKS domain selected from KS1, AT1, KR1 and ACP1, said domains being described by, respectively, amino acids 34-459, 557-885, 1136-1379 and 1419-1486 of SEQ ID No.3. In a preferred embodiment, the PKS domain comprises a sequence selected from the group consisting of bases 18974-20251, 20543-21529, 22280-23011 and 23129-23332 of SEQ ID No.1;

(c) an isolated nucleic acid molecule comprising a sequence that encodes a PKS domain selected from KS2, AT2, DH2, KR2, ACP2, KS3, AT3, DH3, KR3 and ACP3, said domains being described by, respectively, amino acids 34-459, 559-887, 903-1050, 1354-1597, 1628-1694, 1724-2149, 2245-2576, 2593-2734, 3060-3307 and 3340-3406 of SEQ ID No.4. In a preferred embodiment, the PKS domain comprises a sequence selected from the group consisting of bases 23785-25062, 25360-26346, 26392-26835, 27745-28476, 28567-28767, 28855-30132, 30418-31413, 31462-31887, 32863-33606 and 33703-33903 of SEQ ID No.1;

(d) an isolated nucleic acid molecule comprising a sequence that encodes a PKS domain selected from KS4, AT4, KR4 and ACP4, said domains being described by, respectively, amino acids 34-459, 555-886, 1179-1423 and 1459-1525 of SEQ ID No.5. In a preferred embodiment, the PKS domain comprises a sequence selected from the group consisting of bases 34284-35561, 35847-36842, 37719-38453 and 38559-38759 of SEQ ID No.1;

(e) an isolated nucleic acid molecule comprising a sequence that encodes a PKS domain selected from KS5, AT5, DH5, ER5, KR5 and ACP5, said domains being described by, respectively, amino acids 34457, 553-888, 905-1046, 1401-1690, 1696-1942 and 1975-2041 of SEQ ID No.6. In a preferred embodiment, the PKS domain comprises a sequence selected from the group consisting of bases 39221-40492, 40778-41785, 41834-42259, 43322-44191, 44207-44947 and 45044-45244 of SEQ ID No.1;

(f) an isolated nucleic acid molecule comprising a sequence that encodes a PKS domain selected from KS6, AT6, KR6, ACP6 and TE, said domains being described by, respectively, amino acids 37-457, 555-883, 1101-1335, 1371-1437 and 1461-1708 of SEQ ID No.7. In a preferred embodiment, the PKS domain comprises a sequence selected from the group consisting of bases 45622-46884, 47176-48162, 48814-49518, 49624-49824 and 49894-50637 of SEQ ID No.1.

In another of its aspects the invention provides an isolated nucleic acid molecule comprising a sequence that encodes a PKS module, said module being selected from the group consisting of amino acids 322-763 of SEQ ID No.2, 34-1486 of SEQ ID No.3, 34-1694 of SEQ ID No.4, 1724-3406 of SEQ ID No.4, 34-1525 of SEQ ID No.5, 34-2041 of SEQ ID No.6 and 37-1437 or 1708 of SEQ ID No.7. In a preferred embodiment, the module comprises a sequence selected from the group consisting of bases 17147-18472, 18974-23332, 23785-28767, 28855-33903, 34284-38759, 39221-45244, 45622-49824 or 50637 of SEQ ID No.1.

The term 'module' as used herein refers to a single polypeptide comprising a plurality of PKS domains each having a single distinct enzymatic activity in polyketide or macrolide synthesis including, but not restricted to β-ketoacyl-acyl carrier protein synthase (KS), acyltransferase (AT), acyl carrier protein (ACP), β-ketoreductase (KR), dehydratase (DH), or enoyl reductase (ER) or terminal thioesterase (TE). An extension module typically comprises a KS, AT and ACP domain (although some modular PKSs may encode their AT domains as independent proteins). An extension module may further comprise one or more domains capable of reducing a beta-keto group to a hydroxyl, enoyl or methylene group (said group of domains are referred to herein as a "reductive loop"). Thus a module comprising a reductive loop typically contains a KR domain, KR and DH domains, or KR, DH and ER domains.

A PKS may further comprise a TE domain to perform chain termination and/or cyclisation of the final product, or alternatively it may contain another functionality known to perform a similar function such as that for the addition of an amino acid residue and macrolactam formation as observed for rapamycin (Schwecke et al., 1995), for macrolactam formation as for rifamycin (August et al., 1998), and for amino acid incorporation followed by reductive elimination as for myxalamid biosynthesis (Silakowski et al., 2001).

Also provided is a nucleic acid molecule encoding a polyketide synthase comprising a sequence encoding one or more of the domains or modules described above.

The sequences provided herein provide means with which to manipulate and/or to enhance polyketide synthesis. Thus there is provided a method of modifying a parent polyketide synthase, comprising expressing a domain from a borrelidin polyketide synthase or a derivative thereof as described herein in a host cell expressing said parent polyketide synthase, such that the domain is incorporated into said parent polyketide synthase. There is further provided a method of modifying a parent polyketide synthase, comprising introducing into a host cell a nucleic acid encoding a domain from a borrelidin polyketide synthase, or a derivative thereof, wherein the host cell contains nucleic acid encoding said parent polyketide synthase, such that, when expressed, the domain is incorporated into said parent polyketide synthase. The borrelidin PKS domain may be inserted in addition to the native domains of the parent PKS, or may replace a native parent domain. Typically the parent PKS will be a Type I PKS.

The present invention further provides methods of modifying a parent borrelidin PKS. A donor domain (e.g. from a Type I PKS) may be expressed in a host cell expressing said parent borrelidin PKS. There is further provided a method of modifying a parent borrelidin polyketide synthase comprising introducing into a host cell a nucleic acid encoding a domain from a donor polyketide synthase, wherein the host cell contains nucleic acid encoding said parent borrelidin polyketide synthase, such that, when expressed, the domain is incorporated into said parent borrelidin polyketide synthase.

Additionally or alternatively, a domain of the parent PKS may be deleted or otherwise inactivated; e.g. a parent domain may simply be deleted, or be replaced by a domain from a donor PKS, or a domain from a donor PKS may be added to the parent. Where a domain is added or replaced, the donor domain may be derived from the parent synthase, or from a different synthase.

These methods may be used to enhance the biosynthesis of borrelidin, to produce new borrelidin derivatives or analogues, or other novel polyketide or macrolide structures. The number and nature of modules in the system may be altered to change the number and type of extender units recruited, and to change the various synthase, reductase and dehydratase activities that determine the structure of the polyketide chain. Such changes can be made by altering the order of the modules that comprise the PKS, by the duplication or removal of modules that comprise the PKS, by the introduction of modules from heterologous sources, or by some combination of these various approaches.

Thus domains or modules of the borrelidin PKS may be deleted, duplicated, or swapped with other domains or modules from the borrelidin PKS, or from PKS systems responsible for synthesis of other polyketides (heterologous PKS systems, particularly Type I PKS systems), which may be from different bacterial strains or species. Alternatively domains or modules from the borrelidin PKS may be introduced into heterologous PKS systems in order to produce novel polyketide or macrolides. Combinatorial modules may also be swapped between the borrelidin polyketide synthase and other polyketide synthases, these combinatorial modules extend between corresponding domains of two natural-type modules, e.g. from the AT of one module to the AT of the next.

For example, a particular extender module may be swapped for one having specificity for a different extender unit (as described e.g. in WO98/01571 and WO98/01546), or mutated to display specificity or selectivity for a different extender unit e.g. as described below. Additionally or alternatively, introduction, deletion, swapping or mutation of domains or modules, such as the KR, DH and ER domains responsible for the processing of a given β-keto moiety, may be used to alter the level of reductive processing of an extender unit during polyketide synthesis. Such changes may also lead to changes in stereochemistry of the alpha-alkyl and beta-hydroxyl groups thus formed by altered modules. In a preferred embodiment the BorA5 module may be introduced into a parent PKS to provide iterative addition of extender units to a polyketide backbone, e.g. expanding the ring size of a macrolide polyketide relative to that naturally produced by the parent PKS.

The borrelidin loading module is the first PKS loading module to be identified having specificity for an alicyclic di-carboxylic acid starter unit. Thus this module or a derivative thereof may be used to introduce alicyclic starter units into heterologous polyketide synthases. This need not be restricted to use of trans-cyclopentane-1,2,-dicarboxylic acid normally used as the borrelidin starter unit. The borrelidin loading module is herein shown also to be capable of directing incorporation of other starter units including trans-cyclobutane-1,2-dicarboxylic acid, 2,3-methylsuccinic acid and 2-methylsuccinic acid. The borrelidin starter unit may also be modified in a borrelidin producing cell, or replaced by a heterologous loading module, to introduce alternative starter units into the borrelidin synthetic pathway.

The position of the loading module of the PKS may be chosen (e.g. by fusing it to a particular location within the PKS) in order to control the ring size of the resultant polyketide/macrolide molecules.

The AT domains that determine the carboxylic acid-CoA thioester extender units may be deleted, modified or replaced. The ACP domains may also be deleted, modified or replaced. In addition domains that are not normally present in the borrelidin PKS but which are found in other modular PKS and/or mixed PKS/NRPS systems may be inserted. Examples include, but are not limited to: O-methyl transferase domains, C-methyl transferase domains, epimerisation domains, monooxygenase domains and dehydrogenase domains, aminotransferase domains and non-ribosomal peptide synthetase domains.

Further, the thioesterase domain of the borrelidin PKS may be altered or repositioned (e.g. fused to a chosen location within the PKS) in order to change its specificity and/or in order to release polyketide/macrolide molecules with a chosen ring size. Alternatively, heterologous thioesterase domains may be inserted into the borrelidin PKS to produce molecules with altered ring size relative to the molecule normally produced by the parent PKS, or to produce a free acid.

In yet another alternative, the amino acid incorporating and macrolactam forming domains from mixed NRPS/PKS systems such as that for rapamycin, or for related systems such as for rifamycin biosynthesis and myxalamid biosynthesis, or modules from NRPS systems (such as those for bleomycin biosynthesis) may be inserted into the PKS to produce novel polyketide related molecules of mixed origin.

The open reading frames encoding the PKS described herein may also comprise portions encoding non-enzymatically active portions which nevertheless have a functional role as scaffold regions which space and stabilise the enzymatically active domains and/or modules of the PKS at appropriate distances and orientations, and which may have recognition and docking functions that order the domains and modules of the PKS in the correct spatial arrangement. Thus the nucleic acid sequences of the present invention comprise sequences encoding such scaffold regions, either alone or in combination with sequences encoding domains or modules as described above. It will be appreciated that the various manipulations of PKS coding sequences described above may give rise to hybrid PKS genes or systems. Thus the present invention also provides nucleic acids encoding such hydrid PKS systems. The invention therefore provides a nucleic acid construct comprising at least one first nucleic acid portion encoding at least one domain of a borrelidin PKS and a second nucleic acid portion or portions encoding at least one type I PKS domain which is heterologous to said borrelidin PKS. In preferred embodiments the construct comprises a hybrid polyketide synthase gene, said gene encoding at least one domain of a borrelidin PKS and at least one type I PKS domain which is heterologous to said borrelidin PKS. Further preferred embodiments are as described above.

In a further aspect, the present invention provides an isolated nucleic acid molecule comprising a sequence encoding a polypeptide which catalyses a step in the synthesis of a starter unit or substrate for polyketide synthesis, preferably in the synthesis of the trans-cyclopentane-1,2,-dicarboxylic acid moiety used as a starter unit by the borrelidin PKS. The polypeptide may have activity as a dehydrogenase, 3-oxoacyl-ACP-reductase, cyclase, F420 dependent dehydrogenase, or 2-hydroxyhepta-2,4-diene-1,7-dioate isomerase. Preferably the polypeptide comprises the sequence encoded by one of the group of genes consisting of borC, borD, borE, borF, borG, borH, borK, borL, borM and borN, as shown in SEQ ID NO: 8, 9, 10, 12, 13, 14, 17, 18, 19 or 20.

These genes may be rendered deleted, disrupted, or otherwise inactivated in a borrelidin-producing cell in order to abolish borrelidin production. Cell lines resulting from such changes may be chemically complemented by the addition of exogenous carboxylic acids which may be incorporated in place of the natural starter unit. Thus, new borrelidin related molecules may be synthesised, which are initiated from the exogenously fed carboxylic acid. Such an approach is termed mutasynthesis. The genes responsible for trans-cyclopentane-1,2,-dicarboxylic acid synthesis may be introduced into a heterologous polyketide producer cell to allow that cell to synthesise the alicyclic dicarboxylic acid as a starter unit for its own PKS.

Thus the present invention further provides a method for the production of borrelidin and borrelidin analogues at improved titres, said method comprising disrupting borG in the host strain, fermenting the resulting cell line and feeding an exogenous carboxylic acid. In various preferred embodiments the exogenous carboxylic acid is trans-cyclopentane-1,2-dicarboxylic acid or the exogenous carboxylic acid is selected from the group consisting of trans-cyclobutane-1,2-dicarboxylic acid, 2,3-dimethyl succinic acid and 2-methyl-succinic acid and/or the method additional comprises deleting, modifing or replacing one or more borrelidin biosynthetic genes, or borrelidin polyketide synthase domains or modules. A person of skill in the art is aware that polyketide synthases may also be expressed in heterologous hosts, therefore the present invention also contemplates a method for the production of higher titres of borrelidin and borrelidin analogues in a heterologous host, said method comprising transforming a host cell with the entire borrelidin gene cluster with the exception of borG or disrupting the borG gene in situ once the gene cluster has been transferred.

Alternatively, genes responsible for the synthesis of the starter unit may be over-expressed in order to improve the fermentation titres of borrelidin or borrelidin related molecules. Thus the present invention further provides a method for increasing the titre of borrelidin and borrelidin derivatives or borrelidin related molecules and their derivatives, said method comprising upregulating a borrelidin biosynthetic gene involved in production of the starter unit, said gene selected from the group consisting of borC, borD, borE, borF, borH, borK, borL borM and borN, in a preferred embodiment the upregulated gene is borE or borL.

In another approach the genes responsible for the synthesis of the starter unit may be modified, or replaced by other synthetic genes directing the production of altered carboxylic acids, leading to the production of borrelidin related molecules. These techniques may be complemented by the modification of the loading module of the PKS as described above.

In a further aspect, the present invention provides an isolated nucleic acid molecule comprising a sequence encoding a polypeptide which catalyses a step in the modification of a side chain of a polyketide moiety, for example in the conversion of a methyl group to a nitrile moiety, e.g. at C12 of pre-borrelidin (14). The polypeptide may have activity as a cytochrome P450 oxidase, amino transferase, or NAD/quinone oxidoreductase. Preferably the polypeptide comprises the sequence encoded by one of the group of genes consisting of borI, borJ, and borK as shown in SEQ ID NO: 15, 16 or 17.

Various of these genes may be deleted/inactivated such that borrelidin-related molecules, or shunt metabolites thereof, accumulate which represent intermediate stages of the process that introduces the nitrile moiety. The addition of heterologous genes to such systems may allow alternative elaboration of any accumulated biosynthetic intermediates or shunt metabolites thereof. Alternatively, the genes may be mutated in order to alter their substrate specificity such that they function on alternative positions of pre-borrelidin molecules in order to provide borrelidin-related molecules. In addition, the genes responsible for formation of the nitrile group may be over-expressed in order to improve the fermentation titres of borrelidin or borrelidin-related molecules.

Alternatively, one, some or all of these genes may be introduced into cells capable of producing other polyketides to provide for desired side chain processing of that polyketide, e.g. the introduction of a nitrile moiety. This opens up the possibility of specific biosynthetic introduction of nitrile moieties into polyketides, particularly at side chains derived from methylmalonyl-CoA or ethylmalonyl-CoA extender units. Purified enzymes (see below) may also be used to effect the conversion of polyketide side chains to nitrile moieties in vitro.

In a further aspect, the present invention provides an isolated nucleic acid molecule comprising a sequence encoding a polypeptide involved conferring resistance to borrelidin. The polypeptide may have homology to a threonyl tRNA synthase, and preferably has threonyl tRNA synthase activity. Preferably the polypeptide comprises the sequence encoded by the borO gene as shown in SEQ ID NO: 21. A resistance gene such as borO, carried on a suitable vector (see below) may be used as a selective marker. Thus cells transformed with such a vector may be positively selected by culture in the presence of a concentration of borrelidin which inhibits the growth of, or kills, cells lacking such a gene.

In a further aspect, the present invention provides an isolated nucleic acid molecule comprising a sequence encoding a polypeptide involved in regulation of expression of one or more genes of the borrelidin gene cluster. In a preferred embodiment the polypeptide comprises the sequence encoded by the borL gene as shown in SEQ ID NO: 18, or as encoded by orfB8 or orfB12 as shown in SEQ ID NO: 29 or 33. Regulator genes may be engineered to increase the titre of borrelidin and borrelidin derivatives, or borrelidin related molecules and their derivatives produced by fermentation of the resulting cell lines. For example, repressors may be deleted/inactivated, and/or activators may be up-regulated or overexpressed, e.g. by increasing gene copy number or placing the coding sequence under the control of a strong constitutively active or inducible promoter. The borL gene or a portion thereof may also find use as a hybridisation probe to identify similar regulator genes located in or outside other biosynthetic gene clusters.

In a further aspect, the present invention provides an isolated nucleic acid molecule comprising a sequence encoding a polypeptide having type II thioesterase activity. In a preferred embodiment the polypeptide comprises the sequence encoded by the borB gene as shown in SEQ ID NO: 8. This nucleic acid may be introduced into a host cell to modulate the titre of a polyketide synthesised by that cell. In particular, the titre may be increased by 'editing' of the products of unwanted side reactions (e.g. removal of acyl groups formed by inappropriate decarboxylation of extender units attached to KS domains). However in various aspects it may be desirable to remove such an activity from a producer cell, for example to increase the variety of polyketide products produced by that cell, or to facilitate production of an analogue of a naturally produced polyketide which would normally be blocked by such an editing activity.

The nucleotide sequences of the invention may be portions of the sequence shown in SEQ ID NO: 1, or the complement thereof, or mutants, variants, derivatives or alleles of these sequences. The sequences may differ from that shown by a change which is one or more of addition, insertion, deletion and substitution of one or more nucleotides of the sequence shown. Changes to a coding nucleotide sequence may result in an amino acid change at the protein level, or not, as determined by the redundancy of the genetic code. Thus, nucleic acid according to the present invention may include a sequence different from the sequence shown in SEQ ID NO: 1 yet encode a polypeptide with the same amino acid sequence. Preferably mutants, variants, derivatives or alleles of the sequences provided encode polypeptides having the same enzymatic activity as those described herein.

Where the sequence is a coding sequence, the encoded polypeptide may comprise an amino acid sequence which differs by one or more amino acid residues from the amino acid sequences shown in SEQ ID Nos: 2 to 43 and 113. Nucleic acid encoding a polypeptide which is an amino acid sequence mutant, variant, derivative or allele of any of the sequences shown is further provided by the present invention. Such polypeptides are discussed below. Nucleic acid encoding such a polypeptide may show greater than about 60% identity with the coding sequence of SEQ ID NO: 1, greater than about 70% identity, greater than about 80% identity, or greater than about 90%, 91%, 92%, 93%, 94%, 95%, 96%, 97%, 98% or 99% Identity therewith. Percentage identity may be calculated using one of the programs such as BLAST or BestFit from within the Genetics Computer Group (GCG) Version 10 software package available from the University of Wisconsin, using default parameters.

In preferred embodiments, whether coding or non-coding, the nucleotide sequences of the invention are capable of hybridising specifically with at least a portion of the sequence of SEQ ID NO: 1 or the complement thereof.

For example, hybridizations may be performed, according to the method of Sambrook et al. (Sambrook et al., 1989), using a hybridization solution comprising: 5×SSC, 5× Denhardt's reagent, 0.5-1.0% SDS, 100 μg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42-65° C. in 1×SSC and 1% SDS, changing the solution every 30 minutes.

One common formula for calculating the stringency conditions required to achieve hybridization between nucleic acid molecules of a specified sequence homology is (Sambrook et al., 1989): $T_m$=81.5° C.+16.6Log [Na+]+0.41(% G+C)−0.63 (% formamide)−600/# bp in duplex As an illustration of the above formula, using [Na+]=[0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C. Such hybridisation would be considered substantially specific to the nucleic acid sequence of the present invention.

The nucleic acids of the present invention preferably comprise at least 15 contiguous nucleotides of SEQ ID NO: 1. They may comprise 20, 25, 30, 35, 40, 45, 50, 60, 70, 80, 90, 100, 120, 150, 200, 300, 500 or more contiguous nucleotides of SEQ ID NO: 1.

The nucleic acids may be used e.g. as primers or probes for the identification of novel genes or other genetic elements, such as transcriptional regulatory sequences, from polyketide or macrolide biosynthetic gene clusters, e.g. sequences encoding enzymes of the PKS, or domains or modules thereof, enzymes involved in the biosynthesis of a starter unit, enzymes modifying side chains of polyketide moieties, transporters, resistance genes and regulatory molecules as described.

Thus the present invention provides a method of identifying a novel polyketide biosynthetic gene cluster, or a portion thereof, comprising hybridising a sample of target nucleic acid with a nucleic acid of the present invention capable of hybridising specifically to a nucleic acid having the sequence of SEQ ID NO: 1 or a portion thereof. The target nucleic acid may be any suitable nucleic acid, and is preferably bacterial genomic DNA.

Typically, the method further comprises the step of detecting hybridisation between the sample of nucleic acid and the nucleic acid of the invention. Hybridisation may be measured using any of a variety of techniques at the disposal of those skilled in the art. For instance, probes may be radioactively, fluorescently or enzymatically labelled. Other methods not employing labelling of probe include amplification using PCR, RNAase cleavage and allele specific oligonucleotide probing.

A method may include hybridization of one or more (e.g. two) probes or primers to target nucleic acid. Where the nucleic acid is double-stranded DNA, hybridization will generally be preceded by denaturation to produce single-stranded DNA. The hybridization may be as part of a PCR procedure, or as part of a probing procedure not Involving PCR. An example procedure would be a combination of PCR and low stringency hybridization. A screening procedure, chosen from the many available to those skilled in the art, is used to identify successful hybridization events and isolated hybridized nucleic acid.

Those skilled in the art are well able to employ suitable conditions of the desired stringency for selective hybridisation, taking into account factors such as oligonucleotide length and base composition, temperature and so on, as described above.

An isolated nucleic acid molecule of the invention may be an isolated naturally occurring nucleic acid molecule (i.e. isolated or separated from the components with which it is normally found in nature) such as free or substantially free of nucleic acid flanking the gene in the bacterial genome, except possibly one or more regulatory sequence(s) for expression. Nucleic acid may be wholly or partially synthetic and may include genomic DNA, cDNA or RNA. Where nucleic acid according to the invention includes RNA, reference to the sequence shown should be construed as reference to the RNA equivalent, with U substituted for T.

The present invention further provides a vector comprising a nucleic acid according to the present invention. The vector is preferably an expression vector comprising a nucleic acid encoding a polypeptide of a polyketide biosynthetic gene cluster (preferably a borrelidin biosynthetic gene cluster), or a portion thereof, as described. Suitable vectors comprising nucleic acid for introduction into bacteria or eukaryotic host cells can be chosen or constructed, containing appropriate regulatory sequences, including promoter sequences, terminator fragments, enhancer sequences, marker genes and other sequences as appropriate. Vectors may be plasmids, viral eg "phage", or "phagemid", as appropriate. For further details see, for example, Sambrook et al., 1989. Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology, Second Edition, Ausubel et al. Eds, John Wiley & Sons 1992. The disclosures of Sambrook et al. and Ausubel et al. are incorporated herein by reference.

In another of its aspects the present invention provides an isolated polypeptide encoded by a nucleic acid molecule of the invention as described herein. More particularly, there is provided an isolated polypeptide comprising an amino acid sequence as shown in any one or more of SEQ ID Nos.2 to 43 and 113 or a portion thereof. As set out above, these amino acid sequences represent translations of the longest possible open reading frames present in the sequence of SEQ ID NO:

1 and the complement thereof. The first amino acid is always shown as Met, regardless of whether the initiation codon is ATG, GTG, CTG or TTG.

As used herein the term "polypeptide(s)" includes peptides, polypeptides and proteins, these terms are used interchangeably unless otherwise specified.

A polypeptide which is an amino acid sequence variant, allele, derivative or mutant of any one of the amino acid sequences shown may exhibit at least 60%, 65%, 70%, 75%, 80%, 85%, 90%, 91%, 92%, 93%, 94%, 95%, 96%, 97%, 98% or 99% identity with the polypeptide of any one of the SEQ ID Nos.2 to 43 and 113, or with a portion thereof. Particular amino acid sequence variants may differ from those shown by insertion, addition, substitution or deletion of 1 amino acid, 2, 3, 4, 5-10, 10-20 20-30, 30-50, 50-100, 100-150, or more than 150 amino acids. Percentage identity may be calculated using one of the programs such as FASTA or BestFit from within the Genetics Computer Group (GCG) Version 10 software package available from the University of Wisconsin, using default parameters.

The present invention also includes active portions, fragments, and derivatives of the polypeptides of the invention.

An "active portion" means a peptide which is less than the full length polypeptide, but which retains at least some of its essential biological activity. For example, isolated domains or modules of the PKS as described above may be regarded as active portions of the PKS A "fragment" means a stretch of amino acid residues of at least five, at least six, or at least seven contiguous amino acids, often at least eight or at least nine contiguous amino acids, typically at least 10, at least 13 contiguous amino acids and, most preferably, at least 20, at last 25, at least 30, at least 50, at least 75, at least 100 or more contiguous amino acids. Fragments of the sequence may comprise antigenic determinants or epitopes useful for raising antibodies to a portion of the relevant polypeptide. Thus the polypeptide need not comprise a complete sequence provided in any one of SEQ ID Nos 2 to 43 and 113, but may comprise a portion thereof having the desired activity, e.g. an isolated domain or module, such as those of the PKS described above. It should be noted that the terms part, portion and fragment are used interchangeably in this specification; no particular significance should be ascribed to the specific use of one of these terms in any particular context.

A "derivative" of a polypeptide of the invention or a fragment thereof means a polypeptide modified by varying the amino acid sequence of the protein, e.g. by manipulation of the nucleic acid encoding the protein or by altering the protein itself. Such derivatives of the natural amino acid sequence may involve insertion, addition, deletion or substitution of one, two, three, five or more amino acids, without fundamentally altering the essential activity of the wild type polypeptide.

Polypeptides of the invention are provided in isolated form, e.g. isolated from one or more components with which they are normally found associated in nature. They may be isolated from a host in which they are naturally expressed, or may be synthetic or recombinant.

The present invention also encompasses a method of making a polypeptide (as disclosed), the method including expression from nucleic acid encoding the polypeptide (generally nucleic acid according to the invention). This may conveniently be achieved by growing a host cell in culture, containing an expression vector as described above, under appropriate conditions which cause or allow expression of the polypeptide. Polypeptides may also be expressed in in vitro systems, such as reticulocyte lysate systems.

The method may include the step of introducing the nucleic acid into a host cell. The introduction, which may (particularly for in vitro introduction) be generally referred to without limitation as "transformation", may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, conjugation, electroporation and transfection using bacteriophage. As an alternative, direct injection of the nucleic acid could be employed. Marker genes such as antibiotic resistance or sensitivity genes may be used in identifying clones containing nucleic acid of interest, as is well known in the art.

Preferred host cells include Actinomycetes, preferably *Streptomycetes*, and in particular those selected from the group consisting of *Saccharopolyspora erythraea, Streptomyces coelicolor, Streptomyces avernitilis, Streptomyces griseofuscus, Streptomyces cinnamonensis, Micromonospora griseorubida, Streptomyces hygroscopicus, Streptomyces fradiae, Streptomyces longisporoflavus, Streptomyces lasaliensis, Streptomyces tsukubaensis, Streptomyces griseus, Streptomyces venezuelae, Streptomyces antibioticus, Streptomyces lividans, Streptomyces rimosus* and *Streptomyces albus. Streptomyces rochei* ATCC23956, *Streptomyces parvulus* Tü113 and *Streptomyces parvulus* Tü4055, more preferably selected from the group consisting of *Streptomyces rochei* ATCC23956, *Streptomyces parvulus* Tü113 and *Streptomyces parvulus* Tü4055.

A polypeptide, peptide fragment, allele, mutant or variant according to the present invention may be used as an immunogen or otherwise in obtaining specific antibodies, which may be useful in purification and other manipulation of polypeptides and peptides, screening or other applications.

In another of its aspects the invention provides for the molecules that may be derived from the objects of the invention and for modified compounds formed therefrom and for methods for their production. The molecules derived from the objects of the invention are shown by formula 1 and extends to pharmaceutically acceptable salts thereof, wherein:

Formula 1

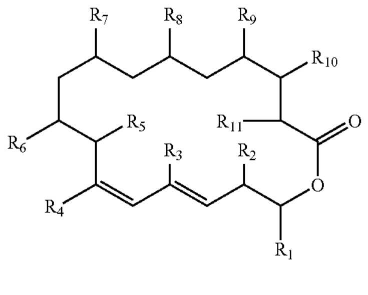

$R_1$ is a cycloalkyl group of varying size (n=1–2) and substituted as shown below;

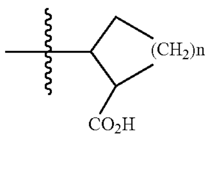

wherein $R_1$ can also optionally be substituted with one or more halo atoms, or one or more $C_1$ to $C_3$ alkyl groups; $R_2$, $R_3$, $R_6$, $R_7$, $R_8$, $R_9$, or $R_{11}$ are each independently H, $OCH_3$, $CH_3$ or $CH_2CH_3$; $R_4$ is CN, $CO_2H$, CHO, $CH_3$, $CONH_2$, CHNH, $R_5$, $R_{10}$ are OH; or analogues differing from the corresponding "natural" compound in the oxidation state of one or more of the ketide units as shown in FIG. 2 (i.e. selection of alternatives from the group: —CO—, —CH(OH)—, =CH—, and —CH2-), with the proviso that said compounds are not borrelidin (1), 12-desnitrile-12-carboxyl borrelidin (2), 10-desmethyl borrelidin (3), 11-epiborrelidin (4) or C14, C15-cis borrelidin analogue (5) as shown in FIG. 1. In preferred embodiments:

(a). $R_7$, $R_8$ and $R_9$ are all $CH_3$.

(b). $R_4$ is $CH_3$ or COOH (c). $R_7$, $R_8$ and $R_9$ are all $CH_3$ and $R_4$ is $CH_3$ or COOH (d). $R_1$ is cyclobutane-1'-carboxylate (e). $R_1$ is cyclobutane-1'-carboxylate and $R_7$, $R_8$ and $R_9$ are all $CH_3$.

(f). $R_6$, $R_7$, $R_8$ and $R_9$ are all $CH_3$, $R_2$ and $R_{11}$ are H, $R_5$ and $R_{10}$ are OH, $R_4$ is either $CH_3$, COOH or CN and $R_1$ is cyclopentane-1'-carboxylate or. cyclobutane-1'-carboxylate (g). $R_1$ is cyclobutane-1'-carboxylate, $R_7$, $R_8$ and $R_9$ are all $CH_3$ and $R_4$ is $CH_3$ or COOH.

The present invention also provides compounds of formula 2 and pharmaceutically acceptable salts thereof, wherein:

Formula 2

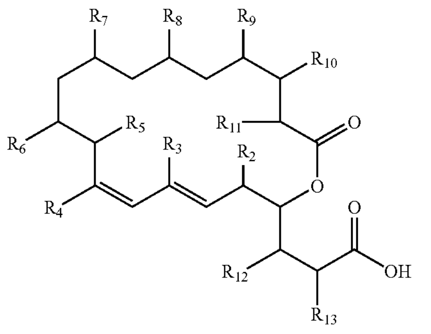

$R_2$, $R_3$, $R_6$, $R_7$, $R_8$, $R_9$, or $R_{11}$ are each independently H, $OCH_3$, $CH_3$ or $CH_2CH_3$; $R_4$ is CN, $CO_2H$, CHO, $CH_3$, $CONH_2$, CHNH, $R_5$, $R_{10}$ are OH; or analogues differing from the corresponding "natural" compound in the oxidation state of one or more of the ketide units as shown in FIG. 2 (i.e. selection of alternatives from the group: —CO—, —CH(OH)—, =CH—, and —$CH_2$—), and $R_{12}$ and $R_{13}$ are independently H or a $C_1$-$C_4$ alkyl group which may be optionally substituted with OH, F, Cl, SH) with the proviso that $R_{12}$ and $R_{13}$ are not simultaneously H.

In preferred embodiments:

(a). $R_7$, $R_8$ and $R_9$ are all $CH_3$.

(b). $R_4$ is $CH_3$ or COOH (c). $R_7$, $R_8$ and $R_9$ are all $CH_3$, and $R_4$ is $CH_3$ or COOH (d). $R_{12}$ and $R_{13}$ are independently $CH_3$ or H (e). $R_{12}$ and $R_{13}$ are independently $CH_3$ or H and $R_7$, $R_8$ and $R_9$ are all $CH_3$ (f). $R_6$, $R_7$, $R_8$ and $R_9$ are all $CH_3$, $R_2$ and $R_{11}$ are H, $R_5$ and $R_{10}$ are OH, $R_4$ is either $CH_3$, COOH or CN and $R_{12}$ and $R_{13}$ are independently $CH_3$ or H (g). $R_6$, $R_7$, $R_8$ and $R_9$ are all $CH_3$, $R_2$ and $R_{11}$ are H, $R_5$ and $R_{10}$ are OH, $R_4$ is either $CH_3$, COOH or CN and $R_{12}$ and $R_{13}$ are both $CH_3$ (h). $R_{12}$ and $R_{13}$ are independently $CH_3$ or H, $R_7$, $R_8$ and $R_9$ are all $CH_3$ and $R_4$ is $CH_3$ or COOH.

The compounds of the present invention may have tRNA synthetase-inhibitory activity (e.g. they may inhibit threonyl-, tyrosinyl-, or tryptophanyl-tRNA synthetase). They may display anti-microbial activity, including activity against intra- or extracellular parasites and organisms such as bacteria, spirochetes (e.g. Treponema), malaria, viruses and fungi. Additionally or alternatively they may have anti-proliferative activity against mammalian cells, and/or anti-angiogenic activity, either as a result of tRNA synthetase inhibition, or through some other mode of action. This may make the compounds of the present invention particularly suitable as anticancer agents (e.g. agents for treatment of bowel cancer, prostate cancer or others), and may also provide application in treatment of other proliferative disorders, such as psoriasis, or conditions in which inappropiate vascularisation occurs, such as psoriasis, rheumatoid arthritis, atherosclerosis and diabetic retinopathy.

The compounds of the present invention may be formulated into pharmaceutically acceptable compositions, e.g. by admixture with a pharmaceutically acceptable excipient, carrier, buffer, stabiliser or other materials well known to those skilled in the art. Such compositions also fall within the scope of the present invention.

Such pharmaceutically acceptable materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required. Examples of the techniques and protocols mentioned above can be found in Remington's Pharmaceutical Sciences, 20th Edition, 2000, pub. Lippincott, Williams & Wilkins.

The invention further provides the compounds and compositions described above for use in a method of medical treatment. Also provided is the use of the compounds of the invention in the preparation of a medicament for the treatment of microbial conditions (including malaria), for the inhibition of angiogenesis, for the treatment of proliferative disorders, or for the treatment of conditions characterised by inappropiate vascularisation, as decribed above.

DETAILED DESCRIPTION OF THE INVENTION

A cosmid library of *S. parvulus* Tü4055 genomic DNA was constructed using fragments obtained from a partial digestion with Sau3AI that were cloned into pWE15 and introduced into *E. coli* cells using the Gigapack® III Gold Packaging Extract kit (Stratagene). A library of 3000 *E. coli* transformants was screened for homology using a labelled probe that was generated using the DIG DNA Labelling and Detection Kit (Roche). The probe used was a 1.7 kbp Bg/II-BamHI fragment obtained from the gene that encodes module 6 of the third subunit of the oleandomycin PKS from *Streptomyces antibioticus* (Swan et al., 1994).

Figure 3:
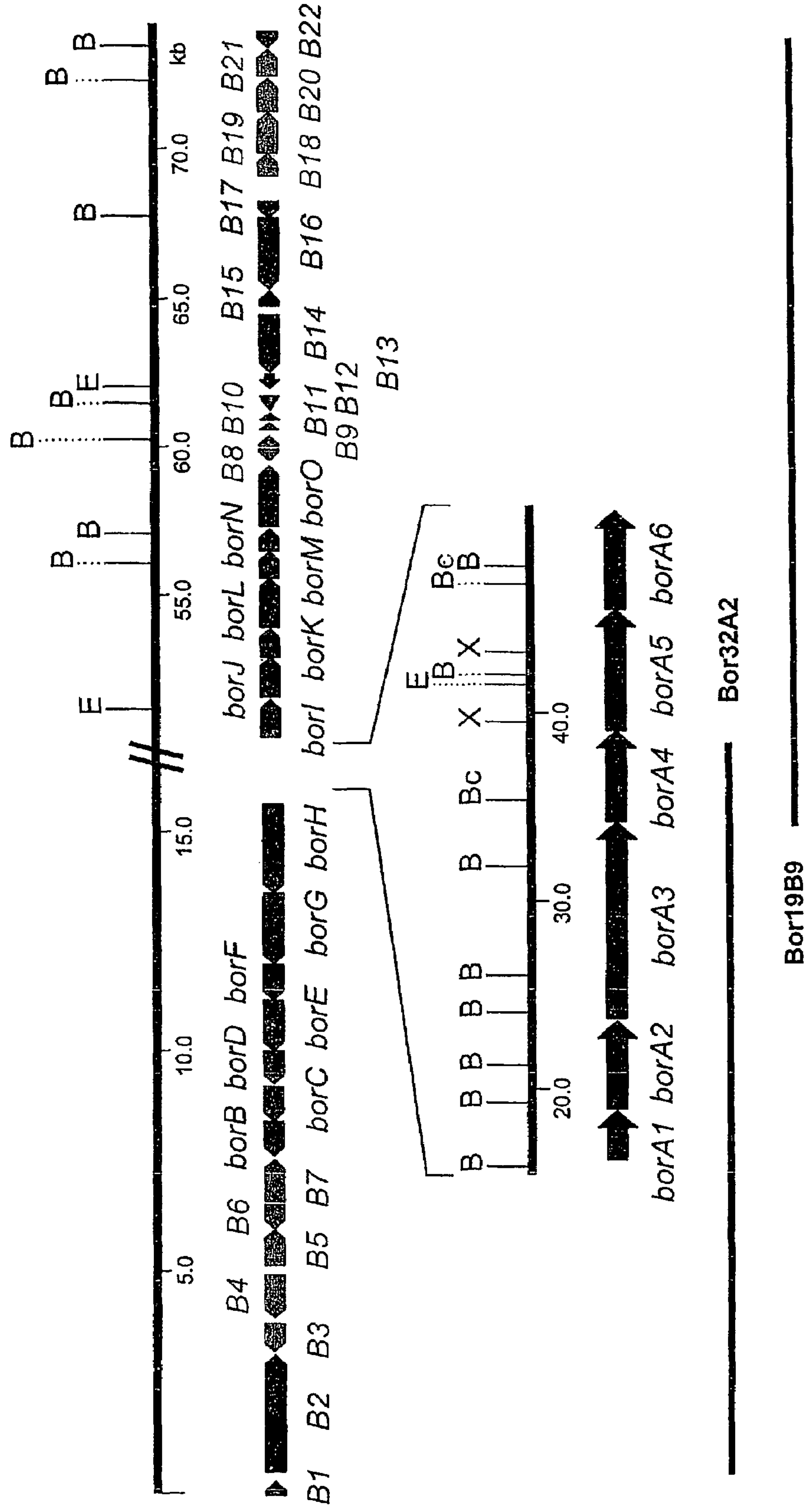
FIG. 3 illustrates the organisation of the borrelidin biosynthetic gene cluster. Restriction sites: B, BamHI; Bc, BclI; E, EcoRI; X, XhoI.

Clones that gave a positive response were selected and cosmid DNA isolated. Cosmid DNA was digested with BamHI and fragments less than 3 kbp in size were sub-cloned into pOJ260 (Bierman et al., 1992). The plasmids were then used to transform *S. parvulus* Tü4055 protoplasts and resulting mutants were screened for the ability to produce borrelidin. Two mutants were identified as borrelidin non-producers, both of which were derived from plasmids that contained fragments of cosBor32A2. These two fragments were of 1.97 and 2.80 kbp in size, and were later identified as adjacent fragments encoding parts of the borrelidin PKS (borA2 & borA3). Using cosBor32A2 as the probe, a second overlapping cosmid, cosBor19B9 was identified from the original library. These two cosmids are sufficient to cover the entire borrelidin biosynthetic gene cluster (see FIG. 3).

The complete nucleotide sequence of cosBor32A2 and cosBor19B9 was determined by shotgun sequencing of a Sau3AI-derived subclone library for each cosmid, consisting of 1.5-2.0 kbp fragments in pHSG397 (Takeshita et al., 1987). Specific details are provided in example 3. The complete, overlapping nucleotide-coding sequence for cosBor32A2 and cosBor19B9 is presented as SEQ ID No.1. The region encoded by cosmid cosBor32A2 represents the sequence from nucleotide positions 0-40217 bp of SEQ ID No.1. The region encoded by cosmid cosBor19B9 overlaps this region by 4452 nucleotides, and corresponds to the nucleotide positions 35766-74787 bp of SEQ ID No.1. As described in more detail in the following text, we have performed gene inactivation experiments on many of the orfs identified to be encoded within SEQ ID No.1, and this leads us to identify the limits of the cluster. The borrelidin biosynthetic gene cluster is contained between nucleotide positions 7603 to 59966 of SEQ ID No.1 (borB to borO, which includes the borA region). Thus, these combined efforts have led us to the identification and sequencing of the DNA region encompassing the entire borrelidin biosynthetic gene cluster, and to the identification and description of the functional sequences encoded within this region.

PKS Genes

Encoded between positions 16184-50742 of SEQ ID No.1 are 6 orfs that display very high homology to the genes that encode the PKSs of known macrolide producing organisms. These genes are designated borA1, borA2, borA3, borA4, borA5 and borA6, and encode the borrelidin PKS as was demonstrated above by disruption of a 1.97 kbp region within borA2. The six orfs are arranged in a head-to-tail manner and each is terminated by an in-frame stop codon. The nucleotide sequence and corresponding polypeptide sequence details are shown below in Table 1:

TABLE 1

| PKS encoding gene | Nucleotide position in SEQ ID No. 1 | Corresponding polypeptide sequence number |
|---|---|---|
| borA1 | 16184-18814 | SEQ ID No. 2 |
| borA2 | 18875-23590 | SEQ ID No. 3 |
| borA3 | 23686-34188 | SEQ ID No. 4 |
| borA4 | 34185-39047 | SEQ ID No. 5 |
| borA5 | 39122-45514 | SEQ ID No. 6 |
| borA6 | 45514-50742 | SEQ ID No. 7 |

The gene borA1 encodes the starter or loading module (SEQ ID No.1, position 16184-18814). The assignment of the start codon is not obvious for this open reading frame. The start codon given here is what we believe to be the true start codon, but there are at least another three possible start codons between the first and the beginning of the AT0 domain sequence and a person of skill in the art will appreciate that it may be possible to generate active protein using one of these alternative start codons. The start codon given here leaves a significant N-terminal tail of 321 amino acids preceding the AT0 domain. For comparison the N-terminal tail preceding the AT0 of the erythromycin loading module is 108 amino acids and that of the avermectin loading module is 28 amino acids. It is therefore possible that one of the other candidate start codons could be correct; the most likely of these are at positions 16298, 16607 and 16901 of SEQ ID No.1. The length of the N-terminal tail suggests it could possibly represent a catalytic activity, although it does not have any significant homology to other sequences in the databases. The nucleotide sequence position and the corresponding amino acid sequence for each of the functional domains within the starter module are identified below in Table 2:

TABLE 2

| Domain in borA1 | Bases in SEQ ID No. 1 | Amino acids in SEQ ID No. 2 |
|---|---|---|
| AT0 | 17147-18175 | 322-664 |
| ACP0 | 18263-18472 | 694-763 |

The gene borA2 encodes the first extension module (SEQ ID No.1, position 18875-23590). The nucleotide sequence position and the corresponding amino acid sequence for each of the functional domains within the first extension module are identified below in Table 3:

TABLE 3

| Domain in borA2 | Bases in SEQ ID No. 1 | Amino acids in SEQ ID No. 3 |
|---|---|---|
| KS1 | 18974-20251 | 34-459 |
| AT1 | 20543-21529 | 557-885 |
| KR1 | 22280-23011 | 1136-1379 |
| ACP1 | 23129-23332 | 1419-1486 |

The gene borA3 encodes the second and third extension modules (SEQ ID No.1, position 23686-34188). The nucleotide sequence position and the corresponding amino acid sequence for each of the functional domains within the second and third extension modules are identified below in Table 4:

TABLE 4

| Domain in borA3 | Bases in SEQ ID No. 1 | Amino acids in SEQ ID No. 4 |
|---|---|---|
| KS2 | 23785-25062 | 34-459 |
| AT2 | 25360-26346 | 559-887 |
| DH2 | 26392-26835 | 903-1050 |
| KR2 | 27745-28476 | 1354-1597 |
| ACP2 | 28567-28767 | 1628-1694 |
| KS3 | 28855-30132 | 1724-2149 |
| AT3 | 30418-31413 | 2245-2576 |
| DH3 | 31462-31887 | 2593-2734 |
| KR3 | 32863-33606 | 3060-3307 |
| ACP3 | 33703-33903 | 3340-3406 |

The gene borA4 encodes the fourth extension module (SEQ ID No.1, position 34185-39047). The nucleotide sequence position and the corresponding amino acid sequence for each of the functional domains within the fourth extension module are identified below in Table 5:

TABLE 5

| Domain in borA4 | Bases in SEQ ID No. 1 | Amino acids in SEQ ID No. 5 |
|---|---|---|
| KS4 | 34284-35561 | 34-459 |
| AT4 | 35847-36842 | 555-886 |
| KR4 | 37719-38453 | 1179-1423 |
| ACP4 | 38559-38759 | 1459-1525 |

The gene borA5 encodes the fifth extension module (SEQ ID No.1, position 39122-45514). The nucleotide sequence position and the corresponding amino acid sequence for each of the functional domains within the fifth extension module are identified below in Table 6:

TABLE 6

| Domain in borA5 | Bases in SEQ ID No. 1 | Amino acids in SEQ ID No. 6 |
|---|---|---|
| KS5 | 39221-40492 | 34-457 |
| AT5 | 40778-41785 | 553-888 |
| DH5 | 41834-42259 | 905-1046 |
| ER5 | 43322-44191 | 1401-1690 |
| KR5 | 44207-44947 | 1696-1942 |
| ACP5 | 45044-45244 | 1975-2041 |

The gene borA6 encodes the sixth extension module and the chain terminating thioesterase (SEQ ID No.1, position 45514-50742). The nucleotide sequence position and the corresponding amino acid sequence for each of the functional domains within the sixth extension module are identified below in Table 7:

TABLE 7

| Domain in borA6 | Bases in SEQ ID No. 1 | Amino acids in SEQ ID No. 7 |
|---|---|---|
| KS6 | 45622-46884 | 37-457 |
| AT6 | 47176-48162 | 555-883 |
| KR6 | 48814-49518 | 1101-1335 |
| ACP6 | 49624-49824 | 1371-1437 |
| TE | 49894-50637 | 1461-1708 |

The identification of functional domains and their boundaries as described in the aforementioned are determined based on the similarities to the conserved amino acid sequences of other modular PKSs such as those for the rapamycin (Schwecke et al., 1995; Aparicio et al., 1996) and erythromycin (Cortés et al., 1990) biosynthesis. The limits of the catalytic domains are established on the basis of homology to other PKS clusters and the chosen point at which a domain starts or finishes is not absolutely defined, but selected based on the aforementioned considerations. In the case of the β-keto processing domains it is least obvious, as there is typically a large region not assigned to a functional domain that precedes the KR domain. This region may be structurally important, or required for stability of the PKS dimer. An unusual characteristic of the borrelidin PKS is that all of the individual enzymatic domains appear to be catalytically competent based on their oligonucleotide/amino acid sequence, and are all necessary in order to provide the β-keto processing required to produce the functional groups observed in borrelidin. This is rather unusual as the majority of modular PKS sequences so far reported contain one or more inactive domains, an exception being for example the spinosyn PKS (Waldron et al., 2001; U.S. Pat. No. 6,274,50).

One skilled in the art is familiar with the degeneracy of the genetic code, therefore, the skilled artisan can modify the specific DNA sequences provided by this disclosure to provide proteins having the same or altered or improved characteristics compared to those polypeptides specifically provided herein. One skilled in the art can also modify the DNA sequences to express an identical polypeptide to those provided, albeit expressed at higher levels. Furthermore, one skilled in the art is familiar with means to prepare synthetically, either partially or in whole, DNA sequences which would be useful in preparing recombinant DNA vectors or coding sequences which are encompassed by the current invention. Additionally, recombinant means for modifying the DNA sequences provided may include for example site-directed deletion or site-directed mutagenesis. These techniques are well known to those skilled in the art and need no further explanation here. Consequently, as used herein, DNA which is isolated from natural sources, prepared synthetically or semi-synthetically, or which is modified by recombinant DNA methods, is within the scope of the present invention.

Likewise, those skilled in the art will recognize that the polypeptides of the invention may be expressed recombinantly. Alternatively, those polypeptides may be synthesised either in whole or in part, by conventional known non-recombinant techniques; for example, solid phase synthesis. Thus, the present invention should not be construed as necessarily limited to any specific vector constructions or means for production of the specific biosynthetic cluster molecules including the polyketide synthase molecules exemplified.

The loading module of the borrelidin PKS exists as a discrete protein. This is rather unusual as the majority of loading modules are found on the same protein as the first extension module. Exceptions to this include, for example, the nystatin (Brautaset et al., 2000) and amphotericin (Caffrey et al., 2001) PKSs. The loading module, which consists of an AT-ACP didomain, is similar to the broad specificity loading module of the avermectin PKS, which accept a number of alternative starter acids, and are of use in generating libraries of novel polyketides (Marsden et al., 1998; Pacey et al., 1998). The AT domain of the borrelidin PKS loading module diverges from the vast majority of AT domains as the active site serine residue is replaced with a cysteine such that the active site motif is GXCXG (specifically GHCYG). In most available type-I PKS AT domain sequences, the conserved active site motif is GXSXG; the same motif is observed in lipases, fatty acid synthases and most thioesterases. The nucleophilic serine is substituted by cysteine in two NRPS thioesterase domains, specifically the synthetases responsible for the production of mycobactin and pyochelin (Shaw-Reid et al., 1999). A GXCXG motif is also observed in a thioesterase-like domain of ORF1 in the bialaphos cluster (Raibaud et al., 1991). It has been suggested that since it is not possible to move between the two types of serine codons by a single base change, active sites containing an essential serine residue may lie on two lines of descent from an ancient ancestral enzyme that had a cysteine instead of a serine in its active site (Brenner, 1988). The presence of enzymes containing cysteine in the active site may support this view. It may alternatively be the case that cysteine arises in these active sites because it is possible to move from one type of serine codon to the other via a cysteine which would remain active.

The AT domains of PKSs select a particular carboxylic acid unit as substrate. This selectivity has been shown to correlate with certain motif signatures within the AT domain (Reeves et al., 2001; WO 02/14482). The borrelidin loading module AT domain motif differs from any described so far, which is not surprising as this AT domain is the first to be sequenced that selects an alicyclic dicarboxylic acid. The AT domains for the borrelidin PKS extension modules display the expected active site motif GXSXG, and also each contain the expected motifs for the selection of malonyl-CoA or methylmalonyl-CoA (Reeves et al., 2001; WO 02/14482). The malonyl-CoA selective AT domains (AT1, AT2 and AT6) show very high similarity to one another, both at the protein and at the DNA level. The same is true for the methylmalonyl-CoA selective AT domains (AT3, AT4 and AT5); two of these AT domains (AT3 and AT4) have identical amino acid sequences throughout the conserved region. The high similarity of AT5 to AT3 and AT4 is evidence that the extender unit selected in module 5 is methylmalonyl-CoA, and that the borrelidin C12-methyl group thus incorporated is subsequently modified to a nitrile function after incorporation into the PKS.

To demonstrate that we can alter the PKS derived structure of borrelidin, the AT domain of module 4 (the AT domain encoded by borA4) is replaced by the AT domain of module 2 of the rapamycin PKS (rapAT2) using a replacement strategy (see example 6). This gives strain *S. parvulus* Tü4055/467. Upon fermentation and LCMS analysis of culture extracts of this mutant, it can be determined that some borrelidin is produced and a new, more polar compound is also observed with a m/z value 14 units lower than borrelidin. This is consistent with incorporation of a malonate rather that a methylmalonate extender unit by module 4 of the PKS to produce 10-desmethyl borrelidin 3.

In addition to production by domain swapping methods, 3 is also generated by introducing specific mutations into the module 4 AT domain selectivity motif (Reeves et al., 2001; WO 02/14482) (see example 7). Such a change affects the selectivity of the AT domain such that it selects a substrate molecule of malonyl-CoA preferentially over methylmalonyl-CoA. Thus, the amino acid motif YASH at positions 739 to 742 of SEQ ID No.5 is mutated to HAFH to give strain *S. parvulus* Tü4055/472. Upon fermentation and LCMS analysis of culture extracts of this mutant it is determined that borrelidin is produced in addition to a new, more polar compound with a m/z value 14 units lower than borrelidin. This new compound is identical to that described above and thus is consistent with incorporation of a malonate rather that a methylmalonate extender unit by module 4 of the PKS to produce 3.

These results clearly indicate that the borrelidin PKS is amenable to genetic manipulation and to the exchange of native sequence for that of a heterologous strain. It is clear to one skilled in the art that the biosynthetic engineering, by the methods described above, of the borrelidin PKS will lead to the production of novel borrelidin-like molecules.

The borrelidin loading module is of interest due to the unique structure of its cognate substrate. To examine its potential use in other systems, the loading module native to the erythromycin PKS is replaced with the borrelidin loading module in *Saccharopolyspora erythraea*; this experiment is analogous to those done previously with the avermectin loading module (WO 98/01546; Marsden et al., 1998). We anticipate that the new strain is capable of producing novel erythromycin like molecules in which the C13-ethyl group is replaced with an exogenously supplied racemic trans-cyclopentane-1,2-dicarboxylic acid moiety. The methodology used to perform this experiment is similar to that described in WO 98/01546, but the transformation is performed using a mutant *Saccharopolyspora erythraea* DM (Gaisser et al., 2000) which accumulates the aglycone product erythronolide B rather than the fully processed macrolide, as well as using *S. erythraea* WT. This experiment is described in example 8.

Figure 7:
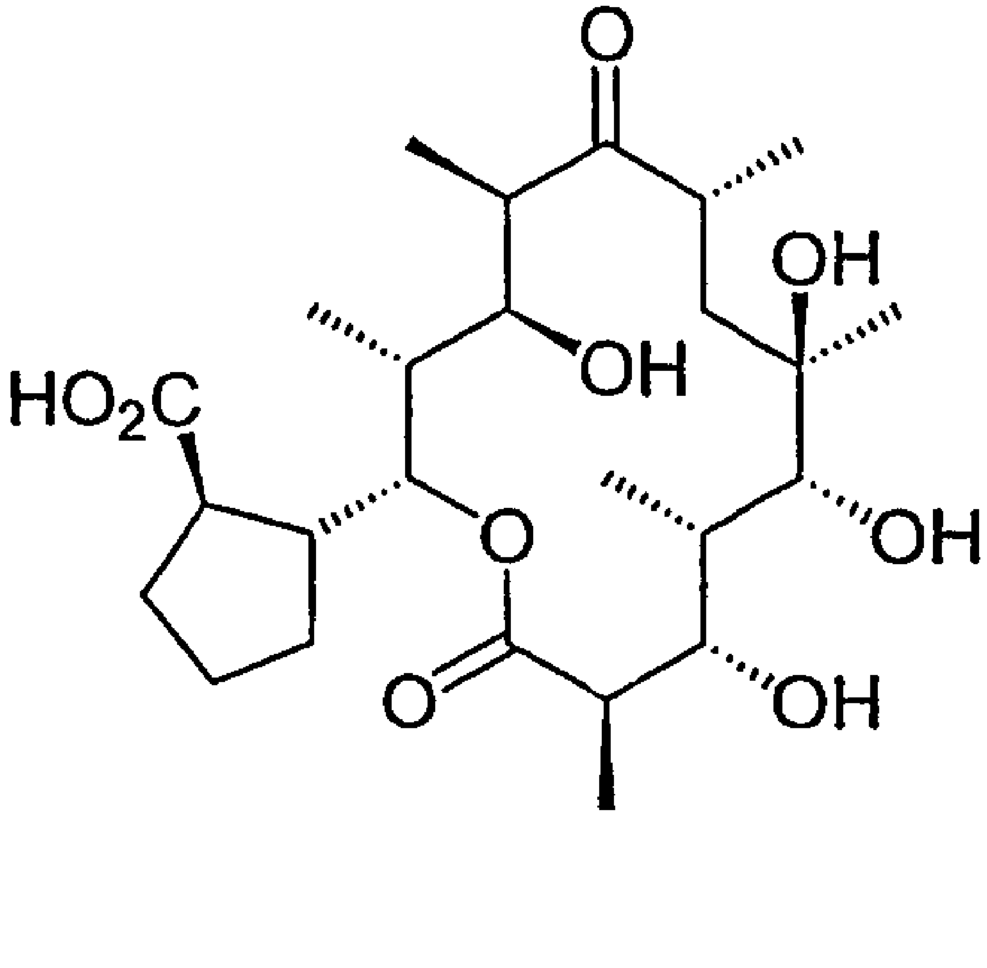
FIG. 7 illustrates the proposed structure of the molecule 6.

It is not evident from SEQ ID No.1, which of four candidate start codons is correct for borA1. The four most obvious candidate start codons are at nucleotides 16184, 16298, 16607 and 16901 of SEQ ID No.1. The earliest of these possible start codons was used in giving the amino acid sequence for SEQ ID No.2. A pile-up of this loading module with the erythromycin and avermectin loading modules indicates that the AT0 domain starts at position 321 of SEQ ID No.2, and that there is a long N-terminal tail. No significant homology is found for the first 298 amino acids of borA1. The borrelidin loading module is encoded by a discrete orf, and in order to retain this architecture the splice site chosen for joining the borrelidin PKS loading module sequence to the erythromycin PKS loading module sequence is at the beginning of the homologous region of the KS1 domain of borA2, at amino acids 42-44 of SEQ ID No.3. This approach maintains the putative docking regions at the end of BorA1 and start of BorA2 that are believed to be essential for the production of a functional PKS assembly. To maintain the continuity of this experiment this loading module is fused to the equivalent point at the beginning of the KS1 domain of eryA1. The resulting mutants *S. erythraea* DM/CJM400-403 are fermented and analysed by negative ion LCMS using standard protocols. This analysis clearly Indicates the presence of a new compound 6 with m/z=485.3 as expected (FIG. 7). It is clear to one skilled in the art that the products of these experiments could be biotransformed using an appropriate strain such as *S. erythraea* JC2 (Rowe et al., 1998) to provide novel, biologically active erythromycin analogues. It is additionally clear to one skilled in the art that the borrelidin loading module has utility for the biosynthetic engineering of other PKSs (i.e. not the borrelidin PKS) to produce further novel polyketides bearing a trans-cyclopentane-1,2-dicarboxylic acid moiety. It is also clear that the diversity of products arising from hybrid PKSs derived from the borrelidin loading module may be further enhanced through the exogenous feeding of carboxylic acids other than the cognate substrate.

Figure 5:
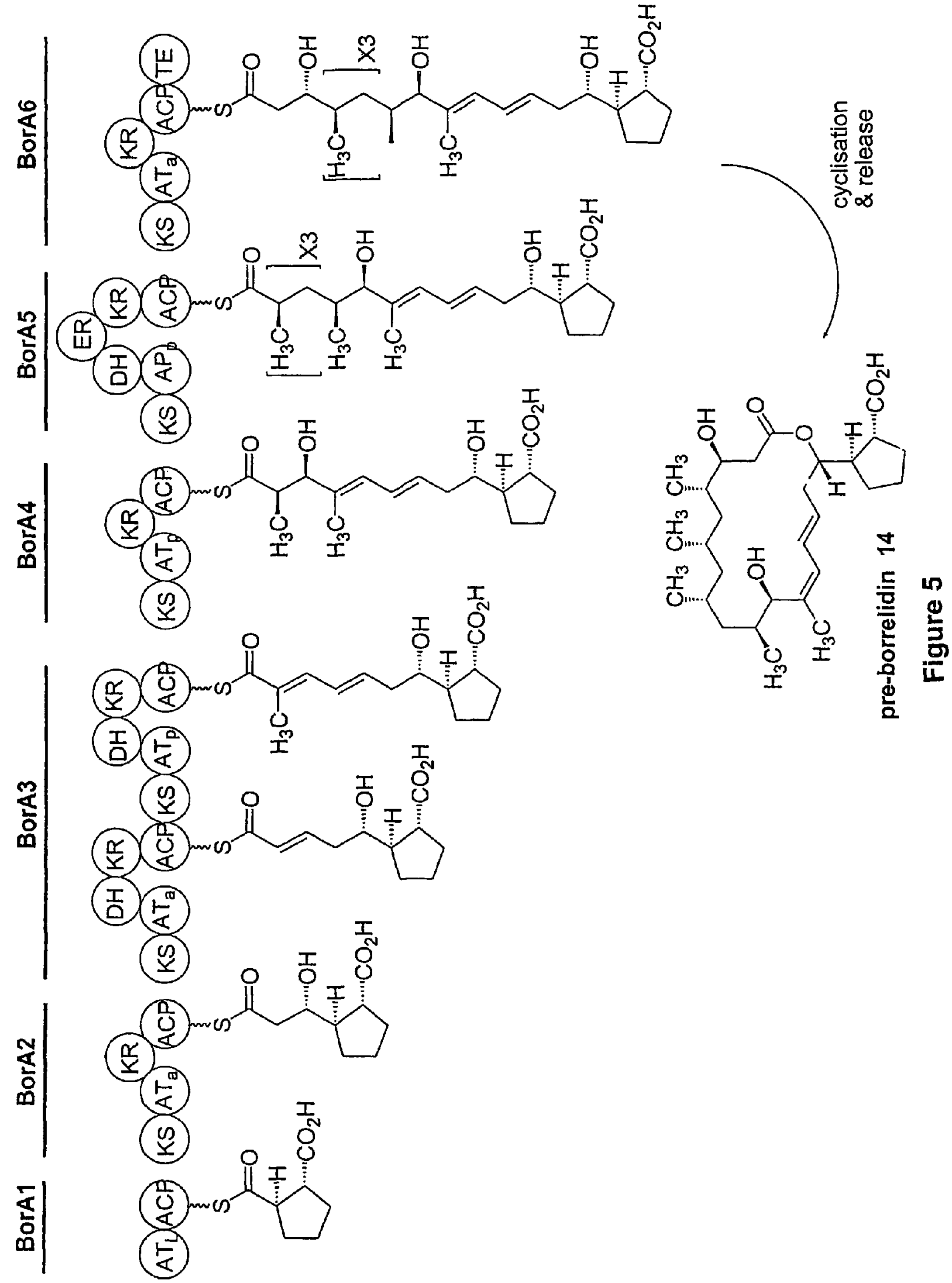
FIG. 5 illustrates the organisation of the borrelidin PKS and the biosynthesis of the pre-borrelidin molecule.

The most striking feature of the borrelidin PKS is the clear divergence from the normal co-linear, processive mode of operation for type-I modular PKSS. Borrelidin is a nonaketide (expected: one loading plus eight extension steps), but only seven modules (one loading and six extension modules) are present in the cluster. Analysis of the PKS domains with respect to the chemical structure of borrelidin correlates with the fifth extension module (BorA5) being used iteratively for three rounds of chain elongation as shown in FIG. 5. Thus, the fifth, sixth and seventh rounds of chain elongation occur on BorA5 with the incorporation of three methylmalonyl-CoA extension units, and with full reductive processing of the β-keto groups to methylene moieties. As described supra, the divergence from co-linear operation for modular PKSs is unusual and limited to a few examples. The present example is interesting as it occurs on a module that reduces the β-keto group fully to a methylene moiety and which is followed by an inter-rather than intra-protein transfer of the growing chain. This is also the case for the two known examples of erroneous iterative use of type-I modules by the erythromycin (Wilkinson et al., 2000) and epothilone (Hardt et al., 2001) PKSs. It is noteworthy that this full reduction makes these modules functionally equivalent to fatty acid synthase (FAS). The type-I PKS modules that can operate iteratively may have retained FAS like activity.

Although it appears that BorA5 is used iteratively (three times), two other possible scenarios may explain borrelidin biosynthesis given the genes present in the borrelidin biosynthetic cluster. Firstly, two modules may be 'missing' from the cluster, but could be present at some other location in the genome. However, in the majority of cases investigated, the genes required for biosynthesis of secondary metabolites in actinomycetes are clustered in a single locus. The second possibility is that three separate BorA5 dimers assemble, and that each catalyses a round of chain elongation; thus the process would be processive. However, this scenario requires that three times the amount of BorA5 is produced with respect to the other PKS proteins, but the organisation of the borrelidin gene cluster does not indicate that the regulation of borA5 differs from that of any of the other PKS genes. In addition, this scenario does not fit with the common thinking as to the roles of inter-protein docking domains, which suggests that there is a specific recognition between the N- and C-terminal ends of the proteins of the biosynthetic complex that need to interact, enabling specific binding between modules encoded on different proteins (Ranganathan et al., 1999; Wu et al., 2001; Broadhurst et al., 2003).

To address the issues described above, the two proteins encoded by borA4 and borA5 were fused after manipulation at the genetic level to provide strain *S. parvulus* Tü4055/borA4-A5 (see example 9), and separately the two proteins encoded by borA5 and borA6 were fused in an analogous manner to provide strain *S. parvulus* Tü4055/borA5-A6 (see example 10). Additionally, a double mutant was generated in which the above described fusions were combined to generate a strain in which borA4, borA5 and borA6 were fused to generate strain *S. parvulus* Tü4055/borA4-A5-A6 (see example 11). Therefore, the new, fused, bi- and tri-modular genes make it impossible to assemble three separate molecules of BorA5, or for another protein(s) encoded by a gene(s) remote from the borrelidin cluster to act in tandem with BorA5. Upon fermentation of strains *S. parvulus* Tü4055/borA4-A5, /borA5-A6, and /borA4-A5-A6 followed by extraction and analysis, the production of borrelidin was verified at a reduced but significant level (21±4%, 27±4% and 18±5% respectively) when compared to the WT strain. Thus, the production of borrelidin by these mutants indicates that module 5 of the fused BorA4-A5 or BorA5-A6 operates in an iterative manner. Since the priority filing of this application, these limited data have been published (Olano et al., 2003).

The ability of BorA5 to operate iteratively has great potential for the engineering of heterologous PKSs to provide macrolactones with expanded ring sizes. To examine this possibility BorA5 is swapped into the erythromycin PKS in place of module 4 of DEBS2. This is done by replacement of the appropriate gene fragment in both the erythromycin producer *S. erythraea* WT and *S. erythraea* DM. This experiment is chosen as both modules recruit methylmalonyl-CoA extender units and process the β-keto functions formed through to methylene groups. In addition, the stereochemistry of the resulting methyl group in the polyketide chain is the same in both cases. Of most significance is the fact that module 4 of DEBS2 is known to perform erroneous iterative rounds of chain elongation (Wilkinson et al., 2000), indicating that such a process can indeed occur at this location within the PKS and give rise to products that can be fully processed by DEBS3, making it an attractive target to introduce specific iterative use of a heterologous module to make 16- and 18-membered macrolides.

Figure 8:
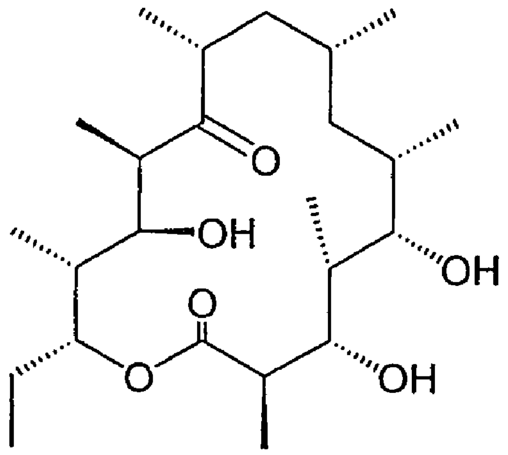
FIG. 8 illustrates the proposed structure of the molecules 7 & 8.
Figure 8:
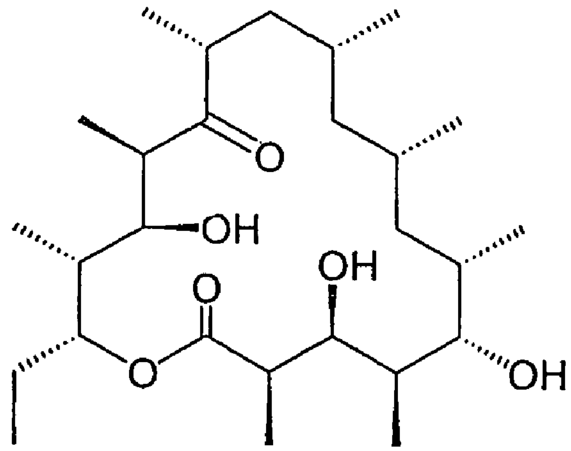

Briefly, the region of DNA encoding borA5 is swapped for that encoded by module 4 of eryA2, which encodes the C-terminal portion of DEBS2 of the erythromycin PKS (see example 12). The resulting mutant *S. erythraea* DM/421 is grown and extracted as for the production of metabolites by *S. erythraea* strains (Wilkinson et al., 2000) and then analysed by LCMS. Two new significant compounds, which are less polar than erythronolide B, are observed. These have an m/z of 435.5 (7, [$MNa^+$]) and 477.5 (8, [$Mna^+$]) respectively, which is consistent with the production of two new ring expanded erythronolide B analogues (FIG. 8). Compound 7 with mmz=435.5 is consistent with the presence of the 16-membered ring-expanded erythronolide B related macrolide reported previously as a minor component of *S. erythraea* WT fermentations (Wilkinson et al., 2000). It is clear to one skilled in the art that such new products can be converted to antibacterial molecules by biotransformation with an appropriate organism. It is also clear to one skilled in the art, that the inclusion of such a module into other positions of the erythromycin PKS, or into other PKSs, may allow the production of novel, ring expanded polyketides in a similar manner. In addition, it is possible to perform this experiment by swapping only the region of the DEBS module 4 from the start of the conserved region of the KS4 to the end of the ACP4 domain; this arrangement retains the C- and N-terminal regions at the end of DEBS2 and DEBS3 respectively, to ensure the mutual recognition and docking of these proteins.

NON-PKS Genes

Both upstream and downstream of the PKS encoding genes are other orfs involved in the biosynthesis of borrelidin. An orf is designated as consisting of at least 100 contiguous nucleotides, that begins with an appropriate start codon and finishes with an appropriate stop codon, and which has an appropriate codon bias for protein-coding regions of an organism whose DNA is rich in the nucleotides guanine and cytosine. In the DNA sequence both upstream and downstream of the borrelidin PKS genes (borA1-borA6) there are a number of orfs that could be identified by comparison to other sequences in the NCBI database (see FIG. 3). The nucleotide sequence details of these orfs are given below in Table 8:

TABLE 8

| Gene | Bases in SEQ ID No. 1 | Corresponding polypeptide sequence number |
|---|---|---|
| borB | 7603-8397c | SEQ ID No. 8 |
| borC | 8397-9194c | SEQ ID No. 9 |
| borD | 9244-9996c | SEQ ID No. 10 |
| borE | 9993-11165c | SEQ ID No. 11 |
| borF | 11162-11980c | SEQ ID No. 12 |
| borG | 11992-13611c | SEQ ID No. 13 |
| borH | 13608-15599c* | SEQ ID No. 14 |
| borI | 50739*-52019 | SEQ ID No. 15 |
| borJ | 52113-53477 | SEQ ID No. 16 |
| borK | 53486-54466 | SEQ ID No. 17 |
| borL | 54506-56176 | SEQ ID No. 18 |
| borM | 56181*-57098 | SEQ ID No. 19 |
| borN | 57112-57858 | SEQ ID No. 20 |
| borO | 57939-59966 | SEQ ID No. 21 |
| orfB1 | 2-313 | SEQ ID No. 22 |
| orfB2 | 501*-3107 | SEQ ID No. 23 |
| orfB3 | 3172-3810c | SEQ ID No. 24 |
| orfB4 | 3935-4924c | SEQ ID No. 25 |
| orfB5 | 5123-5953 | SEQ ID No. 26 |
| orfB6 | 5961-6518*c | SEQ ID No. 27 |
| orfB7 | 6564*-7538 | SEQ ID No. 28 |
| orfB8 | 60153-60533c | SEQ ID No. 29 |
| orfB9 | 60620-61003 | SEQ ID No. 30 |
| orfB10 | 61188*-61436 | SEQ ID No. 31 |
| orfB11 | 61526-61738 | SEQ ID No. 32 |

TABLE 8-continued

| Gene | Bases in SEQ ID No. 1 | Corresponding polypeptide sequence number |
|---|---|---|
| orfB12 | 61767-62285c | SEQ ID No. 33 |
| orfB13a | 62750-63067c | SEQ ID No. 34 |
| orfB13b | 62586-62858c | SEQ ID No. 113 |
| orfB14 | 63155-65071c | SEQ ID No. 35 |
| orfB15 | 65374-65871 | SEQ ID No. 36 |
| orfB16 | 65942-68305c* | SEQ ID No. 37 |
| orfB17 | 68290-68910c* | SEQ ID No. 38 |
| orfB18 | 69681-70436 | SEQ ID No. 39 |
| orfB19 | 70445-71848 | SEQ ID No. 40 |
| orfB20 | 71851-72957 | SEQ ID No. 41 |
| orfB21 | 73037-73942 | SEQ ID No. 42 |
| orfB22 | 73995-74534c | SEQ ID No. 43 |

[Note 1: c indicates that the gene is encoded by the complement DNA strand; Note 2: for each open reading frame given above, the longest probable open reading frame is described. It is sometimes the case that more than one potential candidate start codon can been identified. One skilled in the art will recognise this and be able to identify alternative possible start codons. We have indicated those genes which have more than one possible start codon with a (*) symbol. Throughout we have indicated what we believe to be the start codon, however, a person of skill in the art will appreciate that it may be possible to generate active protein using an alternative start codon, proteins generated using these alternative start codons are also considered within the scope of the present invention. Note 3 the SEQ ID NO: for orfB13b was originally designated SEQ ID NO: 34 but for clarity a separate sequence and SEQ ID NO has been assigned.]

Potential functions of the predicted polypeptides (SEQ ID No.7 to 43) were obtained from the NCBI database using a BLAST search. The best matches obtained from these searches are described below in Table 9:

TABLE 9

| Gene | Significant protein match | Score | Accession GenBank | Proposed function |
|---|---|---|---|---|
| orfB1 | hypothetical protein, no full length hits, high GC codon preference | | | unknown |
| orfB2 | SCM2.07, hypothetical protein (*S. coelicolor*) | 998 | NP_625154 | unknown |
| orfB3 | SCF76.07, hypothetical protein, (*S. coelicolor*) | 359 | NP_624786 | unknown |
| orfB4 | SCF76.06, araC family transcriptional regulator (*S. coelicolor*) | 412 | NP_624785 | unknown |
| orfB5 | SCF76.05c, non-heme chloroperoxidase (*S. coelicolor*) | 495 | NP_624784 | non-heme chloroperoxidase |
| orfB6 | SCF76.09, hypothetical protein (*S. coelicolor*) | 159 | NP_624788 | unknown |
| orfB7 | SCF76.08c, hypothetical protein (*S. coelicolor*) | 473 | NP_624787 | unknown |
| borB | PteH, polyene macrolide thioesterase (*S. avermitilis*) | 244 | BAB69315 | type II thioesterase |
| borC | XF1726, 2,5-dichloro-2,5-cyclohexadiene-1,4,-diol dehydrogenase (*Xylella fastidiosa* strain 9a5c)e | 160 | NP_299015 | dehydrogenase |
| borD | FabG, 3-oxoacyl-ACP reductase precursor, (*Plasmodium falciparum*) | 124 | AAK83686 | 3-oxoacyl-ACP reductase |
| borE | FN1586, O-succinylbenzoyl-CoA synthase, (*Fusobacterium nucleatum* subsp. *nucleatum* ATCC 25586) | 88 | NP_602402 | cyclase (member of enolase superfamily) |
| borF | putative lysophospholipase homologue, (*Arabidopsis thaliana)* | 57 | NP_565066 | unknown |

TABLE 9-continued

| Gene | Significant protein match | Score | Accession GenBank | Proposed function |
| --- | --- | --- | --- | --- |
| borG | MTH1444, acetolactate synthase, large subunit, (*Methanothermobacter thermautotrophicus)* | 120 | NP_276558 | Unknown |
| borH | PA3592, conserved hypothetical protein, (*Pseudomonas aeruginosa*) | 116 | NP_252282 | unknown |
| borI | TylH1, cytochrome P450, (*Streptomyces fradiae*) | 285 | AAD12167 | cytochrome P450 oxidase |
| borJ | BioA, DAPA aminotransferase, (*Kurthia* sp. 538-KA26) | 346 | BAB39453 | amino transferase |
| borK | Adh1, alcohol dehydrogenase, (*Aquifex aeolicus)* | 191 | NP_213938 | NAD/quinone oxidoreductase |
| borL | putative auxin-regulated protein GH3, (*Arabidopsis thaliana)* | 92 | NP_176159 | unknown |
| borM | SCL6.10, hypothetical protein similar to putative F420-dependent dehydrogenase (*S. coelicolor*), | 108 | CAB76875 | F420 dependent dehydrogenase |
| borN | SC1C2.27, hypothetical protein, 2-hydroxyhepta-2,4-diene-1,7-dioate isomerase superfamily (*S. coelicolor*) | 215 | NP_629680 | 2-hydroxyhepta-2,4-diene-1,7-dioate isomerase |
| borO | ThrS, threonyl-tRNA synthetase (*Mycobacterium leprae)* | 627 | NP_301410 | threonyl-tRNA synthetase, self resistance gene |
| orfB8 | conserved hypothetical protein (*Methanosarcina acetivorans* str. C2A). (Pfam pulls out weak MarR family) | 37 | NP_617908 | possible regulator |
| orfB9 | putative anti-sigma factor antagonist (*Streptomyces coelicolor)* | 113 | NP_631789 | anti-sigma factor antagonist |
| orfB10 | conserved hypothetical protein (*S. coelicolor*) | 95 | NP_631790 | unknown |
| orfB11 | hypothetical protein, no full length hits, high GC codon preference | | | unknown |
| orfB12 | putative regulator (*S. coelicolor*) | 92 | NP_631494 | regulator (of a two component system, maybe membrane sensor) |
| orfB13a | putative acetyltransferase (*S. coelicolor*); | 58 | NP_625155 | tentative assignment of acetyltransferase |
| orfB13b | putative acetyltransferase (*S. coelicolor*) | 100 | NP_625155 | in two frames, or sequencing error and should be in a single frame |
| orfB14 | putative lipoprotein (*S. coelicolor*) | 386 | NP_631245 | unknown |
| orfB15 | hypothetical protein (*S. coelicolor*) | 41 | NP_631424 | unknown |
| orfB16 | putative formate dehydrognease (*S. coelicolor*) (Pfam matches to molybdopterin oxidoreductase/ formate dehydrogenase alpha subunit) | 915 | NP_626265 | oxidoreductase |
| orfB17 | conserved hypothetical protein, *S. coelicolor* SCBAC25F8.16 | 175 | NP_631569 | unknown |
| orfB18 | product unknown (*Streptomyces aureofaciens*) | 396 | AAD23399 | unknown |
| orfB19 | putative aldehyde dehydrogenase (*S. aureofaciens*) | 635 | AAD23400 | aldehyde dehydrogenase |
| orfB20 | putative alcohol dehydrogenase (*S. coelicolor*) | 450 | NP_630527 | alcohol dehydrogenase |
| orfB21 | hypothetical protein (*S. coelicolor*) | 395 | NP_630528 | unknown |
| orfB22 | putative calcium binding protein (*S. coelicolor*) | 160 | NP_631687 | calcium binding protein |

Analysis of the functions of the putative gene products indicates that the genes borB to borO most probably form the boundaries of the borrelidin biosynthetic cluster. Evidence to support this came from the disruption of borB2, which produced borrelidin at levels indistinguishable from the wild type parental strain. In addition, borB3 to borB7 have homologues in the *Streptomyces coelicolor* A3(2) genome encoded on cosmid SCF76; the same orfs are present, but in a different order. The orfs borB8 to borB10 are arranged identically to homologues in the *S. coelicolor* A3(2) cosmid SC5E3. The orfs borB18 to borB21 have homologues that are arranged similarly in the *S. coelicolor* A3(2) cosmid SC1A2. The orf borB13 contains a frame-shift and thus any gene product would most probably be inactive. In addition, no function can be readily deduced for the products of these orfs during borrelidin biosynthesis.

Starter Unit Biosynthesis Genes

In order to identify the genes that are involved in the biosynthesis of the trans-cyclopentane-1,2-dicarboxylic starter unit, each of the genes borB to borN was disrupted (e.g. see examples 13-25). This was done in a manner designed to minimise the possibility of polar effects, which was verified by successful in trans complementation with a full-length copy of the disrupted gene under the control of the ermE* promoter, which gave back approximately WT levels of borrelidin production in each case.

Each of the disrupted mutants was grown in triplicate as described in example 1, and borrelidin production assessed. Alongside these, each mutant was grown in triplicate and supplemented, after 24 hours, with exogenous starter acid to a final concentration of 1 mM, and borrelidin production assessed. Extraction and analysis for borrelidin provided the data that are described below in Table 10:

TABLE 10

| Borrelidin biosynthetic gene disrupted | Borrelidin production without feeding (% relative to WT) | Borrelidin production with feeding (% relative to unfed WT) |
|---|---|---|
| Wild type (control) | 100 ± 16, (100 ± 2) | 363 ± 65, (269 ± 49) |
| borB | 75 ± 11, (43 ± 20) | 172 ± 51 |
| borC | 0, (10 ± 3) | 933 ± 42 |
| borD | 7 ± 1, (0) | 75 ± 15 |
| borE | 2 ± 1 | 122 ± 23 |
| borF | 3 ± 2 | 201 ± 52 |
| borG | 11 ± 1, (32 ± 3) | 1532 ± 142 |
| borH | 17 ± 2, (23 ± 13) | 203 ± 40 |
| borI | 0, (0) | 0, (0) |
| borJ | 0, (0) | 0, (0) |
| borK | 0, (6 ± 1) | 319 ± 54, (464 ± 18) |
| borL | 0, (0) | 408 ± 70, (399 ± 69) |
| borM | 0, (6 ± 3) | 461 ± 29, (553 ± 66) |
| borN | 25 ± 9, (34 ± 3) | 68 ± 12, (46 ± 9) |
| borO | N/A | N/A |

[Note 1: The values given in brackets indicate where repeat runs of some experiments were performed; Note 2: N/A = not applicable.]

Based on the data in table 10, it is clear to one skilled in the art that the gene products BorC-F and K-M are essential or very important for the biosynthesis of trans-cyclopentane-1,2-dicarboxylic acid, as these mutants produced no or very low levels of borrelidin without the addition of exogenous starter acid, whereupon they produced borrelidin at levels approaching, or better than, that of the WT organism. In addition the gene products BorG, H, and N appear to be involved in, but not essential for, the biosynthesis of the starter unit, as they produced significantly lower levels of borrelidin unless exogenous starter acid was added, whereupon they produced borrelidin at levels approaching or better than that of the WT organism; this was particularly notable in the case of the borG$^-$ mutant.

Figure 9:
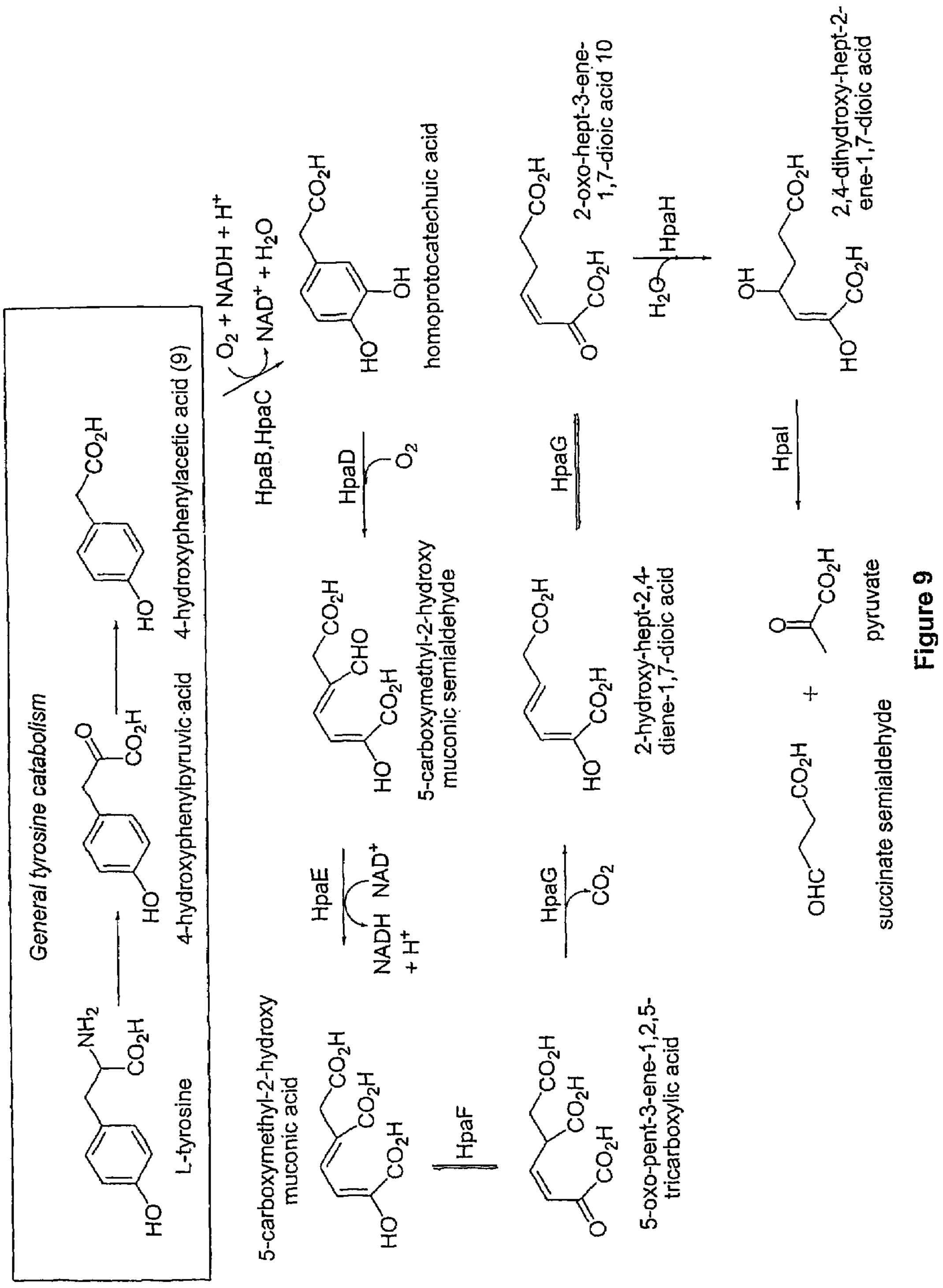
FIG. 9 illustrates the molecular characterisation of the 4-hydroxyphenylacetic acid catabolic pathway in *E. coli* W.

The normal metabolic function of BorN homologues is the production of 2-oxohepta-3-ene-1,7-dioate 10, a key step in the catabolism of tyrosine via 4-hydroxyphenyl acetic acid 9 (FIG. 9) (Prieto et al., 1996). Therefore, 10 may be an intermediate in the biosynthetic pathway to trans-cyclopentane-1,2-dicarboxylic. The ability of the mutant disrupted in borN to produce borrelidin, albeit at a reduced level, most probably lies in the presence of a homologue elsewhere in the genome utilised in the catabolism of tyrosine during primary metabolism.

The intermediate 10 contains all the required functionality for the eventual formation of trans-cyclopentane-1,2-dicarboxylic acid. The most probable next step of the biosynthesis is the reduction of the 3-ene position in a reaction similar to that catalysed by an enoyl reductase. Potential enzymes responsible for this step are BorC, BorD, BorK or BorM; these enzymes are all involved in borrelidin starter unit biosynthesis as seen from the data in table 10. The resulting 2-oxohepta-1,7-dioate 11 is one possible substrate for cyclisation through formation of a new C—C bond between C6 and C2. Another possible substrate for this cyclisation would be 2-hydroxyhepta-1,7-dioate 12 or some activated form thereof. This would presumably be formed from 11 by the action of an oxidoreductase such as BorC, BorD or BorM.

Figure 4:
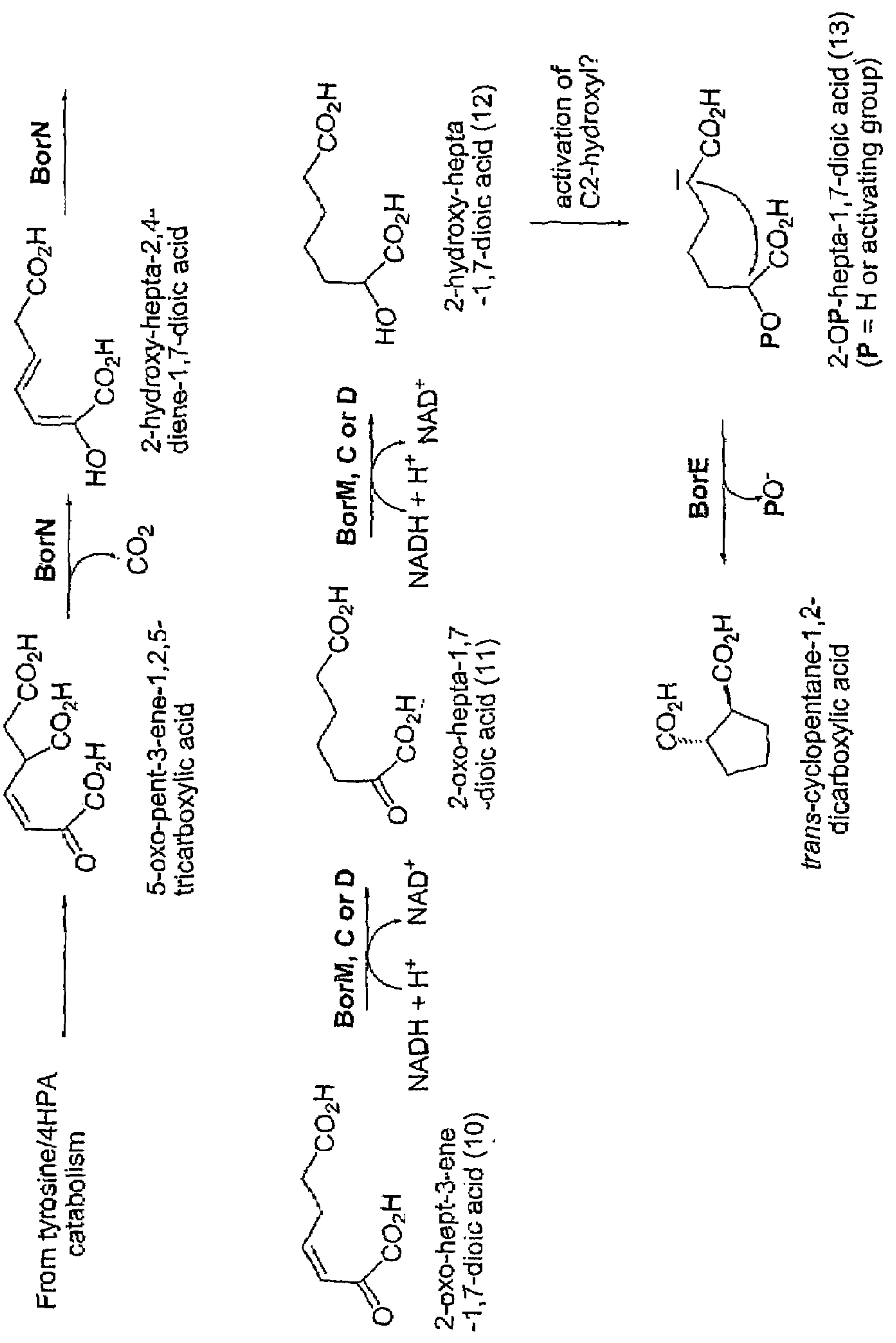
FIG. 4 illustrates a scheme showing the proposed biosynthetic pathway for the trans-cyclopentane-1,2-dicarboxylic acid starter unit.

The key cyclisation step is most probably catalysed by BorE, which displays similarity to O-succinylbenzoyl-CoA synthase and chloromuconate cycloisomerase. These enzymes belong to the enolase super-family, the members of which share the common ability to stabilise the formation of an anion on the carbon atom adjacent to a carboxylate group (Schmidt. et al., 2001). It is further notable that the substrate for muconate cycloisomerase is a hexa-1,6-dioate, which is similar in gross structure to 11 and 12. Abstraction of a proton and formation of an anion equivalent at C6 of 11 or 12 (or an activated form thereof, e.g. 13) with subsequent cyclisation to C2 provides the correctly substituted cyclopentane ring structure, although the intermediacy of 11 as substrate would require some further processing of the substituted cyclopentane, most probably via elimination of water to give the symmetric cyclopent-1-ene-1,2-dicarboxylic acid, or possibly the $\Delta^1$-unsaturated compound, cyclopent-1-ene-1,2-dicarboxylic acid. However, the feeding of cyclopent-1-ene-1,2-dicarboxylic acid, or ethyl esters thereof, to *S. parvulus* Tü4055 strains disrupted in any of borC-E, or to WT strains, did not produce any borrelidin, or did not produce borrelidin in any increased amount when compared to the unfed controls. These data indicate that this compound is probably not an intermediate in starter unit biosynthesis, and that the substrate of BorE is possibly the 2-hydroxyhepta-1,7-dioate 12, or an activated form thereof (e.g. 13). A putative pathway for the biosynthetic pathway to trans-cyclopentane-1,2-dicarboxylic acid is shown in FIG. 4.

The combined, specific genes required for the biosynthetic steps to trans-cyclopentane-1,2-dicarboxylic acid are not clear, but probably are encoded by some combination of borC-H, borK, borM and borN. The lack of certain homologues of genes that are involved in the catabolism of 4-hydroxyphenyl acetic acid 9, and which would act prior to BorN in the pathway, is most probably an indication that primary metabolic genes perform these tasks. The addition of exogenous trans-cylopentane-1,2-dicarboxylic acid to *S. parvulus* Tü4055 and related strains increases the titre of borrelidin in the order of 2- to 3-fold under our conditions, indicating that the biosynthesis of starter acid is a limiting factor in borrelidin biosynthesis. These data are consistent with primary metabolic degradation of tyrosine being the source of trans-cyclopentane-1,2-dicarboxylic acid.

In an attempt to further clarify which genes may be specifically responsible for biosynthesis of the starter unit, a number of co-culture experiments were performed with combinations of the different mutants—these require the knowledge that the gene products of borI and borJ are specifically involved in the formation of the C12-nitrile moiety, which is clarified by the data given in the following section below in combination with the data from table 10. In summary, the co-culture of mutants borE$^-$ & borD$^-$, and of borE$^-$ & borM$^-$ failed to produce any borrelidin whereas the co-culture of mutants borM$^-$ & borI$^-$, and borM$^-$ & borK$^-$ produced borrelidin at approximately WT levels. These data, in combination with that in table 10, and below, clearly indicate that borD, borE and borM are involved in starter unit biosynthesis, whereas borI, and possibly borK, are involved in the formation of the nitrile moiety at C12 of borrelidin.

It is clear from the data in table 10 that exogenous addition of trans-cyclopentane-1,2-dicarboxylic acid is sufficient to re-establish approximately WT levels, or better, of borrelidin production in mutants where genes that are involved in starter unit biosynthesis have been disrupted. These data indicate that there is no problem with the active uptake of added carboxylic acid by *S. parvulus* Tü14055, and that an activity is present which is capable of converting the carboxylic acid to a CoA thioester equivalent. Thus, given the known technologies of mutasynthesis, it is obvious to one skilled in the art that the addition of exogenous carboxylic acids to one of the aforementioned mutants, for example the borE$^-$ strain *S. parvulus* Tü4055/borE:aac3(IV) described in example 16, may lead to the production of borrelidin analogues in which the starter unit carboxylic acid moiety is replaced with a moiety derived from the exogenously added carboxylic acid.

Figure 10:
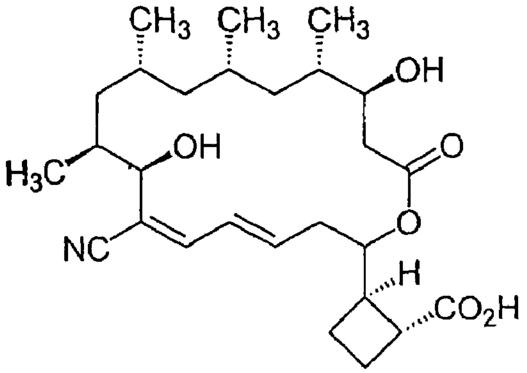
FIG. 10 illustrates the structures of the molecules 18-20
Figure 10:
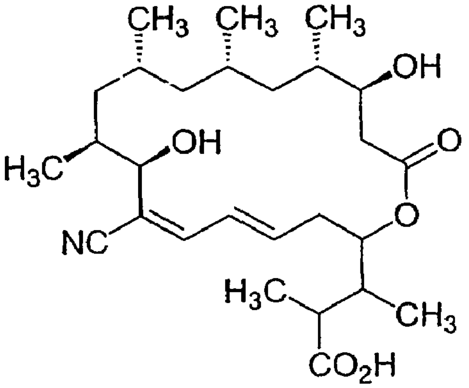
Figure 10:
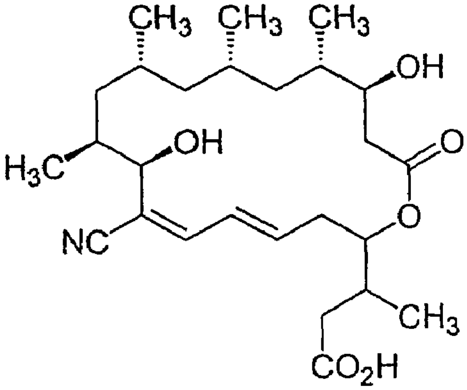

To examine this possibility, strain *S. parvulus* Tü04055/borE:aac3(IV) was fed with a trans-cyclobutane-1,2-dicarboxylic acid according to the protocol described in example 1 and then analysed as described in example 4. The structure 18, described in FIG. 10, shows the new borrelidin structure obtained from feeding this carboxylic acid; this compound 18 displayed the anticipated UV chromophore for borrelidin but eluted at an earlier retention time and displayed the expected mass by LCMS (m/z=474.3 [M−H]$^-$XX). Verification of this methodology was provided by the production, isolation and characterisation of 18 (example 33). (RS)-2It is clear to one skilled in the art that other carboxylic acids could also be used in similar feeding experiments to provide further new borrelidin analogues. Although it is possible that not all carboxylic acids would be incorporated using the exact methodology described herein, a person of skill in the art is aware of a number of available methods to enhance the incorporation of fed starter units.

In addition to the use of the strain deleted in borE, it was observed (see table 10) that the strain *S. parvulus* Tü4055/borG:aac3(IV), in which borG has been disrupted, when fed with the natural starter unit of the bor PKS, trans-cyclopentane-1,2-dicarboxylic acid, produced borrelidin at titres significantly higher than those seen when the wild-type organism was fed (4-fold increase) or unfed (15-fold increase). To examine this further, this experiment was repeated using both the natural and an unnatural starter acid as exogenous substrates, fed, in parallel, to wildtype, the borE mutant and the borG mutant. The resulting data are described in table 11.

TABLE 11

| | Unfed | Fed with 1 mM cyclopentane trans-1,2-dicarboxylic acid | Fed with 1 mM cyclobutane trans-1,2-dicarboxylic acid |
|---|---|---|---|
| *S. parvulus* Tü4055 | 2.3 mg/l | 6.6 mg/l | — |
| *S. parvulus* Tü4055/borE:aac3(IV) | 0 | 4.7 mg/l | 2.2 mg/l |
| *S. parvulus* Tü4055/borG:aac3(IV) | 0 | 88.9 mg/l | 43.0 mg/l |

As one can see from table 11, using *S. parvulus* Tü4055/borG:aac3(IV) instead of *S. parvulus* Tü4055/borE:aac3(IV) for mutasynthesis increases the titre approximately 19-fold, and that *S. parvulus* Tü4055/borG:aac3(IV) fed with the natural starter acid produces 38-fold more borrelidin A than wild type alone, or 13 fold more borrelidin A than the wild type strain fed with the same amount of cyclopentane trans-1,2-dicarboxylic acid. These data clearly indicate that the use of strain *S. parvulus* Tü4055/borG:aac3(IV) for mutasynthesis experiments is beneficial for the production of improved titres of borrelidin analogues. This method has general applicability for both the production of borrelidin and borrelidin analogues.

On the basis of this finding, the feeding experiments with alternative carboxylic acids were repeated in *S. parvulus* Tü4055/borG:aac3(IV), and extended to include 2,3-dimethyl succinic acid and 2-methylsuccinic acid; the new compounds derived from the incorporation of these alternative starter units, 19 and 20 repectively, are described in FIG. 10.

In an attempt to improve the titre of borrelidin produced in fermentation cultures of *S. parvulus* Tü4055 through other means, additional copies of the genes borE and borL were introduced into the organism in vectors that place them under the control of the strong constitutive promoter ermE*. It was anticipated that the over-expression of these genes would increase the intra-cellular levels of the starter acid, which appears to be limiting with respect to borrelidin production.

The genes borE and borL were amplified by PCR, cloned into the vector pEM4, and then introduced into *S. parvulus* Tü4055 as described in examples 29 and 30 respectively. In addition, the vector pEM4 alone (not containing any insert) was also introduced in *S. parvulus* Tü4055 and used as a control. The resulting strains were grown, extracted and analysed as described in examples 1 and 4. Introduction of the vector as a control did not significantly effect the levels of borrelidin production. However, the expression of additional copies of either borE or borL in this manner brought a 4.2±0.3 and 4.3±0.7-fold increase respectively in the titre of borrelidin relative to the wild type strain. Presumably, the steps of biosynthesis catalysed by their gene products are rate limiting, or alternatively their gene products may have a positive regulatory function. For example borL shows greatest homology to auxin response proteins from plants. Auxins are hormones involved in the regulation of various cellular processes in plants, and borL may represent the first example of a related gene having regulatory function in a bacteria. As controls, an additional copy of borJ, borO and borA5, under the control of ermE* in pEM4, were introduced into *S. parvulus* Tü4055, but did not have any significant effect upon borrelidin titre. This was anticipated as none of the respective gene products are anticipated to be involved in starter unit biosynthesis. In addition, up-regulation of the putative 'stuttering' PKS module (borA5) did not increase borrelidin titre, further indicating that iterative use of this module occurs, rather than three independent copies being utilized. The lack of an effect on titre when borO is up-regulated indicates that there is most probably no limitation placed upon borrelidin production due to toxicity in the producing organism and so indicates that there is further scope for titre improvement.

Formation of the Nitrile Moiety at C12

Figure 1:
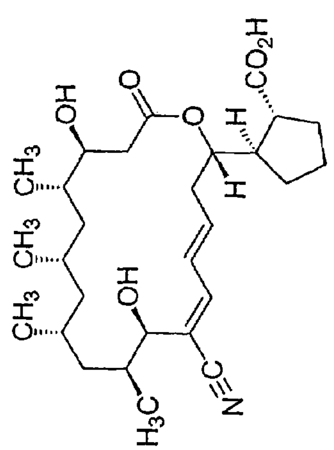
FIG. 1 illustrates the structure of borrelidin and some related metabolites isolated from borrelidin producing organisms.
Figure 1:
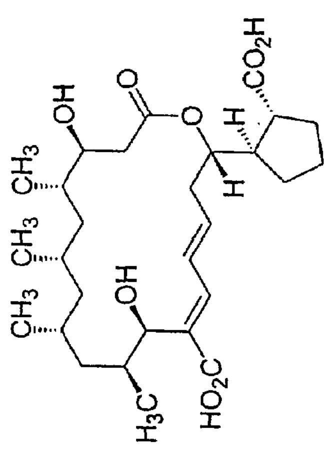
Figure 1:
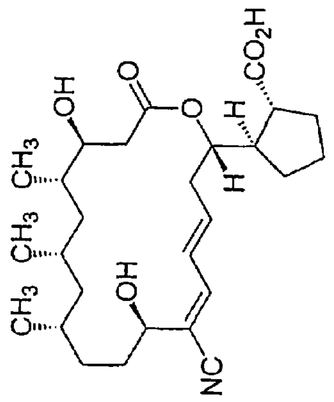
Figure 1:
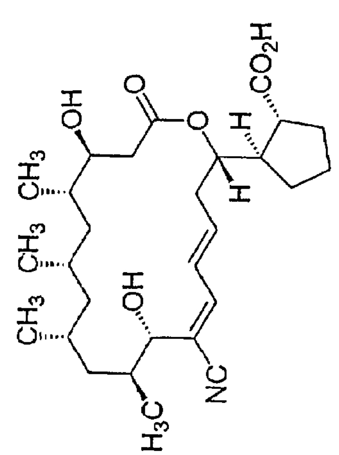
Figure 1:
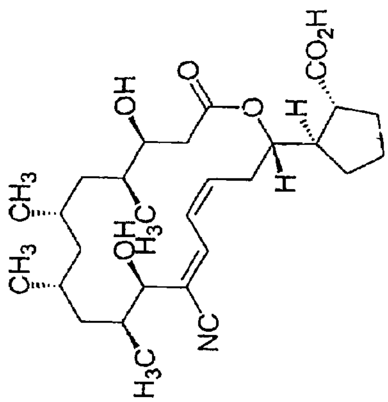
Figure 2:
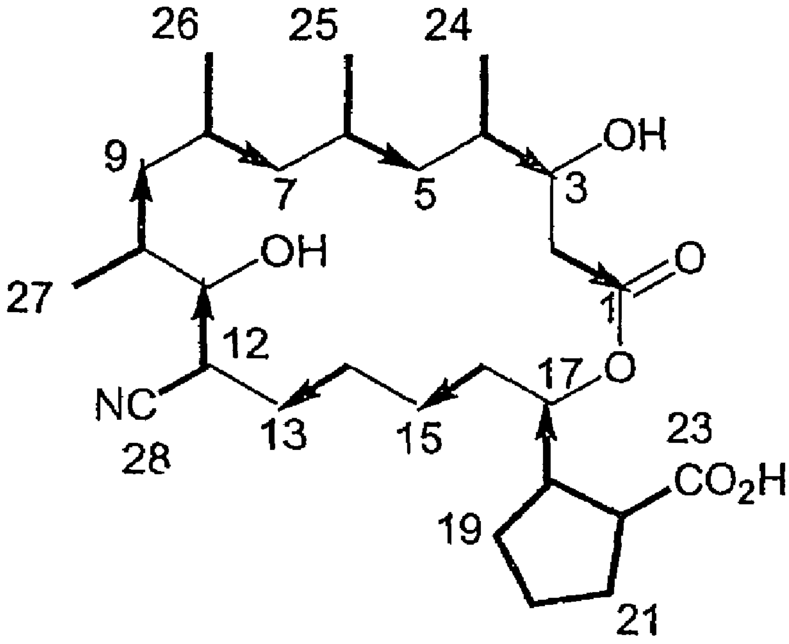
FIG. 2 illustrates the incorporation patterns for $^{13}C$ stable isotope labelled extension substrates and the position of the trans-cyclopentane-1,2-dicarboxylic acid starter unit derived carbons.
Figure 2:
Figure 2:
Figure 2:
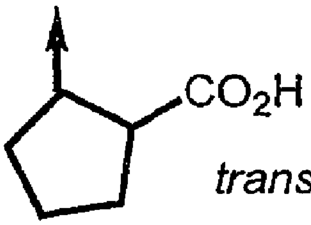

Sequence analysis of the AT domain of the borrelidin PKS module 3 indicates that the substrate utilised for the third round of chain extension is methylmalonyl-CoA. Thus, the carbon atom of the nitrile moiety most probably arises from the methyl group of methylmalonyl-CoA. This was verified by stable isotope feeding experiments. Feeding [2,3-$^{13}C_2$] sodium propionate to *S. parvulus Tü*113 gave borrelidin which displayed intact labelling of the carbons at C4-C24, C6-C25, C8-C26, C10-C27 and C12-C28, and identical specific incorporations (as determined within the limits of our experimental methods), as expected (FIG. 2). These data indicate that the conversion of the C12-methyl group occurs either during chain assembly at, or after, the incorporation of the third extension unit, or that it occurs after polyketide chain assembly and release from the PKS. Based on functional assignments given to the borrelidin biosynthetic genes, in conjunction with the gene disruption data described in table 10, both borI and borJ are clearly implicated in formation of the nitrile moiety at C12, while others such as borK may also be.

The cytochrome P450 hydroxylase BorI shares greatest similarity to TylHI, which catalyses the hydroxylation of an exocyclic methyl group of the tylosin macrolactone prior to addition of a deoxyhexose moiety (Fouces et al., 1999). BorI is therefore believed to catalyse oxidation of the C12-methyl group during borrelidin biosynthesis. In agreement with this the borI$^-$ mutant *S. parvulus* Tü4055/borI::aac3(IV) fails to produce borrelidin but accumulates a new product 14 (FIG. 6) that is less polar than borrelidin. 14 is readily transformed to borrelidin when fed to the borE mutant *S. parvulus* Tü4055/borE::aac3(IV) which lacks the ability to synthesise the PKS starter unit but maintains the rest of the borrelidin biosynthetic genes intact. Fermentation of *S. parvulus* Tü4055/borI::aac3(IV) followed by extraction and isolation provided ~30 mg of 14 (example 31). Full structural analysis of 14 identified it as 12-desnitrile-12-methylborrelidin (pre-borrelidin). This is consistent with the proposed role of BorI in borrelidin biosynthesis and provides a route to novel borrelidin analogues with a methyl group attached to C12 of the macrolactone ring.

The putative PLP dependent aminotransferase BorJ is believed to catalyse the introduction of a nitrogen atom into borrelidin at the activated C28-position, probably via a C12-formyl moiety. In agreement with this the borJ$^-$ mutant *S. parvulus* Tü4055/borJ::aac3(IV) does not produce borrelidin and accumulates a new compound that is more polar than borrelidin. This new compound is not transformed to borrelidin when fed to mutant *S. parvulus* Tü4055/borE::aac3(IV) which indicates that it is probably a shunt metabolite rather than an intermediate in borrelidin biosynthesis. Fermentation of *S. parvulus* Tü4055/borJ::aac3(IV) allowed the isolation of 17 mg of the accumulated compound (example 32). Detailed structural analysis identified the accumulant as 12-desnitrile-12-carboxyl borrelidin 2.

In addition to the compounds isolated from mutation of the borrelidin biosynthetic genes, 12-desnitrile-12-formyl borrelidin 15 is isolated from the fermentation supernatant of *S. parvulus* Tü113. The fermentation media and conditions used for these experiments differ from those we have described so far herein, but are designed to maximise the production of borrelidin. We propose that this altered medium, in combination with a drop in the dissolved oxygen concentration that is observed to occur during this specific fermentation, promoted the accumulation of 15. 15 is readily transformed to borrelidin when fed to the mutant *S. parvulus* Tü4055/borE::aac3(IV) which lacks the ability to synthesise the PKS starter unit but maintains the rest of the borrelidin biosynthetic genes intact.

Figure 6:
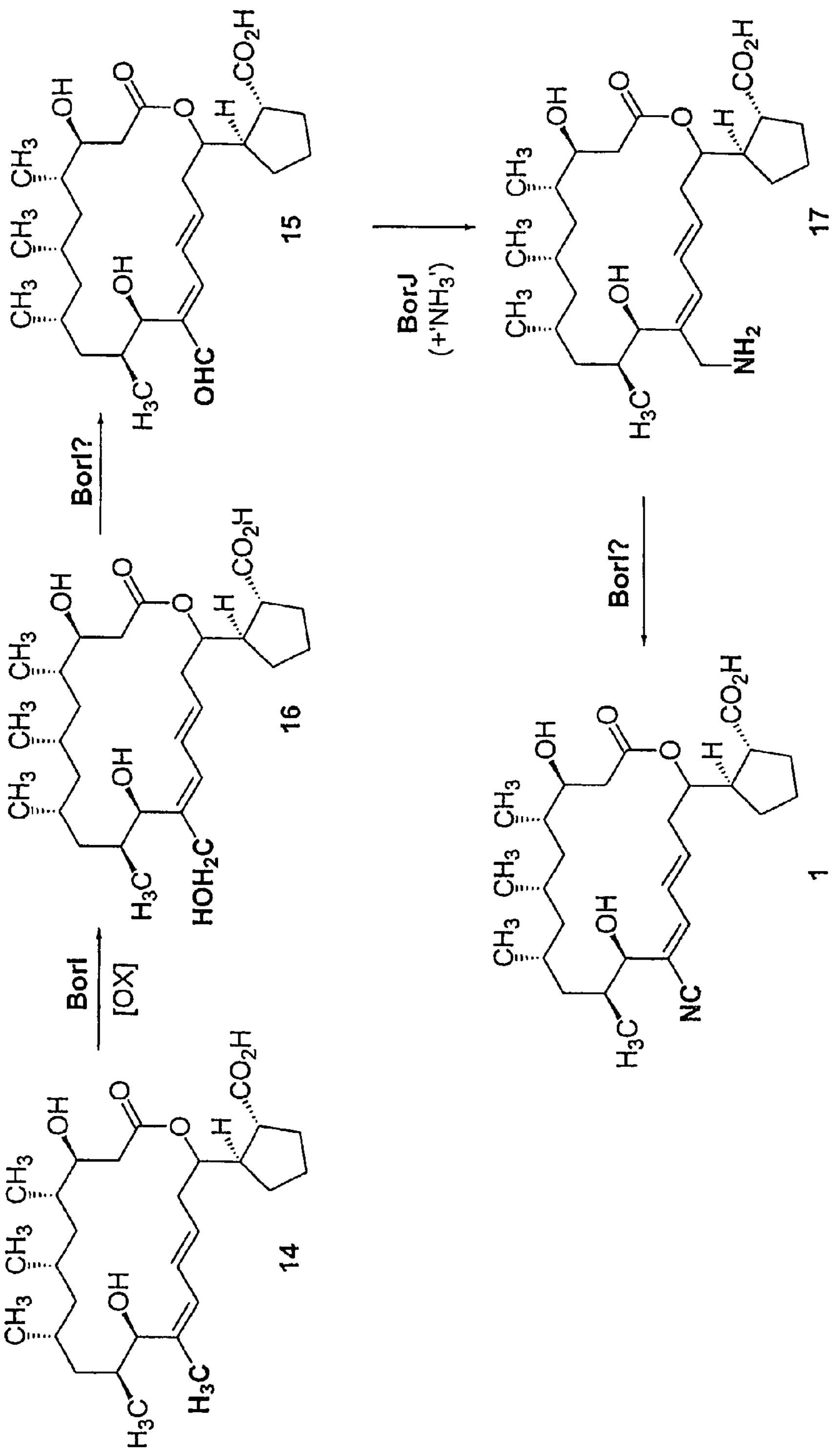
FIG. 6 illustrates the proposed biosynthetic route for the introduction of the nitrile moiety at the C12 position of borrelidin.

The above data lead us to propose a biosynthetic route to the nitrile moiety of borrelidin as presented in FIG. 6. The C12-methyl carbon of pre-borrelidin 14 is first oxidised by BorI to introduce an allylic hydroxyl group at C28 (16). This hydroxyl group is then converted to the formyl moiety attached to C12 (15) using a method selected from the group comprising: spontaneous oxidation (including oxidation mediated by some background enzyme) the action of a specific gene of the borrelidin biosynthetic gene cluster; candidate gene products are thus BorI itself, acting in a multifunctional manner and operating via the formation of a gem-diol structure at C12 followed by dehydration; or alternatively, via one of the oxidoreductase encoding genes such as borC or borK. The next step is anticipated to be BorJ-catalysed transamination of 15 in order to introduce a nitrogen atom at C28, in the form of an amine, through a pyridoxamine phosphate mediated process. The putative product amine 17 then undergoes oxidation, possibly spontaneously, but most probably by an enzymic activity such as BorI (certain parallels can be drawn to the biosynthesis of nitriles in plants (Celenza, 2001; Hahn et al., 1999; Nielson and Møller, 1999)) or by the products of one of the oxidoreductase encoding genes, e.g. borC or borK, or by a general oxidoreductase within the proteome.

In order to examine this proposed pathway in more detail a number of biotransformation experiments were performed using pre-borrelidin 14 as substrate for investigating the action of borI-K individually and in combination, using pEM4 as vector and *S. albus* J1074 (Chater & Wilde, 1980) as an expression strain. Expression of borI or borJ individually did not give borrelidin production on addition of 14. The added 14 was only consumed during biotransformation with borI (and not in any of the control experiments); the 14 added was identified as being converted to the shunt metabolite 2. However, co-expression of borI & borJ did convert the added 14 to borrelidin. It thus appears that either BorI or general proteome activities in *S. albus* are capable of oxidising the proposed amine intermediate 17 in the borrelidin biosynthetic pathway. In addition to the feeding of pre-borrelidin 14, 12-desnitrile-12-carboxyl borrelidin 2 was also fed to the three strains described above. No conversion of 2 to borrelidin was observed in any of these experiments, reinforcing the idea that 2 is a shunt metabolite.

Detailed investigation of genomic DNA from three borrelidin producing strains, *S. rochei* ATCC23956, *S. parvulus* Tü113 and *S. parvulus* Tü4055, using numerous restriction digests and subsequent Southern Blot analysis, indicates that the borrelidin biosynthetic gene clusters of these three organisms are very closely conserved. It therefore appears that the borrelidin biosynthetic pathways of these strains are very similar. This assumption allows us to consider the data above, which are obtained from different strains, as applicable to a single biosynthetic pathway.

It is clear to one skilled in the art that manipulation of the genes involved in formation of the C12-nitrile moiety of borrelidin, for example borI, or borJ, is a generally useful method for the production of novel borrelidin related molecules and borrelidin derivatives with altered functionality at C12. In addition, the transfer of these genes to other organisms producing other natural or engineered polyketide products may allow the incorporation of nitrile moieties into such compounds.

Figure 11:
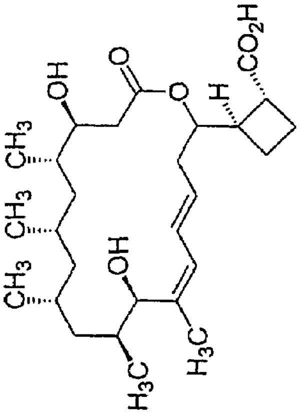
FIG. 11 illustrates the structures of the molecules 21-26
Figure 11:
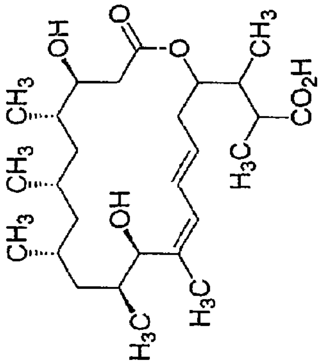
Figure 11:
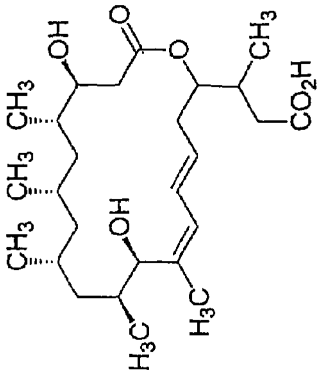
Figure 11:
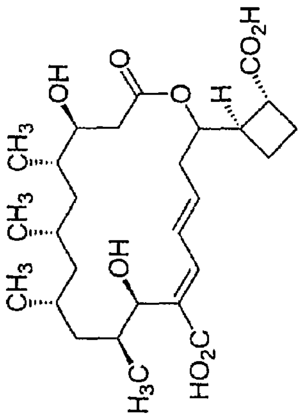
Figure 11:
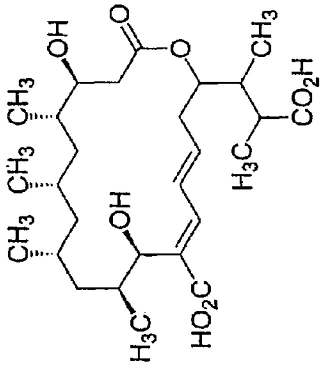
Figure 11:
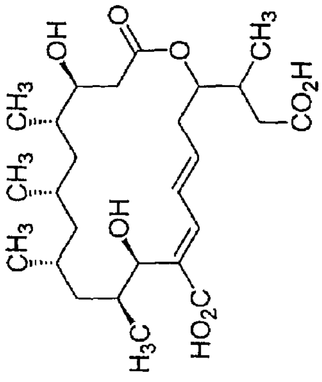

In an extension of this work, disruptions in borI and borJ are separately made in the strain *S. parvulus* Tü4055/borG: aac3(IV) to give the doubly mutated strains *S. parvulus* Tü4055/borG:aac3(IV)/borI::hyg and *S. parvulus* Tü4055/borG:aac3(IV)/borJ::hyg (examples 27 & 28 respectively). These strains are fed alternative carboxylic acids, trans-cyclobutane-1,2-dicarboxylic acid, 2,3-dimethylsuccinic acid and 2-methylsuccinic acid, (as described above) and are found to produce the mutasynthetic borrelidin analogues carrying, either, a methyl (21, 22 and 23 respectively) or a carboxyl function at C12 (24, 25 and 26 respectively) in place of the nitrile group, and which are also derived from alternative starter units corresponding to the exogenously supplied carboxylic acids. This orthogonal library of new compounds is described in FIG. 11 and the observed UV chromophores and mass spectral data for each compound is shown.

Other Genes Involved in Borrelidin Production

In addition to the type-I terminal thioesterase domain of the borrelidin PKS, a discrete type-II thioesterase is located at the upstream boundary of the biosynthetic gene cluster and is encoded by the gene borB. Such discrete type-II TE proteins are commonly found to be associated with type-I PKSs and are believed to play a role in the 'editing' of PKSs by the removal of short chain acyl groups that are formed by unwanted decarboxylation of extender units attached to KS domains (Heathcote et al., 2001). The disruption of such discrete type-II TEs in the picromycin (Xue et al., 1998) and tylosin (Butler et al., 1999) biosynthetic clusters leads to a significant reduction in titre of both macrolides. In accordance with these results, disruption of borB (example 13) gave a mutant that produced between 43-75% of the parental wild type titre.

The self-resistance of *S. parvulus* strains to borrelidin is most probably due to the product of borO, which encodes a threonyl tRNA synthetase homologue. Threonyl-tRNA synthetase is the molecular target of borrelidin in sensitive strains (Paetz & Ness, 1973). It is predicted that BorO is resistant to the action of borrelidin, and acts to produce threonyl-tRNAs in cells that make borrelidin, effectively complementing the normal threonyl-tRNA which are inhibited. To verify this hypothesis borO was amplified by PCR and cloned in to the expression vector pEM4A, which puts borO under the control of the strong constitutive promoter ermE* (example 26). The resulting vector pborOR was then transformed into the borrelidin-sensitive strain *Streptomyces albus* J1074 (Chater & Wilde, 1980). Comparison of this strain with that containing only the expression vector pEM4A, using a soaked disk bioassay, clearly indicated that expression of borO confers resistance to borrelidin.

EXAMPLES

General Methods

Restriction enzymes, other molecular biology reagents, antibiotics and chemicals were purchased from standard commercial sources. Restriction endonuclease digestion and ligation followed standard methods (Sambrook, J. et al., 1989).

Example 1

Fermentation of *S. parvulus* Strains

The Following Method is Generally Useful for Culturing *S. parvulus* for the Production of Borrelidin and/or Borrelidin Analogues:

A seed flask containing NYG medium (30 ml in a 250 ml Erlenmeyer flask) was inoculated from a working stock (0.5 ml). NYG medium contains, in deionised water: beef extract (0.3%), Bacto peptone (0.5%), glucose (1%) and yeast extract (0.5%). After 2 days shaking in a rotary incubator (2-inch throw; 30° C.; 250 rpm) the resulting cream culture was used to inoculate PYDG production medium (30 ml in a 250 ml Erlenmyer flask; 10% innoculum). PYDG medium contains per liter of deionised water: peptonised milk nutrient (1.5%), yeast autolysate (0.15%), dextrin (4.5%) and glucose (0.5%) adjusted to pH 7.0. After 5 days shaking on a rotary incubator (2-inch throw; 30° C.; 250 rpm) the culture was harvested for analysis as described in example 4, or for isolation purposes as required. For quantitative analysis these experiments were performed in triplicate.

The Following Method is Useful for the Feeding of Exogenous Carboxylic acids to *S. parvulus* Strains:

The *S. parvulus* strain was grown as described above. After 24 hours growth in PYDG production medium, the carboxylic acid of choice was added as a 50 µl single aliquot (0.6 M solution in 70% methanol after neutralization with 5 N NaOH). The resulting culture was harvested after 5 days total fermentation and analysed as described in example 4. For quantitative studies these experiments were performed in triplicate, and the equivalent fed and unfed WT strains served as controls.

Example 2

Cryopreservation of *S. parvulus* Strains

Working Stocks

Working stocks of vegetative mycelia were prepared by mixing a 2 day old seed culture grown in NGY medium (0.5 ml) with cryopreservative (0.5 ml). Cryopreservative consists of 20% glycerol and 10% lactose in deionised water.

Spore Stocks

Strains of *S. parvulus* were incubated on HA agar plates at 30° C. After 14 days the resulting spores from a single plate were harvested and suspended in of cryopreservative (1 ml). HA agar contains in deionised water: 0.4% yeast extract, 1% malt extract, 0.4% dextrose and 1.5% agar adjusted to pH 7.3.

Example 3

Cloning of the Borrelidin Biosynthetic Gene Cluster and Disruption of borA2 & borA3

Cosmid Library Generation

A cosmid library was constructed in pWE15 cosmid vector using the Gigapack® III Gold Packaging Extract kit according to the manufacturer's handbook (Stratagene). Chromosomal DNA was extracted from *S. parvulus* Tü4055 according to standard protocols (Kieser et al., 2000) and treated with Sau3AI prior to cloning into pWE15. A number of the resulting *E. coli* transformants (3300) were picked and transferred to 96 well microtitre plates containing Luria Broth (LB)

medium (0.1 ml per well) with ampicillin (100 μg/ml). The resulting clones were replica-plated to Luria agar (LA) plates containing ampicillin (100 μg/ml). After incubation overnight at 37° C. colonies were transferred to nylon membrane filters for in situ colony hybridization analysis according to published protocols (Sambrook et al., 1989).

Library Screening

The cosmid library was screened using a probe that was generated using the DIG DNA Labelling and detection kit (Roche) according to the manufacturers instructions. The probe used was a BglII-BamHI fragment (1.7 kbp) obtained from the gene that encodes module 6 of the third subunit of the oleandomycin PKS from *Streptomyces antibioticus* (Swan et al., 1994).

Disruption of the Borrelidin Biosynthetic Gene Cluster

Cosmids that gave a positive response when screened as described above were digested with BamHI and fragments of less than 3 kbp were subcloned into pOJ260 (Bierman et al., 1992). These were then used to transform protoplasts of *S. parvulus* Tü4055 as described in example 5. The resulting transformants were then assessed for the ability to produce borrelidin. Two clones were borrelidin non-producers; both were obtained from cosBor32A2 and contain sequence typical of a modular PKS. The remaining cosmids were then screened using probes obtained from the two BamHI fragments, which led to the identification of the overlapping cosmid cosBor19B9 that contained the remainder of the borrelidin biosynthetic cluster.

Sequencing of cosBor32A2 and cosBor19B9

The cosmids cosBor32A2 and cosBor19B9 were transformed into *E. coli* DH10B and the resulting clones grown at 37° C. in 2×TY media (30 ml) containing ampicillin. After 15 hours the cells were harvested and Qiagen Tip 100 kits were used to prepare cosmid DNA. Approximately 5 μg of the cosmid DNA was digested with Sau3AI (1 U). Samples were taken at 2, 4, 6, 8 & 10 minute intervals after the enzyme was added and quenched into an equal volume of ice cold 0.5M EDTA. The samples were mixed and then analysed by gel electrophoresis, and those fragments between 1.5-2.0 kbp recovered from the gel. The fragments were cloned into linearised and dephosphorylated pHSG397 (Takeshita et al., 1987), and transformed into *E. coli* DH10B. The resulting clones that contained insert were grown in 2×TY medium (2 ml) containing chloramphenicol (30 μg/ml) and purified using Wizard kits (Promega).

DNA sequencing was carried out using an Applied Biosystems 800 Molecular Biology CATALYST robot to perform the dideoxy terminator reactions, which were then loaded into an ABI Prism 3700 automated sequencer (Applied Biosystems). The raw sequence data was processed using the Staden software package. Assembly and contig editing was performed using GAP (Genome Assembly Program) version 4.2 (Bonfield et al., 1995). The GCG package (Devereux et al., 1984) version 10.0 was used for sequence analysis.

Example 4

Chemical Analysis of *S. parvulus* Strains

The Following Method is Useful for Analysing Fermentations (see example 1) for the Production of Natural Borrelidins and of Engineered Borrelidin Analogues:

In a 2 ml Eppendorf tube, an aliquot of 5 day old fermentation broth (1 ml) was adjusted to pH~3 by the addition of 90% formic acid (ca. 20 μl). Ethyl acetate (1 ml) was added to the sample and mixed vigorously for 10 min using a vortex tray. The mixture was separated by centrifugation in a microfuge and the upper phase removed to a clean 2 ml Eppendorf tube. The ethyl acetate was removed by evaporation using a Speed-Vac. Residues were dissolved into methanol (250 μl) and clarified using a microfuge. Analysis was performed on an Agilent HP1100 HPLC system as described below:

| | |
|---|---|
| Injection volume: | 50 μl |
| Column stationary phase: | 150 × 4.6 mm column, base-deactivated reversed phase silica gel, 3 μm particle size (Hypersil $C_{18}$-BDS). |
| Mobile phase A: | 10% acetonitrile:90% water, containing 10 mM ammonium acetate and 0.1% TFA. |
| Mobile phase B: | 90% acetonitrile:10% water, containing 10 mM ammonium acetate and 0.1% TFA. |
| Mobile phase gradient: | T = 0 min, 25% B; T = 15, 100% B; T = 19, 100% B; T = 19.5, 25% B; T = 25, 25% B. |
| Flow rate: | 1 ml/min. |
| Detection: | UV at 258 nm (DAD acquisition over 190-600 nm); MS detection by electrospray ionisation over m/z range 100-1000 amu, with +/−ve ion mode switching. |

Example 5

Protoplast Transformation Protocol for *S. parvulus* Tü4055

A seed flask containing tryptone soy broth (TSB) medium (10 ml in a 100 ml Erlenmyer flask) was inoculated from a working stock (0.15 ml). After 3 days shaking on a rotary incubator (30° C., 250 rpm), 5 ml of the culture was used to inoculate R5 medium (Kieser et al., 2000) (50 ml in a 250 ml Erlenmeyer flask) that was then shaken on a rotary incubator for 24 hours (30° C., 250 rpm). The PEG mediated transformation of protoplasts was then performed according to standard published protocols (Kieser et al., 2000).

Example 6

Replacement of borAT4 with rapAT2—Production of C10-Desmethyl Borrelidin

The borrelidin PKS AT4 domain is replaced with the AT2 domain of the rapamycin polyketide synthase as follows:

CosBor32A2 is digested with EcoRI and the 5429 bp band isolated. This is used as a template for PCR using the oligos CM410 (5'-AAAATGCATTCGGCCTGAACGGC-CCCGCTGTCA-3') (SEQ ID No.44) and CM411 (5'-AAATGGCCAGCGAACACCAACACCACACCACCA-3') (SEQ ID No.45). CM410 introduces an NsiI restriction site for cloning purposes and CM411 introduces an MscI site for use in the introduction of a heterologous AT. The ~1.1 kbp product is cloned into pUC18 digested with SmaI and dephosphorylated. The insert can ligate in two orientations and the reverse orientation is screened for by restriction enzyme analysis and the insert sequenced. One correct plasmid is designated pCJM462. Methylation deficient DNA (specifically $dcm^{-1}$) of pCJM462 and pCJR26 (Rowe et al. 1998) is isolated by passaging the plasmids through *E. coli* ET12567. Each plasmid is then digested with MscI and XbaI and the ~7.8 kbp fragment from pCJR26, containing the rapamycin AT2 and sequences downstream in pCJR26, is ligated to the ~3.8 kbp backbone generated by digestion of pCJM462. Plasmid pCJM463 is identified by restriction analysis.

CosBor32A2 is digested with EcoRI and EcoRV and the 2871 bp band isolated. This is used as a template for PCR using the oligos CM412 (5'-AAAGTCCTAGGCGGCGGC-CGGCGGGTCGACCT-3') (SEQ ID No.46) and CM413 (5'-TTTAGATCTCGCGACGTCGCACGCGCCGAACGTCA-3') (SEQ ID No.47). CM412 introduces an AvrII restriction site that joins, in frame, the downstream borrelidin homology to the heterologous AT, and CM413 introduces a Bg/II site for cloning purposes. The ~1.1 kbp product is cloned into pUC18 digested with SmaI and dephosphorylated. The insert can ligate in two orientations and the reverse orientation is screened for by restriction enzyme analysis and the insert sequenced. One correct plasmid is designated pCJM464.

Plasmids pCJM463 and pCJM464 are digested with AvrII and XbaI and the ~1.1 kbp fragment from pCJM464 is ligated into the ~4.7 kbp backbone of pCJM463 to give pCJM465, which is identified by restriction enzyme analysis. pCJM465 contains the hybrid rapamycin AT2 with flanking regions of borrelidin sequence which provide homology for integration and secondary recombination.

Plasmid pCJM465 is digested with NsiI and Bg/II and the ~3 kbp fragment is cloned into pSL1180 previously digested with NsiI and BamHI to give pCJM466. Plasmid pCJM466 is then digested with NsiI and the apramycin cassette is incorporated on a PstI fragment from pEFBA (Lozano et al., 2000) to give the replacement vector pCJM467. pCJM467 is introduced into *S. parvulus* Tü4055 by protoplast transformation as described in example 5. Colonies resistant to apramycin (25 μg/ml) are initially identified, and then passaged several times through MA media without antibiotic selection in order to promote the second recombination (Fernandez et al. 1998). Several apramycin-sensitive colonies are isolated and analysed by PCR and Southern blot. The new mutant is named *S. parvulus* Tü4055/467.

*S. parvulus* Tü4055/467 is analysed as described in example 1 and shown to produce a mixture compounds with the correct UV spectrum. One of the new major components that is more polar than borrelidin has the correct retention time for 10-desmethyl borrelidin 3. LCMS analysis indicates an m/z ratio for a compound that is 14 mass units lower than borrelidin as expected, and with an appropriate mass fragmentation pattern. Borrelidin itself is also produced, but at levels lower than the WT organism.

Example 7

Mutation of the Methylmalonyl-CoA Selective Motif of borAT4 to Generate 10-desmethyl Borrelidin Site directed mutagenesis of acyl transferase domains may also be used to alter the specificity of an AT. In this example the specificity of borAT4 is directed from methyl-malonyl-CoA towards malonyl-CoA. An amino acid motif has been identified (Reeves et al., 2001; WO 02/14482) which directs the specificity of an AT. The motif YASH, as observed in borAT4, is found in methylmalonyl-CoA specific ATs and in this example it is altered to HAFH which is found in malonyl-CoA specific ATs.

CosBor32A2 is digested with NcoI and the 5167 bp band isolated. This is used as a template for PCR using the primers CM414 (5'-AAACTGCAGAGTCGAACATCGGTCA-CACGCAGGC-3') (SEQ ID No.48) and CM415 (5'-AAAAT-GCATGATCCACATCGATACGACGCGCCCGA-3') (SEQ ID No.49). CM414 introduces a PstI restriction site for cloning purposes, and CM415 is a mutagenic primer covering the motif encoding region of the AT which will effect the amino acid changes and contains an NsiI site for cloning purposes. The ~1.1 kbp fragment is cloned into pUC18 digested with SmaI and dephosphorylated. The insert can ligate in either orientation and the forward orientation is screened for by restriction enzyme analysis and the insert sequenced. One correct plasmid is designated pCJM468.

A second PCR reaction is performed using the 5167 bp NcoI fragment of CosBor32A2 and the primers CM416 (5'-TAAATGCATTCCATTCGGTGCAGGTG-GAGTTGATCC-3') (SEQ ID No.50) and CM417 (5'-ATAG-GATCCCCTCCGGGTGCTCCAGACCGGCCACCC-3') (SEQ ID No.51). CM416 introduces an NsiI restriction site and is also a mutagenic primer covering the motif encoding region of the AT, and CM417 introduces a BamHI site for cloning purposes. The ~1.1 kbp fragment is cloned into pUC18 previously digested with SmaI and dephosphorylated. The insert can ligate in two orientations and the forward orientation is screened for by restriction enzyme analysis and the insert sequenced. One correct plasmid is designated pCJM469.

Plasmids pCJM468 and pCJM469 are digested with NsiI and XbaI and the ~1.1 kbp fragment from pCJM468 is ligated into the ~3.8 kbp backbone of pCJM469 to give pCJM470, which is identified by restriction enzyme analysis. pCJM470 contains the mutated motif of borAT4 with ~1.1 kbp of homologous DNA on either side which provide homology for integration and secondary recombination.

Plasmid pCJM470 is digested with PstI and BamHI and the ~2.2 kbp fragment is cloned into pSL1180 (Amersham Biosciences) previously digested with PstI and BamHI to give pCJM471. Plasmid pCJM471 is then digested with PstI and the apramycin cassette is incorporated on a PstI fragment from pEFBA (Lozano et al., 2000) to provide the replacement vector pCJM472.

The replacement vector pCJM472 is introduced into *S. parvulus* Tü4055 by protoplast transformation as described in example 5. Colonies resistant to apramycin are initially identified, and then passaged several times through MA media without antibiotic selection in order to promote the second recombination (Fernandez et al., 1998). Several apramycin-sensitive colonies are isolated and analysed by PCR and Southern blot, and one is selected that contains the new AT4 sequence containing the mutated motif and the NsiI site. The new mutant is named *S. parvulus* Tü4055/472.

*S. parvulus* Tü4055/472 is grown and analysed as described in example 1 and shown to produce a mixture of compounds with the correct UV profile for borrelidin. One of the new major components, that is more polar than borrelidin, has the correct retention time for authentic 3. LCMS analysis indicates an m/z ratio for a compound that is 14 mass units lower than borrelidin as expected, and with an appropriate mass fragmentation pattern. Borrelidin itself is also produced, but at levels lower than the WT organism.

Example 8

Introduction of the Borrelidin Loading Module into the Erythromycin PKS

The borrelidin loading module was amplified for each of the four putative start codons. The PCR template was a 3376 bp BamHI fragment of cosBor32A2 covering the region from nucleotides 15858 to 19234 of SEQ ID No.1. The reverse primer CM368 (5'-TTTCCTGCAGGCCATCCCCAC-GATCGCGATCGGCT-3') (SEQ ID No:52) introduces a SbfI site at the sequence corresponding to the start of KS1 of borA2 (conserved MACRL motif) and is used with each of the forward primers CM369 (5'-TTTCATATGACAG-GCAGTGCTGTTTCGGCCCCATT-3') (SEQ ID No.53), CM370 (5'-TTTCATATGGCGGATGCCGTACGTGC-CGCCGGCGCT-3') (SEQ ID No.54), CM371 (5'-TTTCATATGCCCCAGGCGATCGTCCGCACCAC-3') (SEQ ID No.55) and CM372 (5'-TTTCATATGGTCTCGGC-CCCCCACACAAGAGCCCTCCGGGC-3') (SEQ ID No:56). The four PCR products (of 2834, 2720, 2411 and 2117 bp respectively) were cloned into pUC18 that had previously been digested with SmaI and dephosphorylated. The resulting plasmids were designated pCJM370, which contains the largest insert, pCJM371, pCJM372 and pCJM373, which contains the smallest insert.

The four borrelidin loading module fragments were introduced into the vector pKS1W, which contains a PstI site at the start of eryKS1 of DEBS1-TE in the conserved MACRL motif (Rowe et al., 2001); PstI gives the same overhang as SbfI. pKS1W is a pT7-based plasmid containing DEBS1-TE on an NdeI/XbaI fragment, with unique sites flanking the loading module, a unique PstI site at nucleotide position 1698 of the DEBS1-TE encoding gene and a unique NdeI site at the start codon. The borrelidin loading module fragments were excised as follows: pCJM370 was digested with NdeI and SbfI, pCJM371 and pCJM373 were digested with NdeI and PstI, and pCJM372 was digested with NdeI, PstI and DraI. Each loading module containing fragment was cloned into pKS1W previously digested with NdeI and PstI. The resulting plasmids were designated pCJM384, which contains the largest insert, then pCJM386, pCJM388 and pCJM390, which contains the smallest insert.

The hybrid PKS fragments were transferred into pCJR24, which is a suitable vector for transformation of *S. erythraea* WT and *S. erythraea* DM, and for expression of the resulting hybrid PKS (WO 98/01546). Each loading module construct was excised along with a 2346 bp fragment of DNA from DEBS1 in order to allow integration into the chromosome. In order to achieve this, pCJR24 is digested with XbaI and end-filled using Klenow fragment of DNA polymerase 1. This is then digested with NdeI to give the backbone fragment. Into this, the four hybrid PKS fragments containing the borrelidin loading modules plus the region of DEBS1 sequence for integration are cloned as NdeI/EcoRV fragments from pCJM384, pCJM386, pCJM388 and pCJM390 to give pCJM400, pCJM401, pCJM402 and pCJM403 respectively.

Plasmids pCJM400, pCJM401, pCJM402 and pCJM403 were introduced into *S. erythraea* by transformation of *S. erythraea* DM protoplasts as described elsewhere (Gaisser et al., 2000). The resulting mutants were analysed by PCR and Southern blot to confirm the presence of the plasmid on the chromosome and to establish that correct integration had occurred. A number of mutants that appeared correct by these methods were grown, extracted and analysed according to standard methods for polyketide production from *S. erythraea* strains (Wilkinson et al., 2000). When compared to control strains using LCMS methods, the extracts from several of these mutants contained new compounds at reasonable levels. Analysis of their MS spectra showed the presence of a compound with m/z=485.3 ($[M-H]^-$, 6) in negative ion mode. This is in agreement with the expected product compound (M=486.3).

Example 9

Fusion of PKS Modules 4 and 5 (*S. parvulus* Tü4055/borA4-A5)

To examine the iterative action of module 5, the two separate proteins encoding modules 4 and 5 were fused together through manipulation at the genetic level. The fusion was performed by a gene replacement in which the last ~1 kbp of borA4 and the first ~1 kbp of borA5, were fused by converting the overlapping stop and start codons respectively into an arginine residue, introducing a new XbaI site and converting the two separate orfs into one.

In the first step of the mutagenesis, two separate PCR amplifications were performed. In the first PCR reaction, the template DNA was cosBor19B9, and the primers were B1819A (5'-GTCATGCATGCGGCGGGCTC-3') (SEQ ID No.57) and B1819B (5'-GGTCTAGAACGGCCGAACTT-3') (SEQ ID No.58). The 1063 bp product was purified, digested NsiI-XbaI and cloned into pSL1180 (Amersham Biosciences) digested similarly to give plasmid pSL18-19AB. The second PCR reaction amplified the borA5 fragment and used the primers B18-19C (5'-GTTCTAGAAC-CTCGGTCGGC-3') (SEQ ID No.59) and B1819D (5'-CTGGATCCCACGCTGCTGCG-3') (SEQ ID No.60). The 1033 bp product was purified, digested with XbaI-BamHI and cloned into pSL18-19AB that had been digested similarly, to give plasmid pSL18-ABCD. Finally, the apramycin cassette from pEFBA (Lozano et al., 2000) was excised as a PstI fragment and cloned into pSL18-19ABCD digested with NsiI to give the replacement vector pSL18-19Apra.

The replacement vector pSL18-19Apra was introduced into *S. parvulus* Tü4055 by protoplast transformation as described in example 5. Colonies resistant to apramycin (25 μg/ml) were initially selected, and then passaged several times through MA media without selection. Several apramycin-sensitive colonies were obtained, two of which produced borrelidin while the others did not.

Chromosomal DNA was extracted from all of the apramycin sensitive colonies and checked initially by PCR using the primers BLDA (5'-GGAGACTTACGGGGGATGC-3') (SEQ ID No.61) and BLDB (5'-CTCCAGCAGCGACCAGAAC-3') (SEQ ID No.62) that are selective for the loading module (borA1). A 2.9 kbp fragment was observed for the control and the two borrelidin-producing mutants, but not for the non-producing strains. This result is symptomatic and characteristic of non-specific deletions in the chromosome.

The two borrelidin-producing colonies were analysed further by PCR using the primers B19A (5'-CCCATGCATCAC-CGACATAC-3') (SEQ ID No.63) and B19B (5'-GC-GATATCCCGAAGAACGCG-3') (SEQ ID No.64) in order to check the fusion site. The method was as described above. Both the colonies and the controls gave a PCR product of 1010 bp, but upon digestion with XbaI only those that carried the fusion-producing mutation gave digestion to 600 and 400 bp fragments. Only one of the borrelidin-producing colonies harboured the fusion, while the other had reverted to wild type. Final confirmation came from Southern analysis using a BamHI-XhoI internal fragment from borA5 as probe over chromosomal DNA digested with XbaI and BclI. The control and wild type revertant colony showed a fragment of 11.5 kbp as expected, while the fusion mutant showed a fragment of 7.8 kbp as expected. This new mutant was named *S. parvulus* Tü4055/borA4A5. *S. parvulus* Tü4055/borA4-A5 was shown to produce borrelidin at 26±5% of the WT titre, following the protocol described in example 1.

Example 10

Fusion of PKS Modules 5 and 6 (*S. parvulus* Tü4055/borA5-A6)

This experiment was performed for the same reason as, and in an analogous manner to, that of example 9 above. The fusion of these orfs introduced an additional leucine residue into the new protein at the fusion point, in addition to a new SpeI site at the genetic level. In the first step of the process two PCR fragments were generated using cosBor19B9 as template. The first PCR reaction amplified the borA5 region and used the primers B1920A (5'-GCCAAGCTTCCTCGACGCGC-3') (SEQ ID No.65) and B1920B (5'-CACTAGTGCCTCACCCAGTT-3') (SEQ ID No.66). The 804 bp product was purified and digested with HindIII-SpeI. The second PCR reaction amplified the borA6 region and used the primers B1920C (5'-CACTAGTGACGGCCGAAGCG-3') (SEQ ID No.67) and B1920D (5'-TCGGATCCGTCAGACCGTTC-3') (SEQ ID No.68). The 960 bp product was purified and digested with SpeI-BamHI. The two purified and digested gene products were then cloned together into pOJ260 that had been digested with HindIII-BamHI to give the replacement vector pOJF19-20. pOJF19-20 was introduced into *S. parvulus* Tü4055 by protoplast transformation to give apramycin resistant colonies. One such colony was passaged several times through MA media without selection in order to promote double recombination. Two apramycin sensitive colonies were obtained, and chromosomal DNA from these was examined by Southern hybridisation to check for the presence of a 3.2 kbp BamHI fragment (to control for unwanted deletions in the loading module) and a 3.4 kbp SpeI-BamHI fragment to verify correct introduction of the borA5-A6 fusion (5.8 kbp BamHI fragment in the WT). One of the apramycin colonies carried the correct mutation without deletion and was named *S. parvulus* Tü4055/borA5-A6. *S. parvulus* Tü4055/borA5-A6 was shown to produce borrelidin at 25±4% of the WT titre, following the protocol as described in example 1.

Example 11

Fusion of PKS Modules 4, 5 and 6 (*S. parvulus* *Tü*4055/borA4-A5-A6)

To generate the strain *S. parvulus* Tü4055/borA4-A5-A6 we took advantage of the previously obtained strain *S. parvulus* Tü4055/borA4-A5 (Example 9) and plasmid pOJF19-20 (Example 10). pOJF19-20 was introduced into *S. parvulus* Tü4055/borA4-A5 by protoplast transformation to give apramycin resistant colonies. One such colony was passaged several times through MA media without selection in order to promote double recombination. One apramycin sensitive colony was obtained, and chromosomal DNA from it was examined by Southern hybridisation to check for the presence of a 3.2 kbp BamHI fragment (to control for unwanted deletions in the loading module), a 3.4 kbp SpeI-BamHI fragment to verify correct introduction of the borA5-A6 fusion (5.8 kbp BamHI fragment in the WT) and a 6.4 kbp SpeI-XbaI to verify the presence of both fusions, borA4-A5 and borA5-A6, within the same strain. The chosen colony carried the correct mutation without deletion and was named *S. parvulus* Tü4055/borA4-A5-A6. *S. parvulus* Tü4055/borA4-A5-A6 was shown to produce borrelidin at 18±5% of the WT titre, following the protocol as described in example 1.

Example 12

Replacement of the Erythromycin PKS Module 4 with Module 5 of the Borrelidin PKS—Production of Ring Expanded Macrolides Example 12 describes the replacement of erythromycin module 4 with borrelidin module 5. Borrelidin module 5 is believed to be responsible for three rounds of condensation of methylmalonyl-CoA, in an iterative fashion, within the borrelidin PKS. Previously, erythromycin module 4 has been shown to occasionally act in an iterative fashion 'mis'-incorporating a second methylmalonyl-CoA to make very small amounts of a 16-membered macrolide from the erythromycin PKS. A strain in which the erythromycin module 4 is replaced by borrelidin module 5 is engineered by a replacement strategy as follows, and is based on a derivative process as described for module insertion into the erythromycin PKS (Rowe et al., 2001): Initially a series of plasmids are made in order to generate a plasmid in which the borrelidin module 5 is flanked by appropriate regions of homology from the erythromycin PKS. In order to facilitate this, the SbfI site is first removed from the polylinker of pUC18 by digestion with PstI, end-polishing with T4 polymerase and religation. The new plasmid, pCJM409 is identified by restriction enzyme digestion. Borrelidin module 5 is isolated on an SbfI fragment by ligating together 4 PCR fragments. PCRA is generated by amplification of ~1.4 kb of the beginning of borrelidin module 5 using the 6062 bp XcmI fragment of cosBor19B9 as the template and primers CM384 (5'-AACCTGCAGGTACCCCGGTGGGGTGCGGTCGCCCGA-3') (SEQ ID No.69) and CM385 (5'-CGCCGCACGCGTCGAAGCCAACGA-3') (SEQ ID No.70). CM384 introduces an SbfI site in the conserved amino acid sequence MxCR at the beginning of borrelidin module 5. CM385 incorporates a naturally occurring MluI site that is used in the cloning strategy. PCRA is treated with T4 polynucleotide kinase (T4 PNK, NEB) and cloned into pCJM409 previously digested with SmaI and dephosphorylated with Shrimp Alkaline Phosphatase (SAP, Roche). Inserts cloned in the forward direction are screened for by restriction enzyme digestion, and for one correct clone the insert is verified by sequencing. This plasmid is designated pCJM410.

PCRB is generated by amplification of the adjacent ~1.4 kb of borrelidin module 5 using the 6062 bp XcmI fragment of cosBor19B9 as the template and primers CM386 (5'-TGTGGGCTGGTCGTTGGCTTCGAC-3') (SEQ ID No.71) and CM387 (5'-GGTGCCTGCAGCGTGAGTTCCTCGACGGATCCGA-3') (SEQ ID No.72). CM386 binds upstream of the same MluI site as CM385 contains, which is used in the cloning strategy. CM387 is used to remove the SbfI site within the borrelidin PKS module 5 whilst leaving the overlapping PstI site for cloning. PCRB is treated with T4 PNK and cloned into pCJM409 previously digested with SmaI and dephosphorylated with SAP. Inserts cloned in the forward direction are screened for by restriction enzyme digestion, and for one correct clone the insert is verified by sequencing. This plasmid is designated pCJM411.

PCRC is generated by amplification of the downstream adjacent ~1.5 kb of borrelidin module 5 using the 6062 bp XcmI fragment of cosBor19B9 as the template and oligonucleotides CM388 (5'-GAGGAACTCACCCTGCAGGCACCGCT-3') (SEQ ID No.73) and CM395 (5'-CGAACGTCCAGCCCTCGGGCATGCGT-3') (SEQ ID No.74). CM388 binds at the same SbfI site as CM387, but is not mutagenic and retains the SbfI site. CM395 incorporates an SphI site for cloning purposes. PCRC is treated with T4

PNK and cloned into pCJM409 previously digested with SmaI and dephosphorylated with SAP. Inserts cloned in the forward direction are screened for by restriction enzyme digestion and for one correct clone the insert is verified by sequencing. This plasmid is designated pCJM412.

PCRD is generated by amplification of the downstream adjacent ~2.1 kb of borrelidin module 5 using the 7211 bp BbvCI fragment of cosBor19B9 as the template and primers CM396 (5'-TGGCACGCATGCCCGAGGGCTGGACGTT-3') (SEQ ID No.75) and CM397 (5'-TTTCCTGCAGGCCATGCCGACGATCGCGACAGGCT-3') (SEQ ID No.76). CM396 contains the SphI site for cloning purposes, and CM397 Introduces an SbfI site in the conserved amino acid sequence MXCR at the end of borrelidin module 5. PCRD is treated with T4 PNK and cloned into pCJM409 previously digested with SmaI and dephosphorylated with SAP. Inserts cloned in the forward direction are screened for by restriction enzyme digestion, and for one correct clone the insert is verified by sequencing, this plasmid is designated pCJM413.

The four PCR products (PCRA-D) are used to construct the borrelidin module 5 on an SbfI fragment as follows:

pCJM412 is digested with SphI and the ~1.5 kb fragment isolated is cloned into pCJM413 previously digested with SphI and dephosphorylated with SAP. This gives plasmid pCJM414, which is identified by restriction enzyme digestion.

pCJM414 is digested with SbfI and the ~3.6 kb fragment isolated is cloned into pCJM411 previously digested with PstI and dephosphorylated with SAP. This gives pCJM415 which is identified by restriction enzyme digestion.

pCJM410 is digested with MluI and HindIII and the ~1.4 kb fragment isolated is cloned into pCJM415 previously digested with MluI and HindIII. This gives pCJM416, which is identified by restriction enzyme digestion. pCJM416 is a pUC18-based plasmid containing the borrelidin module 5 as an SbfI fragment.

In order to introduce the Borrelidin module 5 into the erythromycin PKS by a replacement strategy, flanking regions of homology from the erythromycin PKS are incorporated for recombination as follows:

PCRE is generated by amplification of ~3.3 kb of the erythromycin PKS directly upstream of the module 4 KS using the 6428 bp XmnI fragment of pIB023 as the template and primers CM398 (5'-AAACATATGGTCCTGGCGCTGCGCAACGGGGAACTG-3') (SEQ ID No.77) and CM399 (5'-TTTCCTGCAGGCGATGCCGACGATGGCGATGGGCT-3') (SEQ ID No.78). CM398 contains an NdeI site for cloning purposes and CM399 introduces an SbfI site in the conserved amino acid sequence M/lxCR at the beginning of erythromycin module 4. PCRE is treated with T4 PNK and cloned into pCJM409 previously digested with SmaI and dephosphorylated with SAP. Inserts cloned in the forward direction are screened for by restriction enzyme digestion, and for one correct clone the insert is verified by sequencing, this plasmid is designated pCJM417.

PCRF is generated by amplification of ~3.4 kb of the erythromycin PKS directly downstream of the module 5 KS using the 7875 bp XmnI/NheI fragment of pIB023 as the template and primers CM400 (5'-AAACCTGCAGGTTCCCCGGCGACGTGGACTCGCCGGAGTCGTT-3') (SEQ ID No.79) and CM401 (5'-TTTTCTAGAGCGACGTCGCAGGCGGCGATGGTCACGCCCGT-3') (SEQ ID No.80). CM400 introduces an SbfI site in the conserved amino acid sequence M/lxCR at the beginning of erythromycin module 4, and primer CM401contains an XbaI site for cloning purposes. PCRF is treated with T4 PNK and cloned into pCJM409 previously digested with SmaI and dephosphorylated with SAP. Inserts cloned in the forward direction are screened for by restriction enzyme digestion, and for one correct clone the insert is verified by sequencing. This plasmid is designated pCJM418.

pCJM417 is digested with NdeI and SbfI and the ~3.3 kb fragment is cloned into pCJM418 digested with NdeI and SbfI (~5.8 kbp) to give pCJM419 which is identified by its restriction digest pattern. pCJM419 contains a unique SbfI site which can be used to accept any complete module with SbfI (or PstI) flanking sites appropriate to place, in-frame, the in-coming module exactly into the conserved region of the KS domain.

The borrelidin module 5 with flanking SbfI sites is cloned from pCJM416 as an SbfI fragment into the unique SbfI site of pCJM419 (which has been dephosphorylated with SAP) to give pCJM420, which is identified by restriction enzyme analysis to confirm the presence and correct orientation of the insert. pCJM420 thus contains borrelidin module 5 with flanking regions of homology to introduce it in-frame between modules 3 and 5 of the erythromycin PKS. The complete insert is removed as an NdeI/XbaI fragment from pCJM420 and cloned into pCJM24 digested with NdeI and XbaI to give the final plasmid pCJM421. pCJR24, and consequently pCJM421, contain an appropriate resistance marker for selection of *S. erythraea* transformants.

Plasmid pCJM421 is used to transform *S. erythraea* strains NRRL2338 (wild type), and *S. erythraea* DM (eryCIII$^-$, eryBV$^-$) protoplasts (Yamamoto et al., 1986; Rowe et al., 1998). Integrants are selected for resistance to thiostrepton (50 mg/L) and a number of integrants (typically 5-8) are analysed further by Southern blot to confirm that the strains are correct and to identify the site of integration. Two correct integrants in each case are sub-cultured in TSB liquid media without antibiotic selection in order to promote the second recombination. Several thiostrepton-sensitive colonies are isolated and analysed by PCR and Southern blot, and in each case one selected that contains the new module correctly inserted. This leads to strains *S. erythraea* WT/421 and *S. erythraea* DM/421.

Strain *S. erythraea* DM/421 is cultured under conditions appropriate for the production of erythronolides (Wilkinson et al., 2000). Analysis of fermentation broth extracts using LCMS methods indicates the presence of two new significant peaks when compared to the control strain, and which are less polar than erythronolide B. These have an m/z of 435.5 ($MNa^+$) and 477.5 ($MNa^+$) respectively, which is consistent with the production of new ring expanded erythronolide B analogues. The compound with m/z=435.5 (7) is consistent with the presence of the 16-membered ring-expanded erythronolide B related macrolide reported previously as a minor component of *S. erythraea* WT fermentations (Wilkinson et al., 2000); the compound with m/z=477.5 (8) is consistent with the presence of an 18-membered, doubly ring-expanded erythronolide B related macrolide (see FIG. 8). It is clear to one skilled in the art that such new products can be converted to antibacterial molecules by biotransformation with an appropriate organism, or through the fermentation of the strain *S. erythraea* WT/421. It is further clear to one skilled in the art that the inclusion of such a module into other positions of the erythromycin PKS or into other PKSs may allow the production of novel, ring expanded polyketides in a similar manner.

An alternative strategy for generating this hybrid PKS is to incorporate the borrelidin module 5 in place of erythromycin module 4 within a large plasmid that contains the entire hybrid PKS, followed by transformation of an eryA$^-$ *S. erythraea* strain. Such an appropriate existing eryA$^-$ is *S. erythraea*

JC2 (Rowe et al., 1998) and the plasmid containing the eryA genes under the actI promoter, pIB023 that also contains a thiostrepton resistance gene and the actII-ORF4 activator. This strategy is accomplished as follows:

pIB023 is digested with NdeI and BsmI and the 13.4 kbp fragment is cloned into pCJM419 digested with NdeI and BsmI to give plasmid pCJM425. pIB023 is digested with BbvCI and XbaI and the approx. 6 kbp fragment is cloned into pCJM425 digested with BbvCI and XbaI to give plasmid pCJM426. The NdeI/XbaI fragment from pCJM426 is cloned into pCJM395 digested with NdeI and XbaI. pCJM395 is a plasmid made by digesting pCJR24 with SbfI, end-polishing with T4 polymerase and religating, to give a version of pCJR24 that does not cut with SbfI. The resulting plasmid, pCJM427, contains an engineered version of the erythromycin PKS in which module 4 is removed. This backbone is then ready to accept any complete module with appropriate flanking sites (SbfI or PstI) to generate a hybrid PKS. Introduction of the single borrelidin module 5 is accomplished by digesting pCJM427 with SbfI, dephosphorylating the backbone with SAP, and ligating in the SbfI fragment from pCJM416, to give pCJM430.

Plasmid pCJM430 is used to transform *S. erythraea* JC2. Integrants are selected for resistance to thiostrepton (50 mg/L) and a number of integrants (typically 5-8) are analysed further by Southern blot to confirm that the strains are correct and to identify the site of integration. The resulting correct strain *S. erythraea* JC2/430 is cultured under conditions appropriate for the production of erythromycins (Wilkinson et al., 2000) and analysed for the production of novel compounds 7 & 8.

Example 13

Disruption of borB (*S. parvulus* Tü4055/borB::aac3(IV))

In order to disrupt borB, an region of 2751 bp containing borB was amplified by PCR using primers B5B (5-'AACTAGTCCGCAGTGGACCG-3') (SEQ ID No.91) and B5A (5'-TCGATATCCTCACCGCCCGT-3') (SEQ ID No.92) and cosmid Bor32A2 as template. The PCR product was purified and then digested at the flanking sites SpeI-EcoRV and subcloned into pSL1180 digested with the same restriction enzymes to generate pSLB. A SpeI-AgeI fragment (the latter site internal to the insert) from pSLB containing the 5'-end of borB was subcloned into the SpeI-XmaI sites of pEFBA, upstream of the apramycin resistance gene aac(3)IV, to produce pEB1. A BsaAI-EcoRV fragment (the former site internal to the insert) from pSLB containing the 3'-end of borB was then subcloned in the correct orientation into the ECORV site of pEB1 downstream of aac(3)IV, to generate pEB2. In this way a 741 bp AgeI-BsaAI fragment internal to borB was deleted and replaced by aac(3)/V. Finally, the SpeI-EcoRV fragment was rescued from pEB2 and subcloned, together with a PstI-SpeI fragment containing the hyg gene from pLHyg, into the PstI-EcoRV sites of pSL1180 to generate pSLBr1. This approach was used in order to avoid possible polar effects.

The vector pSLBr1 was introduced into *S. parvulus* Tü4055 by protoplast transformation as described in example 5. Colonies resistant to apramycin were selected, and then passaged several times through MA media without selection. The replacement was verified by Southern hybridisation and the new mutant was named *S. parvulus* Tü4055/borB::aac3 (IV). Strain *S. parvulus* Tü4055/borB::aac3(IV) was grown, extracted and analysed as described in example 1. Borrelidin production was observed and compared to a wild type control. In addition *S. parvulus* Tü4055/borB::aac3(IV) was chemically complemented with trans-1,2-dicyclopentane dicarboxylic acid, following the protocol described in example 1.

Example 14

Disruption of borC (*S. parvulus* Tü4055/borC::aac3(IV))

In order to disrupt borC, an region of 3553 bp containing borC was amplified by PCR using primers B6B (5'-AACTAGTGTGGCAGACGGTC-3') (SEQ ID No.93) and B5A (5'-TCGATATCCTCACCGCCCGT-3') (SEQ ID No.94) and cosmid Bor32A2 as template. The PCR product was purified and then digested with SpeI-EcoRV and subcloned into the same restriction sites of pSL 180 to produce pSLC. The SpeI-SphI and BalI-EcoRV fragments from this plasmid pSLC, containing the 5'-end and the 3'-end of borC respectively, were then cloned stepwise into the SpeI-SphI and EcoRV sites of pEFBA and in the correct orientations. In this way a 302 bp SphI-BalI internal fragment of borC was replaced by the aac(3)IV gene. The resulting plasmid was then digested with SpeI and EcoRV and the resulting fragment was subcloned together with the hyg gene as described above, into pSL1180 leading to the final construct pSLCr1. This approach was used in order to avoid possible polar effects.

The vector pSLCr1 was introduced into *S. parvulus* Tü4055 by protoplast transformation as described in example 5. Colonies resistant to apramycin were selected, and then passaged several times through MA media without selection. The replacement was verified by Southern hybridisation and the new mutant was named *S. parvulus* Tü4055/borC::aac3 (IV). Strain *S. parvulus* Tü4055/borC::aac3(IV) was grown, extracted and analysed as described in example 1. Borrelidin production was compared to a wild type control. In addition, *S. parvulus* Tü4055/borC::aac3(IV) was chemically complemented with trans-1,2-dicyclopentane dicarboxylic acid, following the protocol described in example 1.

To verify that no polar effects were introduced a full-length copy of borC under the control of the ermE* promoter was introduced in trans to the disrupted mutant. Full-length bor C was amplified by PCR using the primers B6T1 (5'-CGGATGCATCACCGGCACGG-3') (SEQ ID No.95) and B6T2 (5'-TGGGATCCGCGGGGCGGTAC-3') (SEQ ID No.96) using cosmid Bor32A2 as template. The 943 bp product was purified and then digested with NsiI-BamHI and subcloned, together with a BamHI-SpeI fragment from pLHyg (carrying the hyg gene), into pIJ2925 previously digested with PstI-XbaI. A Bg/II fragment (using this site from the vector) was then isolated and subcloned into pEM4, and in the correct orientation to locate borC under the control of the promoter ermE*. Plasmid pborCH and the control plasmid pEM4 were introduced into *S. parvulus* Tü4055/borC::aac(3)IV by protoplast transformation as described in example 5. The resulting strain *S. parvulus* Tü4055/borC::aac(3)IV/pborCH was analysed as described in example 1 and shown to produce borrelidin at a titre similar to a WT control.

Example 15

Disruption of borD (*S. parvulus* Tü4055/borD::aac3(IV))

In order to disrupt borD, a fragment of 2777 bp was amplified by PCR using the primers BBB (5'-AACTAGTGC- GATCCCGGGGA-3') (SEQ ID No.97) and BBA (5'-CGTCGATATCCTCCAGGGGC-3') (SEQ ID No.98) and cosmid Bor32A2 as template. The PCR product was purified and then digested with SpeI-EcoRV and subcloned into pSL1180 to generate pSLD. This was then digested with NdeI-StuI to delete an internal 679 bp region of borD which was replaced by a SmaI-NdeI fragment isolated from pEFBA containing the aac(3)IV gene. The resulting construct was digested with SpeI-EcoRV and the 4.3 kb fragment subcloned together with a SpeI-PstI fragment from pLHyg containing the hyg gene, into pSL1180 digested with PstI-EcoRV. This step leads to the final plasmid pSLDr1. This approach was used in order to avoid possible polar effects.

The vector pSLDr1 was introduced into *S. parvulus* Tü4055 by protoplast transformation as described in example 5. Colonies resistant to apramycin were selected, and then passaged several times through MA media without selection. The replacement was verified by Southern hybridisation and the new mutant was named *S. parvulus* Tü4055/borD::aac3(IV). Strain *S. parvulus* Tü4055/borD::aac3(IV) was grown, extracted and analysed as described in example 1. Borrelidin production was compared to a wild type control. In addition, *S. parvulus* Tü4055/borD::aac3(IV) was chemically complemented with trans-1,2-dicyclopentane dicarboxylic acid, following the protocol described in example 1.

To verify that no polar effects were introduced a full-length copy of borD under the control of the ermE* promoter was introduced in trans to the disrupted mutant. Full-length borD was amplified by PCR using the primers BBT1 (5'-TACTGCAGCACACCCGGTGC-3') (SEQ ID No.99) and BBT2 (5'-TGGGATCCGCTGTGTCATAT-3') (SEQ ID No.100) using cosmid Bor32A2 as template. The 816 bp PCR product was purified and then digested with PstI-BamHI and subcloned together with a BamHI-SpeI fragment containing the hyg gene from pLHyg, into pIJ2925 digested with PstI-XbaI, to give pIJDH. The Bg/II fragment from pIJDH (using these sites from the vector) was then subcloned into pEM4 (predigested with BamHI) and in the correct orientation to generate pborDH. Plasmid pborDH and the control plasmid pEM4 were introduced into *S. parvulus* Tü4055/borD::aac(3)IV by protoplast transformation as described in example 5. The resulting strain *S. parvulus* Tü4055/borD::aac(3)IV/pborDH was analysed as described in example 1 and shown to produce borrelidin at a titre similar to a WT control.

Example 16

Disruption of borE (*S. parvulus* Tü4055/borE::aac3(IV))

In order to disrupt borE, an internal 761 bp fragment of the gene was amplified by PCR using primers B25A (5'-TTCTGCAGCCGCGGCCTTCG-3') (SEQ ID No.81) and B25B (5'-AGAATTCGCCGGCGCCGCTG-3') (SEQ ID No.82) using cosBor32A2 as template. The product was purified, digested PstI-EcoRI and cloned into pOJ260ermE* which had been digested similarly, to provide pOJEd1. This approach was used in order to avoid possible polar effects. The vector pOJEd1 was introduced into *S. parvulus* Tü4055 by protoplast transformation as described in example 5, and colonies were selected for apramycin resistance on R5 and then on MA agar. The disruption was verified by Southern hybridisation and the new mutant was named *S. parvulus* Tü4055/borE::aac3(IV). Strain *S. parvulus* Tü4055/borE::aac3(IV) was grown, extracted and analysed as described in example 1. No borrelidin production was observed whereas a wild type control produced borrelidin as expected.

To verify that no polar effects were introduced a full-length copy of borE under the control of the ermE* promoter was introduced in trans to the disrupted mutant. Full-length borE was amplified by PCR using the primers B7T1 (5'-GGCTGCAGACGCGGCTGAAG-3') (SEQ ID No.83) and B7T2 (5'-CCGGATCCCAGAGCCACGTC-3') (SEQ ID No.84) using cosBor32A2 as template. The 1216 bp product was purified, digested with PstI-BamHI and cloned into PstI-XbaI digested pIJ2925 (Janssen & Bibb, 1993), along with a BamHI-SpeI digested fragment from pLHyg containing the hygromycin resistance cassette, to generate pIJEH. A 2.8 kbp BamHI fragment was excised from pIJEH and cloned into pEM4 (Quiros et al., 1998), which had been digested similarly, to give pborEH (in which the bore gene was cloned in the correct orientation for gene expression). pborEH and the control plasmid pEM4 were introduced into *S. parvulus* Tü4055/borE::aac(3)IV by protoplast transformation as described in example 5. The resulting strain *S. parvulus* Tü4055/borE::aac(3)IV/pborEH was analysed as described in example 1 and shown to produce borrelidin at a titre similar to a WT control; the control strain *S. parvulus* Tü4055/borE::aac(3)IV/pEM4 did not produce borrelidin.

Chemical complementation of *S. parvulus* Tü4055/borE::aac3(IV) with trans-1,2-dicyclopentane dicarboxylic acid, following the protocol described in example 1, demonstrated that the strain thus grown was capable of borrelidin production at 122±23% of the WT parent control. Thus, bore is required for biosynthesis of trans-cyclopentane-1,2-dicarboxylic acid.

Example 17

Disruption of borF (*S. parvulus* Tü4055/borF::aac3(IV))

In order to disrupt borF, a region containing borF was amplified by PCR using the primers BCB (5'-CACTAGTCCTCGCCGGGCAC-3') (SEQ ID No.101) and BCA (5'-GAGGATCCCGGTCAGCGGCA-3') (SEQ ID No.102) and cosmid Bor32A2 as template. The resulting 2132 bp product was purified and then digested with SpeI-BamHI and subcloned into the same sites of pSL1180 leading to pSLF. The aac(3)IV gene from pEFBA was then subcloned as a SphI fragment into the SphI site of pSLF, which is located inside the borF coding region. Finally the BamHI-SpeI fragment was subcloned into pLHyg digested with BamHI-NheI to generate pLHFr1.

The vector pLHFr1 was introduced into *S. parvulus* T4055 by protoplast transformation as described in example 5. Colonies resistant to apramycin were selected, and then passaged several times through MA media without selection. The replacement was verified by Southern hybridisation and the new mutant was named *S. parvulus* Tü4055/borF::aac3(IV). Strain *S. parvulus* Tü4055/borF::aac3(IV) was grown, extracted and analysed as described in example 1. Borrelidin production was compared to a wild type control. In addition, *S. parvulus* Tü4055/borF::aac3(IV) was chemically complemented with trans-1,2-dicyclopentane dicarboxylic acid, following the protocol described in example 1.

To verify that no polar effects were introduced a full-length copy of borF under the control of the ermE* promoter was introduced in trans to the disrupted mutant. Full-length borF was amplified by PCR using the primers BCT1 (5'-GCCTGCAGCGACCTCGCCGG-3') (SEQ ID No.103) and BCT2 (5'-CGGGATCCCGTGGCGTGGTC-3') (SEQ ID No.104) using cosmid Bor32A2 as template. The 1048 bp PCR product was purified and then digested with PstI-BamHI and subcloned together with the hyg gene as described above, into pIJ2925. A Bg/II fragment was then isolated and subcloned into pEM4 to generate pborFH. This was used to complement strain SPMF. Plasmid pborFH and the control plasmid pEM4 were introduced into *S. parvulus* Tü4055/borF::aac(3)IV by protoplast transformation as described in example 5. The resulting strain *S. parvulus* Tü4055/borF::aac(3)IV/pborFH was analysed as described in example 1 and shown to produce borrelidin at a titre similar to a WT control.

Example 18

Disruption of borG (*S. parvulus* Tü4055/borG::aac3(IV))

In order to disrupt borG, an internal region of 885 bp was amplified by PCR using the primers B23A (5'-ATCTGCAGCGGCATCGGTGT-3) (SEQ ID No.105) and B23B (5'-AGAATTCTCCACTGCGGTCG-3') (SEQ ID No.106) and cosmid Bor32A2 as template. The resulting product was purified and the digested at the flanking sites PstI-EcoRI and then subcloned into pOJ260P, downstream of the promoter ermE*, to generate pOJGd1.

The vector pOJGd1 was introduced into *S. parvulus* Tü4055 by protoplast transformation as described in example 5. Colonies resistant to apramycin were selected on MA agar. The disruption was verified by Southern hybridisation and the new mutant was named *S. parvulus* Tü4055/borG::aac3(IV). Strain *S. parvulus* Tü4055/borG::aac3(IV) was grown, extracted and analysed as described in example 1. Borrelidin production was compared to a wild type control. In addition, *S. parvulus* Tü4055/borG::aac3(IV) was chemically complemented with trans-1,2-dicyclopentane dicarboxylic acid, following the protocol described in example 1.

Example 19

Disruption of borH (*S. parvulus* Tü4055/borH::aac3(IV))

In order to disrupt bor H, and internal region of 697 bp was amplified by PCR using the primers B9A (5'-ACCTGCAGGCCGGGCTCATC-3') (SEQ ID No.107) and B9B (5'-AGAATTCGGGCGAGCCGCCG-3') (SEQ ID No.108) and cosmid Bor32A2 as template. The resulting PCR product was purified and then digested with PstI-EcoRI and then subcloned into pOJ260P, downstream of the promoter ermE*, to generate pOJHd2.

The vector pOJHd2 was introduced into *S. parvulus* Tü4055 by protoplast transformation as described in example 5. Colonies resistant to apramycin were selected on MA agar. The disruption was verified by Southern hybridisation and the new mutant was named *S. parvulus* Tü4055/borH::aac3(IV). Strain *S. parvulus* Tü4055/borH::aac3(IV) was grown, extracted and analysed as described in example 1. Borrelidin production was compared to a wild type control. In addition, S. parvulus Tü4055/borH::aac3(IV) was chemically complemented with trans-1,2-dicyclopentane dicarboxylic acid, following the protocol described in example 1.

Example 20

Disruption of borI (*S. parvulus* Tü4055/borI::aac3(IV))

The gene borI and surrounding DNA was amplified from cosBor19B9 using the PCR primers BP4501 (5'-CGTATGCATGGCGCCATGGA-3') (SEQ ID No.85) and BP4502 (5'-AGCCAATTGGTGCACTCCAG-3') (SEQ ID No.86). The 2.32 kbp product was purified, digested with NsiI-MfeI and cloned into pSL1180 digested NsiI-EcoRI, to give plasmid pSLI. The apramycin resistance cassette was excised from pEFBA as an EcoRI fragment and cloned into pSLI digested with EcoRI, to give the plasmid pSLIA. Finally, the hygromycin resistance cassette was excised SpeI-PstI from pLHyg and cloned into pSLIA which had been digested with NsiI-SpeI to give plasmid pSLIr1.

The replacement vector pSLIr1 was introduced into *S. parvulus* Tü4055 by protoplast transformation as described in example 5. Colonies resistant to apramycin (25 μg/ml) were selected, and then passaged several times through MA media without selection. The replacement was verified by Southern hybridisation and the new mutant was named *S. parvulus* Tü4055/borI::aac3(IV).

*S. parvulus* Tü4055/borI::aac3(IV) was grown and analysed as described in example 1. No borrelidin production was observed whereas several new compounds were observed at significantly lower levels. One of the less polar compounds displayed a UV absorbance maximum of 240 nm, and LCMS analysis indicated an m/z ratio 11 mass units lower than that for borrelidin, which is consistent with the presence of a methyl- rather than a nitrile-group at C12.

To verify that no polar effects were introduced a full-length copy of borI under the control of the ermE* promoter was introduced in trans to the disrupted mutant. A 2.1 kb NsiI-AvrII fragment containing borI was recovered from pSLI and subcloned into the PstI-XbaI sites of pEM4, together with the NheI-SpeI fragment from pLHyg containing the hyg gene. Both fragments were subcloned in the same orientation generating pborIH. Plasmid pborIH and the control plasmid pEM4 were introduced into *S. parvulus* Tü4055/borI::aac(3)IV by protoplast transformation as described in example 5. The resulting strain *S. parvulus* Tü4055/borI::aac(3)/V/pborIH was analysed as described in examples 1 & 4, and shown to produce borrelidin at a titre similar to a WT control.

Example 21

Disruption of borJ (*S. parvulus* Tü4055/borJ::aac3(IV))

The gene borJ and surrounding DNA was amplified from cosBor19B9 using the PCR primers BNHT1 (5'-GTCATGCATCAGCGCACCCG-3') (SEQ ID No.87) and BNHT2 (5'-GTGCAATTGCCCTGGTAGTC-3') (SEQ ID No.88). The 2.75 kbp product was purified, digested with NsiI-MfeI and cloned into pSL1180 that had been digested with NsiI-EcoRI, to give plasmid pSL. The hygromycin resistance cassette was excised from pLHyg as a PstI-SpeI fragment and cloned into pSL digested with NsiI-SpeI, to give pSLJH. Finally, the apramycin resistance cassette was excised from pEFBA with SpeI-BamHI and cloned into pSLJH that had been pre-digested with AvrII-Bg/II in order to remove a 453 bp fragment from borJ, to give plasmid pSLJr1.

The replacement vector pSLJr1 was introduced into *S. parvulus* Tü4055 by protoplast transformation as described in example 5. Colonies resistant to apramycin (25 □g/ml) were selected, and then passaged several times through MA media without selection. The replacement was verified by Southern hybridisation. The new mutant was named *S. parvulus* Tü4055/borJ::aac3(IV).

*S. parvulus* Tü4055/borJ::aac3(IV) was grown and analysed as described in example 1. No borrelidin production was observed whereas a new compound more polar than borrelidin was observed with a UV maximum at 262 nm. LCMS analysis indicated a parent compound of 508 amu, which is consistent with a carboxylic acid rather than a nitrile function at C12.

To verify that no polar effects were introduced a full-length copy of borJ under the control of the ermE* promoter was introduced in trans to the disrupted mutant. A 2.4 kb NsiI-SphI fragment from pSLJ containing borJ was subcloned into the PstI-XbaI sites of pEM4, together with the hyg gene as a SphI-SpeI fragment from pLHyg; both fragments were subcloned in the same orientation as the transcription of the genes. The final construct was designed pborJH. Plasmid pborJH and the control plasmid pEM4 were introduced into *S. parvulus* Tü4055/borJ::aac(3)IV by protoplast transformation as described in example 5. The resulting strain *S. parvulus* Tü4055/borJ::aac(3)IV/pborJH was analysed as described in examples 1 & 4, and shown to produce borrelidin at a titre similar to a WT control.

Example 22

Disruption of borK (*S. parvulus* Tü4055/borK::aac3(IV))

In order to disrupt borK, a fragment of 2680 bp was amplified by PCR using the primers B231 (5'-ATCAAGCTTCGTGTCCATGG-3') (SEQ ID No.109) and B232 (5'-GTCATGCATCAGGCGTTCGG-3') (SEQ ID No.110) and cosmid Bor19B9 as template. The resulting PCR product was purified and then digested with HindIII-NsiI and subcloned into the same sites of pSL1180 to produce pSLK. After MluI digestion of pSLK and treatment with the Klenow fragment, the aac(3)IV gene from pEFBA was subcloned as a SmaI-EcoRV fragment leading to pSLKa. Finally a PstI-SpeI fragment from pLHyg containing the hyg gene was subcloned into pSLKa digested NslI-XbaI to obtain pSLKr1.

The vector pSLKr1 was introduced into *S. parvulus* Tü4055 by protoplast transformation as described in example 5. Colonies resistant to apramycin were selected, and then passaged several times through MA media without selection. The replacement was verified by Southern hybridisation and the new mutant was named *S. parvulus* Tü4055/borK::aac3 (IV). Strain *S. parvulus* Tü4055/borK::aac3(IV) was grown, extracted and analysed as described in example 1. Borrelidin production was compared to a wild type control. In addition, *S. parvulus* Tü4055/borK::aac3(IV) was chemically complemented with trans-1,2-dicyclopentane dicarboxylic acid, following the protocol described in example 1.

To verify that no polar effects were introduced a full-length copy of borK under the control of the ermE* promoter was introduced in trans to the disrupted mutant. A 2.2 kb Bg/II (blunt-ended)-NslI fragment from pSLK was subcloned, together with a 1.6 kb PstI-SpeI fragment from pLHyg containing the hyg gene, into pEM4 digested with PstI (treated with the Klenow fragment) and then XbaI. The final vector was named pborKH. Plasmid pborKH and the control plasmid pEM4 were introduced into *S. parvulus* Tü4055/borK::aac(3)IV by protoplast transformation as described in example 5. The resulting strain *S. parvulus* Tü4055/borK::aac(3)IV/pborKH was analysed as described in examples 1 & 4, and shown to produce borrelidin at a titre similar to a WT control.

Example 23

Disruption of borL (*S. Parvulus* Tü4055/borL::aac3(IV))

In order to disrupt borL a 3.95 kbp Bg/II fragment of cosBor19B9, which contained the full-length borL, was subcloned into pSL1180 digested similarly. The resulting clones were analysed by restriction digest and one that displayed the correct orientation was chosen to provide pSL395. Digestion of pSL395 with NheI and SpeI, and subsequent re-ligation to eliminate a fragment of borM that included a Bg/II site, gave pSLL. The apramycin resistance cassette was excised with KpnI from pEFBA (Lozano et al., 2000) and cloned into pSL that had been digested with KpnI, to give pSLLA. pSLLA was digested with Bg/II and then subjected to Klenow treatment following the manufacturers instructions (Roche); an EcoRV fragment isolated from pLHyg containing the hygromycin resistance cassette was then cloned into this prepared vector to give pSLLr1.

The replacement vector pSLLr1 was introduced into *S. parvulus* Tü4055 by protoplast transformation. Colonies resistant to apramycin were selected, and then passaged several times through MA media without selection. The replacement was verified by Southern hybridisation. The new mutant was named *S. parvulus* Tü4055/borL::aac3(IV).

Strain *S. parvulus* Tü4055/borL::aac3(IV) was grown, extracted and analysed as described in example 1. No borrelidin production was observed whereas a wild type control produced borrelidin as expected. Chemical complementation of *S. parvulus* Tü4055/borL::aac(IV) using the natural starter acid as described in example 1 showed that the strain thus grown was capable of borrelidin production at 408±70% of the WT parent control titre.

To verify that no polar effects were introduced a full-length copy of borL under the control of the ermE* promoter was introduced in trans to the disrupted mutant. The vector containing full-length borL was generated as described in example 30. Plasmid pborLH and the control plasmid pEM4 were introduced into *S. parvulus* Tü4055/borL::aac(3)IV by protoplast transformation as described in example 5. The resulting strain *S. parvulus* Tü4055/borL::aac(3)IV/pborLH was analysed as described in example 1.

Example 24

Disruption of borM (*S. parvulus* Tü4055/borM::aac3(IV))

In order to disrupt borM, a 2870 bp fragment containing borM was amplified by PCR using the primers B251 (5'-CTTCTAGATGAACCCCTCCA-3') (SEQ ID No.111) and B252 (5'-GGGCAATTGCGCGGCAGCTT-3') (SEQ ID No.112) and cosmid Bor19B9 as template. The resulting product was purified and then digested with XbaI-MfeI and subcloned into the XbaI-EcoRI sites of pSL1180, leading to pSLM. An internal 780 bp SphI-NheI fragment of borM was then replaced by the aac(3)IV gene which was subcloned from pEFBA as a SpeI-XbaI fragment, leading to pSLMA. pSLMA was digested with NsiI-XbaI and the hyg gene subcloned as a SpeI fragment from pLHyg to generate pSLMr1.

The vector pSLMr1 was introduced into *S. parvulus* Tü4055 by protoplast transformation as described in example 5. Colonies resistant to apramycin were selected, and then passaged several times through MA media without selection. The replacement was verified by Southern hybridisation and the new mutant was named *S. parvulus* Tü4055/borM::aac3(1

V). Strain *S. parvulus* Tü4055/borM::aac3(IV) was grown, extracted and analysed as described in example 1. Borrelidin production was compared to a wild type control. In addition, *S. parvulus* Tü4055/borM::aac3(;V) was chemically complemented with trans-1,2-dicyclopentane dicarboxylic acid, following the protocol described in example 1.

To verify that no polar effects were introduced a full-length copy of borM under the control of the ermE* promoter was introduced in trans to the disrupted mutant. Full-length borM was cloned as a XbaI-AgeI fragment of 2.0 kb from pSLM and subcloned into the EcoRI (end-filled with Klenow)-XbaI sites of pEM4 together with the hyg gene as a XmaI-EcoRV fragment from pLHyg, to give pborMH. Plasmid pborMH and the control plasmid pEM4 were introduced into *S. parvulus* Tü4055/borM::aac(3)IV by protoplast transformation as described in example 5. The resulting strain *S. parvulus* Tü4055/borM::aac(3)IV/pborMH was analysed as described in example 1 and shown to produce borrelidin at a titre similar to a WT control.

Example 25

Disruption of borN (*S. parvulus* Tü4055/borN::aac3(IV))

In order to disrupt bor N, a 1201 bp BamHI fragment from pSLM (containing the 3'-end of borM and the first 161 codons of bor N) was subcloned into the Bg/II-BamHI sites of pSL1180 and in the correct orientation, to generate pSLMN. A BamHI-EcoRI fragment (using these sites from the polylinker) containing borO from pborOR (see below) was subcloned into the BamHI-EcoRI sites of pSLMN, generating pSLNO. After EcoRI digestion of pSLNO and end-filling with Klenow fragment, the hyg gene was subcloned from pLHyg as a EcoRV fragment, leading to pSLNOH. Finally the aac3(IV) gene was subcloned as a NcoI-BamHI fragment from pEFBA into pSLNOH digested with the same restriction enzymes, generating pSLNr1.

The vector pSLNr1 was introduced into *S. parvulus* Tü4055 by protoplast transformation as described in example 5. Colonies resistant to apramycin were selected, and then passaged several times through MA media without selection. The replacement was verified by Southern hybridisation and the new mutant was named *S. parvulus* Tü4055/borN::aac3(IV). Strain *S. parvulus* Tü4055/borN::aac3(IV) was grown, extracted and analysed as described in example 1. Borrelidin production was compared to a wild type control. In addition, *S. parvulus* Tü4055/borN::aac3(IV) was chemically complemented with trans-1,2-dicyclopentane dicarboxylic acid, following the protocol described in example 1.

Example 26

Heterologous expression of borO in *Streptomyces albus* J1074

In order to examine whether the putative resistance protein BorO confers-resistance to a borrelidin-sensitive organism, borO was expressed in *Streptomyces albus* J1074. The gene borO was amplified by PCR using the primers BTRNAS1 (5'-TGTCTAGACTCGCGCGAACA-3') (SEQ ID No.89) and BTRNAS2 (5'-TGAATTCCGAAGGGGGTGGT-3') (SEQ ID No.90) with cosBor19B9 as template. The product was purified, digested XbaI-EcoRI and cloned into pEM4A that had been similarly digested to give plasmid pborOR which puts borO under the control of the promoter ermE*. The vector pborOR was introduced into *S. albus* J1074 by protoplast transformation (Chater & Wilde, 1980) and selected for apramycin resistance. The new strain was named *S. albus* J1074/pborOR.

Resistance to borrelidin was assayed on Bennett's agar containing apramycin at 25 μg/ml. Spores of *S. albus* J1074/pborOR and the control *S. albus* J1074/pEM4A were spread onto plates and then disks containing borrelidin at 100 & 200 μg/ml were laid upon the lawn of spores and incubated overnight at 30° C. Haloes indicating inhibition of growth were observed for the control strain harbouring pEM4A but not for *S. albus* J1074/pborOR.

Example 27

Disruption of borG and borI (*S. parvulus* Tü4055/borG::aac3(IV)/borI::hyg)

The hyg gene is isolated from pLHyg as an EcoRV fragment and cloned into pSLI (example 20) digested with EcoRI and treated with Klenow fragment to give pSLIH; the hyg gene is cloned in the same orientation as borI. pSLIH is introduced into *S. parvulus* Tü4055/borG::aac3(IV) by protoplast transformation, as described in example 5, and selected for both apramycin and hygromycin resistance, and is then passaged several times through MA media without selection in order to promote double recombination. Apramycin and hygromycin resistant colonies are analysed by Southern hybridisation and PCR to verify the replacement.

Example 28

Disruption of borG and borJ (*S. parvulus* Tü4055/borG::aac3(IV)/borJ::hyg)

The hyg gene is isolated from pLHyg as an EcoRV fragment and cloned into pSLJ (example 21) digested with AvrII-Bg/III and treated with Klenow, to give pSLJH; the hyg gene is cloned in the same orientation as borI. pSLJH is introduced into *S. parvulus* Tü4055/borG::aac3(IV) by protoplast transformation, as described in example 5, and selected for both apramycin and hygromycin resistance, and is then passaged several times through MA media without selection in order to promote double recombination. Apramycin and hygromycin resistant colonies are analysed by Southern hybridisation and PCR to verify the replacement.

Example 29

Effects of borE Up-Regulation in *S. parvulus* Tü4055

To examine the possibility that biosynthesis of the trans-1,2-cyclopentane dicarboxylic acid starter unit may have a limiting effect upon borrelidin production, borE was up-regulated in the parental strain and the effect upon borrelidin titre was analysed. The vector used, pborEH was described in example 16.

The vectors pborEH and pEM4 (control) were used to transform protoplasts of *S. parvulus* Tü4055 to give strains *S. parvulus* Tü4055/pborEH and *S. parvulus* Tü4055/pEM4 respectively. Several colonies from each transformation were picked, grown in triplicate and then analysed as described in example 1. Compared to the control strain, up-regulation of borE brought about a 4.2±0.3-fold increase in the titre of borrelidin.

Example 30

Effects of borL Up-Regulation in *S. parvulus* Tü4055

To examine the possibility that borL may have a regulatory, or some other related function involved in borrelidin production, the gene was up-regulated in the parental strain and the effect upon borrelidin titre was analysed.

The expression vector pborLH was generated as follows: pSLL was digested with NofI, treated with Klenow fragment and then digested with BamHI to obtain a fragment of 2190 bp containing borI. This fragment was sub-cloned together with the BamHI-SpeI hyg gene from pLHyg, into pEM4 digested with PstI (treated with Klenow)-XbaI, to obtain pborLH.

The vectors pborLH and pEM4 (control) were used to transform protoplasts of *S. parvulus* Tü4055 to give strains *S. parvulus* Tü4055/pborLH and *S. parvulus* Tü4055/pEM4 respectively. Several colonies from each transformation were picked, grown in triplicate and then analysed as described in example 1. Compared to the control strain, up-regulation of borI brought about a 4.3±0.7-fold increase in the titre of borrelidin.

Example 31

Production of 12-desnitrile-12-methyl borrelidin 14 (Pre-borrelidin)

Working stocks of *S. parvulus* Tü4055/borI::aac3(IV) (0.5 ml) were inoculated into primary vegetative pre-cultures of NYG as described in example 1. Secondary pre-cultures were prepared (as example 1 but with 250 ml NYG in 2 l Erlenmeyer flasks). PYDG production medium (4 l), prepared as in example 1 and with 0.01% Plutronic L0101 added to control foaming, was inoculated with secondary pre-culture (12.5% inoculum). A second fermenter containing centre-point medium (4 l) and 0.01% Plutronic L0101 to control foaming, was set up in parallel and was also inoculated with secondary pre-culture (12.5% inoculum). Centre-point production medium contains per liter of deionised water: Tesco's skimmed milk powder (1.5%), Avidex W-80 (4.5%), glucose (0.5%) and yeast autolysate (0.15%) adjusted to pH 7.0 with 5 M NaOH.

These batches were each allowed to ferment in a 7 I Applikon fermenter for 6.5 days at 30° C. Airflow was set at 0.75 vvm (volume per volume per minute), with tilted baffles and the impeller speed controlled between 400 and 800 rpm to maintain dissolved oxygen tension at or above 30% of air saturation. No further antifoam was added. At 22 hours into the fermentation the starter acid, trans-cyclopentane-1,2-dicarboxylic acid, was added as a neutralised solution of 1:1 MeOH/5 M NaOH, through an in-line filter (0.22 μm). The final concentration in the fermenter vessel of exogenous starter acid was 0.5 mM.

After 6.5 days of fermentation the broths were combined and acidified to pH 3.5 with concentrated HCl (~6 ml), then clarified by centrifugation at 3,500 rpm for 10 minutes. The supernatant was extracted into ethyl acetate (3×1 volume equivalent for 4 hours each) and the cell pellet left to steep in methanol (2×1.5 liters for 4 hours each). The organics were combined and removed under reduced pressure to yield a tarry gum. The gum was re-suspended in 0.1 M Borax buffer (500 ml at pH 9.4) and washed with hexanes (500 ml) and ethyl acetate (500 ml). The aqueous layer was then acidified with concentrated HCl to pH 3.5 and extracted with ethyl acetate (3×500 ml), which were combined and taken to dryness. The resultant gum was dissolved in methanol (15 ml), diluted with water (285 ml) and loaded under gravity onto a $C_{18}$-reversed-phase cartridge (50 g, prepared in 5% aqueous methanol). The cartridge was washed with 20% and 50% aqueous methanol (300 ml each) and eluted with 100% methanol (500 ml). This last fraction was taken to dryness under reduced pressure to yield a black gummy-oil (600 mg) that was taken up in methanol. This residue was finally purified by sequential preparative reversed-phase HPLC (eluted with the mobile phases used in example 4, without added TFA, running isocratically at 40% B). Active fractions were combined and desalted on a $C_1$-cartridge (1 g), to yield 28 mg of a dark oil (3.5 mg/l isolated yield). Table 12 summarises the $^1H$ and $^{13}C$ NMR chemical shift data for 12-desnitrile-12-methyl borrelidin 14 in $CDCl_3$.

TABLE 12

| Position | $\delta_H$ (ppm) | Multiplicity | Coupling (Hz) | $\delta_c$ (ppm) |
|---|---|---|---|---|
| 1 | — | — | — | 174.5 |
| 2a | 2.29 | m | — | 37.8 |
| 2b | 2.26 | m | — | — |
| 3 | 3.85 | dt | 9.0, 3.0 | 71.9 |
| 4 | 1.83 | m | — | 35.1 |
| 5a | 1.19 | bt | 13.5 | 43.6 |
| 5b | 0.91 | m | — | — |
| 6 | 1.75 | m | — | 27.0 |
| 7a | 1.08 | m | — | 49.2 |
| 7b | 0.88 | m | — | — |
| 8 | 1.69 | m | — | 26.5 |
| 9a | 0.97 | m | — | 38.3 |
| 9b | 0.45 | t | 12.5 | — |
| 10 | 1.62 | m | — | 34.1 |
| 11 | 3.53 | d | 9.0 | 85.7 |
| 12 | — | — | — | 138.4 |
| 13 | 5.84 | d | 11.0 | 127.7 |
| 14 | 6.28 | ddd | 14.5, 11.0, 1.0 | 129.6 |
| 15 | 5.48 | ddd | 14.5, 10.5, 3.5 | 129.9 |
| 16a | 2.53 | m | — | 39.1 |
| 16b | 2.22 | m | — | — |
| 17 | 5.07 | ddd | 11.0, 8.0, 3.0 | 76.5 |
| 18 | 2.52 | m | — | 48.0 |
| 19a | 1.92 | m | — | 30.4 |
| 19b | 1.32 | m | — | — |
| 20a | 1.74 | m | — | 26.2 |
| 20b | 1.71 | m | — | — |
| 21a | 1.96 | m | — | 32.0 |
| 21b | 1.84 | m | — | — |
| 22 | 2.45 | m | 8.0 | 49.3 |
| 23 | — | — | — | 182.3 |
| 4-$CH_3$ | 0.78 | d | 6.5 | 18.5 |
| 6-$CH_3$ | 0.77 | d | 6.5 | 18.8 |
| 8-$CH_3$ | 0.75 | d | 6.5 | 20.6 |
| 10-$CH_3$ | 0.94 | d | 6.5 | 16.3 |
| 12-$CH_3$ | 1.64 | s | — | 11.4 |

Chemical shifts are referenced to $CDCl_3$ (for $^1H$ at 7.26 ppm and for $^{13}C$ at 77.0 ppm)

Example 32

Production of 12-desnitrile-12-carboxy borrelidin 2

Working stocks of *S. parvulus* Tü4055/borJ::aac3(IV) (0.5 ml) were inoculated into primary vegetative pre-cultures of NYG as described in example 1. Secondary pre-cultures were prepared (as example 1 but with 250 ml NYG in 2 l Erlenmeyer flasks). PYDG production media (4 L), prepared as in example 1 and with 0.01% Plutronic L0101 added to control foaming, was inoculated with the entire secondary pre-culture (10% inoculum). This was allowed to ferment in a 7 L Applikon fermenter for 6 days at 30° C. Airflow was set at 0.75 vvm, with tilted baffles and the impeller speed controlled between 250 and 600 rpm to maintain dissolved oxygen tension at or above 30% of air saturation. No further antifoam was added. A second fermentation was performed exactly as above, but which was batch fed with 0.2 mol of glucose as an aqueous solution every 12 hours from 60 hours post-inoculation.

After 6 days the fermentations were harvested and combined. The broth was clarified by centrifugation (3,500 rpm, 10 minutes) and the resultant supernatant acidified with 10 M HCl (aq) to pH ~3.5. This solution was then extracted into ethyl acetate by stirring (3×1 volume equivalent for 4 hours each). The cell pellet was extracted twice by steeping the cells in 1:1 methanol/ethyl acetate (500 ml). All the organics were combined and removed under reduced pressure to yield an aqueous slurry. The slurry was diluted to 500 ml with water, acidified to pH ~3.5 with 10 M HCl and extracted into ethyl acetate (3×300 ml). The organics were concentrated under reduced pressure to ~300 ml and extracted with 0.1 M borax (3×150 ml, pH=9.4). The combined borax solutions were-acidified with 10 M HCl to pH ~3.5 and extracted with 6×300 ml of ethyl acetate. Analytical HPLC demonstrated that some of the accumulant still resided in the borax solution and so this was loaded, under gravity, onto a $C_{18}$-reverse-phase cartridge (50 g). The cartridge was washed with water and the accumulant eluted in 100% methanol. The organics containing the accumulant were combined and reduced to a 40 ml methanolic solution. This was loaded onto a Sephadex LH-20 column (70 g, swelled overnight in methanol, column 60 cm×2.5 cm), which was developed with 100% methanol; the active fractions were combined and taken to dryness. The material was then further processed by preparative reversed-phase HPLC (eluted with the mobile phases used in example 4, without added TFA, running isocratically at 40% B). The combined active fractions were taken to dryness, dissolved in methanol (4 ml) and diluted with water (200 ml). This mixture was split into 2 equal fractions and each loaded, under gravity, onto a $C_{18}$-reverse-phase cartridge (20 g). The columns were then eluted with 3 column volumes of 5%, 10%, 20%, 30%, 40%, 50%, 60%, 75%, 90% and 100% aqueous methanol. The accumulant eluted in all fractions from 60% to 100% methanol, which were combined and taken to dryness. The accumulant (dissolved in DMSO) was then finally purified by sequential preparative reversed-phase HPLC (eluted with the mobile phases used in example 4, without added TFA, running isocratically at 40% B). Active fractions were combined and desalted on a $C_{18}$-cartridge (1 g), to yield 17 mg of a brown oil (2.1 mg/l isolated yield). Table 13 summarises the $^1H$ and $^{13}C$ NMR chemical shift data for 12-desnitrile-12-carboxy borrelidin 2 in $d_4$-methanol.

TABLE 13

| Position | $\delta_H$ (ppm) | Multiplicity | Coupling (Hz) | $\delta_c$ (ppm) |
|---|---|---|---|---|
| 1 | — | — | — | 173.27 |
| 2a | 2.40 | dd | 15.8, 4.1 | 39.31 |
| 2b | 2.29 | dd | 15.8, 8.2 | |
| 3 | 3.87 | m | | 71.64 |
| 4 | 1.80 | m | | 36.51 |
| 5a | 1.29 | m | | 44.24 |
| 5b | 0.90 | m | | |
| 6 | 1.59 | m | | 27.48 |
| 7a | 1.09 | m | | ~49.0* |
| 7b | 1.03 | m | | |
| 8 | 1.72 | m | | 28.17 |
| 9a | 1.12 | m | | 38.42 |
| 9b | 0.79 | m | | |
| 10 | 2.03 | m | | 36.43 |
| 11 | 3.90 | m | | 81.95 |

TABLE 13-continued

| Position | $\delta_H$ (ppm) | Multiplicity | Coupling (Hz) | $\delta_c$ (ppm) |
|---|---|---|---|---|
| 12 | — | — | — | 132.35 |
| 13 | 6.43 | d | 11.0 | 140.83 |
| 14 | 6.96 | dd | 14.5, 11.5 | 130.91 |
| 15 | 5.91 | ddd | 15.0, 9.5, 5.0 | 138.93 |
| 16a | 2.61 | m | 15.0 | 38.57 |
| 16b | 2.36 | m | | |
| 17 | 5.04 | m | | 77.40 |
| 18 | 2.50 | m | | 49.80 |
| 19a | 1.90 | m | | 30.59 |
| 19b | 1.32 | m | | |
| 20a | 1.85 | m | | 26.34 |
| 20b | 1.41 | m | | |
| 21a | 1.97 | m | | 32.40 |
| 21b | 1.75 | m | | |
| 22 | 2.52 | m | | ~48.0* |
| 23 | — | — | — | 180.27 |
| 4-$CH_3$ | 0.83 | d | 7.0 | 18.76 |
| 6-$CH_3$ | 0.80 | d | 6.0 | 17.06 |
| 8-$CH_3$ | 0.81 | d | 6.5 | 20.60 |
| 10-$CH_3$ | 0.93 | d | 6.5 | 16.61 |
| 12-$CO_2H$ | — | — | — | 170.49 |

Chemical shifts are referenced to methanol (for $^1H$ at 3.35 ppm (quintet) and for $^{13}C$ at 49.0 ppm (septet));
*Obscured by solvent signal, $d_4$-methanol.

Example 33

Production by mutasynthesis of 17-des-(cyclopentane-2'-carboxylic acid)-17-(cyclobutane-2'-carboxylic acid)borrelidin 18

Working stocks of *S. parvulus* Tü4055/borE™:aac3(IV) (0.5 ml) were inoculated into primary vegetative pre-cultures of NYG as described in example 1. Secondary pre-cultures were prepared (as example 1 but with 250 ml NYG in 2 l Erlenmeyer flasks). PYDG production medium (4 l), prepared as in example 1 and with 0.01% Plutronic L0101 added to control foaming, was inoculated with secondary pre-culture (12.5% inoculum). Two further bioreactors were set up in the same manner. These batches were each allowed to ferment in a 7 l Applikon fermenter for 5 days at 30° C. Airflow was set at 0.75 vvm (volume per volume per minute), with tilted baffles and the impeller speed controlled between 400 and 700 rpm to maintain dissolved oxygen tension at or above 30% of air saturation. No further antifoam was added. At 22 hours into the fermentation the starter acid, trans-cyclobutane-1,2-dicarboxylic acid, was added as a neutralised solution of 1:1 MeOH/5 M NaOH. The final concentration in the fermenter vessel of exogenous starter acid was 0.5 mM.

After 5 days of fermentation the broths were combined and acidified to pH 4.0 with concentrated HCl, then clarified by centrifugation at 3,500 rpm for 10 minutes. The supernatant was absorbed onto diaion HP-20SS resin (1 l), which had been pretreated with methanol (2 l) and then 5% aqueous methanol (2 l), by filtration at a rate of approximately 100 ml/min. The resin was then eluted with 20% aqueous methanol (2.5 l) and then 80% aqueous acetone (4.5 l). The organic solvent was removed from the aqueous acetone and the resultant aqueous slurry (1 liter) extracted into ethyl acetate (3×1 l). The organics were combined and reduced in vacuo to yield a yellow/brown oil (1.7 g). Meanwhile, the cell pellet left to steep in methanol-ethyl acetate, 1:1 (3×1 l for 4 hours each), and the resultant organic supernatants reduced in vacuo to yield an aqueous slurry (400 ml). The particulate matter was dissolved in methanol (50 ml), and added back to the aqueous slurry, which was made up to 500 ml with water. This slurry was absorbed onto diaion HP-20SS resin (300 ml), that had been pretreated with methanol (500 ml) and then 5% aqueous methanol (500 ml). The resin was then eluted with 20% aqueous methanol (1 l) and then 80% aqueous acetone (1.5 l). The organic solvent was removed from the aqueous acetone and the resultant aqueous slurry (made up to 750 ml) extracted into ethyl acetate (3×750 ml). The organics were combined and reduced in vacuo to yield a yellow/brown oil (1.7 g). The crude extracts were combined (3.4 g), dissolved in ethyl acetate (10 ml), then adsorbed onto a silica column (5 cm ID×10 cm, treated with EtOAc), and eluted with EtOAc. The active fractions were combined and the solvent removed in vacuo to yield a brown gum (1.08 g). This residue was finally purified by sequential preparative reversed-phase HPLC (eluted with the mobile phases used in example 4, without added TFA, running from 25% B to 75% B over 25 minutes with a linear gradient). Active fractions were combined and desalted on a $C_{18}$-cartridge (5 g), to yield 83.9 mg (or 7.0 mg/l isolated yield). The $^{13}$C-NMR spectrum of 18 is shown in table 14

TABLE 14

| $\delta_c$ (ppm) | Position |
|---|---|
| 177.1 | COOH (C22) |
| 172.2 | 1 |
| 144.0 | 13 |
| 138.7 | 15 |
| 126.9 | 14 |
| 118.3 | 12 |
| 115.8 | CN |
| 75.5 | 17 |
| 73.1 | 11 |
| 69.7 | 3 |
| 47.6 | 5 |
| 43.1 | 7 |
| 40.1 | 19 |
| 40.0 | 2 |
| 37.3 | 9 |
| 35.7 | 4 |
| 35.1 | 10 |
| 34.4 | 16 |
| 30.9 | 18 |
| 27.3 | 6 |
| 26.2 | 8 |
| 21.7 | 20 |
| 21.0 | 21 |
| 20.1 | 8-Me |
| 18.1 | 6-Me |
| 16.9 | 4-Me |
| 14.9 | 10-Me |

$^{13}$C-NMR assignment for 18, in $CDCl_3$, using that carbon signal as reference at $\delta_c$ = 77.7 ppm

REFERENCES

Anderson, B. F., Herit, A. J., Rickards, R. W., and Robertson, G. B. (1989) Crystal and molecular structures of two isomorphous solvates of the macrolide antibiotic borrelidin: absolute configuration determination by incorporation of a chiral solvent in the in the crystal lattice. *Aust. J. Chem.* 42:717-730.

Anderton, K., and Rickards, R. W. (1965) Some structural features of borrelidin, an anti-viral antibiotic. *Nature* 206: 269.

Aparicio, J. F., Molnár, I., König, A., Haydock, S. H., Khaw., L. E., Staunton, J., and Leadlay, P. F. (1996) Organisation of the biosynthetic gene cluster for rapamycin in *Streptomyces hygroscopicus*: analysis of the enzymatic domains in the modular polyketide synthase. *Gene* 169:9-16.

August, P. R., Tang, L., Yoon, Y. J., Ning, S., Müller, R., Yu, T.-W., Taylor, M., Hoffmann, D., Kim, C. G., Zhang, X. H., Hutchinson, C. R., and Floss, H. G. (1998) Biosynthesis of the ansamycin antibiotic rifamycin: deductions from the molecular analysis of the rif biosynthetic gene cluster of *Amycolatopsis mediteranei* S699. *Chem. Biol.* 5:69-79.

Beck, J. B., Yoon, Y. J., Reynolds, K. A., and Sherman, D. H. (2002) The hidden steps of domain skipping: ring size determination in the pikromycin modular polyketide synthase. *Chem. Biol.* 9:575-583.

Berger, J., Jampoisky, L. M., and Goldberg, M. W. (1949) Borrelidin, a new antibiotic with anti-Borrelia activity and penicillin enhancement properties. *Arc. Biochem.* 22:476-478.

Bierman, M., Logan, R., O'Brian, K., Seno, E. T., Rao, N., and Schoner, B. E. (1992) Plasmid vectors for the conjugal transfer of DNA from *Escherichia coli* to *Streptomyces* spp. *Gene* 116:43-49.

Bonfield, J. K., Smith, K. F., and Staden, R. (1995) A new DNA sequence assembly program. *Nucleic Acids Research* 23:4992-4999.

Brautaset, T., Sekurova, O. N., Sletta, H., Ellingsen, T. E., Strom, A. R., Valla, S., and Zotchev, S. B. (2000) Biosynthesis of the polyene antifungal antibiotic nystatin in *Streptomyces noursei* ATCC 11455: analysis of the gene cluster and deduction of the biosynthetic pathway. *Chem. Biol.* 7:395-403.

Brenner, S. (1998) The molecular evolution of genes and proteins: a tale of two serines. *Nature* 334:528-530.

Broadhurst, R. W., Nietlispach, D., Wheatcroft, M. P., Leadlay, P. F., and Weissman, K. J. (2003) The structure of docking domains in modular polyketide syntheses. *Chem. Biol.* 10:723-731.

Brosius, J. (1989) Super-polylinkers in cloning and expression vectors. *DNA* 8:759-777.

Butler, A. R., Bate, N., and Cundliffe, E. (1999) Impact of thioesterase activity on tylosin biosynthesis in *Streptomyces fradiae. Chem. Biol.* 6:287-292.

Caffrey, P., Lynch, S., Flood, E., Finnan, S., and Oliynyk, M. (2001) Amphotericin biosynthesis in *Streptomyces nodosus*: deductions from analysis of polyketide synthase and late genes. *Chem. Biol.* 8:713-723.

Celenza, J. L. (2001) Metabolism of tyrosine and tryptophan—new genes for old pathways. *Curr. Opin. Plant Biol.* 4:234-240

Chater, K. F. and Wilde, L. C. (1980) *Streptomyces albus* G mutants defective in the SaIG1 restriction modification system. *J. Gen. Microbiol.* 116:323-334.

Cheng, Y. Q., Tang, G. L., and Shen B. (2003) Type I polyketide synthase requiring a discrete acyltransferase for polyketide biosynthesis. *Proc. Natl. Acad. Sci. USA.* 100: 3149-3154.

Cortés J., Haydock, S. F., Roberts, G. A., Bevitt, D. J., and Leadlay, P. F. (1990) An unusually large multifunctional polypeptide in the erythromycin producing polyketide synthase of Saccharopolyspora erythraea. *Nature* 348:176-178.

Cortés, J., Weissman, K. E. H., Roberts, G. A., Brown, M. J. B., Staunton, J., and Leadlay, P. F. (1995) Repositioning of a domain in a modular polyketide synthase to promote specific chain cleavage. *Science* 268:1487-1489.

Cortés, J., Velasco, J., Foster, G., Blackaby, A. P., Rudd, B. A. M., and Wilkinson, B. (2002) Identification and cloning of a type III polyketide synthase required for diffusible pigment biosynthesis in *Saccharopolyspora erythraea. Mol. Micro.* 44:1213-1224.

Devereux, J., Heaberli, P., and Smithies, O. (1984) A comprehensive set of sequence analysis programs for the VAX. *Nucleic Acids Research* 12:387-395.

Dickinson, L., Griffiths, A. J., Mason, C. G., and Mills, R. F. (1965) Anti-viral activity of two antibiotics isolated from a species of *Streptomyces. Nature* 206:265-268.

Donadio, S., Staver, M. J., McAlpine, J. B., Swanson, S. J., and Katz, L. (1991) Modular organization of genes required for complex polyketide biosynthesis. *Science* 252:675-679.

Donadio, S., McAlpine, J. B., Sheldon, P. J., Jackson, M., and Katz, L. (1993) An erythromycin analog produced by reprogramming of polyketide synthesis *Proc. Nat. Acad. Sci. USA* 90:7119-7123.

Duffey, M. O., LeTiran, A., and Morken, J. P. (2003) Enantioselective total synthesis of borrelidin. *J. Am. Chem. Soc.* 125:1458-1459.

Eastwood, E. L., and Schaus, S. E. (2003) Borrelidin induces the transcription of amino acid biosynthetic enzymes via a GCN4-dependent pathway. *Bioorg. Med. Chem. Lett.* 13:2235-2237.

Fernandez, E., Weissbach, U., Sanchez-Reillo, C., Brana, A. F., Mendez, C., Rohr, J., and Salas, J. A. (1998) Identification of two genes from *Streptomyces argillaceus* encoding glycosyltransferases involved in transfer of a disaccharide during the biosynthesis of the antitumor drug mithramycin. *J. Bacteriol.* 180:4929-4937.

Floss, H. G. (2001) Antibiotic biosynthesis: from natural to unnatural compounds. *J. Ind. Micro. Biotech.* 27:183-194.

Fouces, R., Mellado, E., Diez, B, and Barredo, J. L. (1999) The tylosin biosynthetic cluster from *Streptomyces fradiae*: genetic organisation of the left region. *Microbiology* 145:855-868.

Folkman, J. (1986) How is blood vessel growth regulated in normal and neoplastic tissue? G.H.A. Cloves Memorial Lecture. *Cancer Res.* 51:467-473.

Funahashi, Y., Wakabayashi, T., Semba, T., Sonoda, J., Kitoh, K., and Yoshimatsu, K. (1999) Establishment of a quantitative mouse dorsal air sac model and its application to evaluate a new angiogenesis inhibitor. *Oncol. Res.* 11:319-329.

Gaisser, S., Reather, J., Wirtz, G., Kellenberger, L., Staunton, J., and Leadlay, P. F. (2000) A defined system for hybrid macrolide biosynthesis in *Saccharopolyspora erythraea. Mol. Microbiol.* 36:391-401.

Gaisser, S., Martin, C. J., Wilkinson, B., Sheridan, R. M., Lill, R. E., Weston, A. J., Ready, S. J., Waldron, C., Crouse, G. C., Leadlay, P. F., and Staunton, J. (2002) Engineered biosynthesis of novel spinosyns bearing altered deoxyhexose substituents. *Chem. Commun.* 618-619.

Gaitatzis, N., Silakowski, B., Kunze, B., Nordsiek, G., Blöcker, H., Höfle, G., and Müller, R. (2002) The biosynthesis of the aromatic myxobacterial electron transport inhibitor stigmatellin is directed by a novel type of modular polyketide synthase. *J. Biol. Chem.* 277:13082-13090.

Hanessian, S., Yang, Y., Giroux, S., Mascitti, V., Ma, J., and Raeppel, F. (2003) Application of conformation design In acyclic stereoselection: total synthesis of borrelidin as the crystalline benzene solvate. *J. Am. Chem. Soc.* 125:13784-13792.

Hardt, I. H., Steinmetz, H., Gerth, K., Sassa, F., Reichenbach, H., and Höfle, G. (2001) New natural epothilones from *Sorangium cellulosum*, strains So ce90/B2 and So ce90/D13: isolation, structure elucidation, and SAR studies. *J. Nat. Prod.* 64:847-856.

Heathcote, M. L., Staunton, J., and Leadlay, P. F. (2001) Role of type II thioesterases: evidence for the removal of short acyl chains produced by aberrant decarboxylation of chain extender units. *Chem. Biol.* 8:207-220.

Hopwood, D. (1997) Genetic contributions to understanding polyketide biosynthesis. *Chem. Rev.* 97:2465-2497.

Hunziker, D., Yu, T.-W., Hutchinson, C. R., Floss, H. G., and Khosla, C. (1998) Primer unit specificity in biosynthesis principally resides in the later stages of the biosynthetic pathways. *J. Am. Chem. Soc.* 120:1092-1093.

Janssen, G. R., Bibb, M. J., (1993) Derivatives of pUC18 that have Bg/II sites flanking a modified cloning site and that retain the ability to identify recombinant clones by visual screening of *E. coli* colonies. *Gene* 124:133-134.

Kahn, R. A., Fahrendorf, T., Halkier, B. A., and Møller, B. L. (1999) Substrate specificity of the cytochrome P450 enzymes CYP79 μl and CYP71E1 involved in the biosynthesis of the cyanogenic glucoside dhurrin in *Sorghum* bicolour (L.) Moench. *Arch. Biochem. Biophys.* 363:9-18.

Kawamura, T., Liu, D., Towle, M. J., Kageyama, R., Tsukahara, N., Wakabayashi, T., and Littlefield, B. A. (2003) Anti-angiogenesis effects of borrelidin are mediated through distinct pathways: Threonyl-tRNA synthetase and caspases are independently involved in suppression of proliferation and induction of apoptosis in endothelial cells. *J. Antibiot.* 56:709-715.

Kieser, T., Bibb, M. J., Buttner, M. J., Chater, K. F., and Hopwood, D. A. (2000) Practical *Streptomyces* Genetics. The John Innes Foundation. Norwich.

Keller-Scheirlein, W. (1967) Composition of the antibiotic borrelidin. *Helv. Chim. Acta.* 50:731-753.

Kuo, M. S., Yurek, D. A., and Kloosterman, D. A. (1989) Assignment of $^1H$ and $^{13}C$ NMR signals and the alkene geometry at C-7 in borrelidin. *J. Antibiot* 42:1006-1007.

Kuhstoss, S., Huber, M., Turner, J. R., Paschal, J. W., and Rao, R. N. (1996) Production of a novel polyketide through the construction of a hybrid polyketide synthase. *Gene* 183:231-236.

Lozano, M. J., Remsing, L. L., Quiros, L. M., Brana, A. F., Fernandez, E., Sanchez, C., Mendez, C., Rohr, J., and Salas, J. A. (2000) Characterization of two polyketide methyltransferases involved in the biosynthesis of the antitumor drug mithramycin by *Streptomyces argillaceus. J. Biol. Chem.* 275:3065-3074.

Maehr, H., and Evans, R. H. (1987) Identity of borrelidin with treponemycin. *J. Antibiot.* 40:1455-1456.

Marsden, A. F., Wilkinson, B., Cortés, J., Dunster, N. J., Staunton, J., and Leadlay, P. F. (1998) Engineering broader specificity into an antibiotic-producing polyketide synthase. *Science* 279:199-202.

Matter, A,. (2001) Tumor angiogenesis as a therapeutic target. *Drug Dis. Today* 6:1005-1024.

Mochizuki, S., Hiratsu, K., Suwa, M., Ishii, T., Sugino, F., Yamada, K., and Kinashi, H. (2003) The large linear plasmid pSLA2-L of *Streptomyces rochei* has an unusually condensed gene organization for secondary metabolism. *Mol Microbiol.* 48:1501-1510.

Moore, B. S., and Hopke, J. N. (2000) Discovery of a new bacterial polyketide biosynthetic pathway. *Chembiochem* 2:35-38.

Nielsen, J. S., and Møller, B. L. (1999) Biosynthesis of cyanogenic glucosides in *Triglochin maritime* and the involvement of cytochrome P450 enzymes. *Arch. Biochem. Biophys.* 368:121-130.

Olano, C., Wilkinson, B., Moss, S. J., Brana, A. F., Mendez, C., Leadlay, P. F., and Sala, J. A. (2003) Evidence from engineered gene fusions for the repeated use of a module in a modular polyketide synthase. *Chem. Commun.* 2780-2782.

Oliynyk, M., Brown, M. J. B., Cortés, J., Staunton., J., and Leadlay, P. F. (1996) *Chem. Biol.* 3:833-839.

Otani, A., Slike, B. M., Dorrell, H. I., Hood, J., Kinder, K., Cheresh, D. A., Schimmel, P., and Friedlander, M. (2002) A fragment of human TrpRS as a potent antagonist of ocular angiogenesis. *Proc. Nat. Acad. Sci. USA* 99:178-183.

Otoguru, K., Ui, H., Ishiyama, A., Kobayashl, M., Togashi, H., Takahashi, Y., Masuma, R., Tanaka, H., Tomado, H., Yamada, H., and Omura, S. (2003) In vitro and in vivo antimalarial activities of a non-glycosidic 18-membered macrolide antibiotic, borrelidin, against drug-resistant strains of *Plasmodia. J. Antibiot.* 56:727-729.

Pacey, M. S., Dirlam, J. P., Geldart, L. W., Leadlay, P. F., McArthur, H. A. I., McCormick, E. L., Monday, R. A., O'Connell, T. N., Staunton, J., and Winchester, T. J. (1998) Novel erythromycins from a recombinant Saccharopolyspora erythraea strain NRRL 2338 pIG1 I. Fermentation, isolation and biological activity. *J. Antibiot.* 51:1029-1034.

Paetz, W., and Nass, G. (1973) Biochemical and immunological characterization of threonyl-tRNA synthetase of two borrelidin-resistant mutants of *Escherichia coli* K12. *Eur. J. Biochem.* 35:331-337.

Prieto, M. A., Dfaz, E., and Garcia, J. L. (1996) Molecular characterization of the 4-hydroxyphenylacetate catabolic pathway of *Escherichia coli* W: engineering a mobile aromatic degradative cluster. *J. Bacteriol.* 178:111-120.

Quiros, L. M., Aguirrezabalaga, I., Olano, C., Mandez, C., and Salas, J. A. (1998) Two glycosyltransferases and a glycosidase are involved in oleandomycin modification during its biosynthesis by *Streptomyces antibioticus. Mol. Microbiol.* 28:1177-1185.

Raibaud, A., Zalacain, M., Holt, T. G., Tizard, R., and Thompson, C. J. (1991) Nucleotide sequence analysis reveals linked N-acetyl hydrolase, thioesterase, transport, and regulatory genes encoded by the bialophos biosynthetic gene cluster of *Streptomyces hygroscopicus. J. Bacteriol.* 173:4454-4463.

Ranganathan, A., Timoney, M., Bycroft, M., Cortés, J., Thomas, I. P., Wilkinson, B., Kellenberger, L., Hanefeld, U., Galloway, I. S., Staunton, J., and Leadlay, P. F. (1999) Knowledge-based design of bimodular and trimodular polyketide synthases based on domain and module swaps: a route to simple statin analogues. *Chem. Biol.* 6:731-741.

Reeves, C. D., Murli, S., Ashley, G. W., Piagentini, M., Hutchinson, C. R., and McDaniel, R. (2001) Alteration of the substrate specificity of a modular polyketide synthase acyltransferase domain through site-specific mutations. *Biochemistry* 40:15464-15470.

Rowe, C. J., Bohm, I. U., Thomas, I. P., Wilkinson, B., Rudd, B. A. M., Foster, G., Blackaby, A. P., Sidebottom, P. J., Roddis, Y., Buss, A. D., (2001) *Chem. Biol.* 8:475-485.

Rowe, C. J., Cortés, J., Gaisser, S., Staunton, J., and Leadlay, P. F. (1998) Construction of new vectors for high-level expression in actinomycetes. *Gene* 216:215-223.

Rudd, B. A. M., Noble, D., Foster, S. J., Webb, G., Haxell, M. (1990) The biosynthesis of a family of novel antiparasitic macrolides. Proceedings of the $6^{th}$ International Symposium on the Genetics of Industrial Microorganisms. Strausbourg, France. Abstract A70. p. 96. ISBN 2-87805-004-5.

Sambrook, J., Fritsch, E. F., and Maniatis, T. (1989) Molecular cloning: a laboratory manual. $2^{nd}$ ed. Cold Spring Harbour, Laboratory Press. New York.

Schmidt, D. M. Z., Hubbard, B. K., and Gerlt, J. A. (2001) Evolution of enzymatic activities in the enolase superfamily: functional assignment of unknown proteins in *Bacillus subtilis* and *Escherichia coli* as L-Ala-D/L-Glu epimerases. *Biochemistry* 40:15707-15715.

Schwecke, T., Aparicio, J. F., Molnár, I., König, A., Khaw, L. E., Haydock, S. F., Oliynyk, M., Caffrey, P., Cortés, J., Lester, J. B., Böhm, G. A., Staunton, J., and Leadlay, P. F. (1995) The biosynthetic gene cluster for the polyketide immunosuppressant rapamycin. *Proc. Nat. Acad. Sci. USA* 92:7839-7843.

Shaw-Reid, C. A., Kelleher, N. L., Losey, H. C., Gehring, A. M., Berg, C., and Walsh, C. T. (1999) Assembly line enzymology by multimodular nonribosomal peptide synthetases: the thioesterase domain of *E. coli* EntF catalyzes both elongation and cyclolactonization. *Chem. Biol.* 6:385-400.

Silakowski, B., Nordsiek, G., Kunze, B., Blöcker, H., and Müller, R (2001) Novel features in a combined polyketide synthase/non-ribosomal peptide synthetase: the myxalamid biosynthetic gene cluster of the myxobacterium *Stigmatella aurantica* Sga15. *Chem. Biol.* 8:59-69.

Singh, S. K., Gurusiddaiah, S., and Whalen, J. W. (1985) Treponemycin, a nitrile antibiotic active against *Treponema hyodysenteriae. Antimicrob. Agents Chemother.* 27:239-245.

Staunton, J., and Wilkinson, B. (1997) Biosynthesis of erythromycin and rapamycin. *Chem. Rev.* 97:2611-2629.

Swan, D. G., Rodriguez, A. M., Vilches, C., Mendez, C., and Salas, J. A. (1994) Characterization of a *Streptomyces antibioticus* gene encoding a type I polyketide synthase which has an unusual coding sequence. *Mol. Gen. Genet* 242:258-362.

Takeshita, S., Sato, M., Toba, M., Masahashi, W., and Hashimoto-Gotoh, T. (1987) High-copy number and low-copy number plasmid vectors for lacZ alpha-complementation and chloroamphenicol- or kanamycin-resistance selection. *Gene* 61:63-74.

Thomas, I., Martin (née Rowe), C. J., Wilkinson, C. J., Staunton, J., and Leadlay, P. F. (2002) Skipping in a hybrid polyketide synthase: evidence for ACP to ACP chain transfer. *Chem. Biol.* 9:781-787.

Tsuchiya, E., Yukawa, M., Miyakawa, T., Kimura, K. I., and Takahashi, H. (2001) Borrelidin inhibits a cyclin-dependent kinase (CDK), Cdc28/Cln2, of *Saccharomyces cerevisiae. J. Antibiot* 54:84-90.

Wakasugi, K., Slike, B. M., Hood, J., Otani, A., Ewalt, K. L., Friedlander, M., Cheresh, D. A., and Schimmel, P. (2002) A human aminoacyl-tRNA synthetase as a regulator of angiogenesis. *Proc. Nat. Acad. Sci. USA* 99:173-177.

Wakabayashi, T., Kageyama, R., Naruse, N., Tsukahara, N., Funahashi, Y., Kitoh, K., and Watanabe, Y. (1997) Borrelidin is an angiogenesis inhibitor; disruption of angiogenic capilla vessels in a rat aorta matrix culture model. *J. Antibiot.* 50:671-676.

Waldron, C., Matsushima, P., Rosteck, P. R., Broughton, M. C., Turner, J., Madduri, K., Crawford, K. P., Merlo, D. J. and Baltz, R. H. (2001) Cloning and analysis of the spinosad biosynthetic gene cluster of *Saccharopolyspora spinosa. Chem. Biol.* 8:487-499.

Wilkinson, B., Foster, G., Rudd, B. A. M., Taylor, N. L., Blackaby, A. P., Sidebottom, P. J., Dawson, M. J., Buss, A. D., Gaisser, S., Böhm, I. U., Rowe, C. J., Cortés, J., Leadlay, P. F., and Staunton, J. (2000) Novel octaketide macrolides related to 6-deoxyerythronolide B provide evidence for iterative operation of the erythromycin polyketide synthase. *Chem. Biol.* 7:111-117.

Wu, N., Tsuji, S. Y., Cane, D. E., and Khosla, C. (2001) Assessing the balance between protein-protein interactions and enzyme-substrate interactions in the channeling of intermediates between polyketide synthase modules. *J. Am. Chem. Soc.* 123: 6465-6474.

Xue, Y. Q., Zhao, L. S., Liu, H.-W., and Sherman, D. H. (1998) A gene cluster for macrolide antibiotic biosynthesis in *Streptomyces venezuelae*: architecture of metabolic diversity. *Proc. Nat. Acad. Sci. USA* 95:12111-12116.

Xue, Y. Q., and Sherman, D. H. (2000) Alternative modular polyketide synthase expression controls macrolactone structure. *Nature* 403:571-575.

Yamamoto, H., Maurer, K. H., Hutchinson, C. R. (1986) Transformation of *Streptomyces erythraeus*. *J. Antibiot.* 39:1304-1313.

The invention claimed is:

1. An isolated compound, said compound being selected from the group consisting of formula 1,

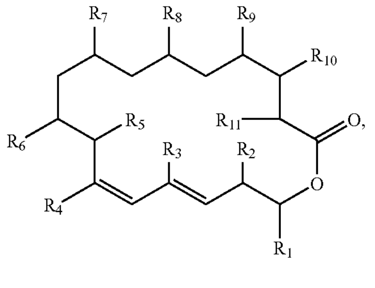

and pharmaceutically acceptable salts thereof, wherein $R_1$ is a cycloalkyl group of the formula, n being 1-2,

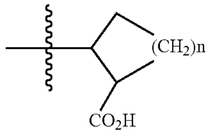

and $R_1$ can also optionally have a substituent of at least one halo atoms or at least one $C_1$ to $C_3$ alkyl groups; $R_2$, $R_3$, $R_6$, $R_7$, $R_8$, $R_9$, or $R_{11}$ are each independently H, $OCH_3$, $CH_3$ or $CH_2CH_3$; $R_4$ is CN, $CO_2H$, CHO, $CH_3$, $CONH_2$, CHNH; $R_5$, $R_{10}$ are OH; with the proviso that said compounds are not borrelidin, 12-desnitrile-12-carboxyl borrelidin, 10-desmethyl borrelidin, 11-epiborrelidin or C14,C15-cis borrelidin; and formula 2

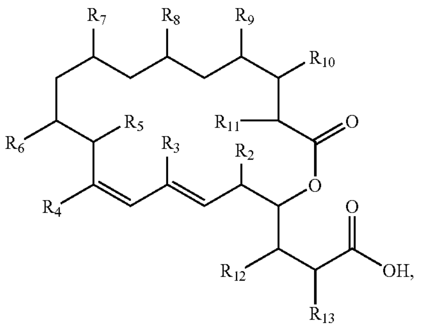

wherein $R_2$, $R_3$, $R_6$, $R_7$, $R_8$, $R_9$, or $R_{11}$ are each independently H, $OCH_3$, $CH_3$ or $CH_2CH_3$; $R_4$ is CN, $CO_2H$, CHO, $CH_3$, $CONH_2$, CHNH; $R_5$, $R_{10}$ are OH; and $R_{12}$ and $R_{13}$ are independently H or a C1-C4 alkyl group which may be optionally substituted with OH, F, Cl, SH, with the proviso that $R_{12}$ and $R_{13}$ are not simultaneously H.

2. The compound of claim 1, or a pharmaceutically acceptable salt thereof, said compound having the formula:

Formula 1

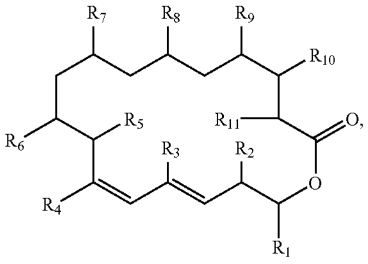

wherein $R_1$ is a cycloalkyl group of the formula, n being 1-2

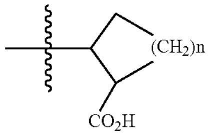

and $R_1$ can also optionally have a substituent of with at least one halo atom or at least one $C_1$ to $C_3$ alkyl group; $R_2$, $R_3$, $R_6$, $R_7$, $R_8$, $R_9$, or $R_{11}$ are each independently H, $OCH_3$, $CH_3$ or $CH_2CH_3$; $R_4$ is CN, $CO_2H$, CHO, $CH_3$, $CONH_2$, CHNH; $R_5$, $R_{10}$ are OH; with the proviso that said compounds are not borrelidin, 12-desnitrile-12-carboxyl borrelidin, 10-desmethyl borrelidin, 11-epiborrelidin or C14,C15-cis borrelidin.

3. The compound or salt according to claim 2 wherein R1 is cyclobutane-1'-carboxylate.

4. The compound or salt according to claim 2, wherein $R_6$, $R_7$, $R_8$ and $R_9$ are all $CH_3$, $R_2$ and $R_{11}$ are H, $R_5$ and $R_{10}$ are OH, $R_4$ is either $CH_3$, COOH or CN and $R_1$ is cyclopentane-1'-carboxylate or cyclobutane-1'-carboxylate.

5. The compound of claim 1, or a pharmaceutically acceptable salt thereof, said compound having the formula:

Formula 2

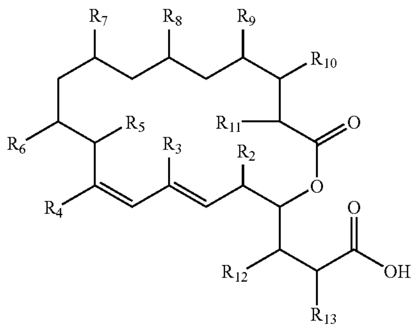

wherein $R_2$, $R_3$, $R_6$, $R_7$, $R_8$, $R_9$, or $R_{11}$ are each independently H, $OCH_3$, $CH_3$ or $CH_2CH_3$; $R_4$ is CN, $CO_2H$, CHO, $CH_3$, $CONH_2$, CHNH; $R_5$, $R_{10}$ are OH; and $R_{12}$ and $R_{13}$ are independently H or a $C_1$-$C_4$ alkyl group which may be optionally substituted with OH, F, Cl, SH, with the proviso that $R_{12}$ and $R_{13}$ are not simultaneously H.

6. The compound or salt according to claim 5, wherein $R_{12}$ and $R_{13}$ are independently $CH_3$ or H.

7. The compound or salt according to claim 5 wherein $R_6$, $R_7$, $R_8$ and $R_9$ are all $CH_3$, $R_2$ and $R_{11}$ are H, $R_5$ and $R_{10}$ are OH, $R_4$ is either $CH_3$, COOH or CN and $R_{12}$ and $R_{13}$ are independently $CH_3$ or H.

8. The compound or salt according to claim 5 wherein $R_6$, $R_7$, $R_8$ and $R_9$ are all $CH_3$, $R_2$ and $R_{11}$ are H, $R_5$ and $R_{10}$ are OH, $R_4$ is either $CH_3$, COOH or CN and $R_{12}$ and $R_{13}$ are both $CH_3$.

9. The compound or salt according to claim 1, wherein $R_7$, $R_8$ and $R_9$ of formulas 1 and 2 are all $CH_3$.

10.: The compound or salt according to claim 9 wherein $R_4$ of formulas 1 and 2 is $CH_3$ or COOH.

11. The compound or salt according to claim 9 wherein $R_4$ of formulas 1 and 2 is CN.

12. The compound or salt according to claim 9, wherein R1 of formula 1 is cyclobutane-1'-carboxylate.

13. The compound or salt according to claim 12, wherein $R_4$ of formulas 1 and 2 is $CH_3$ or COOH.

14. The compound or salt according to claim 9, wherein $R_{12}$ and $R_{13}$ of formula 2 are independently $CH_3$ or H.

15. The compound or salt according to claim 14, wherein $R_4$ of formulas 1 and 2 is $CH_3$ or COOH.

16. The compound or salt according to claim 1, wherein $R_4$ of formulas 1 and 2 is $CH_3$ or COOH.

17. The compound or salt according to claim 1, wherein $R_4$ of formulas 1 and 2 is CN.

* * * * *